US012071646B2

(12) United States Patent
Itkin et al.

(10) Patent No.: US 12,071,646 B2
(45) Date of Patent: Aug. 27, 2024

(54) CELLS COMPRISING MOGROSIDE PATHWAY ENZYMES AND USES THEREOF

(71) Applicant: The State of Israel, Ministry of Agriculture & Rural Development, Agricultural Research Organization (ARO)(Volcani Center), Rishon-LeZion (IL)

(72) Inventors: Maxim Itkin, Kibbutz HaOgen (IL); Rachel Davidovich-Rikanati, Alonei Abba (IL); Shahar Cohen, Rishon-LeZion (IL); Vitaly Portnoy, Nesher (IL); Adi Doron-Faigenboim, Ramat-HaSharon (IL); Marina Petreikov, Rishon-LeZion (IL); Shmuel Shen, Moshav Beit-Elazari (IL); Yaakov Tadmor, Timrat (IL); Yosef Burger, Haifa (IL); Efraim Lewinsohn, Timrat (IL); Nurit Katzir, Kiryat-Tivon (IL); Arthur A. Schaffer, Hashmonaim (IL); Elad Oren, Beit Shearim (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 17/563,127

(22) Filed: Dec. 28, 2021

(65) Prior Publication Data

US 2022/0170063 A1 Jun. 2, 2022

Related U.S. Application Data

(62) Division of application No. 15/510,708, filed as application No. PCT/IL2015/050933 on Sep. 10, 2015, now abandoned.

(Continued)

(51) Int. Cl.

| | |
|---|---|
| ***C12N 9/10*** | (2006.01) |
| ***A23L 2/60*** | (2006.01) |
| ***A23L 27/30*** | (2016.01) |
| ***C07J 17/00*** | (2006.01) |
| ***C12N 9/02*** | (2006.01) |
| ***C12N 9/14*** | (2006.01) |
| ***C12N 9/88*** | (2006.01) |

(Continued)

(52) U.S. Cl.

CPC ................. *C12P 33/12* (2013.01); *A23L 2/60* (2013.01); *A23L 27/36* (2016.08); *C07J 17/005* (2013.01); *C12N 9/0071* (2013.01); *C12N 9/0083* (2013.01); *C12N 9/14* (2013.01); *C12N 9/88* (2013.01); *C12N 9/90* (2013.01); *C12P 19/56* (2013.01); *C12P 33/20* (2013.01); *C12Y 114/99007* (2013.01); *C12Y 204/02017* (2013.01); *C12Y 402/01* (2013.01); *C12Y 504/99033* (2013.01); *A23V 2002/00* (2013.01)

(58) Field of Classification Search

CPC ........... C12P 33/12; C12P 19/56; C12P 33/20; A23L 2/60; A23L 27/36; C07J 17/005; C12N 9/0071; C12N 9/0083; C12N 9/14; C12N 9/88; C12N 9/90; C12Y 114/99007; C12Y 204/02017; C12Y 402/01; C12Y 504/99033; A23V 2002/00

See application file for complete search history.

(56) References Cited

U.S. PATENT DOCUMENTS

| | | | |
|---|---|---|---|
| 9,932,619 | B2 | 4/2018 | Liu et al. |
| 10,011,859 | B2 | 7/2018 | Liu |

(Continued)

FOREIGN PATENT DOCUMENTS

| | | |
|---|---|---|
| CA | 2963300 | 4/2016 |
| WO | WO 2009/037362 | 3/2009 |

(Continued)

OTHER PUBLICATIONS

Singh et al., Current Protein and Peptide Science 19(1):5-15, 2018.*

(Continued)

*Primary Examiner* — Delia M Ramirez

(57) ABSTRACT

Isolated mogroside and mogrol biosynthetic pathway enzyme polypeptides useful in mogroside biosynthesis are provided. Mogroside biosynthetic pathway enzymes of the invention include squalene epoxidase (SE), epoxy hydratase (EH), cytochrome p450 (Cyp), cucurbitadienol synthase (CDS) and udp-glucosyl-transferase (UGT), Also provided are methods of producing a mogroside using the isolated mogroside and mogrol biosynthetic enzyme polypeptides, the methods comprising contacting a mogrol and/or a glycosylated mogrol (mogroside) with at least one UDP glucose glucosyl transferase (UGT) enzyme polypeptide of the invention catalyzing glucosylation of the mogrol and/or the glucosylated mogrol to produce a mogroside with an additional glucosyl moietie(s), thereby producing the mogroside. Alternatively or additionally provided is a method of synthesizing a mogrol, the method comprising contacting a mogrol precursor substrate with one or more mogrol biosynthetic pathway enzyme polypeptides as described herein catalyzing mogrol synthesis from the mogrol precursor substrate, thereby synthesizing the mogrol.

6 Claims, 26 Drawing Sheets
(22 of 26 Drawing Sheet(s) Filed in Color)
Specification includes a Sequence Listing.

Related U.S. Application Data

(60) Provisional application No. 62/089,929, filed on Dec. 10, 2014, provisional application No. 62/048,924, filed on Sep. 11, 2014.

(51) Int. Cl.

| | |
|---|---|
| ***C12N 9/90*** | (2006.01) |
| ***C12P 19/56*** | (2006.01) |
| ***C12P 33/12*** | (2006.01) |
| ***C12P 33/20*** | (2006.01) |

(56) References Cited

U.S. PATENT DOCUMENTS

| | | | |
|---|---|---|---|
| 10,633,685 | B2 | 4/2020 | Houghton-Larsen et al. |
| 11,060,124 | B2 | 7/2021 | Patron |
| 2014/0170286 | A1 | 6/2014 | Jia et al. |
| 2017/0283844 | A1 | 10/2017 | Itkin et al. |

FOREIGN PATENT DOCUMENTS

| | | |
|---|---|---|
| WO | WO 2013/036768 | 3/2013 |
| WO | WO 2013/076577 | 5/2013 |
| WO | WO 2014/086842 | 6/2014 |
| WO | WO 2016/038617 | 3/2016 |
| WO | WO 2016/050890 | 4/2016 |

OTHER PUBLICATIONS

Office Action Dated May 26, 2022 From the Israel Patent Office Re. Application No. 287789. (4 Pages).

Requisition by the Examiner Dated Jul. 27, 2022 From the Innovation, Science and Economic Development Canada, Canadian Intellectual Property Office Re. Application No. 2,972,739. (5 Pages).

Communication Pursuant to Article 94(3) EPC Dated Apr. 6, 2020 From the European Patent Office Re. Application No. 15839739.8. (10 Pages).

Communication Pursuant to Article 94(3) EPC Dated Oct. 8, 2021 From the European Patent Office Re. Application No. 15839739.8. (3 Pages).

Communication Pursuant to Article 94(3) EPC Dated Dec. 23, 2020 From the European Patent Office Re. Application No. 15839739.8. (4 Pages).

Communication Pursuant to Rulc 164(1) EPC and Supplementary Partial European Search Report and the Provisional Opinion Dated Mar. 7, 2018 From the European Patent Office Re. Application No. 15839739.8. (10 Pages).

Decision of Rejection Dated Jun. 2, 2021 From the State Intellectual Property Office of the People's Republic of China Re. Application No. 201580061244.3 and Its Translation Into English. (9 Pages).

Examination Report Under Sections 12 & 13 of the Patents Act, 1970 and the Patents Rules, 2003 Dated Jul. 28, 2020 From the Government of India, Intellectual Property India, Patents, Designs, Trade Marks, Geographical Indications The Patent Office Re. Application No. 201727012291. (8 Pages).

Final Official Action Dated Mar. 15, 2021 From Re. U.S. Appl. No. 15/510,708. (23 Pages).

Hearing Notice Dated Sep. 8, 2021 From the Government of India, Intellectual Property India, Patents, Designs, Trade Marks, Geographical Indications, The Patent Office Re. Application No. 201727012291. (3 Pages).

International Preliminary Report on Patentability Dated Mar. 23, 2017 From the International Bureau of WIPO Re. Application No. PCT/IL2015/050933. (10 Pages).

International Search Report and the Written Opinion Dated Jan. 6, 2016 From the International Searching Authority Rc. Application No. PCT/IL2015/050933.

Notification of Office Action and Search Report Dated Apr. 3, 2020 From the National Intellectual Property Administration of the People's Republic of China Re. Application No. 201580061244.3 and Its Translation Into English. (15 Pages).

Notification of Office Action and Search Report Dated Dec. 10, 2020 From the National Intellectual Property Administration of the People's Republic of China Re. Application No. 201580061244.3 and Its Translation Into English. (18 Pages).

Office Action Dated Apr. 7, 2020 From the Israel Patent Office Re. Application No. 251070 and Its Translation Into English. (7 Pages).

Office Action Dated Feb. 24, 2021 From the Israel Patent Office Re. Application No. 251070 and Its Translation Into English. (5 Pages).

Office Action Dated Dec. 31, 2018 From the Israel Patent Office Re. Application No. 251070 and Its Translation Into English. (8 Pages).

Official Action Dated Sep. 16, 2021 from tRe. U.S. Appl. No. 15/510,708. (12 pages).

Official Action Dated Aug. 6, 2020 from Re. U.S. Appl. No. 15/510,708. (32 pages).

Requisition by the Examiner Dated Aug. 24, 2021 From the Innovation, Science and Economic Development Canada, Canadian Intellectual Property Office Re. Application No. 2,972,739. (14 Pages).

Restriction Official Action Dated Oct. 29, 2019 from Re. U.S. Appl. No. 15/510,708. (8 pages).

Supplementary European Search Report and the European Search Opinion Dated Jun. 14, 2018 From the European Patent Office Re. Application No. 15839739.8 (8 Pages).

Branden et al. "Introduction to Protein Structure", Garland Publishing: p. 247, 1991.

Guo et al. "Protein Tolerance to Random Amino Acid Change", ONAS Research Article, 101(25): 9205-9210, Jun. 22, 2004.

Kasai et al. "Sweet Cucurbitane Glycosides From Fruits of Siraitia Siamensis (Chi-Zi Luo-Han-Guo), A Chinese Folk Medicine", Agricultural and Biological Chemistry, 53(12): 3347-3349, 1989.

Li et al. "Chemistry and Pharmacology of Siraitia Grosvenorii: A Review", Chinese Journal of Natural Medicines, XP002778266, 12(2): 89-102, Available Online Feb. 20, 2014. p. 90, 1-h col. Para 1, Figs. 1, 2.

Motamayor et al. "UDP-Glycosyl Transferase 85A3, Putative [Theobroma Cacao]", Database NCBI [Online], NCBI Reference Sequence: XP_007026849.1, GeneBank Accession No. XP_007026849, Jul. 10, 2014.

NCBI "Predicted: Bifunctional Epoxide Hydrolase 2-Like [Cucumis Melo]", Database NCBI [Online], NCBI Reference Sequence: XP_008454324.1, GeneBank Accession No. XP_008454324, Jun. 25, 2014.

NCBI "Predicted: Bifunctional Epoxide Hydrolase 2-Like [Cucumis Melo]", NCBI Database [Online], NCBI Reference Sequence XP_008454327.1, Database Accession No. XP_008454327, Jun. 25, 2014.

NCBI "Predicted: Bifunctional Epoxide Hydrolase 2-Like [Cucumis Sativus]", NCBI Database [Online], NCBI Reference Sequence XP_0041522243.1, Database Accession No. XP_004152243, Feb. 12, 2013.

NCBI "Predicted: Bifunctional Epoxide Hydrolase 2-Like [Cucumis Sativus]", NCBI Database [Online], NCBI Reference Sequence: XP_004152361.1, Database Accession No. XP_004152361, Feb. 12, 2013.

NCBI "Predicted: Bifunctional Epoxide Hydrolase 2-Like Isoform X1 [Cucumis Melo]", NCBI Database [Online], NCBI Reference Sequence XP_008454322.1, Database Accession No. XP_008454322, Jun. 25, 2014.

NCBI "Predicted: Squalene Monooxygenase-Like [Cucumis Melo]", Database NCBI [Online], NCBI Reference Sequence: XP_008444517.1, GeneBank Accession No. XP_008444517, Jun. 25, 2014.

NCBI "Predicted: Squalene Monooxygenase-Like [Cucumis Melo]", NCBI Databse [Online], NCBI Reference Sequence: XP_008452686.1, GeneBank Accession No. XP_008452686, Jun. 25, 2014.

NCBI "Predicted: Squalene Monooxygenase-Like [Cucumis Sativus]", NCBI Database [Online], NCBI Reference Sequence: XP_004142907.1, Database Accession No. XP_004142907, Feb. 12, 2013.

NCBI "Predicted: UDP-Glycolyltransferase 85A2-Like [Malus Domestica]", Database NCBI [Online], NCBI Reference Sequence: XP_008370121.1, GeneBank Accession No. XP_008370121, Jun. 20, 2014.

(56) References Cited

OTHER PUBLICATIONS

NCBI "Predicted: UDP-Glycosyltransferase 85A7-Like [Cucumis Melo]", Database NCBI [Online], NCBI Reference Sequence: XP_008450117.1, GeneBank Accession No. XP_008450117, Jun. 25, 2014.
Sadowski et al. "The Sequence-Structure Relationship and Protein Function Prediction", Current Opinion in Structural Biology 19: 357-362, 2009.
Seffernick et al. "Melamine Deaminase and Atrazine Chlorohydrolase: 98 Percent Identical but Functionally Different", Journal Of Bacteriology 183 (8): 2405-2410, 2001.
Seki et al. "Licorice Beta-Amyrin 11-Oxidase, A Cytochrome P450 With A Key Role in the Biosynthesis of the Triterpene Sweetener Glycyrrhizin", Proc. Natl. Acad. Sci. USA, PNAS, 105(37): 14204-14209, Sep. 16, 2008.
Shibuya et al. "Cucurbitadienol Synthase, the First Committed Enzyme for Cucurbitacin Biosynthesis, Is A Distinct Enzyme From Cycloartenol Synthase for Phytosterol Biosynthesis", Tetrahedron, 60(33): 6995-7003, 2004. Abstract.
Tang et al. "An Efficient Approach to Finding Siraitia Grosvenorii Triterpenc Biosynthetic Genes by RNA-Seq and Digital Gene Expression Analysis", BMC Genomics, 12(343): 1-13, 2011. Table 3, p. 6, r-h Col. Para 1—p. 8, 1-h Col. Para 1, Fig.1.
Tang et al. "Identification of Dehalobacter Reductive Dehalogenases that Catalyse Dechlorination of Chloroform, 1, 1, 1-Trichloroethane and 1,1-Dichloroethane.", Philosophical Transactions of the Royal Society, Retrieved from the Internet, 2013, 10 pages.
Ukiya et al. "Inhibitory Effects of Cucurbitane Glycosides and Other Triterpenoids from the Fruit of Momordica Grosvenori on Epstein-Barr Virus Early Antigen Induced by Tumor Promoter 12-0-Tetradecanoylphorbolg 13-acetate", Journal of Agricultural and Food Chemistry 50 (23): 6710-6715, 2002.
Witkowski et al. "Conversion of a B-Ketoacyl Synthase to a Malonyl Decarboxylase by Replacement of the Active-Site Cysteine with Glutamine", Biochemistry 38: 11643-11650, 1999.
Wu et al. "Triterpenoid Biosynthesis in Gynostemma Pentaphyllum, A Useful Medicinal Herb Found in Guangxi", Database UniProt [Online], XP002778267, UniProtKB/TrEMBL ID No. C4P9M2_GYNPE, Database Accession No. C4P9M2, Feb. 19, 2014. Abstract.
Communication Pursuant to Article 114(2) EPC Dated Oct. 13, 2022 From the European Patent Office Re. Application No. 15839739.8. (15 pages).
Requisition by the Examiner Dated Aug. 22, 2023 From the Innovation, Science and Economic Development Canada, Canadian Intellectual Property Office Re. Application No. 2,972,739. (3 Pages).
Communication Pursuant to Article 94(3) EPC Dated Mar. 9, 2023 From the European Patent Office Re. Application No. 15839739.8 (3 Pages).

* cited by examiner

| mogrosides | $R_1$ | $R_2$ |
|---|---|---|
| mogroside IIE | -Glc | -Glc |
| mogroside III | -Glc | -Glc-Glc |
| mogroside IV | -Glc-Glc | -Glc-Glc |
| mogroside V | -Glc-Glc | —Glc Glc Glc |
| mogroside VI | —Glc Glc Glc | —Glc Glc Glc |

FIG. 3
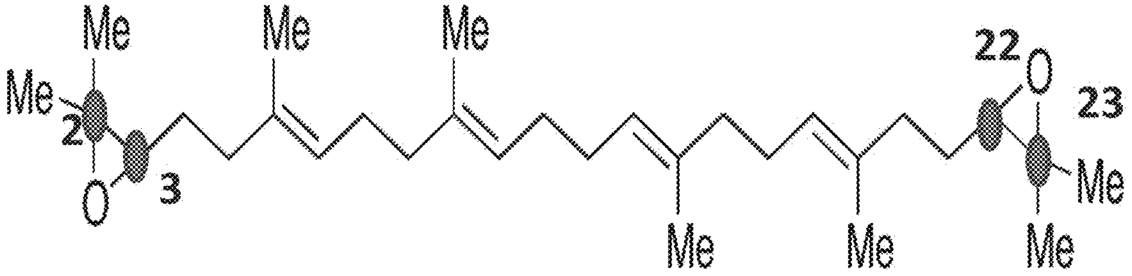
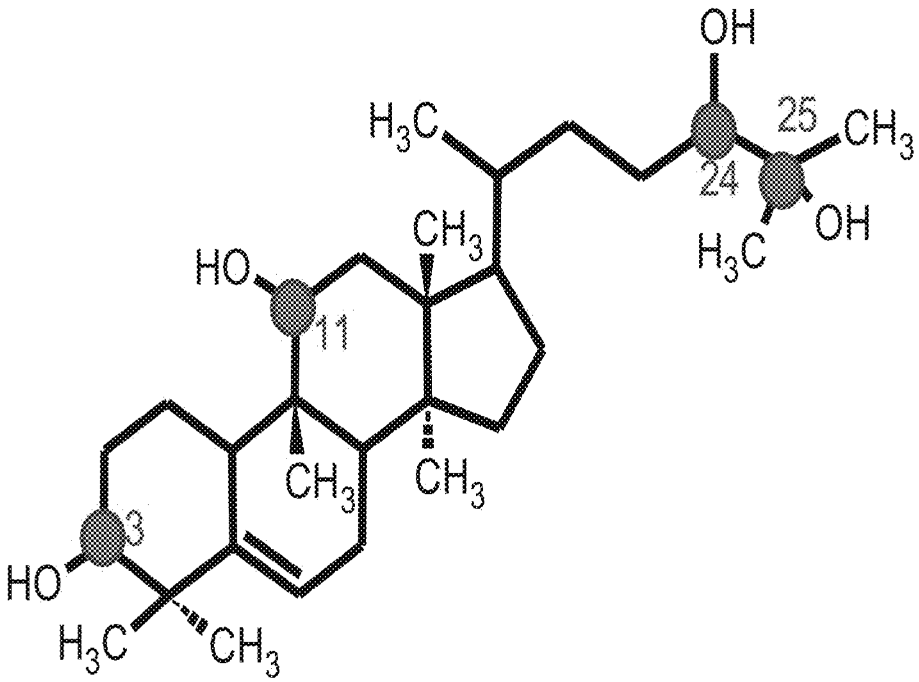

FIG. 4A
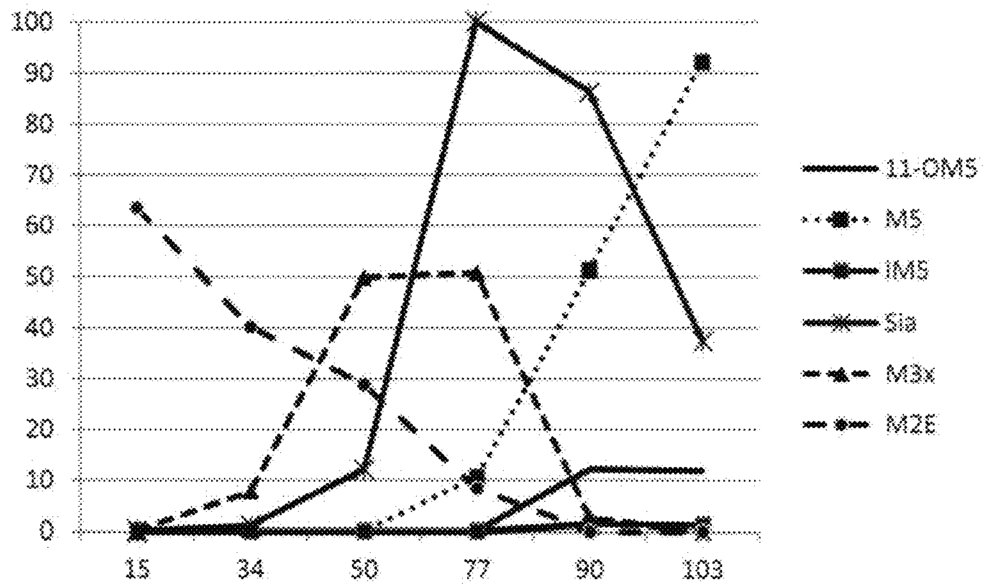
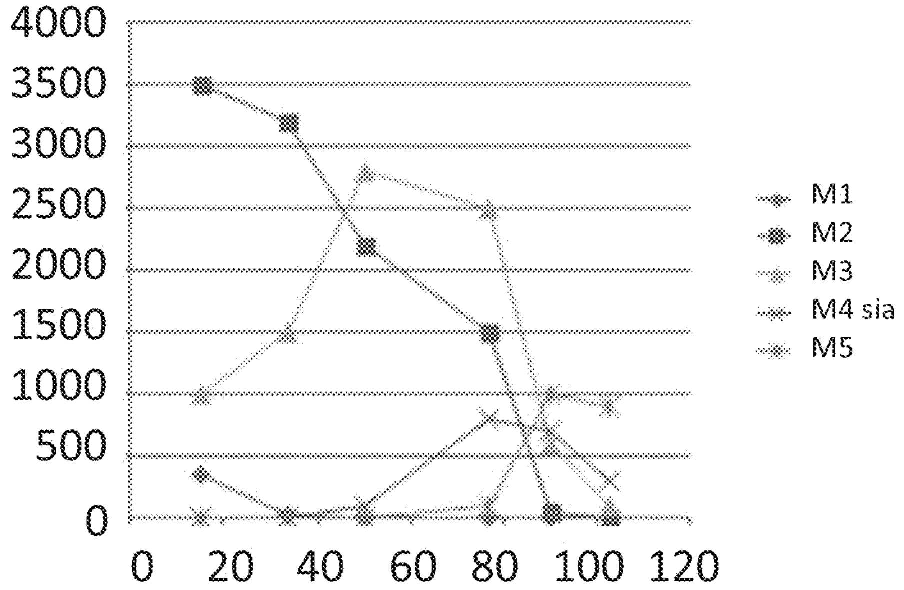
FIG. 4B

FIG. 9

| | seq id #38 | contig102581 | contig101438 | EPH2 86123p | Seq id #40 | EPH1 73966p | EPH3 102640 | EPH4 28382p | contig102175 | contig22474 |
|---|---|---|---|---|---|---|---|---|---|---|
| seq id #38 | 100 | 99 | 65 | 61 | 61 | 60 | 62 | 61 | 63 | 34 |
| contig102581 | 99 | 100 | 65 | 60 | 61 | 60 | 63 | 61 | 63 | 34 |
| contig101438 | 65 | 65 | 100 | 60 | 59 | 60 | 60 | 61 | 64 | 35 |
| EPH2 86123p | 61 | 60 | 60 | 100 | 98 | 76 | 72 | 72 | 72 | 38 |
| Seq id #40 | 61 | 61 | 59 | 98 | 100 | 75 | 72 | 72 | 73 | 39 |
| EPH1 73966p | 60 | 60 | 60 | 76 | 75 | 100 | 71 | 71 | 69 | 37 |
| EPH3 102640 | 62 | 63 | 60 | 72 | 72 | 71 | 100 | 87 | 75 | 37 |
| EPH4 28382p | 61 | 61 | 61 | 72 | 72 | 71 | 87 | 100 | 75 | 39 |
| contig102175 | 63 | 63 | 64 | 72 | 73 | 69 | 75 | 75 | 100 | 37 |
| contig22474 | 34 | 34 | 35 | 38 | 39 | 37 | 37 | 39 | 37 | 100 |

FIG. 12

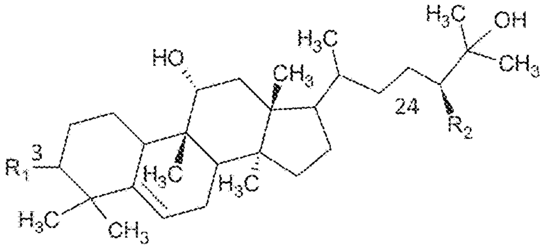

| R1(C3) | R2 (C24) | Name | Verification | Source |
|---|---|---|---|---|
| -OH | -OH | Mogrol (M) | NMR | Mild acid hydrolysis |
| -OH | -Glu | Mogroside I-A1 (M1A1) | NMR | Mild acid hydrolysis |
| -Glu | -OH | Mogroside I-E1 (M1E1) | MS | |
| -OH | -Glu(1-6) Glu | Mogroside II-A1 (M2A1) (previously M2x) | NMR | Mild acid hydrolysis |
| -OH | -Glu(1-2) Glu | Mogroside II-A (M2A) (previously M2c) | NMR | Enzymatic hydrolysis |
| -Glu | -Glu | Mogroside II-E1 (M2E1) | MS | |
| -OH | Glu (1-6) Glu (1-2) Glu | Mogroside III-A1 (M3A1) | MS | |
| -OH | -Glu(1-2) Glu | Mogroside III -1-2 (M3) | NMR | Mild acid or Enzymatic hydrolysis |
| -OH | -Glu(1-6) Glu | Mogroside III (M3x) | MS | |
| -Glu(1-4) Glu | -Glu(1-2) Glu | Isomogroside IV (iM4) | MS | |
| -Glu(1-6) Glu | -Glu(1-6) Glu | Mogroside IV-A (M4A) | MS | |
| -Glu(1-6) Glu | -Glu(1-2) Glu | Mogroside IV (M4) | NMR | Chaturvdula Prakash and Prakash, 2011 |
| -Glu | -Glu (1-6) Glu (1-2) Glu | Siamenoside I (Sia) | NMR | Chaturvdula Prakash and Prakash, 2011 |
| -Glu(1-4) Glu | -Glu (1-6) Glu (1-2) Glu | Isomogroside V (iM5) | NMR | Chaturvdula Prakash and Prakash, 2011 |
| -Glu(1-6) Glu | -Glu (1-6) Glu (1-2) Glu | Mogroside V (M5) | NMR | Chaturvdula Prakash and Prakash, 2011 |
| -Glu (1-6) Glu (1-2) Glu | -Glu (1-6) Glu (1-2) Glu | Mogroside VI (M6) | NMR | Chaturvdula Prakash and Prakash, 2011 |

Protein sequences were aligned using Clustal Omega (http://www.ebi.ac.uk/) and Phylogenetic tree was generated (http://www.ebi.ac.uk/).
Red frames -- our proteins with shown activity, dashed frame -- genes shown to posess UGT activity with mogrosides (At and Sr).

| Substrate structure and name | H UGT85-269-1 | I UGT94-289-3 | J UGT94-289-2 | K UGT94-289-1 | L UGT73-327-2 |
|---|---|---|---|---|---|
| 1 M2-E | M3 C3(1-6) | | | | |
| 2 M3 | iM4, M4* | Sia, M4* | Sia | Sia, M4* | |
| 3 M3x | M4A | M4A, Sia | | | |
| 4 M4 | | M5 | | M5 | |
| 5 Sia | iM5 | M5 | | | |
| 6 M5 | | M6 | | | M6 |

FIG. 18

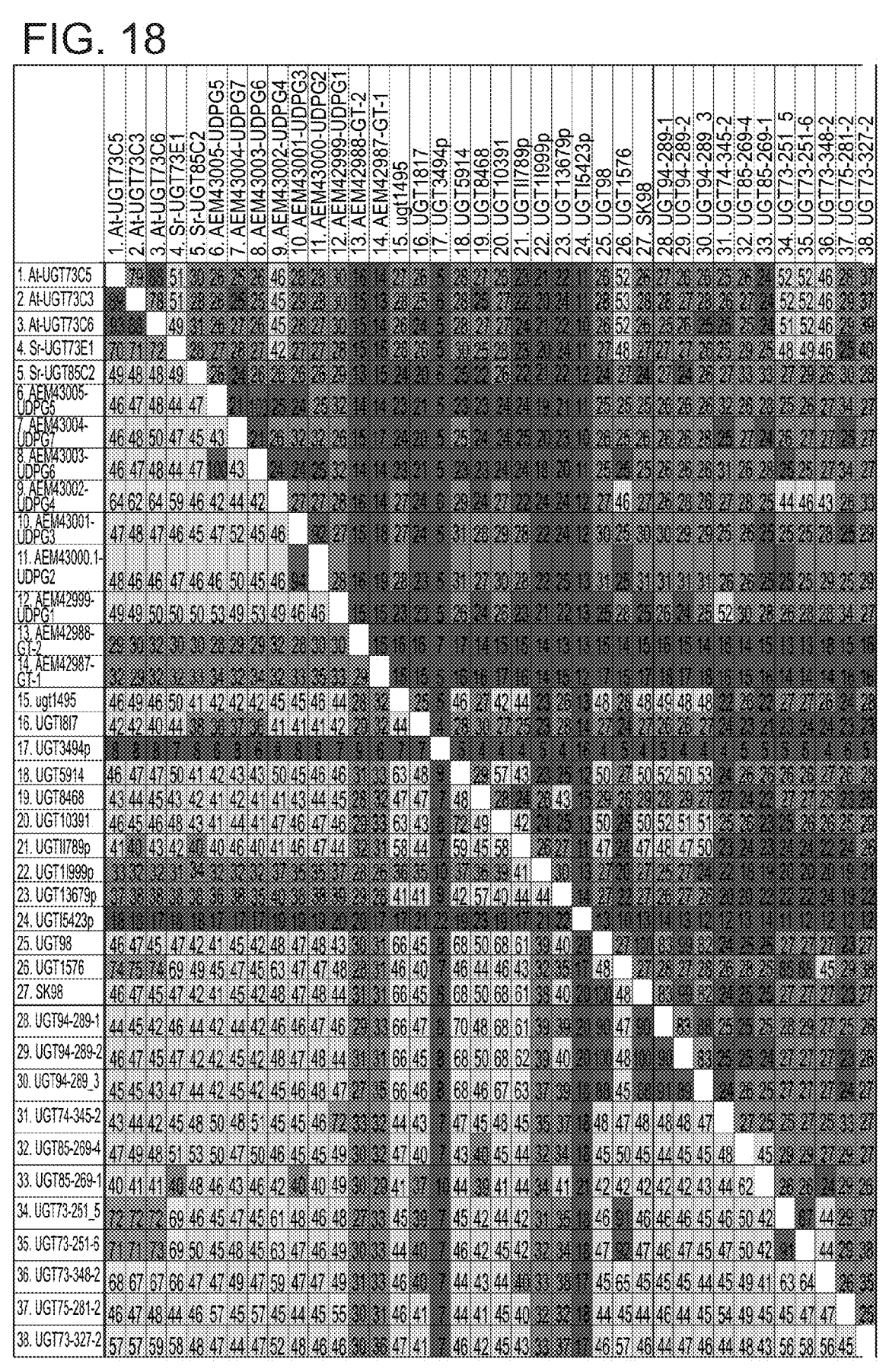

| | 1. At-UGT73C5 | 2. At-UGT73C3 | 3. At-UGT73C6 | 4. Sr-UGT73E1 | 5. Sr-UGT85C2 | 6. AEM43005-UDPG5 | 7. AEM43004-UDPG7 | 8. AEM43003-UDPG6 | 9. AEM43002-UDPG4 | 10. AEM43001-UDPG3 | 11. AEM43000-UDPG2 | 12. AEM42999-UDPG1 | 13. AEM42988-GT-2 | 14. AEM42987-GT-1 | 15. ugt1495 | 16. UGT1817 | 17. UGT3494p | 18. UGT5914 | 19. UGT8468 | 20. UGT10391 | 21. UGTII789p | 22. UGT1I999p | 23. UGT13679p | 24. UGTI5423p | 25. UGT98 | 26. UGT1576 | 27. SK98 | 28. UGT94-289-1 | 29. UGT94-289-2 | 30. UGT94-289 3 | 31. UGT74-345-2 | 32. UGT85-269-4 | 33. UGT85-269-1 | 34. UGT73-251_5 | 35. UGT73-251-6 | 36. UGT73-348-2 | 37. UGT75-281-2 | 38. UGT73-327-2 |
|---|---|---|---|---|---|---|---|---|---|---|---|---|---|---|---|---|---|---|---|---|---|---|---|---|---|---|---|---|---|---|---|---|---|---|---|---|---|---|
| 1. At-UGT73C5 | | 79 | [illegible] | 51 | 30 | 26 | 25 | 26 | 46 | 28 | 28 | 30 | 16 | 14 | 27 | 26 | 5 | 28 | 27 | 26 | 23 | 21 | 22 | 11 | 26 | 52 | 26 | 27 | 26 | 26 | 25 | 26 | 24 | 52 | 52 | 46 | 29 | 37 |
| 2. At-UGT73C3 | [illegible] | | 78 | 51 | 28 | 26 | 25 | 25 | 45 | 29 | 28 | 30 | 15 | 13 | 28 | 25 | 6 | 28 | 25 | 27 | 22 | 20 | 24 | 11 | 28 | 53 | 28 | 28 | 27 | 28 | 26 | 27 | 24 | 52 | 52 | 46 | 29 | 37 |
| 3. At-UGT73C6 | [illegible] | [illegible] | | 49 | 31 | 26 | 27 | 26 | 45 | 28 | 27 | 30 | 15 | 14 | 26 | 24 | 5 | 28 | 27 | 27 | 24 | 21 | 22 | 10 | 26 | 52 | 26 | 25 | 26 | 25 | 26 | 25 | 24 | 51 | 52 | 46 | 29 | 40 |
| 4. Sr-UGT73E1 | 70 | 71 | 72 | | 28 | 27 | 28 | 27 | 42 | 27 | 27 | 28 | 15 | 15 | 28 | 26 | 5 | 30 | 25 | 28 | 23 | 20 | 24 | 11 | 27 | 48 | 27 | 27 | 27 | 26 | 25 | 29 | 25 | 48 | 49 | 46 | 25 | 40 |
| 5. Sr-UGT85C2 | 49 | 48 | 48 | 49 | | 26 | 24 | 26 | 26 | 26 | 26 | 29 | 13 | 15 | 24 | 20 | 6 | 25 | 22 | 26 | 22 | 21 | 22 | 12 | 24 | 27 | 24 | 27 | 24 | 26 | 27 | 33 | 33 | 27 | 29 | 26 | 30 | 28 |
| 6. AEM43005-UDPG5 | 46 | 47 | 48 | 44 | 47 | | 21 | [illegible] | 25 | 24 | 25 | 32 | 14 | 14 | 23 | 21 | 5 | 23 | 23 | 24 | 24 | 19 | 21 | 11 | 25 | 25 | 25 | 26 | 26 | 26 | 32 | 26 | 29 | 25 | 26 | 27 | 34 | 27 |
| 7. AEM43004-UDPG7 | 46 | 48 | 50 | 47 | 45 | 43 | | 21 | 26 | 32 | 32 | 26 | 15 | 17 | 24 | 20 | 5 | 25 | 24 | 24 | 25 | 20 | 23 | 10 | 26 | 25 | 26 | 26 | 26 | 28 | 25 | 27 | 24 | 26 | 27 | 27 | 28 | 27 |
| 8. AEM43003-UDPG6 | 46 | 47 | 48 | 44 | 47 | [illegible] | 43 | | 24 | 24 | 25 | 32 | 14 | 14 | 23 | 21 | 5 | 23 | 23 | 24 | 24 | 18 | 20 | 11 | 25 | 25 | 25 | 26 | 26 | 26 | 31 | 26 | 29 | 25 | 25 | 27 | 34 | 27 |
| 9. AEM43002-UDPG4 | 64 | 62 | 64 | 59 | 46 | 42 | 44 | 42 | | 27 | 27 | 28 | 16 | 14 | 27 | 24 | 6 | 29 | 24 | 27 | 22 | 24 | 24 | 12 | 27 | 46 | 27 | 26 | 28 | 26 | 27 | 28 | 25 | 44 | 46 | 43 | 26 | 33 |
| 10. AEM43001-UDPG3 | 47 | 48 | 47 | 46 | 45 | 47 | 52 | 45 | 46 | | [illegible] | 27 | 16 | 18 | 27 | 24 | 5 | 31 | 28 | 29 | 28 | 22 | 24 | 12 | 30 | 25 | 30 | 30 | 29 | 29 | 25 | 26 | 25 | 25 | 25 | 28 | 28 | 29 |
| 11. AEM43000.1-UDPG2 | 48 | 46 | 46 | 47 | 46 | 46 | 50 | 45 | 46 | [illegible] | | 28 | 16 | 19 | 28 | 23 | 5 | 31 | 27 | 30 | 28 | 22 | 25 | 13 | 31 | 25 | 31 | 31 | 31 | 31 | 26 | 26 | 25 | 25 | 25 | 29 | 25 | 29 |
| 12. AEM42999-UDPG1 | 49 | 49 | 50 | 50 | 50 | 53 | 49 | 53 | 49 | 46 | 46 | | 15 | 15 | 23 | 23 | 5 | 26 | 24 | 26 | 23 | 21 | 22 | 13 | 25 | 24 | 25 | 26 | 24 | 25 | 52 | 30 | 28 | 26 | 28 | 28 | 34 | 27 |
| 13. AEM42988-GT-2 | 29 | 30 | 32 | 30 | 30 | 28 | 29 | 29 | 32 | 28 | 30 | 30 | | 15 | 16 | 16 | 7 | 17 | 14 | 15 | 15 | 14 | 13 | 13 | 15 | 14 | 15 | 16 | 15 | 14 | 16 | 14 | 15 | 13 | 13 | 16 | 15 | 16 |
| 14. AEM42987-GT-1 | 32 | 29 | 32 | 32 | 33 | 34 | 32 | 34 | 32 | 33 | 35 | 33 | 24 | | 18 | 15 | 5 | 16 | 16 | 17 | 16 | 14 | 15 | 17 | 17 | 16 | 17 | 16 | 17 | 18 | 15 | 15 | 16 | 14 | 14 | 14 | 16 | 16 |
| 15. ugt1495 | 46 | 49 | 46 | 50 | 41 | 42 | 42 | 42 | 45 | 45 | 46 | 44 | 28 | 32 | | 25 | 5 | 46 | 27 | 42 | 44 | 23 | 26 | 13 | 48 | 28 | 48 | 49 | 48 | 48 | 22 | 26 | 22 | 27 | 27 | 26 | 24 | 28 |
| 16. UGTI8I7 | 42 | 42 | 40 | 44 | 38 | 36 | 37 | 36 | 41 | 41 | 41 | 42 | 29 | 32 | 44 | | 4 | 28 | 30 | 27 | 25 | 23 | 28 | 14 | 27 | 24 | 27 | 26 | 26 | 27 | 24 | 23 | 21 | 23 | 24 | 24 | 23 | 23 |
| 17. UGT3494p | 8 | 8 | 8 | 7 | 6 | 6 | 8 | 6 | 8 | 8 | 8 | 7 | 9 | 6 | 7 | 7 | | 5 | 4 | 4 | 4 | 5 | 4 | 16 | 4 | 5 | 4 | 5 | 4 | 4 | 4 | 5 | 5 | 5 | 5 | 4 | 6 | 5 |
| 18. UGT5914 | 46 | 47 | 47 | 50 | 41 | 42 | 43 | 43 | 50 | 45 | 46 | 46 | 31 | 33 | 63 | 48 | 9 | | 29 | 57 | 43 | 22 | 25 | 13 | 50 | 27 | 50 | 52 | 50 | 53 | 24 | 26 | 26 | 26 | 26 | 27 | 26 | 28 |
| 19. UGT8468 | 43 | 44 | 45 | 43 | 42 | 41 | 42 | 41 | 41 | 43 | 44 | 45 | 28 | 32 | 47 | 47 | 7 | 48 | | 28 | 24 | 23 | 43 | 15 | 29 | 26 | 29 | 28 | 29 | 27 | 27 | 24 | 22 | 27 | 27 | 25 | 23 | 25 |
| 20. UGT10391 | 46 | 45 | 46 | 48 | 43 | 41 | 44 | 41 | 47 | 46 | 47 | 46 | 29 | 33 | 63 | 43 | 8 | 72 | 49 | | 42 | 24 | 25 | 13 | 50 | 25 | 50 | 52 | 51 | 51 | 25 | 26 | 23 | 26 | 26 | 26 | 25 | 25 |
| 21. UGTII789p | 41 | 40 | 43 | 42 | 40 | 40 | 46 | 40 | 41 | 46 | 47 | 44 | 32 | 31 | 58 | 44 | 7 | 59 | 45 | 58 | | 26 | 27 | 11 | 47 | 24 | 47 | 48 | 47 | 50 | 23 | 24 | 23 | 24 | 24 | 22 | 24 | 26 |
| 22. UGT1I999p | 33 | 32 | 32 | 31 | 34 | 32 | 32 | 32 | 37 | 35 | 35 | 37 | 28 | 26 | 36 | 35 | 10 | 37 | 36 | 39 | 41 | | 30 | 15 | 27 | 20 | 27 | 25 | 27 | 24 | 22 | 16 | 14 | 21 | 20 | 20 | 15 | 21 |
| 23. UGT13679p | 37 | 38 | 38 | 38 | 38 | 36 | 38 | 35 | 40 | 38 | 38 | 39 | 29 | 29 | 41 | 41 | 9 | 42 | 57 | 40 | 44 | 44 | | 14 | 27 | 22 | 27 | 26 | 27 | 26 | 20 | 20 | 22 | 22 | 22 | 24 | 19 | 22 |
| 24. UGTI5423p | 16 | 16 | 17 | 16 | 16 | 17 | 17 | 17 | 19 | 19 | 19 | 20 | 20 | 7 | 17 | 21 | 22 | 19 | 23 | 19 | 17 | 2 | 2 | | 13 | 10 | 13 | 14 | 13 | 12 | 12 | 13 | 14 | 11 | 12 | 12 | 12 | 12 |
| 25. UGT98 | 46 | 47 | 45 | 47 | 42 | 41 | 45 | 42 | 48 | 47 | 48 | 43 | 30 | 31 | 66 | 45 | 8 | 68 | 50 | 68 | 61 | 38 | 40 | 20 | | 27 | [illegible] | 83 | 94 | 82 | 24 | 25 | 26 | 27 | 27 | 27 | 23 | 27 |
| 26. UGT1576 | 74 | 75 | 74 | 69 | 49 | 45 | 47 | 45 | 63 | 47 | 47 | 48 | 28 | 31 | 46 | 40 | 7 | 46 | 44 | 46 | 43 | 32 | 35 | 17 | 48 | | 27 | 28 | 27 | 28 | 26 | 28 | 25 | 85 | 85 | 45 | 29 | 38 |
| 27. SK98 | 46 | 47 | 45 | 47 | 42 | 41 | 45 | 42 | 48 | 47 | 48 | 44 | 31 | 31 | 66 | 45 | 8 | 68 | 50 | 68 | 61 | 38 | 40 | 20 | [illegible] | 48 | | 83 | 94 | 82 | 24 | 25 | 25 | 27 | 27 | 27 | 23 | 27 |
| 28. UGT94-289-1 | 44 | 45 | 42 | 46 | 44 | 42 | 44 | 42 | 46 | 46 | 47 | 46 | 29 | 33 | 66 | 47 | 7 | 70 | 48 | 68 | 61 | 39 | 39 | 20 | [illegible] | 47 | [illegible] | | 83 | 80 | 25 | 25 | 25 | 28 | 29 | 27 | 25 | 26 |
| 29. UGT94-289-2 | 46 | 47 | 45 | 47 | 42 | 42 | 45 | 42 | 48 | 47 | 48 | 44 | 31 | 31 | 66 | 45 | 8 | 68 | 50 | 68 | 62 | 38 | 40 | 20 | [illegible] | 48 | [illegible] | [illegible] | | 83 | 25 | 25 | 24 | 27 | 27 | 27 | 23 | 26 |
| 30. UGT94-289_3 | 45 | 45 | 43 | 47 | 44 | 42 | 45 | 42 | 45 | 46 | 48 | 47 | 27 | 35 | 66 | 46 | 8 | 68 | 46 | 67 | 63 | 37 | 39 | 18 | [illegible] | 45 | [illegible] | [illegible] | [illegible] | | 24 | 26 | 25 | 27 | 27 | 27 | 24 | 27 |
| 31. UGT74-345-2 | 43 | 44 | 42 | 45 | 48 | 50 | 48 | 5 | 45 | 45 | 46 | 72 | 33 | 32 | 44 | 43 | 7 | 47 | 45 | 48 | 45 | 35 | 37 | 13 | 48 | 47 | 48 | 48 | 48 | 47 | | 27 | 25 | 25 | 27 | 25 | 33 | 27 |
| 32. UGT85-269-4 | 47 | 49 | 48 | 51 | 53 | 50 | 47 | 50 | 46 | 45 | 45 | 49 | 30 | 32 | 47 | 40 | 7 | 43 | 40 | 45 | 44 | 32 | 34 | 13 | 45 | 50 | 45 | 44 | 45 | 45 | 48 | | 45 | 29 | 29 | 27 | 29 | 27 |
| 33. UGT85-269-1 | 40 | 41 | 41 | 40 | 48 | 46 | 43 | 46 | 42 | 40 | 40 | 49 | 30 | 29 | 41 | 37 | 10 | 44 | 39 | 41 | 44 | 34 | 41 | 21 | 42 | 42 | 42 | 42 | 42 | 43 | 44 | 62 | | 26 | 26 | 24 | 29 | 25 |
| 34. UGT73-251_5 | 72 | 72 | 72 | 69 | 46 | 45 | 47 | 45 | 61 | 48 | 46 | 48 | 27 | 33 | 45 | 39 | 7 | 45 | 42 | 44 | 42 | 31 | 35 | 13 | 46 | [illegible] | 46 | 46 | 46 | 45 | 46 | 50 | 42 | | 87 | 44 | 29 | 37 |
| 35. UGT73-251-6 | 71 | 71 | 73 | 69 | 50 | 45 | 48 | 45 | 63 | 47 | 46 | 49 | 30 | 33 | 44 | 40 | 7 | 46 | 42 | 45 | 42 | 32 | 34 | 13 | 47 | [illegible] | 47 | 46 | 47 | 45 | 47 | 50 | 42 | [illegible] | | 44 | 29 | 38 |
| 36. UGT73-348-2 | 68 | 67 | 67 | 66 | 47 | 47 | 49 | 47 | 59 | 47 | 47 | 49 | 31 | 33 | 46 | 40 | 7 | 44 | 43 | 44 | 40 | 33 | 38 | 17 | 45 | 65 | 45 | 45 | 45 | 44 | 45 | 49 | 41 | 63 | 64 | | 26 | 35 |
| 37. UGT75-281-2 | 46 | 47 | 48 | 44 | 46 | 57 | 45 | 57 | 45 | 44 | 45 | 55 | 30 | 31 | 46 | 41 | 7 | 44 | 41 | 45 | 40 | 32 | 32 | 13 | 44 | 45 | 44 | 46 | 44 | 45 | 54 | 49 | 45 | 45 | 47 | 47 | | 25 |
| 38. UGT73-327-2 | 57 | 57 | 59 | 58 | 48 | 47 | 44 | 47 | 52 | 48 | 46 | 46 | 30 | 36 | 47 | 41 | 7 | 46 | 42 | 45 | 43 | 33 | 37 | 12 | 46 | 57 | 46 | 44 | 47 | 46 | 44 | 48 | 43 | 56 | 58 | 56 | 45 | |

SEQUENCE LISTING

<160> NUMBER OF SEQ ID NOS: 59

<210> SEQ ID NO 1
<211> LENGTH: 1647
<212> TYPE: DNA
<213> ORGANISM: Siraitia grosvenori

<400> SEQUENCE: 1
atggacgaaa attataattt tttaaaagtt caaaccttca atctcaagaa attcaacaaa 60
aattttccat cgcaacgacg ccgttcacct gcaccaagta actacttcat gtgtacttca 120
cttgctgaat tccttccgtg taaaacgtgg ttccagtttg tctcagcaat attctattta 180
aatggtcctt cgcacgattt ccaccatttg cctgctgcac cgggcggcga ttccgacgga 240
agagagaaga gccgatcgcc ggaaatggac gagacgacgg tgaacggagg gcggagagcg 300
agtgatgtgg tggtgttcgc tttcccgagg cacggccata tgagtccgat gctccaattc 360
tccaagcgtt tggtctccaa aggcctccgc gtcacgtttc tcatcaccac ctctgcaact 420
gaatccctcc gactaaatct tcctccctct tcttctctcg atcttcaagt tatctccgac 480
gtccctgaaa gtaacgacat cgcgacgctc gaagggtatc ttcgaagctt caaggccact 540
gtttccaaaa ccttggcgga tttcatcgac ggaatcggaa atcctccaaa gttcatcgtt 600
tacgattcgg tcatgccgtg ggtgcaggag gtagccagag ggcgcggcct cgatgcggcg 660
ccgtttttca ctcaatcgtc cgccgttaat cacatcctca atcatgtgta cggaggatct 720
ttgagcattc cggccccgga gaacacggca gtttcgcttc cttcgatgcc ggttcttcaa 780
gccgaggatc tgccggcctt ccccgacgac ccagaagtgg ttatgaactt catgaccagt 840
caattctcca atttccagga tgcaaaatgg attttcttca acacattcga tcagctggag 900
tgcaagaaac aaagtcaggt tgttaattgg atggccgaca gatggcccat caagacagtg 960
ggaccgacca ttccatcggc atatttggac gacggtcggt tggaggatga cagggcgttt 1020
ggtctgaatc tcctaaaacc tgaagatggg aagaacacta ggcagtggca gtggttagac 1080
tcaaaagaca ctgcttctgt cctttatatt tcatttggaa gcttggctat cttacaagaa 1140
gaacaagtga aggaactggc atatttcctc aaagacacca atctttcctt cttatgggtc 1200
cttagagact cagaactcca aaagcttccc cacaactttg tacaagagac atcacacaga 1260
ggtctggttg taaactggtg ctctcaacta caagttctgt ctcacagggc tgtaagttgc 1320
tttgtgactc attgtggttg gaattcgacg ctcgaagctt tgagcttggg ggtgccgatg 1380
gtcgcaattc cacagtgggt tgatcaaacg acaaacgcca agttcgttgc agatgtttgg 1440
agagtgggag ttagagtgaa gaagaaggac gaacgcatcg taaccaagga agaactagaa 1500
gcctccatcc gacaggttgt tcaaggagag gggagaaatg agtttaaaca taatgcaatc 1560
aagtggaaga agctggctaa agaagcagtg gatgaaggtg gcagctctga taaaaacatt 1620
gaagaatttg tcaagacaat tgcatga 1647

<210> SEQ ID NO 2
<211> LENGTH: 456
<212> TYPE: PRT
<213> ORGANISM: Siraitia grosvenori

<400> SEQUENCE: 2

```
Met Asp Glu Thr Thr Val Asn Gly Gly Arg Arg Ala Ser Asp Val Val
1               5                   10                  15

Val Phe Ala Phe Pro Arg His Gly His Met Ser Pro Met Leu Gln Phe
            20                  25                  30

Ser Lys Arg Leu Val Ser Lys Gly Leu Arg Val Thr Phe Leu Ile Thr
        35                  40                  45

Thr Ser Ala Thr Glu Ser Leu Arg Leu Asn Leu Pro Pro Ser Ser Ser
    50                  55                  60

Leu Asp Leu Gln Val Ile Ser Asp Val Pro Glu Ser Asn Asp Ile Ala
65                  70                  75                  80

Thr Leu Glu Gly Tyr Leu Arg Ser Phe Lys Ala Thr Val Ser Lys Thr
                85                  90                  95

Leu Ala Asp Phe Ile Asp Gly Ile Gly Asn Pro Pro Lys Phe Ile Val
            100                 105                 110

Tyr Asp Ser Val Met Pro Trp Val Gln Glu Val Ala Arg Gly Arg Gly
        115                 120                 125

Leu Asp Ala Ala Pro Phe Phe Thr Gln Ser Ser Ala Val Asn His Ile
    130                 135                 140

Leu Asn His Val Tyr Gly Gly Ser Leu Ser Ile Pro Ala Pro Glu Asn
145                 150                 155                 160

Thr Ala Val Ser Leu Pro Ser Met Pro Val Leu Gln Ala Glu Asp Leu
                165                 170                 175

Pro Ala Phe Pro Asp Asp Pro Glu Val Val Met Asn Phe Met Thr Ser
            180                 185                 190

Gln Phe Ser Asn Phe Gln Asp Ala Lys Trp Ile Phe Phe Asn Thr Phe
        195                 200                 205

Asp Gln Leu Glu Cys Lys Val Val Asn Trp Met Ala Asp Arg Trp Pro
    210                 215                 220

Ile Lys Thr Val Gly Pro Thr Ile Pro Ser Ala Tyr Leu Asp Asp Gly
225                 230                 235                 240

Arg Leu Glu Asp Asp Arg Ala Phe Gly Leu Asn Leu Leu Lys Pro Glu
                245                 250                 255

Asp Gly Lys Asn Thr Arg Gln Trp Gln Trp Leu Asp Ser Lys Asp Thr
            260                 265                 270

Ala Ser Val Leu Tyr Ile Ser Phe Gly Ser Leu Ala Ile Leu Gln Glu
        275                 280                 285

Glu Gln Val Lys Glu Leu Ala Tyr Phe Leu Lys Asp Thr Asn Leu Ser
    290                 295                 300

Phe Leu Trp Val Leu Arg Asp Ser Glu Leu Gln Lys Leu Pro His Asn
305                 310                 315                 320

Phe Val Gln Glu Thr Ser His Arg Gly Leu Val Val Asn Trp Cys Ser
                325                 330                 335

Gln Leu Gln Val Leu Ser His Arg Ala Val Ser Cys Phe Val Thr His
            340                 345                 350

Cys Gly Trp Asn Ser Thr Leu Glu Ala Leu Ser Leu Gly Val Pro Met
        355                 360                 365

Val Ala Ile Pro Gln Trp Val Asp Gln Thr Thr Asn Ala Lys Phe Val
    370                 375                 380
```

```
Ala Asp Val Trp Arg Val Gly Val Arg Val Lys Lys Lys Asp Glu Arg
385                 390                 395                 400

Ile Val Thr Lys Glu Glu Leu Glu Ala Ser Ile Arg Gln Val Val Gln
                405                 410                 415

Gly Glu Gly Arg Asn Glu Phe Lys His Asn Ala Ile Lys Trp Lys Lys
            420                 425                 430

Leu Ala Lys Glu Ala Val Asp Glu Gly Gly Ser Ser Asp Lys Asn Ile
        435                 440                 445

Glu Glu Phe Val Lys Thr Ile Ala
    450                 455
```

<210> SEQ ID NO 3
<211> LENGTH: 1479
<212> TYPE: DNA
<213> ORGANISM: Siraitia grosvenori

<400> SEQUENCE: 3

```
atggcttctc ttctcagcca gattcacatt gttgtgattc cattgatgac tcaaggtcac     60

ctgatccctg cagccgacat ggcaaagcta ttggcagagc gcggcgttac cgtcactatc    120

atcaccaccc ctctcaacgc caagcggatt cagacgctcg ttgatcgcgc tcgagaggcc    180

aatctcgatc tccgacttgt cgaccgactc aacattccgc tcgctgagtt cggcttgccg    240

gaagggtgtg agagcgtaga tcgagtcccc tcgcgggaac tgtttaagaa tttctttttg    300

gctctcaacg acttgcaaaa accccctcgag aggctcgtcg ctaggttgca accacgcccc    360

agctgcgtaa ttgctgataa aaatctgcca tgggtggtag gtgtttgtga aaagttccaa    420

gtgacgaggt tttcgtttga tggcactagt tgtttttctc tgttatgttc taacaacata    480

cgtgcgtcta aggtcctcga gagtgtgaat tcggtatcag agagcttttt ggttcctggg    540

ttacctgata ggattgaagt tactgcagct caattaccag cagacttgaa tccaggttca    600

tatttaaaag agctacatga aagtggaaga attgctcatg agaatgccta tgggttgctg    660

gttaatagtt tcgaggagtt ggaatctgaa tacttgaagg aatatcgaaa ggtgaaaggc    720

gataaaatct ggtgcattgg ccctgtgtcc ctatccaata agacaggcgt ggaaagggcc    780

caacgcggcg gcatagccgc acaagatgct gacaagtgct tgcgctggct cgattcatgg    840

cctaagagct ctgttgttta cgtttgtatt gggagcctca gccggctttc atctcaacaa    900

agttcagagc ttgctttagc cttagaagaa tcaaaccaac cattcatttg ggtcgtaaag    960

gaagaggaga agcatgaaac atcaaagact acatcgacgg tcggatccat gagagctttt   1020

gaagaaagga cgaagggaag agggattctg ctgaagggtt gggctccgca gctgcagatc   1080

ttgtcgcacc cggccgtcgg agcatttcta acccactgcg gctggaactc tgttctggaa   1140

ggcgtctgcg ccggtgttcc attgatcaca tggcccatgt tcgccgacca gttctttaac   1200

gagaaggaag ttgttgaagt tttgaagatt ggggaagaag ttggaaacaa gaagacggtg   1260

ccattggggg atgaagagaa gagcgaggtg gtgatcggca gagaggagat taagaaggct   1320

attggtgcgg taatggagga aggagcagag gcagagagaa gaaagagagc gagaaggctg   1380

gctgagaagg caaacaaagc tatggaagat ggggggagtt cttatgttaa tgttacacga   1440

ttggttgaac atatcaagca actggtgctt gaaaaatga                          1479
```

<210> SEQ ID NO 4
<211> LENGTH: 492
<212> TYPE: PRT
<213> ORGANISM: Siraitia grosvenori

<400> SEQUENCE: 4

Met Ala Ser Leu Leu Ser Gln Ile His Ile Val Val Ile Pro Leu Met
1 5 10 15

Thr Gln Gly His Leu Ile Pro Ala Ala Asp Met Ala Lys Leu Leu Ala
20 25 30

Glu Arg Gly Val Thr Val Thr Ile Ile Thr Thr Pro Leu Asn Ala Lys
35 40 45

Arg Ile Gln Thr Leu Val Asp Arg Ala Arg Glu Ala Asn Leu Asp Leu
50 55 60

Arg Leu Val Asp Arg Leu Asn Ile Pro Leu Ala Glu Phe Gly Leu Pro
65 70 75 80

Glu Gly Cys Glu Ser Val Asp Arg Val Pro Ser Arg Glu Leu Phe Lys
85 90 95

Asn Phe Phe Leu Ala Leu Asn Asp Leu Gln Lys Pro Leu Glu Arg Leu
100 105 110

Val Ala Arg Leu Gln Pro Arg Pro Ser Cys Val Ile Ala Asp Lys Asn
115 120 125

Leu Pro Trp Val Val Gly Val Cys Glu Lys Phe Gln Val Thr Arg Phe
130 135 140

Ser Phe Asp Gly Thr Ser Cys Phe Ser Leu Leu Cys Ser Asn Asn Ile
145 150 155 160

Arg Ala Ser Lys Val Leu Glu Ser Val Asn Ser Val Ser Glu Ser Phe
165 170 175

Leu Val Pro Gly Leu Pro Asp Arg Ile Glu Val Thr Ala Ala Gln Leu
180 185 190

Pro Ala Asp Leu Asn Pro Gly Ser Tyr Leu Lys Glu Leu His Glu Ser
195 200 205

Gly Arg Ile Ala His Glu Asn Ala Tyr Gly Leu Leu Val Asn Ser Phe
210 215 220

Glu Glu Leu Glu Ser Glu Tyr Leu Lys Glu Tyr Arg Lys Val Lys Gly
225 230 235 240

Asp Lys Ile Trp Cys Ile Gly Pro Val Ser Leu Ser Asn Lys Thr Gly
245 250 255

Val Glu Arg Ala Gln Arg Gly Gly Ile Ala Ala Gln Asp Ala Asp Lys
260 265 270

Cys Leu Arg Trp Leu Asp Ser Trp Pro Lys Ser Ser Val Val Tyr Val
275 280 285

Cys Ile Gly Ser Leu Ser Arg Leu Ser Ser Gln Gln Ser Ser Glu Leu
290 295 300

Ala Leu Ala Leu Glu Glu Ser Asn Gln Pro Phe Ile Trp Val Val Lys
305 310 315 320

Glu Glu Glu Lys His Glu Thr Ser Lys Thr Thr Ser Thr Val Gly Ser
325 330 335

Met Arg Ala Phe Glu Glu Arg Thr Lys Gly Arg Gly Ile Leu Leu Lys
340 345 350

Gly Trp Ala Pro Gln Leu Gln Ile Leu Ser His Pro Ala Val Gly Ala
355 360 365

Phe Leu Thr His Cys Gly Trp Asn Ser Val Leu Glu Gly Val Cys Ala
370 375 380

Gly Val Pro Leu Ile Thr Trp Pro Met Phe Ala Asp Gln Phe Phe Asn
385 390 395 400

Glu Lys Glu Val Val Glu Val Leu Lys Ile Gly Glu Glu Val Gly Asn

-continued

```
            405                 410                 415

Lys Lys Thr Val Pro Leu Gly Asp Glu Glu Lys Ser Glu Val Val Ile
        420                 425                 430

Gly Arg Glu Glu Ile Lys Lys Ala Ile Gly Ala Val Met Glu Glu Gly
    435                 440                 445

Ala Glu Ala Glu Arg Arg Lys Arg Ala Arg Arg Leu Ala Glu Lys Ala
    450                 455                 460

Asn Lys Ala Met Glu Asp Gly Gly Ser Ser Tyr Val Asn Val Thr Arg
465                 470                 475                 480

Leu Val Glu His Ile Lys Gln Leu Val Leu Glu Lys
            485                 490
```

<210> SEQ ID NO 5
<211> LENGTH: 1362
<212> TYPE: DNA
<213> ORGANISM: Siraitia grosvenori

<400> SEQUENCE: 5

```
atggatgccc agcgaggtca caccacaacc attttgatgt ttccatggct cggctatggc     60

catctttcgg ctttcctaga gttggccaaa agcctctcaa ggaggaactt ccatatctac    120

ttctgttcaa cctctgttaa cctcgacgcc attaaaccaa agcttccttc ttcttcctct    180

tctgattcca tccaacttgt ggaactttgt cttccatctt ctcctgatca gctccctcct    240

catcttcaca caaccaacgc cctccccccct cacctcatgc ccactctcca ccaagccttc    300

tccatggctg cccaacactt tgctgccatt ttacacacac ttgctccgca tctcctcatt    360

tacgactctt tccaaccttg ggctcctcaa ctagcttcat ccctcaacat tccagccatc    420

aacttcaata ctacgggagc ttcagtcctg acccgaatgc ttcacgctac tcactaccca    480

agttctaaat tcccaatttc agagtttgtt ctccacgatt attggaaagc catgtacagc    540

gccgccggtg ggctgttac aaaaaaagac cacaaaattg gagaaacact tgcgaattgc    600

ttgcatgctt cttgtagtgt aattctaatc aatagtttca gagagctcga ggagaaatat    660

atggattatc tctccgttct cttgaacaag aaagttgttc cggttggtcc tttggtttac    720

gaaccgaatc aagacgggga agatgaaggt tattcaagca tcaaaaattg gcttgacaaa    780

aaggaaccgt cctccaccgt cttcgtttca tttggaagcg aatacttccc gtcaaaggaa    840

gaaatggaag agatagccca tgggttagag gcgagcgagg ttcatttcat ctgggtcgtt    900

aggtttcctc aaggagacaa caccagcgcc attgaagatg ccttgccgaa ggggtttctg    960

gagagggtgg gagagagagg gatggtggtg aagggttggg ctcctcaggc gaagatactg   1020

aagcattgga gcacaggggg attcgtgagc cactgtggat ggaactcggt gatggaaagc   1080

atgatgtttg gcgttcccat aatagggggtt ccgatgcatc tggaccagcc ctttaacgcc   1140

ggactcgcgg aagaagctgg cgtcggcgtg gaggccaagc gagatccaga cggcaaaatt   1200

caaagagacg aagttgcaaa gttgatcaaa gaagtggtgg ttgagaaaac cagagaagac   1260

gtgcggaaga aagcaagaga aatgagtgag attttgagga gcaaaggaga ggagaagatg   1320

gatgagatgg tggctgcaat ctctctcttt cttaaaatat ga                       1362
```

<210> SEQ ID NO 6
<211> LENGTH: 453
<212> TYPE: PRT
<213> ORGANISM: Siraitia grosvenori

<400> SEQUENCE: 6

-continued

```
Met Asp Ala Gln Arg Gly His Thr Thr Thr Ile Leu Met Phe Pro Trp
1               5                   10                  15

Leu Gly Tyr Gly His Leu Ser Ala Phe Leu Glu Leu Ala Lys Ser Leu
            20                  25                  30

Ser Arg Arg Asn Phe His Ile Tyr Phe Cys Ser Thr Ser Val Asn Leu
        35                  40                  45

Asp Ala Ile Lys Pro Lys Leu Pro Ser Ser Ser Ser Ser Asp Ser Ile
    50                  55                  60

Gln Leu Val Glu Leu Cys Leu Pro Ser Ser Pro Asp Gln Leu Pro Pro
65                  70                  75                  80

His Leu His Thr Thr Asn Ala Leu Pro Pro His Leu Met Pro Thr Leu
                85                  90                  95

His Gln Ala Phe Ser Met Ala Ala Gln His Phe Ala Ala Ile Leu His
            100                 105                 110

Thr Leu Ala Pro His Leu Leu Ile Tyr Asp Ser Phe Gln Pro Trp Ala
        115                 120                 125

Pro Gln Leu Ala Ser Ser Leu Asn Ile Pro Ala Ile Asn Phe Asn Thr
    130                 135                 140

Thr Gly Ala Ser Val Leu Thr Arg Met Leu His Ala Thr His Tyr Pro
145                 150                 155                 160

Ser Ser Lys Phe Pro Ile Ser Glu Phe Val Leu His Asp Tyr Trp Lys
                165                 170                 175

Ala Met Tyr Ser Ala Ala Gly Gly Ala Val Thr Lys Lys Asp His Lys
            180                 185                 190

Ile Gly Glu Thr Leu Ala Asn Cys Leu His Ala Ser Cys Ser Val Ile
        195                 200                 205

Leu Ile Asn Ser Phe Arg Glu Leu Glu Glu Lys Tyr Met Asp Tyr Leu
    210                 215                 220

Ser Val Leu Leu Asn Lys Lys Val Val Pro Val Gly Pro Leu Val Tyr
225                 230                 235                 240

Glu Pro Asn Gln Asp Gly Glu Asp Glu Gly Tyr Ser Ser Ile Lys Asn
                245                 250                 255

Trp Leu Asp Lys Lys Glu Pro Ser Ser Thr Val Phe Val Ser Phe Gly
            260                 265                 270

Ser Glu Tyr Phe Pro Ser Lys Glu Glu Met Glu Glu Ile Ala His Gly
        275                 280                 285

Leu Glu Ala Ser Glu Val His Phe Ile Trp Val Val Arg Phe Pro Gln
    290                 295                 300

Gly Asp Asn Thr Ser Ala Ile Glu Asp Ala Leu Pro Lys Gly Phe Leu
305                 310                 315                 320

Glu Arg Val Gly Glu Arg Gly Met Val Val Lys Gly Trp Ala Pro Gln
                325                 330                 335

Ala Lys Ile Leu Lys His Trp Ser Thr Gly Gly Phe Val Ser His Cys
            340                 345                 350

Gly Trp Asn Ser Val Met Glu Ser Met Met Phe Gly Val Pro Ile Ile
        355                 360                 365

Gly Val Pro Met His Leu Asp Gln Pro Phe Asn Ala Gly Leu Ala Glu
    370                 375                 380

Glu Ala Gly Val Gly Val Glu Ala Lys Arg Asp Pro Asp Gly Lys Ile
385                 390                 395                 400

Gln Arg Asp Glu Val Ala Lys Leu Ile Lys Glu Val Val Val Glu Lys
                405                 410                 415

Thr Arg Glu Asp Val Arg Lys Lys Ala Arg Glu Met Ser Glu Ile Leu
```

-continued

```
            420                 425                 430

Arg Ser Lys Gly Glu Glu Lys Met Asp Glu Met Val Ala Ala Ile Ser
        435                 440                 445

Leu Phe Leu Lys Ile
    450
```

<210> SEQ ID NO 7
<211> LENGTH: 1476
<212> TYPE: DNA
<213> ORGANISM: Siraitia grosvenori

<400> SEQUENCE: 7

```
atgggctccg ccggcgtcga actgaaggtg gctttcctgc catttgcagc tccaggtcac     60
atgattccct tgatgaacat agccagactc ttcgccatgc acggcgccga cgtcaccttc    120
atcaccaccc cggccactgc ctcccgcttc caaaacgtcg tcgactccga tctccgacgc    180
ggccacaaaa tcaaactcca tacatttcaa ctgccctctg cagaagccgg tctccccccc    240
ggcgtcgaga gcttcaacga atgcacttct aaagagatga ccgaaaaact cttcggcgca    300
tttgaaatgc tcaacggaga catcgaacag ttcctcaaag gggctaaagt cgactgcatt    360
gtgagcgata cgattctcgt ttggaccttg gacgccgctg caaggctcgg gattccgagg    420
atagctttcc gatcttcagg attcttttcg gaatgtattc atcactcttt aaggtgtcac    480
aagcctcaca agaaggtggg atccgataca gagccgttta tatttcctgg tttaccgcat    540
aagattgaga taacgagatt gaatatacca caatggtatt cagaagaagg ctatattcag    600
catattgaaa agatgaaaga aatggacaaa aagagttatg cggtactgct aaataccttc    660
tatgagcttg aggctgatta tgttgaatat tttgaatctg ttattgggtt gaaaacatgg    720
atcgtagggc cagtttcctt atgggctaac gagggtggag gcaaaaacga ctcaagaact    780
gagaacaaca acgctgagtt gatggaatgg ctggactcca aacagcctaa ttcagttctg    840
tatgttagtt ttggtagcat gacgaagttc ccatctgctc aggtgctcga aatagctcac    900
ggccttgaag attctggctg ccatttcatt tgggtggttc gaaagatgaa cgaaagtgaa    960
gcagctgatg aagaatttcc agaggggttc gaggagagag tgagagagag caagagaggt   1020
ttgatcataa gagattgggc gccgcaagaa ttgattttga atcatgcagc tgttgggggg   1080
tttgtcactc actgtggctg gaattcaatt ctcgaaagtg tatgtgctgg tcggccgatc   1140
atcgcgtggc cgttgtcggc ggaacagttt ttcaacgaga agtttgtaac tcgtgtattg   1200
aaagttggag tttcaattgg tgtaagaaaa tggtggggct cgacgagttc agaaacttta   1260
gatgtggtga aaagggatcg aattgcagaa gcagtggcga ggttgatggg agatgacaga   1320
gaggtggttg aaatgagaga tggagttaga gaactttcac atgcagcgaa gagagcaata   1380
aaggaaggtg gatcttctca ctcaaccttg ctctcattga tccatgaact caagaccatg   1440
aaatttaaac gccaaagtag taatgtggat ggataa                              1476
```

<210> SEQ ID NO 8
<211> LENGTH: 491
<212> TYPE: PRT
<213> ORGANISM: Siraitia grosvenori

<400> SEQUENCE: 8

```
Met Gly Ser Ala Gly Val Glu Leu Lys Val Ala Phe Leu Pro Phe Ala
1               5                   10                  15

Ala Pro Gly His Met Ile Pro Leu Met Asn Ile Ala Arg Leu Phe Ala
            20                  25                  30
```

-continued

```
Met His Gly Ala Asp Val Thr Phe Ile Thr Thr Pro Ala Thr Ala Ser
        35                  40                  45

Arg Phe Gln Asn Val Val Asp Ser Asp Leu Arg Arg Gly His Lys Ile
    50                  55                  60

Lys Leu His Thr Phe Gln Leu Pro Ser Ala Glu Ala Gly Leu Pro Pro
65                  70                  75                  80

Gly Val Glu Ser Phe Asn Glu Cys Thr Ser Lys Glu Met Thr Glu Lys
                85                  90                  95

Leu Phe Gly Ala Phe Glu Met Leu Asn Gly Asp Ile Glu Gln Phe Leu
            100                 105                 110

Lys Gly Ala Lys Val Asp Cys Ile Val Ser Asp Thr Ile Leu Val Trp
        115                 120                 125

Thr Leu Asp Ala Ala Ala Arg Leu Gly Ile Pro Arg Ile Ala Phe Arg
    130                 135                 140

Ser Ser Gly Phe Phe Ser Glu Cys Ile His His Ser Leu Arg Cys His
145                 150                 155                 160

Lys Pro His Lys Lys Val Gly Ser Asp Thr Glu Pro Phe Ile Phe Pro
                165                 170                 175

Gly Leu Pro His Lys Ile Glu Ile Thr Arg Leu Asn Ile Pro Gln Trp
            180                 185                 190

Tyr Ser Glu Glu Gly Tyr Ile Gln His Ile Glu Lys Met Lys Glu Met
        195                 200                 205

Asp Lys Lys Ser Tyr Ala Val Leu Leu Asn Thr Phe Tyr Glu Leu Glu
    210                 215                 220

Ala Asp Tyr Val Glu Tyr Phe Glu Ser Val Ile Gly Leu Lys Thr Trp
225                 230                 235                 240

Ile Val Gly Pro Val Ser Leu Trp Ala Asn Glu Gly Gly Gly Lys Asn
                245                 250                 255

Asp Ser Arg Thr Glu Asn Asn Asn Ala Glu Leu Met Glu Trp Leu Asp
            260                 265                 270

Ser Lys Gln Pro Asn Ser Val Leu Tyr Val Ser Phe Gly Ser Met Thr
        275                 280                 285

Lys Phe Pro Ser Ala Gln Val Leu Glu Ile Ala His Gly Leu Glu Asp
    290                 295                 300

Ser Gly Cys His Phe Ile Trp Val Val Arg Lys Met Asn Glu Ser Glu
305                 310                 315                 320

Ala Ala Asp Glu Glu Phe Pro Glu Gly Phe Glu Glu Arg Val Arg Glu
                325                 330                 335

Ser Lys Arg Gly Leu Ile Ile Arg Asp Trp Ala Pro Gln Glu Leu Ile
            340                 345                 350

Leu Asn His Ala Ala Val Gly Gly Phe Val Thr His Cys Gly Trp Asn
        355                 360                 365

Ser Ile Leu Glu Ser Val Cys Ala Gly Arg Pro Ile Ile Ala Trp Pro
    370                 375                 380

Leu Ser Ala Glu Gln Phe Phe Asn Glu Lys Phe Val Thr Arg Val Leu
385                 390                 395                 400

Lys Val Gly Val Ser Ile Gly Val Arg Lys Trp Trp Gly Ser Thr Ser
                405                 410                 415

Ser Glu Thr Leu Asp Val Val Lys Arg Asp Arg Ile Ala Glu Ala Val
            420                 425                 430

Ala Arg Leu Met Gly Asp Asp Arg Glu Val Val Glu Met Arg Asp Gly
        435                 440                 445
```

-continued

```
Val Arg Glu Leu Ser His Ala Ala Lys Arg Ala Ile Lys Glu Gly Gly
    450                 455                 460

Ser Ser His Ser Thr Leu Leu Ser Leu Ile His Glu Leu Lys Thr Met
465                 470                 475                 480

Lys Phe Lys Arg Gln Ser Ser Asn Val Asp Gly
                485                 490


<210> SEQ ID NO 9
<211> LENGTH: 1422
<212> TYPE: DNA
<213> ORGANISM: Siraitia grosvenori

<400> SEQUENCE: 9

atgtggactg tcgtgctcgg tttggcgacg ctgtttgtcg cctactacat ccattggatt      60

aacaaatgga gagattccaa gttcaacgga gttctgccgc cgggcaccat gggtttgccg     120

ctcatcggag agacgattca actgagtcga cccagtgact ccctcgacgt tcaccctttc     180

atccagaaaa aagttgaaag atacgggccg atcttcaaaa catgtctggc cggaaggccg     240

gtggtggtgt cggcggacgc agagttcaac aactacataa tgctgcagga aggaagagca     300

gtggaaatgt ggtatttgga tacgctctcc aaatttttcg gcctcgacac cgagtggctc     360

aaagctctgg gcctcatcca caagtacatc agaagcatta ctctcaatca cttcggcgcc     420

gaggccctgc gggagagatt tcttcctttt attgaagcat cctccatgga agcccttcac     480

tcctggtcta ctcaacctag cgtcgaagtc aaaaatgcct ccgctctcat ggtttttagg     540

acctcggtga ataagatgtt cggtgaggat gcgaagaagc tatcgggaaa tatccctggg     600

aagttcacga agcttctagg aggatttctc agtttaccac tgaattttcc cggcaccacc     660

taccacaaat gcttgaagga tatgaaggaa atccagaaga agctaagaga ggttgtagac     720

gatagattgg ctaatgtggg ccctgatgtg gaagatttct tggggcaagc ccttaaagat     780

aaggaatcag agaagttcat ttcagaggag ttcatcatcc aactgttgtt ttctatcagt     840

tttgctagct ttgagtccat ctccaccact cttactttga ttctcaagct ccttgatgaa     900

cacccagaag tagtgaaaga gttggaagct gaacacgagg cgattcgaaa agctagagca     960

gatccagatg gaccaattac ttgggaagaa tacaaatcca tgacttttac attacaagtc    1020

atcaatgaaa ccctaaggtt ggggagtgtc acacctgcct tgttgaggaa aacagttaaa    1080

gatcttcaag taaaaggata cataatcccg gaaggatgga caataatgct tgtcaccgct    1140

tcacgtcaca gagacccaaa agtctataag gaccctcata tcttcaatcc atggcgttgg    1200

aaggacttgg actcaattac catccaaaag aacttcatgc cttttggggg aggcttaagg    1260

cattgtgctg gtgctgagta ctctaaagtc tacttgtgca ccttcttgca catcctctgt    1320

accaaatacc gatggaccaa acttggggga ggaaggattg caagagctca tatattgagt    1380

tttgaagatg ggttacatgt gaagttcaca cccaaggaat ga                       1422


<210> SEQ ID NO 10
<211> LENGTH: 473
<212> TYPE: PRT
<213> ORGANISM: Siraitia grosvenori

<400> SEQUENCE: 10

Met Trp Thr Val Val Leu Gly Leu Ala Thr Leu Phe Val Ala Tyr Tyr
1               5                   10                  15

Ile His Trp Ile Asn Lys Trp Arg Asp Ser Lys Phe Asn Gly Val Leu
            20                  25                  30
```

-continued

```
Pro Pro Gly Thr Met Gly Leu Pro Leu Ile Gly Glu Thr Ile Gln Leu
        35                  40                  45

Ser Arg Pro Ser Asp Ser Leu Asp Val His Pro Phe Ile Gln Lys Lys
    50                  55                  60

Val Glu Arg Tyr Gly Pro Ile Phe Lys Thr Cys Leu Ala Gly Arg Pro
65                  70                  75                  80

Val Val Val Ser Ala Asp Ala Glu Phe Asn Asn Tyr Ile Met Leu Gln
                85                  90                  95

Glu Gly Arg Ala Val Glu Met Trp Tyr Leu Asp Thr Leu Ser Lys Phe
            100                 105                 110

Phe Gly Leu Asp Thr Glu Trp Leu Lys Ala Leu Gly Leu Ile His Lys
        115                 120                 125

Tyr Ile Arg Ser Ile Thr Leu Asn His Phe Gly Ala Glu Ala Leu Arg
    130                 135                 140

Glu Arg Phe Leu Pro Phe Ile Glu Ala Ser Ser Met Glu Ala Leu His
145                 150                 155                 160

Ser Trp Ser Thr Gln Pro Ser Val Glu Val Lys Asn Ala Ser Ala Leu
                165                 170                 175

Met Val Phe Arg Thr Ser Val Asn Lys Met Phe Gly Glu Asp Ala Lys
            180                 185                 190

Lys Leu Ser Gly Asn Ile Pro Gly Lys Phe Thr Lys Leu Leu Gly Gly
        195                 200                 205

Phe Leu Ser Leu Pro Leu Asn Phe Pro Gly Thr Thr Tyr His Lys Cys
    210                 215                 220

Leu Lys Asp Met Lys Glu Ile Gln Lys Lys Leu Arg Glu Val Val Asp
225                 230                 235                 240

Asp Arg Leu Ala Asn Val Gly Pro Asp Val Glu Asp Phe Leu Gly Gln
                245                 250                 255

Ala Leu Lys Asp Lys Glu Ser Glu Lys Phe Ile Ser Glu Glu Phe Ile
            260                 265                 270

Ile Gln Leu Leu Phe Ser Ile Ser Phe Ala Ser Phe Glu Ser Ile Ser
        275                 280                 285

Thr Thr Leu Thr Leu Ile Leu Lys Leu Leu Asp Glu His Pro Glu Val
    290                 295                 300

Val Lys Glu Leu Glu Ala Glu His Glu Ala Ile Arg Lys Ala Arg Ala
305                 310                 315                 320

Asp Pro Asp Gly Pro Ile Thr Trp Glu Glu Tyr Lys Ser Met Thr Phe
                325                 330                 335

Thr Leu Gln Val Ile Asn Glu Thr Leu Arg Leu Gly Ser Val Thr Pro
            340                 345                 350

Ala Leu Leu Arg Lys Thr Val Lys Asp Leu Gln Val Lys Gly Tyr Ile
        355                 360                 365

Ile Pro Glu Gly Trp Thr Ile Met Leu Val Thr Ala Ser Arg His Arg
    370                 375                 380

Asp Pro Lys Val Tyr Lys Asp Pro His Ile Phe Asn Pro Trp Arg Trp
385                 390                 395                 400

Lys Asp Leu Asp Ser Ile Thr Ile Gln Lys Asn Phe Met Pro Phe Gly
                405                 410                 415

Gly Gly Leu Arg His Cys Ala Gly Ala Glu Tyr Ser Lys Val Tyr Leu
            420                 425                 430

Cys Thr Phe Leu His Ile Leu Cys Thr Lys Tyr Arg Trp Thr Lys Leu
        435                 440                 445

Gly Gly Gly Arg Ile Ala Arg Ala His Ile Leu Ser Phe Glu Asp Gly
```

-continued 450 455 460

Leu His Val Lys Phe Thr Pro Lys Glu
465 470

<210> SEQ ID NO 11
<211> LENGTH: 2277
<212> TYPE: DNA
<213> ORGANISM: Artificial Sequence
<220> FEATURE:
<223> OTHER INFORMATION: Optimised Nucleic Acid sequence encoding SgCDS
cucurbitadienol synthase

<400> SEQUENCE: 11
atgtggaggt taaaggtcgg agcggaatcc gttggtgaga acgacgaaaa atggttaaag 60
tcaatatcaa accatttggg taggcaagtt tgggaatttt gtccagatgc gggtactcaa 120
caacagctgc tacaagttca taaagcacgt aaagctttcc acgatgaccg tttccacaga 180
aaacagtcat cagacttgtt catcacgatc cagtacggca aagaggttga aaacggaggc 240
aaaaccgctg gagtaaaatt aaaagaaggc gaggaagtca ggaaagaagc cgtagaaagc 300
tcacttgaaa gagctctatc tttttactca tctatacaaa cgagtgacgg aaactgggct 360
tccgatctag gtggaccaat gttcttactg cctggtttag ttattgcact ttatgtcaca 420
ggggttttaa actccgtatt atctaaacat catagacaag agatgtgtag atacgtttat 480
aatcatcaaa acgaggatgg cggatggggg ttacacatcg agggaccttc aacaatgttt 540
ggttcagctc taaactatgt agctcttagg ttattgggcg aagatgctaa tgctggtgca 600
atgcccaaag caagagcatg gatcttagat catggaggtg ccacggggat tacaagttgg 660
gggaaattgt ggctaagtgt tctgggtgta tatgagtggt ccggaaataa tccactacca 720
cccgaattct ggttatttcc atactttctg ccttttcatc caggcagaat gtggtgtcat 780
tgcagaatgg tctatttacc tatgagttac ctatacggta aaagattcgt aggtccaatt 840
actcccatcg tgttgtcttt gagaaaggaa ttatacgcag ttccgtatca cgaaattgac 900
tggaataaat ctagaaatac ttgtgctaaa gaagatctat actatcctca tcccaagatg 960
caagacattt tgtggggaag tttacaccat gtctatgaac ccttatttac aagatggcct 1020
gcgaaaagat tgagagaaaa agcgctacag actgccatgc agcatattca ttatgaagat 1080
gaaaacacaa gatatatttg tttaggacct gtaaataaag tattgaatct tttatgttgt 1140
tgggttgaag acccttattc agacgccttc aagttgcatt tacaaagagt acatgactac 1200
ttatgggtcg ctgaagacgg aatgaaaatg caaggctata atggaagtca gctgtgggac 1260
acagcctttt caatacaagc aattgtttct accaagctag tagataacta cggcccaact 1320
ttgagaaagg cccatgactt tgttaagtcc agccagatcc aacaagattg tcctggtgat 1380
ccaaacgtct ggtataggca tattcacaag ggtgcctggc cctttagcac tagagaccat 1440
ggttggttga tttccgactg tacggccgaa ggcttaaaag ctgcattgat gctaagtaag 1500
ttaccctccg aaacagtagg ggagagttta gaaagaaata gactatgcga cgctgtaaat 1560
gtcttattat ctttacaaaa cgacaatgga ggttttgctt catacgaatt aacaagatcc 1620
tacccttggt tagaactgat taacccagct gaaacttttg gtgatattgt catcgattat 1680
ccctatgttg aatgtacgtc tgcgactatg gaagccttga ctttatttaa gaaacttcat 1740
ccaggccaca ggactaagga gatagatact gctattgttc gtgcggctaa cttcttggaa 1800
aacatgcaaa gaactgatgg aagttggtac ggttgttggg gggtgtgttt cacatatgct 1860
ggctggtttg gaataaaggg tttggttgcc gctgggagaa cgtataataa ttgtttagca 1920

-continued

```
ataaggaaag cttgcgactt tcttttgagt aaggaattac ctggcggtgg atggggagag   1980

tcttaccttt catgccaaaa taaggtgtac acgaacctag aaggtaatag acctcacttg   2040

gtaaataccg cctgggtttt aatggccttg atcgaagcag gacaagccga gagagatcca   2100

acaccattgc atcgtgctgc cagactatta ataaatagtc aactagagaa cggtgacttc   2160

ccacagcaag aaatcatggg tgtttttaat aaaaactgta tgataactta tgccgcatat   2220

cgtaatatat tcccaatttg ggcgttagga gagtattgtc acagagtact tactgaa      2277


<210> SEQ ID NO 12
<211> LENGTH: 759
<212> TYPE: PRT
<213> ORGANISM: Siraitia grosvenori

<400> SEQUENCE: 12

Met Trp Arg Leu Lys Val Gly Ala Glu Ser Val Gly Glu Asn Asp Glu
1               5                   10                  15

Lys Trp Leu Lys Ser Ile Ser Asn His Leu Gly Arg Gln Val Trp Glu
            20                  25                  30

Phe Cys Pro Asp Ala Gly Thr Gln Gln Gln Leu Leu Gln Val His Lys
        35                  40                  45

Ala Arg Lys Ala Phe His Asp Asp Arg Phe His Arg Lys Gln Ser Ser
    50                  55                  60

Asp Leu Phe Ile Thr Ile Gln Tyr Gly Lys Glu Val Glu Asn Gly Gly
65                  70                  75                  80

Lys Thr Ala Gly Val Lys Leu Lys Glu Gly Glu Glu Val Arg Lys Glu
                85                  90                  95

Ala Val Glu Ser Ser Leu Glu Arg Ala Leu Ser Phe Tyr Ser Ser Ile
            100                 105                 110

Gln Thr Ser Asp Gly Asn Trp Ala Ser Asp Leu Gly Gly Pro Met Phe
        115                 120                 125

Leu Leu Pro Gly Leu Val Ile Ala Leu Tyr Val Thr Gly Val Leu Asn
    130                 135                 140

Ser Val Leu Ser Lys His His Arg Gln Glu Met Cys Arg Tyr Val Tyr
145                 150                 155                 160

Asn His Gln Asn Glu Asp Gly Gly Trp Gly Leu His Ile Glu Gly Pro
                165                 170                 175

Ser Thr Met Phe Gly Ser Ala Leu Asn Tyr Val Ala Leu Arg Leu Leu
            180                 185                 190

Gly Glu Asp Ala Asn Ala Gly Ala Met Pro Lys Ala Arg Ala Trp Ile
        195                 200                 205

Leu Asp His Gly Gly Ala Thr Gly Ile Thr Ser Trp Gly Lys Leu Trp
    210                 215                 220

Leu Ser Val Leu Gly Val Tyr Glu Trp Ser Gly Asn Asn Pro Leu Pro
225                 230                 235                 240

Pro Glu Phe Trp Leu Phe Pro Tyr Phe Leu Pro Phe His Pro Gly Arg
                245                 250                 255

Met Trp Cys His Cys Arg Met Val Tyr Leu Pro Met Ser Tyr Leu Tyr
            260                 265                 270

Gly Lys Arg Phe Val Gly Pro Ile Thr Pro Ile Val Leu Ser Leu Arg
        275                 280                 285

Lys Glu Leu Tyr Ala Val Pro Tyr His Glu Ile Asp Trp Asn Lys Ser
    290                 295                 300

Arg Asn Thr Cys Ala Lys Glu Asp Leu Tyr Tyr Pro His Pro Lys Met
```

-continued

```
305                 310                 315                 320

Gln Asp Ile Leu Trp Gly Ser Leu His His Val Tyr Glu Pro Leu Phe
                325                 330                 335

Thr Arg Trp Pro Ala Lys Arg Leu Arg Glu Lys Ala Leu Gln Thr Ala
            340                 345                 350

Met Gln His Ile His Tyr Glu Asp Glu Asn Thr Arg Tyr Ile Cys Leu
        355                 360                 365

Gly Pro Val Asn Lys Val Leu Asn Leu Leu Cys Cys Trp Val Glu Asp
    370                 375                 380

Pro Tyr Ser Asp Ala Phe Lys Leu His Leu Gln Arg Val His Asp Tyr
385                 390                 395                 400

Leu Trp Val Ala Glu Asp Gly Met Lys Met Gln Gly Tyr Asn Gly Ser
                405                 410                 415

Gln Leu Trp Asp Thr Ala Phe Ser Ile Gln Ala Ile Val Ser Thr Lys
            420                 425                 430

Leu Val Asp Asn Tyr Gly Pro Thr Leu Arg Lys Ala His Asp Phe Val
        435                 440                 445

Lys Ser Ser Gln Ile Gln Gln Asp Cys Pro Gly Asp Pro Asn Val Trp
    450                 455                 460

Tyr Arg His Ile His Lys Gly Ala Trp Pro Phe Ser Thr Arg Asp His
465                 470                 475                 480

Gly Trp Leu Ile Ser Asp Cys Thr Ala Glu Gly Leu Lys Ala Ala Leu
                485                 490                 495

Met Leu Ser Lys Leu Pro Ser Glu Thr Val Gly Glu Ser Leu Glu Arg
            500                 505                 510

Asn Arg Leu Cys Asp Ala Val Asn Val Leu Leu Ser Leu Gln Asn Asp
        515                 520                 525

Asn Gly Gly Phe Ala Ser Tyr Glu Leu Thr Arg Ser Tyr Pro Trp Leu
    530                 535                 540

Glu Leu Ile Asn Pro Ala Glu Thr Phe Gly Asp Ile Val Ile Asp Tyr
545                 550                 555                 560

Pro Tyr Val Glu Cys Thr Ser Ala Thr Met Glu Ala Leu Thr Leu Phe
                565                 570                 575

Lys Lys Leu His Pro Gly His Arg Thr Lys Glu Ile Asp Thr Ala Ile
            580                 585                 590

Val Arg Ala Ala Asn Phe Leu Glu Asn Met Gln Arg Thr Asp Gly Ser
        595                 600                 605

Trp Tyr Gly Cys Trp Gly Val Cys Phe Thr Tyr Ala Gly Trp Phe Gly
    610                 615                 620

Ile Lys Gly Leu Val Ala Ala Gly Arg Thr Tyr Asn Asn Cys Leu Ala
625                 630                 635                 640

Ile Arg Lys Ala Cys Asp Phe Leu Leu Ser Lys Glu Leu Pro Gly Gly
                645                 650                 655

Gly Trp Gly Glu Ser Tyr Leu Ser Cys Gln Asn Lys Val Tyr Thr Asn
            660                 665                 670

Leu Glu Gly Asn Arg Pro His Leu Val Asn Thr Ala Trp Val Leu Met
        675                 680                 685

Ala Leu Ile Glu Ala Gly Gln Ala Glu Arg Asp Pro Thr Pro Leu His
    690                 695                 700

Arg Ala Ala Arg Leu Leu Ile Asn Ser Gln Leu Glu Asn Gly Asp Phe
705                 710                 715                 720

Pro Gln Gln Glu Ile Met Gly Val Phe Asn Lys Asn Cys Met Ile Thr
                725                 730                 735
```

-continued

```
Tyr Ala Ala Tyr Arg Asn Ile Phe Pro Ile Trp Ala Leu Gly Glu Tyr
            740                 745                 750

Cys His Arg Val Leu Thr Glu
        755


<210> SEQ ID NO 13
<211> LENGTH: 1575
<212> TYPE: DNA
<213> ORGANISM: Artificial Sequence
<220> FEATURE:
<223> OTHER INFORMATION: Optimised Nucleic Acid sequence encoding
      squalene epoxidase

<400> SEQUENCE: 13

atggtcgatc agtgtgctct gggctggatc ctggcgtcag tgcttggtgc agctgcatta     60

tatttcctat ttggaagaaa aaacgggggga gtttcaaacg aaagaagaca tgaatcaatt    120

aagaacattg caactacgaa tggtgaatac aagtcttcca actctgatgg tgatatcatt    180

atcgtgggcg ccggtgtagc aggatctgct ttggcatata cattagggaa agacggtcgt    240

agagttcatg tgatagagag agatcttacg gaaccggaca ggattgttgg tgaacttttg    300

cagccgggcg gatacttaaa actgacggaa ctaggtttag aggattgcgt tgatgacatt    360

gatgctcaaa gagtttacgg ctacgccttg ttcaaagacg gtaaagatac taggttaagt    420

tatcctctag aaaaatttca ttccgacgtt gctggcagat cctttcacaa cggaagattt    480

atacaaagaa tgagagaaaa agccgctagt ctaccaaatg tatccttgga acaaggtaca    540

gttacatcct tattagaaga gaatggtatt atcaaaggcg tgcaatataa aacgaaaacc    600

ggacaagaaa tgactgctta tgccccatta acaatcgtgt gtgatggctg cttctctaat    660

ttgagaagat ctctttgtaa tccaaaggtt gacgttccta gctgctttgt tggtttggtt    720

ttggaaaatt gcgatttacc gtatgctaac catggacatg ttatcctagc agatccgtct    780

ccaattctgt tctacagaat tagttcaact gaaattagat gtttggttga tgtccctggt    840

cagaaggttc caagtatctc caacggtgaa atggctaatt acctaaaaaa cgttgttgct    900

ccgcaaattc ccagccagtt gtacgactct ttcgttgccg cgatagacaa aggtaatatc    960

agaacgatgc cgaataggtc catgcctgct gacccatatc ccaccccagg agcgttattg   1020

atgggtgatg cttttaatat gagacatcca ttaacaggcg gagggatgac tgttgctttg   1080

tctgatgttg tcgtcttgag agatttatta aaaccgcttc gtgatctaaa cgatgcacct   1140

acattgtcaa agtatttaga ggccttttac acgttgagga agcctgttgc tagtaccatt   1200

aatacgttgg ctggagctct gtataaggtg ttttgcgcct caccagacca agctagaaaa   1260

gaaatgcgtc aagcttgttt cgactaccta agtctgggtg gtatatttag taacggtcct   1320

gtctctctat tgtcagggct aaacccacgt cctattagtc ttgtcttgca cttcttcgca   1380

gtggcgattt atggtgttgg taggttgctg attccgtttc ccagtcctaa acgtgtgtgg   1440

ataggtgcaa gaattatctc tggtgcgtca gcgattattt ttccaattat taaggctgaa   1500

ggtgtgagac aaatgttttt ccctgctact gttgccgcgt attacagagc accaagggtt   1560

gtcaagggca gataa                                                    1575


<210> SEQ ID NO 14
<211> LENGTH: 524
<212> TYPE: PRT
<213> ORGANISM: Siraitia grosvenori

<400> SEQUENCE: 14
```

-continued

```
Met Val Asp Gln Cys Ala Leu Gly Trp Ile Leu Ala Ser Val Leu Gly
1               5                   10                  15

Ala Ala Ala Leu Tyr Phe Leu Phe Gly Arg Lys Asn Gly Gly Val Ser
            20                  25                  30

Asn Glu Arg Arg His Glu Ser Ile Lys Asn Ile Ala Thr Thr Asn Gly
        35                  40                  45

Glu Tyr Lys Ser Ser Asn Ser Asp Gly Asp Ile Ile Ile Val Gly Ala
    50                  55                  60

Gly Val Ala Gly Ser Ala Leu Ala Tyr Thr Leu Gly Lys Asp Gly Arg
65                  70                  75                  80

Arg Val His Val Ile Glu Arg Asp Leu Thr Glu Pro Asp Arg Ile Val
                85                  90                  95

Gly Glu Leu Leu Gln Pro Gly Gly Tyr Leu Lys Leu Thr Glu Leu Gly
            100                 105                 110

Leu Glu Asp Cys Val Asp Asp Ile Asp Ala Gln Arg Val Tyr Gly Tyr
        115                 120                 125

Ala Leu Phe Lys Asp Gly Lys Asp Thr Arg Leu Ser Tyr Pro Leu Glu
    130                 135                 140

Lys Phe His Ser Asp Val Ala Gly Arg Ser Phe His Asn Gly Arg Phe
145                 150                 155                 160

Ile Gln Arg Met Arg Glu Lys Ala Ala Ser Leu Pro Asn Val Ser Leu
                165                 170                 175

Glu Gln Gly Thr Val Thr Ser Leu Leu Glu Glu Asn Gly Ile Ile Lys
            180                 185                 190

Gly Val Gln Tyr Lys Thr Lys Thr Gly Gln Glu Met Thr Ala Tyr Ala
        195                 200                 205

Pro Leu Thr Ile Val Cys Asp Gly Cys Phe Ser Asn Leu Arg Arg Ser
    210                 215                 220

Leu Cys Asn Pro Lys Val Asp Val Pro Ser Cys Phe Val Gly Leu Val
225                 230                 235                 240

Leu Glu Asn Cys Asp Leu Pro Tyr Ala Asn His Gly His Val Ile Leu
                245                 250                 255

Ala Asp Pro Ser Pro Ile Leu Phe Tyr Arg Ile Ser Ser Thr Glu Ile
            260                 265                 270

Arg Cys Leu Val Asp Val Pro Gly Gln Lys Val Pro Ser Ile Ser Asn
        275                 280                 285

Gly Glu Met Ala Asn Tyr Leu Lys Asn Val Val Ala Pro Gln Ile Pro
    290                 295                 300

Ser Gln Leu Tyr Asp Ser Phe Val Ala Ala Ile Asp Lys Gly Asn Ile
305                 310                 315                 320

Arg Thr Met Pro Asn Arg Ser Met Pro Ala Asp Pro Tyr Pro Thr Pro
                325                 330                 335

Gly Ala Leu Leu Met Gly Asp Ala Phe Asn Met Arg His Pro Leu Thr
            340                 345                 350

Gly Gly Gly Met Thr Val Ala Leu Ser Asp Val Val Val Leu Arg Asp
        355                 360                 365

Leu Leu Lys Pro Leu Arg Asp Leu Asn Asp Ala Pro Thr Leu Ser Lys
    370                 375                 380

Tyr Leu Glu Ala Phe Tyr Thr Leu Arg Lys Pro Val Ala Ser Thr Ile
385                 390                 395                 400

Asn Thr Leu Ala Gly Ala Leu Tyr Lys Val Phe Cys Ala Ser Pro Asp
                405                 410                 415
```

```
Gln Ala Arg Lys Glu Met Arg Gln Ala Cys Phe Asp Tyr Leu Ser Leu
            420                 425                 430

Gly Gly Ile Phe Ser Asn Gly Pro Val Ser Leu Leu Ser Gly Leu Asn
        435                 440                 445

Pro Arg Pro Ile Ser Leu Val Leu His Phe Phe Ala Val Ala Ile Tyr
    450                 455                 460

Gly Val Gly Arg Leu Leu Ile Pro Phe Pro Ser Pro Lys Arg Val Trp
465                 470                 475                 480

Ile Gly Ala Arg Ile Ile Ser Gly Ala Ser Ala Ile Ile Phe Pro Ile
                485                 490                 495

Ile Lys Ala Glu Gly Val Arg Gln Met Phe Phe Pro Ala Thr Val Ala
            500                 505                 510

Ala Tyr Tyr Arg Ala Pro Arg Val Val Lys Gly Arg
        515                 520


<210> SEQ ID NO 15
<211> LENGTH: 1587
<212> TYPE: DNA
<213> ORGANISM: Artificial Sequence
<220> FEATURE:
<223> OTHER INFORMATION: Optimised Nucleic Acid sequence encoding
      squalene epoxidase

<400> SEQUENCE: 15

atggttgatc aatgtgcctt aggttggatc ttagcttccg ctttgggttt agtcattgct      60

ttgtgtttct tcgttgcccc aagaagaaac catagaggtg tcgattccaa agaaaagagat    120

gaatgtgtcc aatctgctgc tactaccaag ggtgaatgca gatttaacga cagagatgtc    180

gatgtcattg ttgttggtgc tggtgttgcc ggttctgctt tggctcacac tttgggtaag    240

gatggtagaa gagttcatgt tatcgaaaga gacttaaccg aaccagacag aattgttggt    300

gagttgttgc aaccaggtgg ttacttgaaa ttgattgagt tgggtttgca agactgtgtt    360

gaagagatcg acgctcaaag agtttacggt tatgctttat tcaaggacgg taagaatacc    420

cgtttatcct acccattgga aaatttccat tctgacgttt ctggtagatc tttccacaac    480

ggtagattta ttcaaagaat gagagaaaaa gccgcttctt taccaaacgt tagattggaa    540

caaggtactg ttacttcttt gttagaagaa aaaggtacca ttaaaggtgt tcaatacaag    600

tccaaaaacg gtgaagaaaa gaccgcttac gctcctttga ccatcgtttg tgacggttgt    660

ttttctaact tgagaagatc tttgtgtaac cctatggttg atgttccatc ttactttgtc    720

ggtttggttt tggaaaattg tgaattgcca tttgccaacc atggtcacgt tattttgggt    780

gacccttccc caattttgtt ctaccaaatt tcccgtactg aaatcagatg tttggtcgat    840

gttccaggtc aaaaagttcc ttctatcgcc aacggtgaaa tggagaagta tttaaagacc    900

gtcgttgctc cacaagtccc tccacaaatt tacgactcct tcatcgctgc tattgacaag    960

ggtaacatca gaactatgcc aaatagatcc atgccagctg ctccacaccc aaccccaggt   1020

gccttattaa tgggtgacgc ttttaacatg cgtcacccat tgaccggtgg tggtatgact   1080

gtcgctttgt ctgacattgt tgtcttgcgt aacttattga agccattgaa ggacttgtct   1140

gacgcctcta ccttgtgtaa gtacttggaa tccttctaca ctttgagaaa gccagttgct   1200

tccactatca acaccttggc tggtgccttg tacaaggttt tctgtgcttc tccagaccaa   1260

gctagaaaag aaatgagaca agcttgtttt gactacttat ctttgggtgg tattttctct   1320

aacggtccag tttccttgtt gtccggtttg aaccctagac cattgtcctt agttttgcac   1380

tttttcgccg tcgctatcta cggtgttggt agattgttgt tgccattccc ttctgtcaag   1440
```

```
ggtatctgga ttggtgctag attgatctac tctgcttctg gtattatctt cccaatcatt   1500

agagccgaag gtgtcagaca aatgttcttc ccagccactg ttcctgctta ctaccgttcc   1560

ccaccagttt tcaagccaat cgtttaa                                       1587


<210> SEQ ID NO 16
<211> LENGTH: 528
<212> TYPE: PRT
<213> ORGANISM: Siraitia grosvenori

<400> SEQUENCE: 16

Met Val Asp Gln Cys Ala Leu Gly Trp Ile Leu Ala Ser Ala Leu Gly
1               5                   10                  15

Leu Val Ile Ala Leu Cys Phe Phe Val Ala Pro Arg Arg Asn His Arg
            20                  25                  30

Gly Val Asp Ser Lys Glu Arg Asp Glu Cys Val Gln Ser Ala Ala Thr
        35                  40                  45

Thr Lys Gly Glu Cys Arg Phe Asn Asp Arg Asp Val Asp Val Ile Val
    50                  55                  60

Val Gly Ala Gly Val Ala Gly Ser Ala Leu Ala His Thr Leu Gly Lys
65                  70                  75                  80

Asp Gly Arg Arg Val His Val Ile Glu Arg Asp Leu Thr Glu Pro Asp
                85                  90                  95

Arg Ile Val Gly Glu Leu Leu Gln Pro Gly Gly Tyr Leu Lys Leu Ile
            100                 105                 110

Glu Leu Gly Leu Gln Asp Cys Val Glu Glu Ile Asp Ala Gln Arg Val
        115                 120                 125

Tyr Gly Tyr Ala Leu Phe Lys Asp Gly Lys Asn Thr Arg Leu Ser Tyr
    130                 135                 140

Pro Leu Glu Asn Phe His Ser Asp Val Ser Gly Arg Ser Phe His Asn
145                 150                 155                 160

Gly Arg Phe Ile Gln Arg Met Arg Glu Lys Ala Ala Ser Leu Pro Asn
                165                 170                 175

Val Arg Leu Glu Gln Gly Thr Val Thr Ser Leu Leu Glu Glu Lys Gly
            180                 185                 190

Thr Ile Lys Gly Val Gln Tyr Lys Ser Lys Asn Gly Glu Glu Lys Thr
        195                 200                 205

Ala Tyr Ala Pro Leu Thr Ile Val Cys Asp Gly Cys Phe Ser Asn Leu
    210                 215                 220

Arg Arg Ser Leu Cys Asn Pro Met Val Asp Val Pro Ser Tyr Phe Val
225                 230                 235                 240

Gly Leu Val Leu Glu Asn Cys Glu Leu Pro Phe Ala Asn His Gly His
                245                 250                 255

Val Ile Leu Gly Asp Pro Ser Pro Ile Leu Phe Tyr Gln Ile Ser Arg
            260                 265                 270

Thr Glu Ile Arg Cys Leu Val Asp Val Pro Gly Gln Lys Val Pro Ser
        275                 280                 285

Ile Ala Asn Gly Glu Met Glu Lys Tyr Leu Lys Thr Val Val Ala Pro
    290                 295                 300

Gln Val Pro Pro Gln Ile Tyr Asp Ser Phe Ile Ala Ala Ile Asp Lys
305                 310                 315                 320

Gly Asn Ile Arg Thr Met Pro Asn Arg Ser Met Pro Ala Ala Pro His
                325                 330                 335

Pro Thr Pro Gly Ala Leu Leu Met Gly Asp Ala Phe Asn Met Arg His
```

-continued

```
            340                 345                 350

Pro Leu Thr Gly Gly Gly Met Thr Val Ala Leu Ser Asp Ile Val Val
        355                 360                 365

Leu Arg Asn Leu Leu Lys Pro Leu Lys Asp Leu Ser Asp Ala Ser Thr
    370                 375                 380

Leu Cys Lys Tyr Leu Glu Ser Phe Tyr Thr Leu Arg Lys Pro Val Ala
385                 390                 395                 400

Ser Thr Ile Asn Thr Leu Ala Gly Ala Leu Tyr Lys Val Phe Cys Ala
                405                 410                 415

Ser Pro Asp Gln Ala Arg Lys Glu Met Arg Gln Ala Cys Phe Asp Tyr
            420                 425                 430

Leu Ser Leu Gly Gly Ile Phe Ser Asn Gly Pro Val Ser Leu Leu Ser
        435                 440                 445

Gly Leu Asn Pro Arg Pro Leu Ser Leu Val Leu His Phe Phe Ala Val
    450                 455                 460

Ala Ile Tyr Gly Val Gly Arg Leu Leu Leu Pro Phe Pro Ser Val Lys
465                 470                 475                 480

Gly Ile Trp Ile Gly Ala Arg Leu Ile Tyr Ser Ala Ser Gly Ile Ile
                485                 490                 495

Phe Pro Ile Ile Arg Ala Glu Gly Val Arg Gln Met Phe Phe Pro Ala
            500                 505                 510

Thr Val Pro Ala Tyr Tyr Arg Ser Pro Pro Val Phe Lys Pro Ile Val
        515                 520                 525
```

<210> SEQ ID NO 17
<211> LENGTH: 951
<212> TYPE: DNA
<213> ORGANISM: Artificial Sequence
<220> FEATURE:
<223> OTHER INFORMATION: Optimised Nucleic Acid sequence encoding epoxy hydratase

<400> SEQUENCE: 17

```
atggaaaaca tcgaacacac cactgtccaa actaacggta tcaagatgca cgtcgctgct     60

attggtactg gtccaccagt tttgttgttg catggtttcc cagaattgtg gtattcttgg    120

agacaccaat tgttgtactt gtcttctgct ggttacagag ctatcgctcc agacttgaga    180

ggttacggtg ataccgacgc tccaccttcc ccatcttcct ataccgcttt acacattgtc    240

ggtgatttgg tcggtttgtt ggacgtcttg ggtatcgaaa aagtcttctt aatcggtcac    300

gactggggtg ccatcatcgc ctggtacttc tgtttattca gacctgatag aatcaaagct    360

ttggttaact tgtctgttca attcttccca agaaacccaa ccaccccatt tgttaagggt    420

ttcagagccg tcttgggtga tcaattttac atggttagat tccaagaacc aggtaaagct    480

gaagaagaat tcgcttccgt tgatattaga gaattcttca agaatgtttt gtccaacaga    540

gatccacaag ctccatattt gccaaatgaa gttaagttcg aaggtgtccc accaccagct    600

ttggctccat ggttgacccc agaagatatc gatgtctacg ctgacaaatt cgctgaaact    660

ggtttcactg gtggtttgaa ctactacaga gcctttgaca gaacctggga attaactgct    720

ccatggaccg gtgcccgtat tggtgtccca gtcaagttca ttgtcggtga tttggacttg    780

acttaccact ttccaggtgc tcaaaaatac attcacggtg aaggtttcaa gaaggctgtc    840

ccaggtttgg aagaagttgt cgttatggag gatacctctc acttcattaa ccaagaaaga    900

ccacacgaaa ttaattctca catccacgat ttcttctcta agttctgtta a             951
```

-continued

<210> SEQ ID NO 18
<211> LENGTH: 316
<212> TYPE: PRT
<213> ORGANISM: Siraitia grosvenori

<400> SEQUENCE: 18

```
Met Glu Asn Ile Glu His Thr Thr Val Gln Thr Asn Gly Ile Lys Met
1               5                   10                  15

His Val Ala Ala Ile Gly Thr Gly Pro Pro Val Leu Leu Leu His Gly
            20                  25                  30

Phe Pro Glu Leu Trp Tyr Ser Trp Arg His Gln Leu Leu Tyr Leu Ser
        35                  40                  45

Ser Ala Gly Tyr Arg Ala Ile Ala Pro Asp Leu Arg Gly Tyr Gly Asp
    50                  55                  60

Thr Asp Ala Pro Pro Ser Pro Ser Ser Tyr Thr Ala Leu His Ile Val
65                  70                  75                  80

Gly Asp Leu Val Gly Leu Leu Asp Val Leu Gly Ile Glu Lys Val Phe
                85                  90                  95

Leu Ile Gly His Asp Trp Gly Ala Ile Ile Ala Trp Tyr Phe Cys Leu
            100                 105                 110

Phe Arg Pro Asp Arg Ile Lys Ala Leu Val Asn Leu Ser Val Gln Phe
        115                 120                 125

Phe Pro Arg Asn Pro Thr Thr Pro Phe Val Lys Gly Phe Arg Ala Val
    130                 135                 140

Leu Gly Asp Gln Phe Tyr Met Val Arg Phe Gln Glu Pro Gly Lys Ala
145                 150                 155                 160

Glu Glu Glu Phe Ala Ser Val Asp Ile Arg Glu Phe Phe Lys Asn Val
                165                 170                 175

Leu Ser Asn Arg Asp Pro Gln Ala Pro Tyr Leu Pro Asn Glu Val Lys
            180                 185                 190

Phe Glu Gly Val Pro Pro Pro Ala Leu Ala Pro Trp Leu Thr Pro Glu
        195                 200                 205

Asp Ile Asp Val Tyr Ala Asp Lys Phe Ala Glu Thr Gly Phe Thr Gly
    210                 215                 220

Gly Leu Asn Tyr Tyr Arg Ala Phe Asp Arg Thr Trp Glu Leu Thr Ala
225                 230                 235                 240

Pro Trp Thr Gly Ala Arg Ile Gly Val Pro Val Lys Phe Ile Val Gly
                245                 250                 255

Asp Leu Asp Leu Thr Tyr His Phe Pro Gly Ala Gln Lys Tyr Ile His
            260                 265                 270

Gly Glu Gly Phe Lys Lys Ala Val Pro Gly Leu Glu Glu Val Val Val
        275                 280                 285

Met Glu Asp Thr Ser His Phe Ile Asn Gln Glu Arg Pro His Glu Ile
    290                 295                 300

Asn Ser His Ile His Asp Phe Phe Ser Lys Phe Cys
305                 310                 315
```

<210> SEQ ID NO 19
<211> LENGTH: 951
<212> TYPE: DNA
<213> ORGANISM: Artificial Sequence
<220> FEATURE:
<223> OTHER INFORMATION: Optimised Nucleic Acid sequence encoding epoxy hydratase

<400> SEQUENCE: 19

```
atggatcaaa ttgaacacat cactattaac accaacggta tcaaaatgca tatcgcctct      60
```

-continued

```
gttggtactg gtcctgttgt tttgttgttg catggtttcc cagaattgtg gtactcttgg    120

cgtcatcaat tgttgtattt gtcctctgtc ggttacagag ctattgctcc agatttaaga    180

ggttacggtg atactgactc tccagcctct ccaacttctt ataccgcttt gcatatcgtt    240

ggtgacttgg tcggtgcttt ggatgaattg ggtattgaaa aggtcttctt ggtcggtcat    300

gattgggctg ccatcatcgc ttggtacttt tgtttgttta gaccagatcg tattaaagct    360

ttagttaatt tgtctgttca attcatccca agaaacccag ctatcccatt tattgaaggt    420

ttcagaaccg cttttggtga tgatttctac atgtgtagat tccaagttcc aggtgaagct    480

gaagaagact ttgcttctat tgatactgct caattgttca aaacctcctt gtgtaacaga    540

tcctccgctc caccatgctt gccaaaagaa atcggtttca gagctattcc accaccagaa    600

aatttgccat cttggttgac cgaggaagac attaattact acgctgctaa gttcaagcaa    660

accggtttca ctggtgcttt aaactactat agagctttcg atttgacctg ggaattaact    720

gctccatgga ccggtgctca aattcaagtc ccagtcaagt tcattgttgg tgattctgac    780

ttgacttacc attttccagg tgctaaggaa tacatccaca acggtggttt caagaaggac    840

gttccattgt tggaagaagt tgttgttgtc aaggacgctt gtcacttcat caaccaagaa    900

agaccacaag aaattaacgc tcacattcat gactttatta acaagttcta a             951
```

<210> SEQ ID NO 20
<211> LENGTH: 316
<212> TYPE: PRT
<213> ORGANISM: Siraitia grosvenori

<400> SEQUENCE: 20

```
Met Asp Gln Ile Glu His Ile Thr Ile Asn Thr Asn Gly Ile Lys Met
1               5                   10                  15

His Ile Ala Ser Val Gly Thr Gly Pro Val Val Leu Leu Leu His Gly
            20                  25                  30

Phe Pro Glu Leu Trp Tyr Ser Trp Arg His Gln Leu Leu Tyr Leu Ser
        35                  40                  45

Ser Val Gly Tyr Arg Ala Ile Ala Pro Asp Leu Arg Gly Tyr Gly Asp
    50                  55                  60

Thr Asp Ser Pro Ala Ser Pro Thr Ser Tyr Thr Ala Leu His Ile Val
65                  70                  75                  80

Gly Asp Leu Val Gly Ala Leu Asp Glu Leu Gly Ile Glu Lys Val Phe
                85                  90                  95

Leu Val Gly His Asp Trp Ala Ala Ile Ile Ala Trp Tyr Phe Cys Leu
            100                 105                 110

Phe Arg Pro Asp Arg Ile Lys Ala Leu Val Asn Leu Ser Val Gln Phe
        115                 120                 125

Ile Pro Arg Asn Pro Ala Ile Pro Phe Ile Glu Gly Phe Arg Thr Ala
    130                 135                 140

Phe Gly Asp Asp Phe Tyr Met Cys Arg Phe Gln Val Pro Gly Glu Ala
145                 150                 155                 160

Glu Glu Asp Phe Ala Ser Ile Asp Thr Ala Gln Leu Phe Lys Thr Ser
                165                 170                 175

Leu Cys Asn Arg Ser Ser Ala Pro Pro Cys Leu Pro Lys Glu Ile Gly
            180                 185                 190

Phe Arg Ala Ile Pro Pro Pro Glu Asn Leu Pro Ser Trp Leu Thr Glu
        195                 200                 205

Glu Asp Ile Asn Tyr Tyr Ala Ala Lys Phe Lys Gln Thr Gly Phe Thr
```

```
    210                 215                 220

Gly Ala Leu Asn Tyr Tyr Arg Ala Phe Asp Leu Thr Trp Glu Leu Thr
225                 230                 235                 240

Ala Pro Trp Thr Gly Ala Gln Ile Gln Val Pro Val Lys Phe Ile Val
                245                 250                 255

Gly Asp Ser Asp Leu Thr Tyr His Phe Pro Gly Ala Lys Glu Tyr Ile
            260                 265                 270

His Asn Gly Gly Phe Lys Lys Asp Val Pro Leu Leu Glu Glu Val Val
        275                 280                 285

Val Val Lys Asp Ala Cys His Phe Ile Asn Gln Glu Arg Pro Gln Glu
    290                 295                 300

Ile Asn Ala His Ile His Asp Phe Ile Asn Lys Phe
305                 310                 315


<210> SEQ ID NO 21
<211> LENGTH: 945
<212> TYPE: DNA
<213> ORGANISM: Artificial Sequence
<220> FEATURE:
<223> OTHER INFORMATION: Optimised Nucleic Acid sequence encoding epoxy
      hydratase

<400> SEQUENCE: 21

atggagaaga ttgaacactc tactatcgct actaatggta tcaatatgca cgttgcctct     60

gctggttctg gtccagctgt tttgtttttg cacggtttcc cagaattatg gtattcctgg    120

agacaccaat tgttgtactt gtcttctttg ggttacagag ctattgctcc agatttgaga    180

ggtttcggtg acaccgatgc tccaccatct ccatcctcct acaccgccca ccacatcgtt    240

ggtgatttgg tcggtttgtt ggatcaatta ggtgtcgatc aagtcttttt ggttggtcat    300

gattggggtg ctatgatggc ctggtacttc tgtttgttcc gtccagacag agtcaaggcc    360

ttagttaatt tatctgtcca cttcacccca cgtaacccag ctatctctcc attagatggt    420

ttccgtttga tgttgggtga tgatttctac gtttgtaagt ttcaagaacc aggtgtcgct    480

gaagccgatt tcggttctgt tgatactgcc actatgttta aaaagttctt gaccatgaga    540

gatccacgtc cacctattat tccaaacggt ttcagatcct tggccacccc agaagctttg    600

ccatcctggt tgactgaaga ggatatcgat tactttgctg ccaaattcgc taagactggt    660

tttactggtg gtttcaacta ctacagagct atcgacttga cctgggagtt gactgctcca    720

tggtccggtt ctgaaatcaa ggttccaact aagtttattg ttggtgactt agacttggtt    780

taccatttcc caggtgttaa ggaatacatt cacggtggtg gtttcaagaa ggacgttcca    840

ttcttggaag aagttgtcgt catggaaggt gctgctcatt ttatcaacca agaaaaagct    900

gacgaaatta attctttgat ctatgacttc attaaacaat tctag                    945


<210> SEQ ID NO 22
<211> LENGTH: 314
<212> TYPE: PRT
<213> ORGANISM: Siraitia grosvenori

<400> SEQUENCE: 22

Met Glu Lys Ile Glu His Ser Thr Ile Ala Thr Asn Gly Ile Asn Met
1               5                   10                  15

His Val Ala Ser Ala Gly Ser Gly Pro Ala Val Leu Phe Leu His Gly
            20                  25                  30

Phe Pro Glu Leu Trp Tyr Ser Trp Arg His Gln Leu Leu Tyr Leu Ser
        35                  40                  45
```

```
Ser Leu Gly Tyr Arg Ala Ile Ala Pro Asp Leu Arg Gly Phe Gly Asp
    50                  55                  60

Thr Asp Ala Pro Pro Ser Pro Ser Ser Tyr Thr Ala His His Ile Val
65                  70                  75                  80

Gly Asp Leu Val Gly Leu Leu Asp Gln Leu Gly Val Asp Gln Val Phe
                85                  90                  95

Leu Val Gly His Asp Trp Gly Ala Met Met Ala Trp Tyr Phe Cys Leu
            100                 105                 110

Phe Arg Pro Asp Arg Val Lys Ala Leu Val Asn Leu Ser Val His Phe
        115                 120                 125

Thr Pro Arg Asn Pro Ala Ile Ser Pro Leu Asp Gly Phe Arg Leu Met
    130                 135                 140

Leu Gly Asp Asp Phe Tyr Val Cys Lys Phe Gln Glu Pro Gly Val Ala
145                 150                 155                 160

Glu Ala Asp Phe Gly Ser Val Asp Thr Ala Thr Met Phe Lys Lys Phe
                165                 170                 175

Leu Thr Met Arg Asp Pro Arg Pro Pro Ile Ile Pro Asn Gly Phe Arg
            180                 185                 190

Ser Leu Ala Thr Pro Glu Ala Leu Pro Ser Trp Leu Thr Glu Glu Asp
        195                 200                 205

Ile Asp Tyr Phe Ala Ala Lys Phe Ala Lys Thr Gly Phe Thr Gly Gly
    210                 215                 220

Phe Asn Tyr Tyr Arg Ala Ile Asp Leu Thr Trp Glu Leu Thr Ala Pro
225                 230                 235                 240

Trp Ser Gly Ser Glu Ile Lys Val Pro Thr Lys Phe Ile Val Gly Asp
                245                 250                 255

Leu Asp Leu Val Tyr His Phe Pro Gly Val Lys Glu Tyr Ile His Gly
            260                 265                 270

Gly Gly Phe Lys Lys Asp Val Pro Phe Leu Glu Glu Val Val Val Met
        275                 280                 285

Glu Gly Ala Ala His Phe Ile Asn Gln Glu Lys Ala Asp Glu Ile Asn
    290                 295                 300

Ser Leu Ile Tyr Asp Phe Ile Lys Gln Phe
305                 310
```

<210> SEQ ID NO 23
<211> LENGTH: 951
<212> TYPE: DNA
<213> ORGANISM: Artificial Sequence
<220> FEATURE:
<223> OTHER INFORMATION: Optimised Nucleic Acid sequence encoding epoxy hydratase

<400> SEQUENCE: 23

```
atggaaaaga ttgaacacac cactatttct accaatggta tcaacatgca tgttgcctct     60

attggttctg gtccagctgt cttgttcttg cacggtttcc cagaattgtg gtattcttgg    120

agacaccaat tattattctt gtcttccatg ggttacagag ctatcgctcc agacttaaga    180

ggttttggtg acaccgacgc tccaccatct ccatcttctt acaccgctca ccacattgtc    240

ggtgacttgg tcggtttgtt agaccaattg ggtattgacc aagttttttt ggttggtcac    300

gactggggtg ctatgatggc ctggtacttt tgtttgttcc gtccagatag agttaaggct    360

ttggtcaatt tatctgtcca cttcttacgt agacacccat ctatcaaatt tgttgatggt    420

ttcagagcct tattaggtga tgatttttac ttctgtcaat tccaagaacc aggtgtcgct    480
```

-continued

```
gaagccgact tcggttctgt cgatgttgct accatgttga agaaattctt gaccatgaga    540

gatccaagac ctccaatgat tcctaaggaa aagggtttca gagccttgga aactccagat    600

ccattgccag cctggttaac tgaagaagac attgactact tcgccggtaa gtttcgtaag    660

accggtttta ccggtggttt taattactac agagccttca acttgacttg ggagttgacc    720

gctccatggt ctggttctga aatcaaggtc gctgccaagt tcattgttgg tgatttagac    780

ttggtttatc acttccctgg tgccaaggag tatatccatg gtggtggttt caaaaaggac    840

gtccctttgt tggaggaagt tgttgttgtt gatggtgctg ctcacttcat caaccaagaa    900

agaccagctg aaatttcttc cttgatttac gactttatca agaagttcta a             951
```

```
<210> SEQ ID NO 24
<211> LENGTH: 316
<212> TYPE: PRT
<213> ORGANISM: Siraitia grosvenori

<400> SEQUENCE: 24

Met Glu Lys Ile Glu His Thr Thr Ile Ser Thr Asn Gly Ile Asn Met
1               5                   10                  15

His Val Ala Ser Ile Gly Ser Gly Pro Ala Val Leu Phe Leu His Gly
            20                  25                  30

Phe Pro Glu Leu Trp Tyr Ser Trp Arg His Gln Leu Leu Phe Leu Ser
        35                  40                  45

Ser Met Gly Tyr Arg Ala Ile Ala Pro Asp Leu Arg Gly Phe Gly Asp
    50                  55                  60

Thr Asp Ala Pro Pro Ser Pro Ser Ser Tyr Thr Ala His His Ile Val
65                  70                  75                  80

Gly Asp Leu Val Gly Leu Leu Asp Gln Leu Gly Ile Asp Gln Val Phe
                85                  90                  95

Leu Val Gly His Asp Trp Gly Ala Met Met Ala Trp Tyr Phe Cys Leu
            100                 105                 110

Phe Arg Pro Asp Arg Val Lys Ala Leu Val Asn Leu Ser Val His Phe
        115                 120                 125

Leu Arg Arg His Pro Ser Ile Lys Phe Val Asp Gly Phe Arg Ala Leu
    130                 135                 140

Leu Gly Asp Asp Phe Tyr Phe Cys Gln Phe Gln Glu Pro Gly Val Ala
145                 150                 155                 160

Glu Ala Asp Phe Gly Ser Val Asp Val Ala Thr Met Leu Lys Lys Phe
                165                 170                 175

Leu Thr Met Arg Asp Pro Arg Pro Pro Met Ile Pro Lys Glu Lys Gly
            180                 185                 190

Phe Arg Ala Leu Glu Thr Pro Asp Pro Leu Pro Ala Trp Leu Thr Glu
        195                 200                 205

Glu Asp Ile Asp Tyr Phe Ala Gly Lys Phe Arg Lys Thr Gly Phe Thr
    210                 215                 220

Gly Gly Phe Asn Tyr Tyr Arg Ala Phe Asn Leu Thr Trp Glu Leu Thr
225                 230                 235                 240

Ala Pro Trp Ser Gly Ser Glu Ile Lys Val Ala Ala Lys Phe Ile Val
                245                 250                 255

Gly Asp Leu Asp Leu Val Tyr His Phe Pro Gly Ala Lys Glu Tyr Ile
            260                 265                 270

His Gly Gly Gly Phe Lys Lys Asp Val Pro Leu Leu Glu Glu Val Val
        275                 280                 285

Val Val Asp Gly Ala Ala His Phe Ile Asn Gln Glu Arg Pro Ala Glu
```

290 295 300

Ile Ser Ser Leu Ile Tyr Asp Phe Ile Lys Lys Phe
305 310 315

<210> SEQ ID NO 25
<211> LENGTH: 1599
<212> TYPE: DNA
<213> ORGANISM: Siraitia grosvenori

<400> SEQUENCE: 25
atgctgatgc acgctctcac ccctacagct cctttcttct ctataaaacc taacacagaa 60 ccccccttctg ctaccacacg gcagccaccc atggattccc caccccaaaa acctcacttc 120
cttctcttcc ctttcatggc tcagggccac atgatcccca tgattgacct tgccaagctt 180
ctggcccagc gaggagccat tattactgtc gtcaccacgc cccacaatgc tgctcgctac 240
cactctgttc tcgctcgcgc cattgattct gggttacaca tccatgtcct ccaacttcag 300
tttccatgca acgaaggcgg gttgccagaa gggtgcgaga atttcgactt gttaccttca 360
cttggttctg cctccacatt cttcagagca acattcctcc tttacgaacc atcggaaaaa 420
gtgttcgagg aactcatccc ccgcccccacc tgcataatct ccgatatgtg tctgccctgg 480
accgtacgac ttgctcagaa atatcacgtc ccaaggctcg ttttctacag tttgagctgc 540
ttctttcttc tctgtatgcg gagtttaaaa aacaatcaag ctcttataag ctccaagtct 600
gattctgagt tggtaacttt ctcagacttg cctgatccag tcgagtttct caagtcgcag 660
ctgcctaaat ccaacgatga agaaatggca aagtttggtt atgaaatagg ggaggccgat 720
cggcaatcac acggcgttat tgtgaatgta tttgaggaga tggagccgaa gtatcttgcg 780
gagtatagaa aggaaagaga atcgccggaa aaagtgtggt gcgtcggccc agtttcgctt 840
tgcaacgaca acaaactcga caaggctcag agaggcaaca aagcctccat cgacgaacgc 900
gaatgcatcg agtggctcga cgggcagcag ccgtcttcag tggtttacgt gtctttagga 960
agtctgtgca atttggtgac ggcgcaactt attgagctgg gtttgggttt ggaggcatca 1020
aacaaaccat tcatttgggt catacgaaaa ggaaacataa cagaggagtt acagaaatgg 1080
ctggtggagt atgatttcga ggagaaaact aaagggagag ggctcgtgat tcttggctgg 1140
gctccccaag ttctgatact atcgcaccct gcaatcggat gctttttgac gcactgcggt 1200
tggaactcaa gcatcgaagg aatatcggcc ggcatgccca tgatcacttg gccacttttt 1260
gccgatcaag tcttcaacga gaagctaatc gtagagatac tcagaatcgg tgtaagtgtg 1320
ggcatggaaa cagctatgca ctggggagag gaagaggaga aaggggtggt ggtaaagaga 1380
gagaaagtga gagaagccat agaaagggcg atggatggag atgagagaga agagaggagg 1440
gagagatgca aagagcttgc tgaaatggcg aagagagccg tagaagaagg ggggtcgtct 1500
catcggaacc tgacgctgct aactgaagat attcttgtta atggaggagg tcaagagaga 1560
atggatgatg ctgatgattt tcctactata gttaattga 1599

<210> SEQ ID NO 26
<211> LENGTH: 502
<212> TYPE: PRT
<213> ORGANISM: Siraitia grosvenori

<400> SEQUENCE: 26

Met Asp Ser Pro Pro Gln Lys Pro His Phe Leu Leu Phe Pro Phe Met
1 5 10 15

Ala Gln Gly His Met Ile Pro Met Ile Asp Leu Ala Lys Leu Leu Ala

-continued

```
            20                  25                  30

Gln Arg Gly Ala Ile Ile Thr Val Val Thr Thr Pro His Asn Ala Ala
        35                  40                  45

Arg Tyr His Ser Val Leu Ala Arg Ala Ile Asp Ser Gly Leu His Ile
    50                  55                  60

His Val Leu Gln Leu Gln Phe Pro Cys Asn Glu Gly Gly Leu Pro Glu
65                  70                  75                  80

Gly Cys Glu Asn Phe Asp Leu Leu Pro Ser Leu Gly Ser Ala Ser Thr
                85                  90                  95

Phe Phe Arg Ala Thr Phe Leu Leu Tyr Glu Pro Ser Glu Lys Val Phe
            100                 105                 110

Glu Glu Leu Ile Pro Arg Pro Thr Cys Ile Ile Ser Asp Met Cys Leu
        115                 120                 125

Pro Trp Thr Val Arg Leu Ala Gln Lys Tyr His Val Pro Arg Leu Val
    130                 135                 140

Phe Tyr Ser Leu Ser Cys Phe Phe Leu Leu Cys Met Arg Ser Leu Lys
145                 150                 155                 160

Asn Asn Gln Ala Leu Ile Ser Ser Lys Ser Asp Ser Glu Leu Val Thr
                165                 170                 175

Phe Ser Asp Leu Pro Asp Pro Val Glu Phe Leu Lys Ser Gln Leu Pro
            180                 185                 190

Lys Ser Asn Asp Glu Glu Met Ala Lys Phe Gly Tyr Glu Ile Gly Glu
        195                 200                 205

Ala Asp Arg Gln Ser His Gly Val Ile Val Asn Val Phe Glu Glu Met
    210                 215                 220

Glu Pro Lys Tyr Leu Ala Glu Tyr Arg Lys Glu Arg Glu Ser Pro Glu
225                 230                 235                 240

Lys Val Trp Cys Val Gly Pro Val Ser Leu Cys Asn Asp Asn Lys Leu
                245                 250                 255

Asp Lys Ala Gln Arg Gly Asn Lys Ala Ser Ile Asp Glu Arg Glu Cys
            260                 265                 270

Ile Glu Trp Leu Asp Gly Gln Gln Pro Ser Ser Val Val Tyr Val Ser
        275                 280                 285

Leu Gly Ser Leu Cys Asn Leu Val Thr Ala Gln Leu Ile Glu Leu Gly
    290                 295                 300

Leu Gly Leu Glu Ala Ser Asn Lys Pro Phe Ile Trp Val Ile Arg Lys
305                 310                 315                 320

Gly Asn Ile Thr Glu Glu Leu Gln Lys Trp Leu Val Glu Tyr Asp Phe
                325                 330                 335

Glu Glu Lys Thr Lys Gly Arg Gly Leu Val Ile Leu Gly Trp Ala Pro
            340                 345                 350

Gln Val Leu Ile Leu Ser His Pro Ala Ile Gly Cys Phe Leu Thr His
        355                 360                 365

Cys Gly Trp Asn Ser Ser Ile Glu Gly Ile Ser Ala Gly Met Pro Met
    370                 375                 380

Ile Thr Trp Pro Leu Phe Ala Asp Gln Val Phe Asn Glu Lys Leu Ile
385                 390                 395                 400

Val Glu Ile Leu Arg Ile Gly Val Ser Val Gly Met Glu Thr Ala Met
                405                 410                 415

His Trp Gly Glu Glu Glu Glu Lys Gly Val Val Val Lys Arg Glu Lys
            420                 425                 430

Val Arg Glu Ala Ile Glu Arg Ala Met Asp Gly Asp Glu Arg Glu Glu
        435                 440                 445
```

```
Arg Arg Glu Arg Cys Lys Glu Leu Ala Glu Met Ala Lys Arg Ala Val
    450                 455                 460

Glu Glu Gly Gly Ser Ser His Arg Asn Leu Thr Leu Leu Thr Glu Asp
465                 470                 475                 480

Ile Leu Val Asn Gly Gly Gly Gln Glu Arg Met Asp Asp Ala Asp Asp
                485                 490                 495

Phe Pro Thr Ile Val Asn
            500


<210> SEQ ID NO 27
<211> LENGTH: 1575
<212> TYPE: DNA
<213> ORGANISM: Siraitia grosvenori

<400> SEQUENCE: 27

atggagaaac tgcaggagaa gcttcggaaa ataaaacgtg ctgtccacgg ggctggcact     60

ctccaaagac caaaatgcta ttgtcaagtc aagctcttcc catctcccca agcaattaaa    120

agagaaagac ctcactttct gctcttccct ttcatggctc agggccacat gatccccatg    180

attgacctcg ccaagcttct ggctcagcga ggagccattg tcactatcct caccacgccc    240

cacaatgctg ctcgcaccca ctcagttctt gctcgcgcca tcgattctgg gttacaaatc    300

cgtgtccgcc cacttcagtt tccatgcaaa gaagccggcc tgccagaagg gtgcgagaat    360

ctcgacttgt taccttcact tggttctgcc tccacattct tcagagcaac atgtctcctt    420

tacgacccat cggaaaaact gttcgaggaa ctcagccccc ggccgacttg cataatctcc    480

gatatgtgtc tgccctggac catacgactt gctcagaaat atcacgtacc aaggctcgtt    540

ttctacagtt tgagctgctt ctttcttctc tgtatgcgga gtttaaaaaa caatccagcg    600

cttattagct ccaagtctga ttctgagttc gtaactttct ctgacttgcc tgatccagtc    660

gagtttctca agtcggagct acctaaatcc accgatgaag acttggtgaa gtttagttat    720

gaaatggggg aggccgatcg gaagtcatac ggcgttattt taaatatatt tgaggagatg    780

gaaccaaagt atcttgcgga atatggaaac gaaagagaat cgccggaaaa agtctggtgc    840

gtcggcccag tttcgctttg caacgacaac aaactcgaca aggctcagag aggcaacaaa    900

gcctccatcg acgaacgtga atgcatcaag tggctcggcg ggcagcagcc gtcttcagtg    960

gtttacgcgt ctttaggaag cttatgcaat ctggttacgg cgcaattcat agagttgggt   1020

ttgggtttgg aggcatcaaa taaaccattt atttgggtca ttagaaaagg aaacataaca   1080

gaagagctac aaaaatggct tgtggagtat gatttcgagg agaaaactaa agggagaggg   1140

ctggtgattc ttggctgggc tccccaagtt ctgatactgt cccacccttc aatcggatgc   1200

tttttgacgc actgtggttg gaactcaagc atcgaaggga tatcggccgg cgtgccaatg   1260

gtcacctggc cgcttttttc ggatcaagtc ttcaacgaga agctaattgt acaaatactc   1320

agaatcggcg taagtgtagg cgcggaaact gctatgaact ggggagagga agaggagaaa   1380

ggggtagtag tgaagagaga gaaagtgagg gaagccatag aaaggatgat ggatggagat   1440

gagagagaag agaggagaga gagatgcaaa gagcttgctg agacggcgaa gagagctata   1500

gaagaagggg gctcgtctca ccggaacctc acgctgttga ttgaagatat aggtacttca   1560

ttgaggaggt tgtga                                                    1575


<210> SEQ ID NO 28
<211> LENGTH: 488
<212> TYPE: PRT
```

<213> ORGANISM: Siraitia grosvenori

<400> SEQUENCE: 28

```
Met Asp Ser Pro Pro His Arg Pro His Phe Leu Leu Phe Pro Phe Met
1               5                   10                  15

Ala Gln Gly His Met Ile Pro Met Ile Asp Leu Ala Lys Leu Leu Ala
            20                  25                  30

Gln Arg Gly Ala Ile Val Thr Ile Leu Thr Thr Pro His Asn Ala Ala
        35                  40                  45

Arg Thr His Ser Val Leu Ala Arg Ala Ile Asp Ser Gly Leu Gln Ile
    50                  55                  60

Arg Val Arg Pro Leu Gln Phe Pro Cys Lys Glu Ala Gly Leu Pro Glu
65                  70                  75                  80

Gly Cys Glu Asn Leu Asp Leu Leu Pro Ser Leu Gly Ser Ala Ser Thr
                85                  90                  95

Phe Phe Arg Ala Thr Cys Leu Leu Tyr Asp Pro Ser Glu Lys Leu Phe
            100                 105                 110

Glu Glu Leu Ser Pro Arg Pro Thr Cys Ile Ile Ser Asp Met Cys Leu
        115                 120                 125

Pro Trp Thr Ile Arg Leu Ala Gln Lys Tyr His Val Pro Arg Leu Val
    130                 135                 140

Phe Tyr Ser Leu Ser Cys Phe Phe Leu Leu Cys Met Arg Ser Leu Lys
145                 150                 155                 160

Asn Asn Pro Ala Leu Ile Ser Ser Lys Ser Asp Ser Glu Phe Val Thr
                165                 170                 175

Phe Ser Asp Leu Pro Asp Pro Val Glu Phe Leu Lys Ser Glu Leu Pro
            180                 185                 190

Lys Ser Thr Asp Glu Asp Leu Val Lys Phe Ser Tyr Glu Met Gly Glu
        195                 200                 205

Ala Asp Arg Lys Ser Tyr Gly Val Ile Leu Asn Ile Phe Glu Glu Met
    210                 215                 220

Glu Pro Lys Tyr Leu Ala Glu Tyr Gly Asn Glu Arg Glu Ser Pro Glu
225                 230                 235                 240

Lys Val Trp Cys Val Gly Pro Val Ser Leu Cys Asn Asp Asn Lys Leu
                245                 250                 255

Asp Lys Ala Gln Arg Gly Asn Lys Ala Ser Ile Asp Glu Arg Glu Cys
            260                 265                 270

Ile Lys Trp Leu Gly Gly Gln Gln Pro Ser Ser Val Val Tyr Ala Ser
        275                 280                 285

Leu Gly Ser Leu Cys Asn Leu Val Thr Ala Gln Phe Ile Glu Leu Gly
    290                 295                 300

Leu Gly Leu Glu Ala Ser Asn Lys Pro Phe Ile Trp Val Ile Arg Lys
305                 310                 315                 320

Gly Asn Ile Thr Glu Glu Leu Gln Lys Trp Leu Val Glu Tyr Asp Phe
                325                 330                 335

Glu Glu Lys Thr Lys Gly Arg Gly Leu Val Ile Leu Gly Trp Ala Pro
            340                 345                 350

Gln Val Leu Ile Leu Ser His Pro Ser Ile Gly Cys Phe Leu Thr His
        355                 360                 365

Cys Gly Trp Asn Ser Ser Ile Glu Gly Ile Ser Ala Gly Val Pro Met
    370                 375                 380

Val Thr Trp Pro Leu Phe Ser Asp Gln Val Phe Asn Glu Lys Leu Ile
385                 390                 395                 400
```

-continued

```
Val Gln Ile Leu Arg Ile Gly Val Ser Val Gly Ala Glu Thr Ala Met
                405                 410                 415

Asn Trp Gly Glu Glu Glu Glu Lys Gly Val Val Val Lys Arg Glu Lys
            420                 425                 430

Val Arg Glu Ala Ile Glu Arg Met Met Asp Gly Asp Glu Arg Glu Glu
        435                 440                 445

Arg Arg Glu Arg Cys Lys Glu Leu Ala Glu Thr Ala Lys Arg Ala Ile
    450                 455                 460

Glu Glu Gly Gly Ser Ser His Arg Asn Leu Thr Leu Leu Ile Glu Asp
465                 470                 475                 480

Ile Gly Thr Ser Leu Arg Arg Leu
                485


<210> SEQ ID NO 29
<211> LENGTH: 1416
<212> TYPE: DNA
<213> ORGANISM: Siraitia grosvenori

<400> SEQUENCE: 29

atgatgagaa accaccattt ccttctggta tgtttccctt ctcaaggcta tataaaccct      60

tcccttcaac tcgccaggcg actgataagc ctcggcgtta atgtcacctt cgccaccacc     120

gtcctcgccg gccgccgcat gaagaacaaa acccaccaaa ctgcaacaac accaggcttg     180

tctttcgcta ctttctccga tggcttcgat gacgaaaccc tcaaacccaa cggcgacttg     240

acccactact tctcggagct caggcgctgc ggctctgaat ctctaaccca tctcattact     300

tctgcagcaa acgaaggtcg tccgattacc ttcgtaatct atagcctcct gctctcttgg     360

gcggctgata ttgccagcac atatgacatc ccgtcagcac tttttttgc tcagcctgcg     420

acggttttgg ctttgtactt ctattacttc catggttatg gtgataccat ttgcagcaaa     480

ctccaagacc catcttcgta catagaatta ccaggtttgc cgttgctcac tagtcaggac     540

atgccctctt tcttctcccc ttccggcccc catgctttca ttctccctcc aatgagagag     600

caggctgaat tcctcggccg acaaagccaa ccaaaagtac tagtgaacac cttcgacgcg     660

ttagaggcag acgccttgag agccattgat aagttgaaga tgttggcgat tggacccttg     720

attccatctg ctttactggg tggaaacgat tcctctgatg catcattttg tggtgatctt     780

tttcaagtct cgtcagagga ttatatagaa tggttgaact ccaagcctga ctcgtcggtc     840

gtttacatat cagttggatc catctgcgtg ctgtctgatg aacaagagga cgagcttgtg     900

catgctttat taaacagtgg ccacacgttc ttgtgggtaa agagatcgaa agagaacaac     960

gaaggagtaa aacaagaaac agacgaggag aagttgaaga agctggaaga gcaagggaaa    1020

atggtgtcgt ggtgccgtca agttgaagtg ttgaaacacc ctgcgttggg ttgttttctg    1080

acgcactgtg ggtggaactc gactattgaa agcttggttt cagggctgcc ggtggttgct    1140

tttccgcagc agatagatca agccaccaac gcgaagctca tagaggacgt gtggaagacg    1200

ggagtgaggg tgaaggccaa tacagaagga attgtggaga gggaagaaat caggaggtgc    1260

ttggatttgg tgatggggag cagagatggg caaaaggaag agatagagag aaatgccaaa    1320

aagtggaaag aattggctag acaggccatc ggtgaaggtg ggtcatcaga ttcgaatctt    1380

aagacttttc tatgggagat tgatctagaa atttag                              1416


<210> SEQ ID NO 30
<211> LENGTH: 471
<212> TYPE: PRT
<213> ORGANISM: Siraitia grosvenori
```

<400> SEQUENCE: 30

Met Met Arg Asn His His Phe Leu Leu Val Cys Phe Pro Ser Gln Gly
1               5                   10                  15

Tyr Ile Asn Pro Ser Leu Gln Leu Ala Arg Arg Leu Ile Ser Leu Gly
            20                  25                  30

Val Asn Val Thr Phe Ala Thr Thr Val Leu Ala Gly Arg Arg Met Lys
        35                  40                  45

Asn Lys Thr His Gln Thr Ala Thr Thr Pro Gly Leu Ser Phe Ala Thr
    50                  55                  60

Phe Ser Asp Gly Phe Asp Asp Glu Thr Leu Lys Pro Asn Gly Asp Leu
65                  70                  75                  80

Thr His Tyr Phe Ser Glu Leu Arg Arg Cys Gly Ser Glu Ser Leu Thr
                85                  90                  95

His Leu Ile Thr Ser Ala Ala Asn Glu Gly Arg Pro Ile Thr Phe Val
            100                 105                 110

Ile Tyr Ser Leu Leu Leu Ser Trp Ala Ala Asp Ile Ala Ser Thr Tyr
        115                 120                 125

Asp Ile Pro Ser Ala Leu Phe Phe Ala Gln Pro Ala Thr Val Leu Ala
    130                 135                 140

Leu Tyr Phe Tyr Tyr Phe His Gly Tyr Gly Asp Thr Ile Cys Ser Lys
145                 150                 155                 160

Leu Gln Asp Pro Ser Ser Tyr Ile Glu Leu Pro Gly Leu Pro Leu Leu
                165                 170                 175

Thr Ser Gln Asp Met Pro Ser Phe Phe Ser Pro Ser Gly Pro His Ala
            180                 185                 190

Phe Ile Leu Pro Pro Met Arg Glu Gln Ala Glu Phe Leu Gly Arg Gln
        195                 200                 205

Ser Gln Pro Lys Val Leu Val Asn Thr Phe Asp Ala Leu Glu Ala Asp
    210                 215                 220

Ala Leu Arg Ala Ile Asp Lys Leu Lys Met Leu Ala Ile Gly Pro Leu
225                 230                 235                 240

Ile Pro Ser Ala Leu Leu Gly Gly Asn Asp Ser Ser Asp Ala Ser Phe
                245                 250                 255

Cys Gly Asp Leu Phe Gln Val Ser Ser Glu Asp Tyr Ile Glu Trp Leu
            260                 265                 270

Asn Ser Lys Pro Asp Ser Ser Val Val Tyr Ile Ser Val Gly Ser Ile
        275                 280                 285

Cys Val Leu Ser Asp Glu Gln Glu Asp Glu Leu Val His Ala Leu Leu
    290                 295                 300

Asn Ser Gly His Thr Phe Leu Trp Val Lys Arg Ser Lys Glu Asn Asn
305                 310                 315                 320

Glu Gly Val Lys Gln Glu Thr Asp Glu Glu Lys Leu Lys Lys Leu Glu
                325                 330                 335

Glu Gln Gly Lys Met Val Ser Trp Cys Arg Gln Val Glu Val Leu Lys
            340                 345                 350

His Pro Ala Leu Gly Cys Phe Leu Thr His Cys Gly Trp Asn Ser Thr
        355                 360                 365

Ile Glu Ser Leu Val Ser Gly Leu Pro Val Val Ala Phe Pro Gln Gln
    370                 375                 380

Ile Asp Gln Ala Thr Asn Ala Lys Leu Ile Glu Asp Val Trp Lys Thr
385                 390                 395                 400

Gly Val Arg Val Lys Ala Asn Thr Glu Gly Ile Val Glu Arg Glu Glu

```
            405                 410                 415

Ile Arg Arg Cys Leu Asp Leu Val Met Gly Ser Arg Asp Gly Gln Lys
        420                 425                 430

Glu Glu Ile Glu Arg Asn Ala Lys Lys Trp Lys Glu Leu Ala Arg Gln
    435                 440                 445

Ala Ile Gly Glu Gly Gly Ser Ser Asp Ser Asn Leu Lys Thr Phe Leu
    450                 455                 460

Trp Glu Ile Asp Leu Glu Ile
465                 470
```

<210> SEQ ID NO 31
<211> LENGTH: 1458
<212> TYPE: DNA
<213> ORGANISM: Siraitia grosvenori

<400> SEQUENCE: 31

```
atggcggagc aagctcatga tcttcttcac gtcctccttt ttccgtttcc ggcggagggc      60

cacatcaagc ccttcctctg tctcgccgag ctcctctgca acgccggctt ccatgtcacc     120

ttcctcaaca ccgactacaa ccaccgccgc ctccacaacc tccatctcct cgccgcccgc     180

tttccctcac ttcatttcga gtccatttcc gacggcctcc cgcccgatca gcctcgagat     240

atactggacc ccaagttttt tatatccatc tgtcaagtca ctaaacccct tttccgggag     300

ctcctccttt cctacaaacg catttccagt gtccagaccg gccgcccgcc aataacttgc     360

gttattacag atgtgatttt tcgttttccg atcgacgtag ctgaagaact ggatattcct     420

gtgtttagtt tctgtacttt cagtgcccgt ttcatgtttc tttacttctg gattcccaag     480

ctcattgaag atggccagct tccataccca aacggcaata tcaaccagaa actctacggt     540

gttgctcctg aggcggaagg ccttttaaga tgtaaagatt tgccgggaca ttgggctttc     600

gcagacgaac taaaagatga tcaacttaac tttgtggacc agacaacggc gtcatctcga     660

tcctccggtc tcattctcaa cacattcgac gacctcgaag ctccatttct ggggcgtctc     720

tccaccatct ttaagaaaat ctacgccgtt ggacccatcc actctctgtt gaactcccac     780

cactgtgggc tttggaaaga agatcacagt tgcctggcgt ggctcgactc ccgggccgcg     840

aaatccgtcg tgttcgtcag cttcgggagc ttggtgaaga taacaagtag gcagctgatg     900

gagttttggc atggcttgct caacagtgga aagtcgttcc tcttcgtgtt gagatctgac     960

gtagttgagg gcgatgatga aaaacaagtc gtcaaagaaa tttacgagac gaaggcagag    1020

gggaaatggt tggttgtggg gtgggctccg caagagaagg tgttagccca tgaagctgtt    1080

ggtggatttc tgacccattc gggctggaac tccattttag agagcattgc tgctggggtt    1140

cctatgatct cctgccccaa aattggagac cagtccagta actgtacgtg gatcagtaaa    1200

gtatggaaaa ttgggcttga aatggaggat cggtacgacc gggtttcggt cgaaacaatg    1260

gttagatcta taatggaaca agaaggtgag aaaatgcaga agacaattgc agaattagca    1320

aaacaagcta agtataaagt tagtaaagat ggaacatcat atcaaaattt agaatgttta    1380

atccaagata ttaaaaaact gaaccaaatt gagggtttta tcaacaaccc caattttagt    1440

gatttattaa gggtttag                                                  1458
```

<210> SEQ ID NO 32
<211> LENGTH: 485
<212> TYPE: PRT
<213> ORGANISM: Siraitia grosvenori

<400> SEQUENCE: 32

```
Met Ala Glu Gln Ala His Asp Leu Leu His Val Leu Leu Phe Pro Phe
1               5                   10                  15

Pro Ala Glu Gly His Ile Lys Pro Phe Leu Cys Leu Ala Glu Leu Leu
            20                  25                  30

Cys Asn Ala Gly Phe His Val Thr Phe Leu Asn Thr Asp Tyr Asn His
        35                  40                  45

Arg Arg Leu His Asn Leu His Leu Leu Ala Ala Arg Phe Pro Ser Leu
    50                  55                  60

His Phe Glu Ser Ile Ser Asp Gly Leu Pro Pro Asp Gln Pro Arg Asp
65                  70                  75                  80

Ile Leu Asp Pro Lys Phe Phe Ile Ser Ile Cys Gln Val Thr Lys Pro
                85                  90                  95

Leu Phe Arg Glu Leu Leu Leu Ser Tyr Lys Arg Ile Ser Ser Val Gln
            100                 105                 110

Thr Gly Arg Pro Pro Ile Thr Cys Val Ile Thr Asp Val Ile Phe Arg
        115                 120                 125

Phe Pro Ile Asp Val Ala Glu Glu Leu Asp Ile Pro Val Phe Ser Phe
    130                 135                 140

Cys Thr Phe Ser Ala Arg Phe Met Phe Leu Tyr Phe Trp Ile Pro Lys
145                 150                 155                 160

Leu Ile Glu Asp Gly Gln Leu Pro Tyr Pro Asn Gly Asn Ile Asn Gln
                165                 170                 175

Lys Leu Tyr Gly Val Ala Pro Glu Ala Glu Gly Leu Leu Arg Cys Lys
            180                 185                 190

Asp Leu Pro Gly His Trp Ala Phe Ala Asp Glu Leu Lys Asp Asp Gln
        195                 200                 205

Leu Asn Phe Val Asp Gln Thr Thr Ala Ser Ser Arg Ser Ser Gly Leu
    210                 215                 220

Ile Leu Asn Thr Phe Asp Asp Leu Glu Ala Pro Phe Leu Gly Arg Leu
225                 230                 235                 240

Ser Thr Ile Phe Lys Lys Ile Tyr Ala Val Gly Pro Ile His Ser Leu
                245                 250                 255

Leu Asn Ser His His Cys Gly Leu Trp Lys Glu Asp His Ser Cys Leu
            260                 265                 270

Ala Trp Leu Asp Ser Arg Ala Ala Lys Ser Val Val Phe Val Ser Phe
        275                 280                 285

Gly Ser Leu Val Lys Ile Thr Ser Arg Gln Leu Met Glu Phe Trp His
    290                 295                 300

Gly Leu Leu Asn Ser Gly Lys Ser Phe Leu Phe Val Leu Arg Ser Asp
305                 310                 315                 320

Val Val Glu Gly Asp Asp Glu Lys Gln Val Val Lys Glu Ile Tyr Glu
                325                 330                 335

Thr Lys Ala Glu Gly Lys Trp Leu Val Val Gly Trp Ala Pro Gln Glu
            340                 345                 350

Lys Val Leu Ala His Glu Ala Val Gly Gly Phe Leu Thr His Ser Gly
        355                 360                 365

Trp Asn Ser Ile Leu Glu Ser Ile Ala Ala Gly Val Pro Met Ile Ser
    370                 375                 380

Cys Pro Lys Ile Gly Asp Gln Ser Ser Asn Cys Thr Trp Ile Ser Lys
385                 390                 395                 400

Val Trp Lys Ile Gly Leu Glu Met Glu Asp Arg Tyr Asp Arg Val Ser
                405                 410                 415
```

-continued

```
Val Glu Thr Met Val Arg Ser Ile Met Glu Gln Glu Gly Glu Lys Met
            420                 425                 430

Gln Lys Thr Ile Ala Glu Leu Ala Lys Gln Ala Lys Tyr Lys Val Ser
        435                 440                 445

Lys Asp Gly Thr Ser Tyr Gln Asn Leu Glu Cys Leu Ile Gln Asp Ile
    450                 455                 460

Lys Lys Leu Asn Gln Ile Glu Gly Phe Ile Asn Asn Pro Asn Phe Ser
465                 470                 475                 480

Asp Leu Leu Arg Val
                485


<210> SEQ ID NO 33
<211> LENGTH: 1425
<212> TYPE: DNA
<213> ORGANISM: Siraitia grosvenori

<400> SEQUENCE: 33

atggtgcaac ctcgggtact gctgtttcct ttcccggcac tgggccacgt gaagcccttc     60

ttatcactgg cggagctgct ttccgacgcc ggcatagacg tcgtcttcct cagcaccgag    120

tataaccacc gtcggatctc caacactgaa gccctagcct cccgcttccc gacgcttcat    180

ttcgaaacta taccggatgg cctgccgcct aatgagtcgc gcgctcttgc cgacggccca    240

ctgtatttct ccatgcgtga gggaactaaa ccgagattcc ggcaactgat tcaatctctt    300

aacgacggtc gttggcccat cacctgtatt atcactgaca tcatgttatc ttctccgatt    360

gaagtagcgg aagaatttgg gattccagta attgccttct gcccctgcag tgctcgctac    420

ttatcgattc actttttat accgaagctc gttgaggaag gtcaaattcc atacgcagat     480

gacgatccga ttggagagat ccagggggtg cccttgttcg aaggtctttt gcgacggaat    540

catttgcctg gttcttggtc tgataaatct gcagatatat ctttctcgca tggcttgatt    600

aatcagaccc ttgcagctgg tcgagcctcg gctcttatac tcaacacctt cgacgagctc    660

gaagctccat ttctgaccca tctctcttcc attttcaaca aaatctacac cattggaccc    720

ctccatgctc tgtccaaatc aaggctcggc gactcctcct cctccgcttc tgccctctcc    780

ggattctgga aagaggatag agcctgcatg tcctggctcg actgtcagcc gccgagatct    840

gtggttttcg tcagtttcgg gagtacgatg aagatgaaag ccgatgaatt gagagagttc    900

tggtatgggt tggtgagcag cgggaaaccg ttcctctgcg tgttgagatc cgacgttgtt    960

tccggcggag aagcggcgga attgatcgaa cagatggcgg aggaggaggg agctggaggg   1020

aagctgggaa tggtagtgga gtgggcagcg caagagaagg tcctgagcca ccctgccgtc   1080

ggtgggtttt tgacgcactg cgggtggaac tcaacggtgg aaagcattgc cgcgggagtt   1140

ccgatgatgt gctggccgat tctcggcgac caacccagca acgccacttg gatcgacaga   1200

gtgtggaaaa ttggggttga aaggaacaat cgtgaatggg acaggttgac ggtggagaag   1260

atggtgagag cattgatgga aggccaaaag agagtggaga ttcagagatc aatggagaag   1320

ctttcaaagt tggcaaatga gaaggttgtc aggggtgggt tgtcttttga taacttggaa   1380

gttctcgttg aagacatcaa aaaattgaaa ccatataaat tttaa                   1425


<210> SEQ ID NO 34
<211> LENGTH: 419
<212> TYPE: PRT
<213> ORGANISM: Siraitia grosvenori

<400> SEQUENCE: 34
```

-continued

```
Met Val Gln Pro Arg Val Leu Leu Phe Pro Phe Pro Ala Leu Gly His
1               5                   10                  15

Val Lys Pro Phe Leu Ser Leu Ala Glu Leu Leu Ser Asp Ala Gly Ile
            20                  25                  30

Asp Val Val Phe Leu Ser Thr Glu Tyr Asn His Arg Arg Ile Ser Asn
        35                  40                  45

Thr Glu Ala Leu Ala Ser Arg Phe Pro Thr Leu His Phe Glu Thr Ile
    50                  55                  60

Pro Asp Gly Leu Pro Pro Asn Glu Ser Arg Ala Leu Ala Asp Gly Pro
65                  70                  75                  80

Leu Tyr Phe Ser Met Arg Glu Gly Thr Lys Pro Arg Phe Arg Gln Leu
                85                  90                  95

Ile Gln Ser Leu Asn Asp Gly Arg Trp Pro Ile Thr Cys Ile Ile Thr
            100                 105                 110

Asp Ile Met Leu Ser Ser Pro Ile Glu Val Ala Glu Glu Phe Gly Ile
        115                 120                 125

Pro Val Ile Ala Phe Cys Pro Cys Ser Ala Arg Tyr Leu Ser Ile His
    130                 135                 140

Phe Phe Ile Pro Lys Leu Val Glu Glu Gly Gln Ile Pro Tyr Ala Asp
145                 150                 155                 160

Asp Asp Pro Ile Gly Glu Ile Gln Gly Val Pro Leu Phe Glu Gly Leu
                165                 170                 175

Leu Arg Arg Asn His Leu Pro Gly Ser Trp Ser Asp Lys Ser Ala Asp
            180                 185                 190

Ile Ser Phe Ser His Gly Leu Ile Asn Gln Thr Leu Ala Ala Gly Arg
        195                 200                 205

Ala Ser Ala Leu Ile Leu Asn Thr Phe Asp Glu Leu Glu Ala Pro Phe
    210                 215                 220

Leu Thr His Leu Ser Ser Ile Phe Asn Lys Ile Tyr Thr Ile Gly Pro
225                 230                 235                 240

Leu His Ala Leu Ser Lys Ser Arg Leu Gly Asp Ser Ser Ser Ser Ala
                245                 250                 255

Ser Ala Leu Ser Gly Phe Trp Lys Glu Asp Arg Ala Cys Met Ser Trp
            260                 265                 270

Leu Asp Cys Gln Pro Pro Arg Ser Val Val Phe Val Ser Phe Gly Ser
        275                 280                 285

Thr Met Lys Met Lys Ala Asp Glu Leu Arg Glu Phe Trp Tyr Gly Leu
    290                 295                 300

Val Ser Ser Gly Lys Pro Phe Leu Cys Val Leu Arg Ser Asp Val Val
305                 310                 315                 320

Ser Gly Gly Glu Ala Ala Glu Leu Ile Glu Gln Met Ala Glu Glu Glu
                325                 330                 335

Gly Ala Gly Gly Lys Leu Gly Met Val Val Glu Trp Ala Ala Gln Glu
            340                 345                 350

Lys Val Leu Ser His Pro Ala Val Gly Gly Phe Leu Thr His Cys Gly
        355                 360                 365

Trp Asn Ser Thr Val Glu Ser Ile Ala Ala Gly Val Pro Met Met Cys
    370                 375                 380

Trp Pro Ile Leu Gly Asp Gln Pro Ser Asn Ala Thr Trp Ile Asp Arg
385                 390                 395                 400

Val Trp Lys Ile Gly Val Glu Arg Asn Asn Arg Glu Trp Asp Arg Leu
                405                 410                 415

Thr Val Glu
```

<210> SEQ ID NO 35
<211> LENGTH: 1422
<212> TYPE: DNA
<213> ORGANISM: Siraitia grosvenori

<400> SEQUENCE: 35

```
atggatgccc agcaaggtca caccaccacc attttgatgc ttccatgggt cggctacggc     60
catctcttgc ctttcctcga gctggccaaa agcctctcca ggaggaaatt attccacatc    120
tacttctgtt caacgtctgt tagcctcgac gccattaaac caaagcttcc tccttctatc    180
tcttctgatg attccatcca acttgtggaa cttcgtctcc cttcttctcc tgagttacct    240
cctcatcttc acacaaccaa cggccttccc tctcacctca tgcccgctct ccaccaagcc    300
ttcgtcatgg ctgcccaaca ctttcaggtc attttacaaa cacttgcccc gcatctcctc    360
atttatgaca ttctccaacc ttgggctcct caagtggctt catccctcaa cattccagcc    420
atcaacttca gtactaccgg agcttcaatg ctttctcgaa cgcttcaccc tactcactac    480
ccaagttcta aattcccaat ctcagagttt gttcttcaca atcactggag agccatgtac    540
accaccgccg atggggctct tacagaagaa ggccacaaaa ttgaagaaac acttgcgaat    600
tgcttgcata cttcttgcgg ggtagttttg gtcaatagtt tcagagagct tgagacgaaa    660
tatatcgatt atctctctgt tctcttgaac aagaaagttg ttccggtcgg tcctttggtt    720
tacgaaccga atcaagaagg ggaagatgaa ggttattcaa gcatcaaaaa ttggcttgac    780
aaaaaggaac cgtcctcaac cgtcttcgtt tcatttggaa ccgaatactt cccgtcaaag    840
gaagaaatgg aagagatagc gtatgggtta gagctgagcg aggttaattt catctgggtc    900
cttagatttc ctcaaggaga cagcaccagc accattgaag acgccttgcc gaaggggttt    960
ctggagagag cgggagagag ggcgatggtg gtgaagggtt gggctcctca ggcgaagata   1020
ctgaagcatt ggagcacagg ggggcttgtg agtcactgtg gatggaactc gatgatggag   1080
ggcatgatgt ttggcgtacc cataatagcg gttccgatgc atctggacca gccctttaac   1140
gccggactcg tggaagaagc tggcgtcggc gtggaagcca agcgagattc ggacggcaaa   1200
attcaaagag aagaagttgc aaagtcgatc aaagaagtgg tgattgagaa aaccagggaa   1260
gacgtgagga agaaagcaag agaaatggac accaaacacg gacctaccta ttttagtcgg   1320
tcgaaagtta gcagttttgg aaggctatat aaaatcaacc gaccaactac actgacggtt   1380
ggtcgatttt ggtcgaaaca gatcaagatg aagcgagagt aa                      1422
```

<210> SEQ ID NO 36
<211> LENGTH: 459
<212> TYPE: PRT
<213> ORGANISM: Siraitia grosvenori

<400> SEQUENCE: 36

```
Met Asp Ala Gln Gln Gly His Thr Thr Thr Ile Leu Met Leu Pro Trp
1               5                   10                  15

Val Gly Tyr Gly His Leu Leu Pro Phe Leu Glu Leu Ala Lys Ser Leu
            20                  25                  30

Ser Arg Arg Lys Leu Phe His Ile Tyr Phe Cys Ser Thr Ser Val Ser
        35                  40                  45

Leu Asp Ala Ile Lys Pro Lys Leu Pro Pro Ser Ile Ser Ser Asp Asp
    50                  55                  60

Ser Ile Gln Leu Val Glu Leu Arg Leu Pro Ser Ser Pro Glu Leu Pro
65                  70                  75                  80
```

```
Pro His Leu His Thr Thr Asn Gly Leu Pro Ser His Leu Met Pro Ala
                85                  90                  95

Leu His Gln Ala Phe Val Met Ala Ala Gln His Phe Gln Val Ile Leu
            100                 105                 110

Gln Thr Leu Ala Pro His Leu Leu Ile Tyr Asp Ile Leu Gln Pro Trp
        115                 120                 125

Ala Pro Gln Val Ala Ser Ser Leu Asn Ile Pro Ala Ile Asn Phe Ser
    130                 135                 140

Thr Thr Gly Ala Ser Met Leu Ser Arg Thr Leu His Pro Thr His Tyr
145                 150                 155                 160

Pro Ser Ser Lys Phe Pro Ile Ser Glu Phe Val Leu His Asn His Trp
                165                 170                 175

Arg Ala Met Tyr Thr Thr Ala Asp Gly Ala Leu Thr Glu Glu Gly His
            180                 185                 190

Lys Ile Glu Glu Thr Leu Ala Asn Cys Leu His Thr Ser Cys Gly Val
        195                 200                 205

Val Leu Val Asn Ser Phe Arg Glu Leu Glu Thr Lys Tyr Ile Asp Tyr
    210                 215                 220

Leu Ser Val Leu Leu Asn Lys Lys Val Val Pro Val Gly Pro Leu Val
225                 230                 235                 240

Tyr Glu Pro Asn Gln Glu Gly Glu Asp Glu Gly Tyr Ser Ser Ile Lys
                245                 250                 255

Asn Trp Leu Asp Lys Lys Glu Pro Ser Ser Thr Val Phe Val Ser Phe
            260                 265                 270

Gly Thr Glu Tyr Phe Pro Ser Lys Glu Glu Met Glu Glu Ile Ala Tyr
        275                 280                 285

Gly Leu Glu Leu Ser Glu Val Asn Phe Ile Trp Val Leu Arg Phe Pro
    290                 295                 300

Gln Gly Asp Ser Thr Ser Thr Ile Glu Asp Ala Leu Pro Lys Gly Phe
305                 310                 315                 320

Leu Glu Arg Ala Gly Glu Arg Ala Met Val Val Lys Gly Trp Ala Pro
                325                 330                 335

Gln Ala Lys Ile Leu Lys His Trp Ser Thr Gly Gly Leu Val Ser His
            340                 345                 350

Cys Gly Trp Asn Ser Met Met Glu Gly Met Met Phe Gly Val Pro Ile
        355                 360                 365

Ile Ala Val Pro Met His Leu Asp Gln Pro Phe Asn Ala Gly Leu Val
    370                 375                 380

Glu Glu Ala Gly Val Gly Val Glu Ala Lys Arg Asp Ser Asp Gly Lys
385                 390                 395                 400

Ile Gln Arg Glu Glu Val Ala Lys Ser Ile Lys Glu Val Val Ile Glu
                405                 410                 415

Lys Thr Arg Glu Asp Val Arg Lys Lys Ala Arg Glu Met Gly Glu Ile
            420                 425                 430

Leu Arg Ser Lys Gly Asp Glu Lys Ile Asp Glu Leu Val Ala Glu Ile
        435                 440                 445

Ser Leu Leu Arg Lys Lys Ala Pro Cys Ser Ile
    450                 455
```

<210> SEQ ID NO 37
<211> LENGTH: 1359
<212> TYPE: DNA
<213> ORGANISM: Siraitia grosvenori

<400> SEQUENCE: 37

```
atggatgctg cccaacaagg tgacaccaca accattttga tgcttccatg gctcggctat     60
ggccatcttt cagcttttct cgagctggcc aaaagcctct caaggaggaa cttccatatc    120
tacttctgtt caacctctgt taatcttgac gccattaaac caaagcttcc ttcttctttc    180
tctgattcca ttcaatttgt ggagctccat ctcccttctt ctcctgagtt ccctcctcat    240
cttcacacaa ccaacggcct tccccctacc ctcatgcccg ctctccacca agccttctcc    300
atggctgccc agcactttga gtccatttta caaacacttg ccccgcacct tctcatttat    360
gactctcttc aaccttgggc tcctcgggta gcttcatccc tcaaaattcc ggccatcaac    420
ttcaatacca cgggagtttt cgtcatttct caagggyttc accctattca ctacccacat    480
tctaaattcc cattctcaga gttcgttctt cacaatcatt ggaaagccat gtactccact    540
gccgatggag cttctaccga aagaacccgc aaacgtggag aagcgtttct gtattgcttg    600
catgcttctt gtagtgtaat tctaatcaat agtttcagag agctcgaggg gaaatatatg    660
gattatctct ctgttctctt gaacaagaaa gttgttccgg ttggtccttt ggtttacgaa    720
ccgaatcaag acggggaaga tgaaggttat tcaagcatca aaaattggct tgacaaaaag    780
gaaccgtcct ccaccgtctt cgtgtcattt ggaagcgaat acttcccgtc aaaggaagaa    840
atggaagaga tagcccatgg gttagaggcg agcgaggtta atttcatctg ggtcgttagg    900
tttcctcaag gagacaacac cagcggcatt gaagatgcct tgccgaaggg ttttctggag    960
agggcgggag agagagggat ggtggtgaag ggttgggctc ctcaggcgaa gatactgaag   1020
cattggagca caggggggatt cgtgagccac tgtggatgga actcggtgat ggagagcatg  1080
atgtttggcg ttcccataat aggggttccg atgcatgtgg accagccctt taacgccgga   1140
ctcgtggaag aagctggcgt cggcgtggag gccaagcgag atccagacgg caaaaattcaa  1200
agagacgaag ttgcaaagtt gatcaaagaa gtggtggttg agaaaaccag agaagatgtg   1260
cggaagaaag caagagaaat gagtgagatt ttgaggagca agggagagga gaagtttgat   1320
gagatggtcg ctgaaatttc tctcttgctt aaaatatga                           1359
```

<210> SEQ ID NO 38
<211> LENGTH: 452
<212> TYPE: PRT
<213> ORGANISM: Siraitia grosvenori

<400> SEQUENCE: 38

```
Met Asp Ala Ala Gln Gln Gly Asp Thr Thr Thr Ile Leu Met Leu Pro
1               5                   10                  15

Trp Leu Gly Tyr Gly His Leu Ser Ala Phe Leu Glu Leu Ala Lys Ser
            20                  25                  30

Leu Ser Arg Arg Asn Phe His Ile Tyr Phe Cys Ser Thr Ser Val Asn
        35                  40                  45

Leu Asp Ala Ile Lys Pro Lys Leu Pro Ser Ser Phe Ser Asp Ser Ile
    50                  55                  60

Gln Phe Val Glu Leu His Leu Pro Ser Ser Pro Glu Phe Pro Pro His
65                  70                  75                  80

Leu His Thr Thr Asn Gly Leu Pro Pro Thr Leu Met Pro Ala Leu His
                85                  90                  95

Gln Ala Phe Ser Met Ala Ala Gln His Phe Glu Ser Ile Leu Gln Thr
            100                 105                 110

Leu Ala Pro His Leu Leu Ile Tyr Asp Ser Leu Gln Pro Trp Ala Pro
        115                 120                 125
```

```
Arg Val Ala Ser Ser Leu Lys Ile Pro Ala Ile Asn Phe Asn Thr Thr
    130                 135                 140

Gly Val Phe Val Ile Ser Gln Gly Leu His Pro Ile His Tyr Pro His
145                 150                 155                 160

Ser Lys Phe Pro Phe Ser Glu Phe Val Leu His Asn His Trp Lys Ala
                165                 170                 175

Met Tyr Ser Thr Ala Asp Gly Ala Ser Thr Glu Arg Thr Arg Lys Arg
            180                 185                 190

Gly Glu Ala Phe Leu Tyr Cys Leu His Ala Ser Cys Ser Val Ile Leu
        195                 200                 205

Ile Asn Ser Phe Arg Glu Leu Glu Gly Lys Tyr Met Asp Tyr Leu Ser
    210                 215                 220

Val Leu Leu Asn Lys Lys Val Val Pro Val Gly Pro Leu Val Tyr Glu
225                 230                 235                 240

Pro Asn Gln Asp Gly Glu Asp Glu Gly Tyr Ser Ser Ile Lys Asn Trp
                245                 250                 255

Leu Asp Lys Lys Glu Pro Ser Ser Thr Val Phe Val Ser Phe Gly Ser
            260                 265                 270

Glu Tyr Phe Pro Ser Lys Glu Glu Met Glu Glu Ile Ala His Gly Leu
        275                 280                 285

Glu Ala Ser Glu Val Asn Phe Ile Trp Val Val Arg Phe Pro Gln Gly
    290                 295                 300

Asp Asn Thr Ser Gly Ile Glu Asp Ala Leu Pro Lys Gly Phe Leu Glu
305                 310                 315                 320

Arg Ala Gly Glu Arg Gly Met Val Val Lys Gly Trp Ala Pro Gln Ala
                325                 330                 335

Lys Ile Leu Lys His Trp Ser Thr Gly Gly Phe Val Ser His Cys Gly
            340                 345                 350

Trp Asn Ser Val Met Glu Ser Met Met Phe Gly Val Pro Ile Ile Gly
        355                 360                 365

Val Pro Met His Val Asp Gln Pro Phe Asn Ala Gly Leu Val Glu Glu
    370                 375                 380

Ala Gly Val Gly Val Glu Ala Lys Arg Asp Pro Asp Gly Lys Ile Gln
385                 390                 395                 400

Arg Asp Glu Val Ala Lys Leu Ile Lys Glu Val Val Val Glu Lys Thr
                405                 410                 415

Arg Glu Asp Val Arg Lys Lys Ala Arg Glu Met Ser Glu Ile Leu Arg
            420                 425                 430

Ser Lys Gly Glu Glu Lys Phe Asp Glu Met Val Ala Glu Ile Ser Leu
        435                 440                 445

Leu Leu Lys Ile
    450
```

<210> SEQ ID NO 39
<211> LENGTH: 317
<212> TYPE: PRT
<213> ORGANISM: Siraitia grosvenori

<400> SEQUENCE: 39

```
Met Asp Ala Ile Glu His Arg Thr Val Ser Val Asn Gly Ile Asn Met
1               5                   10                  15

His Val Ala Glu Lys Gly Glu Gly Pro Val Val Leu Leu Leu His Gly
            20                  25                  30

Phe Pro Glu Leu Trp Tyr Ser Trp Arg His Gln Ile Leu Ala Leu Ser
```

```
        35                  40                  45

Ser Leu Gly Tyr Arg Ala Val Ala Pro Asp Leu Arg Gly Tyr Gly Asp
    50                  55                  60

Thr Asp Ala Pro Gly Ser Ile Ser Ser Tyr Thr Cys Phe His Ile Val
65                  70                  75                  80

Gly Asp Leu Val Ala Leu Val Glu Ser Leu Gly Met Asp Arg Val Phe
                85                  90                  95

Val Val Ala His Asp Trp Gly Ala Met Ile Ala Trp Cys Leu Cys Leu
            100                 105                 110

Phe Arg Pro Glu Met Val Lys Ala Phe Val Cys Leu Ser Val Pro Phe
        115                 120                 125

Arg Gln Arg Asn Pro Lys Met Lys Pro Val Gln Ser Met Arg Ala Phe
    130                 135                 140

Phe Gly Asp Asp Tyr Tyr Ile Cys Arg Phe Gln Asn Pro Gly Glu Ile
145                 150                 155                 160

Glu Glu Glu Met Ala Gln Val Gly Ala Arg Glu Val Leu Arg Gly Ile
                165                 170                 175

Leu Thr Ser Arg Arg Pro Gly Pro Pro Ile Leu Pro Lys Gly Gln Ala
            180                 185                 190

Phe Arg Ala Arg Pro Gly Ala Ser Thr Ala Leu Pro Ser Trp Leu Ser
        195                 200                 205

Glu Lys Asp Leu Ser Phe Phe Ala Ser Lys Tyr Asp Gln Lys Gly Phe
    210                 215                 220

Thr Gly Pro Leu Asn Tyr Tyr Arg Ala Met Asp Leu Asn Trp Glu Leu
225                 230                 235                 240

Thr Ala Ser Trp Thr Gly Val Gln Val Lys Val Pro Val Lys Tyr Ile
                245                 250                 255

Val Gly Asp Val Asp Met Val Phe Thr Thr Pro Gly Val Lys Glu Tyr
            260                 265                 270

Val Asn Gly Gly Gly Phe Lys Lys Asp Val Pro Phe Leu Gln Glu Val
        275                 280                 285

Val Ile Met Glu Gly Val Gly His Phe Ile Asn Gln Glu Lys Pro Glu
    290                 295                 300

Glu Ile Ser Ser His Ile His Asp Phe Ile Ser Lys Phe
305                 310                 315


<210> SEQ ID NO 40
<211> LENGTH: 316
<212> TYPE: PRT
<213> ORGANISM: Siraitia grosvenori

<400> SEQUENCE: 40

Met Asp Glu Ile Glu His Ile Thr Ile Asn Thr Asn Gly Ile Lys Met
1               5                   10                  15

His Ile Ala Ser Val Gly Thr Gly Pro Val Val Leu Leu Leu His Gly
            20                  25                  30

Phe Pro Glu Leu Trp Tyr Ser Trp Arg His Gln Leu Leu Tyr Leu Ser
        35                  40                  45

Ser Val Gly Tyr Arg Ala Ile Ala Pro Asp Leu Arg Gly Tyr Gly Asp
    50                  55                  60

Thr Asp Ser Pro Ala Ser Pro Thr Ser Tyr Thr Ala Leu His Ile Val
65                  70                  75                  80

Gly Asp Leu Val Gly Ala Leu Asp Glu Leu Gly Ile Glu Lys Val Phe
                85                  90                  95
```

```
Leu Val Gly His Asp Trp Gly Ala Ile Ile Ala Trp Tyr Phe Cys Leu
            100                 105                 110

Phe Arg Pro Asp Arg Ile Lys Ala Leu Val Asn Leu Ser Val Gln Phe
        115                 120                 125

Ile Pro Arg Asn Pro Ala Ile Pro Phe Ile Glu Gly Phe Arg Thr Ala
    130                 135                 140

Phe Gly Asp Asp Phe Tyr Ile Cys Arg Phe Gln Val Pro Gly Glu Ala
145                 150                 155                 160

Glu Glu Asp Phe Ala Ser Ile Asp Thr Ala Gln Leu Phe Lys Thr Ser
                165                 170                 175

Leu Cys Asn Arg Ser Ser Ala Pro Pro Cys Leu Pro Lys Glu Ile Gly
            180                 185                 190

Phe Arg Ala Ile Pro Pro Pro Glu Asn Leu Pro Ser Trp Leu Thr Glu
        195                 200                 205

Glu Asp Ile Asn Phe Tyr Ala Ala Lys Phe Lys Gln Thr Gly Phe Thr
    210                 215                 220

Gly Ala Leu Asn Tyr Tyr Arg Ala Phe Asp Leu Thr Trp Glu Leu Thr
225                 230                 235                 240

Ala Pro Trp Thr Gly Ala Gln Ile Gln Val Pro Val Lys Phe Ile Val
                245                 250                 255

Gly Asp Ser Asp Leu Thr Tyr His Phe Pro Gly Ala Lys Glu Tyr Ile
            260                 265                 270

His Asn Gly Gly Phe Lys Arg Asp Val Pro Leu Leu Glu Glu Val Val
        275                 280                 285

Val Val Lys Asp Ala Cys His Phe Ile Asn Gln Glu Arg Pro Gln Glu
    290                 295                 300

Ile Asn Ala His Ile His Asp Phe Ile Asn Lys Phe
305                 310                 315
```

<210> SEQ ID NO 41
<211> LENGTH: 325
<212> TYPE: PRT
<213> ORGANISM: Siraitia grosvenori

<400> SEQUENCE: 41

```
Met Glu Lys Glu Ser Glu Ile His Ser Ile Arg His Thr Thr Val Ser
1               5                   10                  15

Val Asn Gly Ile Asn Met His Val Ala Glu Lys Gly Glu Gly Pro Leu
            20                  25                  30

Val Leu Phe Ile His Gly Phe Pro Glu Leu Trp Tyr Ser Trp Arg His
        35                  40                  45

Gln Ile Leu Asp Leu Ala Ser Leu Gly Tyr Arg Ala Val Ala Pro Asp
    50                  55                  60

Leu Arg Gly Tyr Gly Asp Ser Asp Ala Pro Pro Ser Ala Ser Ser Tyr
65                  70                  75                  80

Thr Ser Phe His Ile Val Gly Asp Leu Ile Ala Leu Leu Asp Ala Ile
                85                  90                  95

Val Gly Val Glu Glu Lys Val Phe Val Val Ala His Asp Trp Gly Ala
            100                 105                 110

Ile Ile Ala Trp Tyr Leu Cys Leu Tyr Arg Pro Asp Arg Ile Lys Ala
        115                 120                 125

Leu Val Asn Leu Ser Val Ala Phe Ile Arg Arg Asn Pro Lys Gly Lys
    130                 135                 140

Pro Val Glu Trp Ile Arg Ala Leu Tyr Gly Asp Asp His Tyr Met Cys
145                 150                 155                 160
```

```
Arg Cys Gln Glu Pro Gly Glu Ile Glu Gly Glu Phe Ala Glu Ile Gly
                165                 170                 175

Thr Glu Arg Val Leu Thr Gln Phe Leu Thr Tyr His Ser Pro Lys Pro
            180                 185                 190

Leu Met Leu Pro Lys Gly Lys Ala Phe Gly His Pro Leu Asp Thr Pro
        195                 200                 205

Ile Pro Leu Pro Pro Trp Leu Ser His Gln Asp Ile Glu Tyr Tyr Ala
    210                 215                 220

Ser Lys Phe Asp Lys Lys Gly Phe Thr Gly Pro Val Asn Tyr Tyr Arg
225                 230                 235                 240

Asn Leu Asp Arg Asn Trp Glu Leu Asn Ala Pro Phe Thr Arg Ala Gln
                245                 250                 255

Val Lys Val Pro Val Lys Phe Ile Val Gly Asp Leu Asp Leu Thr Tyr
            260                 265                 270

His Ser Phe Gly Thr Lys Glu Tyr Ile His Ser Gly Glu Met Lys Lys
        275                 280                 285

Asp Val Pro Phe Leu Gln Glu Val Val Val Met Glu Gly Val Gly His
    290                 295                 300

Phe Ile Gln Ser Glu Lys Pro His Glu Ile Ser Asp His Ile Tyr Gln
305                 310                 315                 320

Phe Ile Lys Lys Phe
                325


<210> SEQ ID NO 42
<211> LENGTH: 316
<212> TYPE: PRT
<213> ORGANISM: Siraitia grosvenori

<400> SEQUENCE: 42

Met Glu Lys Ile Glu His Thr Ile Ile Thr Thr Asn Gly Ile Asn Met
1               5                   10                  15

His Val Ala Ser Ile Gly Thr Gly Pro Ala Val Leu Phe Leu His Gly
            20                  25                  30

Phe Pro Glu Leu Trp Tyr Ser Trp Arg His Gln Leu Leu Ser Phe Ser
        35                  40                  45

Ser Leu Gly Tyr Arg Ala Ile Ala Pro Asp Leu Arg Gly Tyr Gly Asp
    50                  55                  60

Ser Asp Ala Pro Pro Ser Pro Ser Ser Tyr Thr Val Phe His Ile Val
65                  70                  75                  80

Gly Asp Leu Val Gly Leu Leu Asp Gln Leu Gly Ile Asp Gln Val Phe
                85                  90                  95

Leu Val Gly His Asp Trp Gly Ala Ser Ile Ala Trp Tyr Phe Ser Leu
            100                 105                 110

Leu Arg Pro Asp Arg Ile Lys Ala Leu Val Asn Leu Ser Val Gln Tyr
        115                 120                 125

Phe Pro Arg Asn Pro Ala Arg Asn Thr Val Glu Ala Leu Arg Ala Leu
    130                 135                 140

Phe Gly Asp Asp Tyr Tyr Val Cys Arg Phe Gln Glu Pro Gly Glu Met
145                 150                 155                 160

Glu Glu Asp Phe Ala Ser Ile Asp Thr Ala Val Ile Phe Lys Ile Phe
                165                 170                 175

Leu Ser Ser Arg Asp Pro Arg Pro Pro Cys Ile Pro Lys Ala Val Gly
            180                 185                 190

Phe Arg Ala Phe Pro Val Pro Asp Ser Leu Pro Ser Trp Leu Ser Glu
```

```
        195                 200                 205

Glu Asp Ile Ser Tyr Tyr Ala Ser Lys Phe Ser Lys Lys Gly Phe Thr
    210                 215                 220

Gly Gly Leu Asn Tyr Tyr Arg Ala Leu Ala Leu Asn Trp Glu Leu Thr
225                 230                 235                 240

Ala Pro Trp Thr Gly Thr Gln Ile Lys Val Pro Thr Lys Phe Ile Val
                245                 250                 255

Gly Asp Leu Asp Leu Thr Tyr His Ile Pro Gly Ser Lys Glu Tyr Ile
            260                 265                 270

His Lys Gly Gly Phe Glu Arg Asp Val Pro Ser Leu Glu Glu Val Val
        275                 280                 285

Val Ile Glu Gly Ala Ala His Phe Val Asn Gln Glu Arg Pro Glu Glu
    290                 295                 300

Ile Ser Lys His Ile Tyr Asp Phe Ile Lys Lys Phe
305                 310                 315


<210> SEQ ID NO 43
<211> LENGTH: 317
<212> TYPE: PRT
<213> ORGANISM: Siraitia grosvenori

<400> SEQUENCE: 43

Met Asp Ala Ile Glu His Arg Thr Val Ser Val Asn Gly Ile Asn Met
1               5                   10                  15

His Val Ala Glu Lys Gly Glu Gly Pro Val Val Leu Leu Leu His Gly
            20                  25                  30

Phe Pro Glu Leu Trp Tyr Ser Trp Arg His Gln Ile Leu Ala Leu Ser
        35                  40                  45

Ser Leu Gly Tyr Arg Ala Val Ala Pro Asp Leu Arg Gly Tyr Gly Asp
    50                  55                  60

Thr Asp Ala Pro Gly Ser Ile Ser Ser Tyr Thr Cys Phe His Ile Val
65                  70                  75                  80

Gly Asp Leu Val Ala Leu Val Glu Ser Leu Gly Val Asp Arg Val Phe
                85                  90                  95

Val Val Ala His Asp Trp Gly Ala Met Ile Ala Trp Cys Leu Cys Leu
            100                 105                 110

Phe Arg Pro Glu Met Val Lys Ala Phe Val Cys Leu Ser Val Pro Phe
        115                 120                 125

Arg Gln Arg Asn Pro Lys Met Lys Pro Val Gln Ser Met Arg Ala Phe
    130                 135                 140

Phe Gly Asp Asp Tyr Tyr Ile Cys Arg Phe Gln Asn Pro Gly Glu Ile
145                 150                 155                 160

Glu Glu Glu Met Ala Gln Val Gly Ala Arg Glu Val Leu Arg Gly Ile
                165                 170                 175

Leu Thr Ser Arg Arg Pro Gly Pro Pro Ile Leu Pro Lys Gly Gln Ala
            180                 185                 190

Phe Arg Ala Arg Pro Gly Ala Ser Thr Ala Leu Pro Ser Trp Leu Ser
        195                 200                 205

Glu Lys Asp Leu Ser Phe Phe Ala Ser Lys Tyr Asp Gln Lys Gly Phe
    210                 215                 220

Thr Gly Pro Leu Asn Tyr Tyr Arg Ala Met Asp Leu Asn Trp Glu Leu
225                 230                 235                 240

Thr Ala Ser Trp Thr Gly Val Gln Val Lys Val Pro Val Lys Tyr Ile
                245                 250                 255
```

-continued

```
Val Gly Asp Val Asp Met Val Phe Thr Thr Pro Gly Val Lys Glu Tyr
            260                 265                 270

Val Asn Gly Gly Gly Phe Lys Lys Asp Val Pro Phe Leu Gln Glu Val
        275                 280                 285

Val Ile Met Glu Gly Val Gly His Phe Ile Asn Gln Glu Lys Pro Glu
    290                 295                 300

Glu Ile Ser Ser His Ile His Asp Phe Ile Ser Arg Phe
305                 310                 315


<210> SEQ ID NO 44
<211> LENGTH: 311
<212> TYPE: PRT
<213> ORGANISM: Siraitia grosvenori

<400> SEQUENCE: 44

Met Asp Gln Ile Gln His Lys Phe Ile Asp Ile Arg Gly Leu Lys Leu
1               5                   10                  15

His Ile Ala Glu Ile Gly Thr Gly Ser Pro Ala Val Val Phe Leu His
            20                  25                  30

Gly Phe Pro Glu Ile Trp Tyr Ser Trp Arg His Gln Met Val Ala Ala
        35                  40                  45

Ala Ala Val Gly Tyr Arg Ala Ile Ser Pro Asp Leu Arg Gly Tyr Gly
    50                  55                  60

Phe Ser Asp Pro His Pro Gln Pro Gln Asn Ala Ser Phe Asp Asp Phe
65                  70                  75                  80

Val Glu Asp Thr Leu Ala Ile Leu Asp Phe Leu His Ile Pro Lys Ala
                85                  90                  95

Phe Leu Val Gly Lys Asp Phe Gly Ser Trp Pro Val Tyr Leu Phe Ser
            100                 105                 110

Leu Val His Pro Thr Arg Val Ala Gly Ile Val Ser Leu Gly Val Pro
        115                 120                 125

Phe Leu Pro Pro Asn Pro Lys Arg Tyr Arg Asp Leu Pro Glu Gly Phe
    130                 135                 140

Tyr Ile Phe Arg Trp Lys Glu Ser Gly Arg Ala Glu Ala Asp Phe Gly
145                 150                 155                 160

Arg Phe Asp Val Lys Thr Val Leu Arg Arg Ile Tyr Thr Leu Phe Ser
                165                 170                 175

Arg Ser Glu Ile Pro Ile Ala Glu Lys Asp Gln Glu Ile Met Asp Met
            180                 185                 190

Val Asp Glu Ser Thr Pro Pro Pro Pro Trp Leu Thr Asp Glu Asp Leu
        195                 200                 205

Ala Ala Tyr Ala Thr Ala Tyr Glu His Ser Gly Phe Glu Ser Ala Leu
    210                 215                 220

Gln Val Pro Tyr Arg Arg Arg His Gln Glu Leu Gly Met Ser Asn Pro
225                 230                 235                 240

Arg Val Asp Val Pro Val Leu Leu Ile Ile Gly Gly Lys Asp Tyr Phe
                245                 250                 255

Leu Lys Phe Pro Gly Ile Glu Asp Tyr Ile Lys Ser Glu Lys Met Arg
            260                 265                 270

Glu Ile Val Pro Asp Leu Glu Val Ala Asp Leu Ala Asp Gly Thr His
        275                 280                 285

Phe Met Gln Glu Gln Phe Pro Ala Gln Val Asn His Leu Leu Ile Ser
    290                 295                 300

Phe Leu Gly Lys Arg Asn Thr
305                 310
```

<210> SEQ ID NO 45
<211> LENGTH: 759
<212> TYPE: PRT
<213> ORGANISM: Siraitia grosvenorii

<400> SEQUENCE: 45

Met Trp Arg Leu Lys Val Gly Ala Glu Ser Val Gly Glu Asn Asp Glu
1 5 10 15

Lys Trp Leu Lys Ser Ile Ser Asn His Leu Gly Arg Gln Val Trp Glu
20 25 30

Phe Cys Pro Asp Ala Gly Thr Gln Gln Gln Leu Leu Gln Val His Lys
35 40 45

Ala Arg Lys Ala Phe His Asp Asp Arg Phe His Arg Lys Gln Ser Ser
50 55 60

Asp Leu Phe Ile Thr Ile Gln Tyr Gly Lys Glu Val Glu Asn Gly Gly
65 70 75 80

Lys Thr Ala Gly Val Lys Leu Lys Glu Gly Glu Glu Val Arg Lys Glu
85 90 95

Ala Val Glu Ser Ser Leu Glu Arg Ala Leu Ser Phe Tyr Ser Ser Ile
100 105 110

Gln Thr Ser Asp Gly Asn Trp Ala Ser Asp Leu Gly Gly Pro Met Phe
115 120 125

Leu Leu Pro Gly Leu Val Ile Ala Leu Tyr Val Thr Gly Val Leu Asn
130 135 140

Ser Val Leu Ser Lys His His Arg Gln Glu Met Cys Arg Tyr Val Tyr
145 150 155 160

Asn His Gln Asn Glu Asp Gly Gly Trp Gly Leu His Ile Glu Gly Pro
165 170 175

Ser Thr Met Phe Gly Ser Ala Leu Asn Tyr Val Ala Leu Arg Leu Leu
180 185 190

Gly Glu Asp Ala Asn Ala Gly Ala Met Pro Lys Ala Arg Ala Trp Ile
195 200 205

Leu Asp His Gly Gly Ala Thr Gly Ile Thr Ser Trp Gly Lys Leu Trp
210 215 220

Leu Ser Val Leu Gly Val Tyr Glu Trp Ser Gly Asn Asn Pro Leu Pro
225 230 235 240

Pro Glu Phe Trp Leu Phe Pro Tyr Phe Leu Pro Phe His Pro Gly Arg
245 250 255

Met Trp Cys His Cys Arg Met Val Tyr Leu Pro Met Ser Tyr Leu Tyr
260 265 270

Gly Lys Arg Phe Val Gly Pro Ile Thr Pro Ile Val Leu Ser Leu Arg
275 280 285

Lys Glu Leu Tyr Ala Val Pro Tyr His Glu Ile Asp Trp Asn Lys Ser
290 295 300

Arg Asn Thr Cys Ala Lys Glu Asp Leu Tyr Tyr Pro His Pro Lys Met
305 310 315 320

Gln Asp Ile Leu Trp Gly Ser Leu His His Val Tyr Glu Pro Leu Phe
325 330 335

Thr Arg Trp Pro Ala Lys Arg Leu Arg Glu Lys Ala Leu Gln Thr Ala
340 345 350

Met Gln His Ile His Tyr Glu Asp Glu Asn Thr Arg Tyr Ile Cys Leu
355 360 365

Gly Pro Val Asn Lys Val Leu Asn Leu Leu Cys Cys Trp Val Glu Asp

```
    370                 375                 380

Pro Tyr Ser Asp Ala Phe Lys Leu His Leu Gln Arg Val His Asp Tyr
385                 390                 395                 400

Leu Trp Val Ala Glu Asp Gly Met Lys Met Gln Gly Tyr Asn Gly Ser
                405                 410                 415

Gln Leu Trp Asp Thr Ala Phe Ser Ile Gln Ala Ile Val Ser Thr Lys
            420                 425                 430

Leu Val Asp Asn Tyr Gly Pro Thr Leu Arg Lys Ala His Asp Phe Val
        435                 440                 445

Lys Ser Ser Gln Ile Gln Gln Asp Cys Pro Gly Asp Pro Asn Val Trp
    450                 455                 460

Tyr Arg His Ile His Lys Gly Ala Trp Pro Phe Ser Thr Arg Asp His
465                 470                 475                 480

Gly Trp Leu Ile Ser Asp Cys Thr Ala Glu Gly Leu Lys Ala Ala Leu
                485                 490                 495

Met Leu Ser Lys Leu Pro Ser Glu Thr Val Gly Glu Ser Leu Glu Arg
            500                 505                 510

Asn Arg Leu Cys Asp Ala Val Asn Val Leu Leu Ser Leu Gln Asn Asp
        515                 520                 525

Asn Gly Gly Phe Ala Ser Tyr Glu Leu Thr Arg Ser Tyr Pro Trp Leu
    530                 535                 540

Glu Leu Ile Asn Pro Ala Glu Thr Phe Gly Asp Ile Val Ile Asp Tyr
545                 550                 555                 560

Pro Tyr Val Glu Cys Thr Ser Ala Thr Met Glu Ala Leu Thr Leu Phe
                565                 570                 575

Lys Lys Leu His Pro Gly His Arg Thr Lys Glu Ile Asp Thr Ala Ile
            580                 585                 590

Val Arg Ala Ala Asn Phe Leu Glu Asn Met Gln Arg Thr Asp Gly Ser
        595                 600                 605

Trp Tyr Gly Cys Trp Gly Val Cys Phe Thr Tyr Ala Gly Trp Phe Gly
    610                 615                 620

Ile Lys Gly Leu Val Ala Ala Gly Arg Thr Tyr Asn Asn Cys Leu Ala
625                 630                 635                 640

Ile Arg Lys Ala Cys Asp Phe Leu Leu Ser Lys Glu Leu Pro Gly Gly
                645                 650                 655

Gly Trp Gly Glu Ser Tyr Leu Ser Cys Gln Asn Lys Val Tyr Thr Asn
            660                 665                 670

Leu Glu Gly Asn Arg Pro His Leu Val Asn Thr Ala Trp Val Leu Met
        675                 680                 685

Ala Leu Ile Glu Ala Gly Gln Ala Glu Arg Asp Pro Thr Pro Leu His
    690                 695                 700

Arg Ala Ala Arg Leu Leu Ile Asn Ser Gln Leu Glu Asn Gly Asp Phe
705                 710                 715                 720

Pro Gln Gln Glu Ile Met Gly Val Phe Asn Lys Asn Cys Met Ile Thr
                725                 730                 735

Tyr Ala Ala Tyr Arg Asn Ile Phe Pro Ile Trp Ala Leu Gly Glu Tyr
            740                 745                 750

Cys His Arg Val Leu Thr Glu
        755


<210> SEQ ID NO 46
<211> LENGTH: 524
<212> TYPE: PRT
<213> ORGANISM: Cucumis melo
```

<400> SEQUENCE: 46

Met Val Asp Gln Cys Ala Leu Gly Trp Ile Leu Ala Ser Val Leu Gly
1 5 10 15

Ala Ser Ala Leu Tyr Leu Leu Phe Gly Lys Lys Asn Cys Gly Val Leu
20 25 30

Asn Glu Arg Arg Arg Glu Ser Leu Lys Asn Ile Ala Thr Thr Asn Gly
35 40 45

Glu Cys Lys Ser Ser Asn Ser Asp Gly Asp Ile Ile Ile Val Gly Ala
50 55 60

Gly Val Ala Gly Ser Ala Leu Ala Tyr Thr Leu Ala Lys Asp Gly Arg
65 70 75 80

Gln Val His Val Ile Glu Arg Asp Leu Ser Glu Pro Asp Arg Ile Val
85 90 95

Gly Glu Leu Leu Gln Pro Gly Gly Tyr Leu Lys Leu Thr Glu Leu Gly
100 105 110

Leu Glu Asp Cys Val Asp Asp Ile Asp Ala Gln Arg Val Tyr Gly Tyr
115 120 125

Ala Leu Phe Lys Asp Gly Lys Asp Thr Arg Leu Ser Tyr Pro Leu Glu
130 135 140

Lys Phe His Ser Asp Val Ser Gly Arg Ser Phe His Asn Gly Arg Phe
145 150 155 160

Ile Gln Arg Met Arg Glu Lys Ala Ala Ser Leu Pro Asn Val Arg Leu
165 170 175

Glu Gln Gly Thr Val Thr Ser Leu Leu Glu Glu Asn Gly Thr Ile Lys
180 185 190

Gly Val Gln Tyr Lys Asn Lys Ser Gly Gln Glu Met Thr Ala Tyr Ala
195 200 205

Pro Leu Thr Ile Val Cys Asp Gly Cys Phe Ser Asn Leu Arg Arg Ser
210 215 220

Leu Cys Asn Pro Lys Val Asp Val Pro Ser Cys Phe Val Gly Leu Ile
225 230 235 240

Leu Glu Asn Cys Asp Leu Pro Tyr Ala Asn His Gly His Val Ile Leu
245 250 255

Ala Asp Pro Ser Pro Ile Leu Phe Tyr Pro Ile Ser Ser Thr Glu Ile
260 265 270

Arg Cys Leu Val Asp Val Pro Gly Gln Lys Val Pro Ser Ile Ser Asn
275 280 285

Gly Glu Met Ala Asn Tyr Leu Lys Asn Val Val Ala Pro Gln Ile Pro
290 295 300

Pro Gln Leu Tyr Asn Ser Phe Ile Ala Ala Ile Asp Lys Gly Asn Ile
305 310 315 320

Arg Thr Met Pro Asn Arg Ser Met Pro Ala Asp Pro Tyr Pro Thr Pro
325 330 335

Gly Ala Leu Leu Met Gly Asp Ala Phe Asn Met Arg His Pro Leu Thr
340 345 350

Gly Gly Gly Met Thr Val Ala Leu Ser Asp Ile Val Val Leu Arg Asp
355 360 365

Leu Leu Lys Pro Leu Arg Asp Leu Asn Asp Ala Pro Thr Leu Cys Lys
370 375 380

Tyr Leu Glu Ala Phe Tyr Thr Leu Arg Lys Pro Val Ala Ser Thr Ile
385 390 395 400

Asn Thr Leu Ala Gly Ala Leu Tyr Lys Val Phe Cys Ala Ser Pro Asp

```
                405                 410                 415

Gln Ala Arg Lys Glu Met Arg Gln Ala Cys Phe Asp Tyr Leu Ser Leu
            420                 425                 430

Gly Gly Ile Phe Ser Asn Gly Pro Val Ser Leu Leu Ser Gly Leu Asn
        435                 440                 445

Pro Arg Pro Leu Ser Leu Val Leu His Phe Phe Ala Val Ala Ile Tyr
    450                 455                 460

Gly Val Gly Arg Leu Leu Ile Pro Phe Pro Ser Pro Lys Arg Val Trp
465                 470                 475                 480

Ile Gly Ala Arg Leu Ile Ser Gly Ala Ser Ala Ile Ile Phe Pro Ile
            485                 490                 495

Ile Lys Ala Glu Gly Val Arg Gln Met Phe Phe Pro Lys Thr Val Ala
            500                 505                 510

Ala Tyr Tyr Arg Ala Pro Pro Val Val Arg Glu Arg
        515                 520


<210> SEQ ID NO 47
<211> LENGTH: 528
<212> TYPE: PRT
<213> ORGANISM: Cucumis sativus

<400> SEQUENCE: 47

Met Val Asp His Cys Thr Phe Gly Trp Ile Phe Ser Ala Phe Leu Ala
1               5                   10                  15

Phe Val Ile Ala Phe Ser Phe Phe Leu Ser Pro Arg Lys Asn Arg Arg
            20                  25                  30

Gly Arg Gly Thr Asn Ser Thr Pro Arg Arg Asp Cys Leu Ser Ser Ser
        35                  40                  45

Ala Thr Thr Asn Gly Glu Cys Arg Ser Val Asp Gly Asp Ala Asp Val
    50                  55                  60

Ile Ile Val Gly Ala Gly Val Ala Gly Ser Ala Leu Ala His Thr Leu
65                  70                  75                  80

Gly Lys Asp Gly Arg Arg Val His Val Ile Glu Arg Asp Leu Thr Glu
                85                  90                  95

Pro Asp Arg Ile Val Gly Glu Leu Leu Gln Pro Gly Gly Tyr Leu Lys
            100                 105                 110

Leu Ile Glu Leu Gly Leu Gln Asp Cys Val Glu Glu Ile Asp Ala Gln
        115                 120                 125

Lys Val Tyr Gly Tyr Ala Leu Phe Lys Asp Gly Lys Ser Thr Arg Leu
    130                 135                 140

Ser Tyr Pro Leu Glu Asn Phe Gln Ser Asp Val Ser Gly Arg Ser Phe
145                 150                 155                 160

His Asn Gly Arg Phe Ile Gln Arg Met Arg Glu Lys Ala Ala Phe Leu
                165                 170                 175

Pro Asn Val Arg Leu Glu Gln Gly Thr Val Thr Ser Leu Leu Glu Glu
            180                 185                 190

Lys Gly Thr Ile Thr Gly Val Gln Tyr Lys Ser Lys Asn Gly Glu Gln
        195                 200                 205

Lys Thr Ala Tyr Ala Pro Leu Thr Ile Val Cys Asp Gly Cys Phe Ser
    210                 215                 220

Asn Leu Arg Arg Ser Leu Cys Asn Pro Met Val Asp Val Pro Ser Cys
225                 230                 235                 240

Phe Val Gly Leu Val Leu Glu Asn Cys Gln Leu Pro Tyr Ala Asn Leu
                245                 250                 255
```

-continued

```
Gly His Val Val Leu Gly Asp Pro Ser Pro Ile Leu Phe Tyr Pro Ile
            260                 265                 270

Ser Ser Thr Glu Ile Arg Cys Leu Val Asp Val Pro Gly Gln Lys Val
        275                 280                 285

Pro Ser Ile Ser Asn Gly Glu Met Glu Lys Tyr Leu Lys Thr Val Val
    290                 295                 300

Ala Pro Gln Val Pro Pro Gln Ile His Asp Ala Phe Ile Ala Ala Ile
305                 310                 315                 320

Glu Lys Gly Asn Ile Arg Thr Met Pro Asn Arg Ser Met Pro Ala Ala
                325                 330                 335

Pro Gln Pro Thr Pro Gly Ala Leu Leu Met Gly Asp Ala Phe Asn Met
            340                 345                 350

Arg His Pro Leu Thr Gly Gly Gly Met Thr Val Ala Leu Ser Asp Ile
        355                 360                 365

Val Val Leu Arg Asn Leu Leu Lys Pro Leu Lys Asp Leu Asn Asp Ala
    370                 375                 380

Pro Thr Leu Cys Lys Tyr Leu Glu Ser Phe Tyr Thr Leu Arg Lys Pro
385                 390                 395                 400

Val Ala Ser Thr Ile Asn Thr Leu Ala Gly Ala Leu Tyr Lys Val Phe
                405                 410                 415

Cys Ala Ser Ser Asp Gln Ala Arg Lys Glu Met Arg Gln Ala Cys Phe
            420                 425                 430

Asp Tyr Leu Ser Leu Gly Gly Ile Phe Ser Asn Gly Pro Val Ser Leu
        435                 440                 445

Leu Ser Gly Leu Asn Pro Arg Pro Leu Ser Leu Val Leu His Phe Phe
    450                 455                 460

Ala Val Ala Ile Tyr Gly Val Gly Arg Leu Leu Leu Pro Phe Pro Ser
465                 470                 475                 480

Pro Lys Gly Ile Trp Ile Gly Ala Arg Leu Val Tyr Ser Ala Ser Gly
                485                 490                 495

Ile Ile Phe Pro Ile Ile Lys Ala Glu Gly Val Arg Gln Met Phe Phe
            500                 505                 510

Pro Ala Thr Val Pro Ala Tyr Tyr Arg Thr Pro Pro Val Phe Asn Ser
        515                 520                 525


<210> SEQ ID NO 48
<211> LENGTH: 318
<212> TYPE: PRT
<213> ORGANISM: Cucumis sativus

<400> SEQUENCE: 48

Met Glu Thr Ile Asn His Ile Thr Val Gln Thr Asn Gly Ile Asn Leu
1               5                   10                  15

His Val Ala Thr Ala Gly Pro Val Thr Gly Pro Pro Val Leu Leu Leu
            20                  25                  30

His Gly Phe Pro Glu Leu Trp Tyr Ser Trp Arg His Gln Ile Ile Phe
        35                  40                  45

Leu Ser Ser Val Gly Tyr Arg Val Ile Ala Pro Asp Leu Arg Gly Tyr
    50                  55                  60

Gly Asp Ser Asp Ala Pro Pro Ser Ser Asp Thr Tyr Thr Ala Leu His
65                  70                  75                  80

Ile Val Gly Asp Val Val Gly Leu Leu Asn Glu Leu Gly Ile Asp Lys
                85                  90                  95

Val Leu Leu Val Gly His Asp Trp Gly Ala Leu Ile Ala Trp Tyr Phe
            100                 105                 110
```

```
Cys Leu Phe Arg Pro Asp Arg Ile Lys Ala Ser Val Ile Leu Ser Val
        115                 120                 125

Gln Phe Phe Pro Arg Asn Pro Lys Val Ser Phe Val Glu Gly Phe Lys
    130                 135                 140

Ala Val Leu Gly Asp Gln Phe Tyr Met Val Arg Phe Gln Glu Pro Gly
145                 150                 155                 160

Lys Ala Glu Lys Glu Phe Ala Ser Val Asp Ile Arg Glu Phe Phe Lys
                165                 170                 175

Asn Val Met Ser Asn Arg Asp Pro Ser Ala Pro Tyr Leu Pro Gly Glu
            180                 185                 190

Glu Lys Phe Glu Gly Val Pro Pro Pro Ser Leu Ala Pro Trp Leu Thr
        195                 200                 205

Pro Gln Asp Ile Asp Tyr Tyr Ala Gln Lys Phe Ser His Ser Gly Phe
    210                 215                 220

Thr Gly Gly Leu Asn Tyr Tyr Arg Ala Phe Asp Arg Thr Trp Glu Leu
225                 230                 235                 240

Thr Ala Pro Trp Thr Ala Ala Glu Ile Lys Val Pro Val Lys Phe Ile
                245                 250                 255

Val Gly Asp Leu Asp Leu Thr Tyr His Phe Pro Gly Gly Gln Asp Tyr
            260                 265                 270

Ile Asn Gly Asp Ala Phe Arg Lys Asp Val Pro Gly Leu Glu Glu Val
        275                 280                 285

Ile Val Met Lys Asp Thr Ser His Phe Ile Asn Gln Glu Arg Pro Asp
    290                 295                 300

Glu Ile Asn Cys His Ile His Asp Phe Phe Asn Lys Phe Cys
305                 310                 315


<210> SEQ ID NO 49
<211> LENGTH: 316
<212> TYPE: PRT
<213> ORGANISM: Cucumis melo

<400> SEQUENCE: 49

Met Asp Ala Ile Gln His Thr Thr Ile Lys Thr Asn Gly Ile Lys Met
1               5                   10                  15

His Ile Ala Ser Val Gly Asn Gly Pro Val Val Leu Leu Leu His Gly
            20                  25                  30

Phe Pro Glu Leu Trp Tyr Ser Trp Arg His Gln Leu Leu Tyr Leu Ser
        35                  40                  45

Ser Val Gly Tyr Arg Ala Ile Ala Pro Asp Leu Arg Gly Tyr Gly Asp
    50                  55                  60

Thr Asp Ser Pro Glu Ser His Thr Ser Tyr Thr Ala Leu His Ile Val
65                  70                  75                  80

Gly Asp Leu Val Gly Ala Leu Asp Glu Leu Gly Ile Glu Lys Val Phe
                85                  90                  95

Leu Val Gly His Asp Trp Gly Ala Ile Ile Ala Trp Tyr Phe Cys Leu
            100                 105                 110

Phe Arg Pro Glu Arg Ile Lys Ala Leu Val Asn Leu Ser Val Gln Phe
        115                 120                 125

Phe Pro Arg Asn Pro Ala Ile Ser Phe Ile Gln Arg Phe Arg Ala Ala
    130                 135                 140

Tyr Gly Asp Asp Phe Tyr Met Cys Arg Phe Gln Val Pro Gly Glu Ala
145                 150                 155                 160

Glu Ala Asp Phe Ala Cys Ile Asp Thr Ala Gln Leu Phe Lys Thr Thr
```

```
                165                 170                 175

Leu Ser Asn Arg Ser Thr Lys Ala Pro Cys Leu Pro Lys Glu Tyr Gly
            180                 185                 190

Phe Arg Ala Ile Pro Pro Pro Glu Asn Leu Pro Ser Trp Leu Thr Glu
        195                 200                 205

Glu Asp Ile Asn Tyr Tyr Ala Ala Lys Phe Lys Glu Thr Gly Phe Thr
    210                 215                 220

Gly Ala Leu Asn Tyr Tyr Arg Ala Phe Asp Leu Thr Trp Glu Leu Thr
225                 230                 235                 240

Ala Pro Trp Thr Gly Val Gln Ile Gln Val Pro Val Lys Phe Ile Val
                245                 250                 255

Gly Asp Ser Asp Leu Thr Tyr His Phe Lys Gly Ala Lys Glu Tyr Ile
            260                 265                 270

His Glu Gly Gly Phe Lys Arg Asp Val Pro Leu Leu Glu Glu Val Val
        275                 280                 285

Ile Val Glu Asn Ala Gly His Phe Val His Glu Glu Lys Pro His Glu
    290                 295                 300

Ile Asn Thr His Ile His Asp Phe Ile Lys Lys Phe
305                 310                 315


<210> SEQ ID NO 50
<211> LENGTH: 315
<212> TYPE: PRT
<213> ORGANISM: Cucumis melo

<400> SEQUENCE: 50

Met Asp Lys Ile Gln His Ser Thr Ile Ser Thr Asn Gly Ile Asn Ile
1               5                   10                  15

His Phe Ala Ser Ile Gly Ser Gly Pro Val Val Leu Phe Leu His Gly
            20                  25                  30

Phe Pro Glu Leu Trp Tyr Ser Trp Arg His Gln Leu Leu Phe Leu Ala
        35                  40                  45

Ser Lys Gly Phe Arg Ala Ile Ala Pro Asp Leu Arg Gly Phe Gly Asp
    50                  55                  60

Ser Asp Ala Pro Pro Ser Pro Ser Ser Tyr Thr Pro His His Ile Val
65                  70                  75                  80

Gly Asp Leu Ile Gly Leu Leu Asp His Leu Gly Ile Asp Gln Val Phe
                85                  90                  95

Leu Val Gly His Asp Trp Gly Ala Met Met Ala Trp Tyr Phe Cys Leu
            100                 105                 110

Phe Arg Pro Asp Arg Val Lys Ala Leu Val Asn Leu Ser Val His Tyr
        115                 120                 125

Thr Pro Arg Asn Pro Ala Gly Ser Pro Leu Ala Val Thr Arg Arg Tyr
    130                 135                 140

Leu Gly Asp Asp Phe Tyr Ile Cys Lys Phe Gln Glu Pro Gly Val Ala
145                 150                 155                 160

Glu Ala Asp Phe Gly Ser Val Asp Thr Ala Thr Met Met Lys Lys Phe
                165                 170                 175

Leu Thr Met Arg Asp Pro Arg Pro Ala Ile Ile Pro Asn Gly Phe Lys
            180                 185                 190

Thr Leu Leu Glu Thr Pro Glu Ile Leu Pro Ser Trp Leu Thr Glu Glu
        195                 200                 205

Asp Ile Glu Tyr Phe Ala Ser Lys Phe Ser Lys Thr Gly Phe Thr Gly
    210                 215                 220
```

```
Gly Phe Asn Tyr Tyr Arg Ala Leu Asp Ile Thr Trp Glu Leu Thr Gly
225                 230                 235                 240

Pro Trp Ser Arg Ala Gln Ile Lys Val Pro Thr Lys Phe Ile Val Gly
                245                 250                 255

Asp Leu Asp Leu Val Tyr Asn Phe Pro Gly Ala Lys Glu Tyr Ile His
            260                 265                 270

Gly Gly Gly Phe Lys Lys Asp Val Pro Leu Leu Glu Asp Val Val Val
        275                 280                 285

Ile Glu Gly Ala Ala His Phe Ile Asn Gln Glu Lys Pro Asp Glu Ile
    290                 295                 300

Ser Ser Leu Ile Tyr Asp Phe Ile Thr Lys Phe
305                 310                 315


<210> SEQ ID NO 51
<211> LENGTH: 322
<212> TYPE: PRT
<213> ORGANISM: Cucumis sativus

<400> SEQUENCE: 51

Met Glu Lys Ile Glu His Thr Thr Ile Pro Thr Asn Gly Ile Asn Met
1               5                   10                  15

His Val Ala Ser Ile Gly Ser Gly Pro Ala Val Leu Phe Leu His Gly
            20                  25                  30

Phe Pro Gln Leu Trp Tyr Ser Trp Arg His Gln Leu Leu Phe Leu Ala
        35                  40                  45

Ser Lys Gly Phe Arg Ala Leu Ala Pro Asp Leu Arg Gly Phe Gly Asp
    50                  55                  60

Thr Asp Ala Pro Pro Ser Pro Ser Ser Tyr Thr Phe His His Ile Ile
65                  70                  75                  80

Gly Asp Leu Ile Gly Leu Leu Asp His Phe Gly Leu Asp Lys Val Phe
                85                  90                  95

Leu Val Gly His Asp Trp Gly Ala Val Ile Ala Trp Tyr Phe Cys Leu
            100                 105                 110

Phe Arg Pro Asp Arg Val Lys Ala Leu Val Asn Leu Ser Val His Tyr
        115                 120                 125

Leu Lys Arg His Pro Ser Ile Asn Phe Val Asp Gly Phe Arg Ala Ser
    130                 135                 140

Ala Gly Glu Asn Phe Tyr Ile Cys Gln Phe Gln Glu Ala Gly Val Ala
145                 150                 155                 160

Glu Ala Asp Phe Gly Ser Val Asp Thr Ala Thr Met Met Lys Lys Phe
                165                 170                 175

Met Gly Met Arg Asp Pro Val Ala Pro Pro Ile Tyr Asn Thr Lys Glu
            180                 185                 190

Lys Gly Phe Ser Ser Leu Glu Thr Pro Asn Pro Leu Pro Cys Trp Leu
        195                 200                 205

Thr Glu Glu Asp Val Asp Phe Phe Ala Ser Lys Phe Ser Lys Thr Gly
    210                 215                 220

Phe Thr Gly Gly Phe Asn Tyr Tyr Arg Ala Leu Asn Leu Ser Trp Glu
225                 230                 235                 240

Leu Thr Ala Ala Trp Asn Gly Ser Lys Ile Glu Val Pro Val Lys Phe
                245                 250                 255

Ile Val Gly Asp Leu Asp Leu Val Tyr His Phe Pro Gly Ala Lys Glu
            260                 265                 270

Tyr Ile Asn Gly Gly Glu Phe Lys Lys Asp Val Pro Phe Leu Glu Glu
        275                 280                 285
```

```
Val Val Val Ile Lys Asp Ala Ala His Phe Ile Asn Gln Glu Lys Pro
    290                 295                 300

His Gln Ile Asn Ser Leu Ile Tyr His Phe Ile Asn Lys Phe Val Ser
305                 310                 315                 320

Ser Ile


<210> SEQ ID NO 52
<211> LENGTH: 473
<212> TYPE: PRT
<213> ORGANISM: Siraitia grosvenorii

<400> SEQUENCE: 52

Met Trp Thr Val Val Leu Gly Leu Ala Thr Leu Phe Val Ala Tyr Tyr
1               5                   10                  15

Ile His Trp Ile Asn Lys Trp Arg Asp Ser Lys Phe Asn Gly Val Leu
            20                  25                  30

Pro Pro Gly Thr Met Gly Leu Pro Leu Ile Gly Glu Thr Ile Gln Leu
        35                  40                  45

Ser Arg Pro Ser Asp Ser Leu Asp Val His Pro Phe Ile Gln Lys Lys
    50                  55                  60

Val Glu Arg Tyr Gly Pro Ile Phe Lys Thr Cys Leu Ala Gly Arg Pro
65                  70                  75                  80

Val Val Val Ser Ala Asp Ala Glu Phe Asn Asn Tyr Ile Met Leu Gln
                85                  90                  95

Glu Gly Arg Ala Val Glu Met Trp Tyr Leu Asp Thr Leu Ser Lys Phe
            100                 105                 110

Phe Gly Leu Asp Thr Glu Trp Leu Lys Ala Leu Gly Leu Ile His Lys
        115                 120                 125

Tyr Ile Arg Ser Ile Thr Leu Asn His Phe Gly Ala Glu Ala Leu Arg
    130                 135                 140

Glu Arg Phe Leu Pro Phe Ile Glu Ala Ser Ser Met Glu Ala Leu His
145                 150                 155                 160

Ser Trp Ser Thr Gln Pro Ser Val Glu Val Lys Asn Ala Ser Ala Leu
                165                 170                 175

Met Val Phe Arg Thr Ser Val Asn Lys Met Phe Gly Glu Asp Ala Lys
            180                 185                 190

Lys Leu Ser Gly Asn Ile Pro Gly Lys Phe Thr Lys Leu Leu Gly Gly
        195                 200                 205

Phe Leu Ser Leu Pro Leu Asn Phe Pro Gly Thr Thr Tyr His Lys Cys
    210                 215                 220

Leu Lys Asp Met Lys Glu Ile Gln Lys Lys Leu Arg Glu Val Val Asp
225                 230                 235                 240

Asp Arg Leu Ala Asn Val Gly Pro Asp Val Glu Asp Phe Leu Gly Gln
                245                 250                 255

Ala Leu Lys Asp Lys Glu Ser Glu Lys Phe Ile Ser Glu Glu Phe Ile
            260                 265                 270

Ile Gln Leu Leu Phe Ser Ile Ser Phe Ala Ser Phe Glu Ser Ile Ser
        275                 280                 285

Thr Thr Leu Thr Leu Ile Leu Lys Leu Leu Asp Glu His Pro Glu Val
    290                 295                 300

Val Lys Glu Leu Glu Ala Glu His Glu Ala Ile Arg Lys Ala Arg Ala
305                 310                 315                 320

Asp Pro Asp Gly Pro Ile Thr Trp Glu Glu Tyr Lys Ser Met Thr Phe
                325                 330                 335
```

```
Thr Leu Gln Val Ile Asn Glu Thr Leu Arg Leu Gly Ser Val Thr Pro
            340                 345                 350

Ala Leu Leu Arg Lys Thr Val Lys Asp Leu Gln Val Lys Gly Tyr Ile
        355                 360                 365

Ile Pro Glu Gly Trp Thr Ile Met Leu Val Thr Ala Ser Arg His Arg
    370                 375                 380

Asp Pro Lys Val Tyr Lys Asp Pro His Ile Phe Asn Pro Trp Arg Trp
385                 390                 395                 400

Lys Asp Leu Asp Ser Ile Thr Ile Gln Lys Asn Phe Met Pro Phe Gly
                405                 410                 415

Gly Gly Leu Arg His Cys Ala Gly Ala Glu Tyr Ser Lys Val Tyr Leu
            420                 425                 430

Cys Thr Phe Leu His Ile Leu Cys Thr Lys Tyr Arg Trp Thr Lys Leu
        435                 440                 445

Gly Gly Gly Thr Ile Ala Arg Ala His Ile Leu Ser Phe Glu Asp Gly
    450                 455                 460

Leu His Val Lys Phe Thr Pro Lys Glu
465                 470


<210> SEQ ID NO 53
<211> LENGTH: 480
<212> TYPE: PRT
<213> ORGANISM: Cucumis melo

<400> SEQUENCE: 53

Met Ala Ser Thr His Ile Leu Leu Phe Pro Phe Met Ala Gln Gly His
1               5                   10                  15

Met Ile Pro Met Ile Asp Leu Ala Lys Leu Leu Ala His His Gly Phe
            20                  25                  30

Ile Ile Thr Ile Val Thr Thr Pro His Asn Ala Asp Arg Tyr His Ser
        35                  40                  45

Val Leu Ala Arg Ala Thr His Ser Gly Leu Gln Ile His Val Ala Leu
    50                  55                  60

Leu Pro Phe Pro Ser Thr Gln Val Gly Leu Pro Glu Gly Cys Glu Asn
65                  70                  75                  80

Leu Asp Leu Leu Pro Leu His Leu Ser Ser Ser Met Ser Ala Phe Cys
                85                  90                  95

Arg Ala Thr Ser Leu Leu Tyr Glu Pro Ser Glu Lys Leu Leu Gln Gln
            100                 105                 110

Leu Cys Pro Arg Pro Ser Cys Ile Ile Ser Asp Met Cys Leu Pro Trp
        115                 120                 125

Thr Leu Arg Leu Ala Gln Asn His Gln Ile Pro Arg Leu Val Phe Tyr
    130                 135                 140

Ser Leu Ser Cys Phe Phe Leu Leu Cys Met Arg Ser Leu Lys Thr Asn
145                 150                 155                 160

His Ser Leu Val Thr Ser Ile Ser Asp Ser Glu Phe Leu Thr Leu Ser
                165                 170                 175

Asp Leu Pro Asp Pro Val Glu Ile Arg Lys Ser Gln Leu Ser Arg Val
            180                 185                 190

Lys Asn Glu Glu Met Gly Lys Leu Ser Tyr Glu Met Val Glu Ala Asp
        195                 200                 205

Arg Leu Ser His Gly Val Ile Leu Asn Val Phe Glu Glu Met Glu Ala
    210                 215                 220

Glu Tyr Val Ala Glu Tyr Arg Lys Asn Arg Asp Leu Pro Gln Lys Val
```

```
225                 230                 235                 240

Trp Cys Val Gly Pro Leu Ser Leu Cys Asn Asp Asn Lys Leu Asp Lys
                245                 250                 255

Ala Glu Arg Gly Glu Lys Ser Ser Ile His Glu Asp Glu Cys Ile Lys
            260                 265                 270

Trp Leu Asn Gly Gln Gln Pro Ser Ser Val Val Tyr Val Ser Met Gly
        275                 280                 285

Ser Leu Cys Asn Leu Ser Thr Pro Gln Leu Val Glu Leu Gly Leu Gly
    290                 295                 300

Leu Glu Ala Ser Lys Lys Pro Phe Ile Trp Val Ile Arg Lys Gly Asn
305                 310                 315                 320

Leu Thr Glu Glu Leu Gln Arg Trp Ile Met Glu Tyr Asp Phe Glu Arg
                325                 330                 335

Lys Thr Glu Gly Trp Gly Leu Val Ile Arg Gly Trp Ala Pro Gln Val
            340                 345                 350

Ala Ile Leu Ser His Ser Ala Ile Gly Gly Phe Leu Thr His Cys Gly
        355                 360                 365

Trp Asn Ser Ser Ile Glu Gly Ile Ala Ala Gly Val Pro Met Met Thr
    370                 375                 380

Trp Pro Leu Phe Ala Asp Gln Val Phe Asn Ala Lys Leu Ile Val Glu
385                 390                 395                 400

Val Leu Lys Val Gly Val Ser Val Gly Glu Glu Thr Ala Leu His Trp
                405                 410                 415

Gly Glu Glu Ala Glu Lys Glu Val Met Val Lys Arg Glu Glu Val Arg
            420                 425                 430

Glu Ala Ile Glu Arg Val Met Asp Gly Glu Asn Arg Glu Glu Met Lys
        435                 440                 445

Gln Arg Ser Lys Lys Leu Ala Glu Met Ala Lys Arg Ala Val Glu Glu
    450                 455                 460

Gly Gly Ser Ser His Arg Asn Leu Lys Arg Leu Ile Glu Glu Ile Val
465                 470                 475                 480


<210> SEQ ID NO 54
<211> LENGTH: 497
<212> TYPE: PRT
<213> ORGANISM: Cucumis melo

<400> SEQUENCE: 54

Met Ala Ser Thr Leu Ser Asn Gln Leu Glu Leu Gln Pro His Phe Val
1               5                   10                  15

Leu Val Pro Leu Met Ala Gln Gly His Met Ile Pro Met Ile Asp Ile
            20                  25                  30

Ala Thr Leu Leu Ala Arg Arg Gly Val Phe Val Thr Phe Val Thr Thr
        35                  40                  45

Pro Tyr Asn Ala Thr Arg Leu Glu Ser Phe Phe Ala Arg Ala Lys Gln
    50                  55                  60

Ser Ser Leu Ser Ile Ser Leu Leu Glu Ile Pro Phe Pro Cys Leu Gln
65                  70                  75                  80

Val Gly Leu Pro Leu Gly Cys Glu Asn Leu Asp Thr Leu Pro Ser Arg
                85                  90                  95

Ser Leu Leu Arg Asn Phe Tyr Lys Ala Leu Ser Leu Leu Gln Gln Pro
            100                 105                 110

Leu Glu Gln Phe Leu Ser Arg His His Leu Asn Pro Thr Cys Ile Ile
        115                 120                 125
```

```
Ser Asp Lys Tyr Leu Tyr Trp Thr Ala Gln Thr Ala His Lys Phe Lys
    130                 135                 140

Cys Pro Arg Val Val Phe His Gly Thr Gly Cys Phe Ser Leu Leu Ser
145                 150                 155                 160

Ser His Asn Leu Gln Leu Tyr Ser Pro His Thr Ser Ile Asp Ser Asn
                165                 170                 175

Ser Gln Pro Phe Leu Val Pro Gly Leu Pro His Lys Ile Glu Ile Thr
            180                 185                 190

Lys Ser Gln Leu Pro Gly Ser Leu Ile Lys Ser Pro Asp Phe Asp Asp
        195                 200                 205

Phe Arg Asp Lys Ile Thr Lys Ala Glu Gln Glu Ala Tyr Gly Val Val
    210                 215                 220

Val Asn Ser Phe Ser Glu Leu Glu Asn Gly Tyr Tyr Gln Asn Tyr Glu
225                 230                 235                 240

Arg Ala Ile Ser Lys Lys Leu Trp Cys Ile Gly Pro Val Ser Leu Cys
                245                 250                 255

Asn Glu Asn Ser Ile Glu Lys Tyr Asn Arg Gly Asn Lys Ala Ser Ile
            260                 265                 270

Glu Gln Ser Asn Cys Leu Asn Trp Leu Asp Ser Met Ile Pro Lys Ser
        275                 280                 285

Val Leu Tyr Ile Cys Leu Gly Ser Leu Cys Arg Met Leu Pro Ser Gln
    290                 295                 300

Leu Ile Gln Leu Gly Gln Cys Leu Glu Ser Ser Thr Arg Pro Phe Ile
305                 310                 315                 320

Trp Val Ile Lys Asn Arg Asp Glu Asn Cys Ser Glu Leu Glu Lys Trp
                325                 330                 335

Leu Ser Glu Glu Phe Glu Arg Lys Thr Lys Gly Arg Gly Leu Ile
            340                 345                 350

Ile Arg Gly Trp Ala Pro Gln Leu Leu Ile Leu Ser His Trp Ser Thr
        355                 360                 365

Gly Gly Phe Leu Thr His Cys Gly Trp Asn Ser Thr Val Glu Gly Ile
    370                 375                 380

Gly Asn Gly Val Pro Met Ile Thr Trp Pro Gln Phe Ala Glu Gln Phe
385                 390                 395                 400

Leu Asn Glu Lys Leu Val Val Glu Ile Leu Lys Ile Gly Val Arg Val
                405                 410                 415

Gly Val Glu Gly Ala Val Arg Trp Gly Glu Glu Glu Arg Val Gly Val
            420                 425                 430

Met Ala Lys Lys Glu Glu Ile Glu Lys Ala Ile Glu Met Val Met Asp
        435                 440                 445

Gly Gly Glu Glu Gly Glu Glu Arg Arg Arg Arg Val Gly Asp Leu Ser
    450                 455                 460

Lys Met Ala Pro Lys Ala Met Glu Asn Gly Gly Ser Ser Tyr Val Asn
465                 470                 475                 480

Leu Ser Leu Phe Ile Glu Asp Val Met Ala Gln Ser Ala His Leu Lys
                485                 490                 495

Ala


<210> SEQ ID NO 55
<211> LENGTH: 477
<212> TYPE: PRT
<213> ORGANISM: Cucumis sativus

<400> SEQUENCE: 55
```

-continued

```
Met Asp Pro Lys Asn Thr Gln Leu Arg Ile Phe Phe Phe Pro Phe Met
1               5                   10                  15

Ala Gln Gly His Thr Ile Pro Ala Ile Asp Met Ala Lys Leu Phe Ala
            20                  25                  30

Ser Arg Gly Ala Asp Val Ala Ile Ile Thr Thr Pro Leu Asn Ala Pro
        35                  40                  45

Leu Ile Ala Lys Ser Ile Asn Lys Phe Asp Arg Pro Gly Arg Lys Ile
    50                  55                  60

Glu Leu Leu Ile Ile Asp Phe Pro Ser Val Ala Val Gly Leu Pro Asp
65                  70                  75                  80

Gly Cys Glu Ser Leu Asp Leu Ala Arg Ser Pro Glu Met Phe Gln Ser
                85                  90                  95

Phe Phe Arg Ala Thr Thr Leu Leu Glu Pro Gln Ile Asp Gln Ile Leu
            100                 105                 110

Asp His His Arg Pro His Cys Leu Val Ala Asp Thr Phe Phe Pro Trp
        115                 120                 125

Thr Thr Asp Leu Ala Ala Lys Tyr Gly Ile Pro Arg Val Val Phe His
    130                 135                 140

Gly Thr Cys Phe Phe Ala Leu Cys Ala Ala Ala Ser Leu Ile Ala Asn
145                 150                 155                 160

Arg Pro Tyr Lys Lys Val Ser Ser Asp Leu Glu Pro Phe Val Ile Pro
                165                 170                 175

Gly Leu Pro Asp Glu Ile Lys Leu Thr Arg Ser Gln Val Pro Gly Phe
            180                 185                 190

Leu Lys Glu Glu Val Glu Thr Asp Phe Ile Lys Leu Tyr Trp Ala Ser
        195                 200                 205

Lys Glu Val Glu Ser Arg Cys Tyr Gly Phe Leu Ile Asn Ser Phe Tyr
    210                 215                 220

Glu Leu Glu Pro Ala Tyr Ala Asp Tyr Tyr Arg Asn Val Leu Gly Arg
225                 230                 235                 240

Arg Ala Trp His Ile Gly Pro Leu Ser Leu Tyr Ser Asn Val Glu Glu
                245                 250                 255

Asp Asn Val Gln Arg Gly Ser Ser Ser Ser Ile Ser Glu Asp Gln Cys
            260                 265                 270

Leu Lys Trp Leu Asp Ser Lys Asn Pro Asp Ser Val Leu Tyr Val Ser
        275                 280                 285

Phe Gly Ser Leu Ala Ser Leu Thr Asn Ser Gln Leu Leu Glu Ile Ala
    290                 295                 300

Lys Gly Leu Glu Gly Thr Gly Gln Asn Phe Ile Trp Val Val Lys Lys
305                 310                 315                 320

Ala Lys Gly Asp Gln Glu Glu Trp Leu Pro Glu Gly Phe Glu Lys Arg
                325                 330                 335

Val Glu Gly Lys Gly Leu Ile Ile Arg Gly Trp Ala Pro Gln Val Leu
            340                 345                 350

Ile Leu Asp His Arg Ser Ile Gly Gly Phe Val Thr His Cys Gly Trp
        355                 360                 365

Asn Ser Ala Leu Glu Gly Val Thr Ala Gly Val Pro Met Val Thr Trp
    370                 375                 380

Pro Asn Ser Ala Glu Gln Phe Tyr Asn Glu Lys Leu Ile Thr Asp Val
385                 390                 395                 400

Leu Gln Ile Gly Val Gly Val Gly Ala Leu Tyr Trp Gly Arg Ala Gly
                405                 410                 415

Lys Asp Glu Ile Lys Ser Glu Ala Ile Glu Lys Ala Val Asn Arg Val
```

```
            420                 425                 430

Met Val Gly Glu Glu Ala Glu Glu Met Arg Ser Arg Ala Lys Ala Leu
        435                 440                 445

Gly Ile Gln Ala Arg Lys Ala Ile Val Glu Gly Gly Ser Ser Ser Ser
    450                 455                 460

Asp Leu Asn Ala Phe Phe Lys Asp Leu Arg Ser Gln Ile
465                 470                 475


<210> SEQ ID NO 56
<211> LENGTH: 467
<212> TYPE: PRT
<213> ORGANISM: Cucumis melo

<400> SEQUENCE: 56

Met Glu Met Thr Ala Ala Asn Gly Gly Gly Glu Arg Ile Lys Gln Ser
1               5                   10                  15

His Val Ile Val Phe Pro Phe Pro Arg His Gly His Met Ser Pro Met
            20                  25                  30

Leu Gln Phe Ser Lys Arg Leu Ile Ser Lys Gly Leu Leu Leu Thr Phe
        35                  40                  45

Leu Ile Thr Ser Ser Ala Ser Gln Ser Leu Thr Ile Asn Ile Pro Pro
    50                  55                  60

Ser Pro Ser Phe His Phe Lys Ile Ile Ser Asp Leu Pro Glu Ser Asp
65                  70                  75                  80

Asp Val Ala Thr Leu Asp Ala Tyr Leu Arg Ser Phe Arg Ala Ala Val
                85                  90                  95

Thr Lys Ser Leu Ser Asn Phe Ile Asp Glu Val Leu Thr Ser Ser Ser
            100                 105                 110

Asn Glu Glu Val Pro Pro Thr Leu Ile Val Tyr Asp Ser Val Met Pro
        115                 120                 125

Trp Val Gln Ser Val Ala Ala Glu Arg Gly Leu Asp Ser Ala Pro Phe
    130                 135                 140

Phe Thr Glu Ser Ala Ala Val Asn His Leu Leu His Leu Val Tyr Gly
145                 150                 155                 160

Gly Ser Leu Ser Ile Pro Pro Pro Asp Asn Val Val Val Ser Leu Pro
                165                 170                 175

Ser Glu Ile Val Leu Gln Pro Glu Asp Leu Pro Ser Phe Pro Asp Asp
            180                 185                 190

Pro Glu Val Val Leu Asp Phe Met Thr Ser Gln Phe Ser His Leu Glu
        195                 200                 205

Asn Val Lys Trp Ile Phe Ile Asn Thr Phe Asp Arg Leu Glu Ser Lys
    210                 215                 220

Val Val Asn Trp Met Ala Lys Thr Leu Pro Ile Lys Thr Val Gly Pro
225                 230                 235                 240

Thr Ile Pro Ser Ala Tyr Leu Asp Gly Arg Leu Glu Lys Asp Lys Ala
                245                 250                 255

Tyr Gly Leu Asn Val Ser Lys Ser Asn Asn Gly Lys Cys Pro Ile Lys
            260                 265                 270

Trp Leu Asp Ser Lys Glu Thr Ala Ser Val Ile Tyr Ile Ser Phe Gly
        275                 280                 285

Ser Leu Val Ile Leu Ser Glu Glu Gln Val Lys Glu Leu Thr Asn Leu
    290                 295                 300

Leu Arg Asp Thr Asp Phe Ser Phe Leu Trp Val Leu Arg Glu Ser Glu
305                 310                 315                 320
```

```
Met Val Lys Leu Pro Lys Asn Phe Val Gln Asp Thr Ser Asp Arg Gly
                325                 330                 335

Leu Ile Val Asn Trp Cys Cys Gln Leu Gln Val Leu Ser His Lys Ala
            340                 345                 350

Val Ser Cys Phe Val Thr His Cys Gly Trp Asn Ser Thr Leu Glu Ala
        355                 360                 365

Leu Ser Leu Gly Val Pro Met Val Ala Ile Pro Gln Trp Ile Asp Gln
    370                 375                 380

Thr Thr Asn Ala Lys Phe Val Ala Asp Val Trp Arg Val Gly Val Arg
385                 390                 395                 400

Val Lys Lys Asn Glu Lys Ser Val Ala Ile Lys Glu Glu Leu Glu Ala
                405                 410                 415

Ser Ile Arg Lys Ile Val Val Gln Gly Asn Gly Thr Asn Glu Phe Lys
            420                 425                 430

Gln Asn Ala Ile Lys Trp Lys Asn Leu Ala Lys Glu Ala Val Asp Glu
        435                 440                 445

Arg Gly Ser Ser Asp Lys Asn Ile Glu Glu Phe Val Gln Ala Leu Val
    450                 455                 460

Ala Ser Asn
465


<210> SEQ ID NO 57
<211> LENGTH: 464
<212> TYPE: PRT
<213> ORGANISM: Cucumis sativus

<400> SEQUENCE: 57

Met Arg Asn His His Phe Leu Ile Val Cys Phe Pro Ser Gln Gly Tyr
1               5                   10                  15

Ile Asn Pro Ser Leu Gln Leu Ala Asn Lys Leu Thr Ser Leu Asn Ile
            20                  25                  30

Glu Val Thr Phe Ala Thr Thr Val Thr Ala Ser Arg Arg Met Lys Ile
        35                  40                  45

Thr Gln Gln Ile Ser Ser Pro Ser Thr Leu Ser Phe Ala Thr Phe Ser
    50                  55                  60

Asp Gly Phe Asp Asp Glu Asn His Lys Thr Ser Asp Phe Asn His Phe
65                  70                  75                  80

Phe Ser Glu Leu Lys Arg Cys Gly Ser Gln Ser Leu Thr Asp Leu Ile
                85                  90                  95

Thr Ser Phe Arg Asp Arg His Arg Arg Pro Phe Thr Phe Val Ile Tyr
            100                 105                 110

Ser Leu Leu Leu Asn Trp Ala Ala Asp Val Ala Thr Ser Phe Asn Ile
        115                 120                 125

Pro Ser Ala Leu Phe Ser Ala Gln Pro Ala Thr Val Leu Ala Leu Tyr
    130                 135                 140

Tyr Tyr Tyr Phe His Gly Phe Glu Asp Glu Ile Thr Asn Lys Leu Gln
145                 150                 155                 160

Asn Asp Gly Pro Ser Ser Leu Ser Ile Glu Leu Pro Gly Leu Pro Leu
                165                 170                 175

Leu Phe Lys Ser His Glu Met Pro Ser Phe Phe Ser Pro Ser Gly Gln
            180                 185                 190

His Ala Phe Ile Ile Pro Trp Met Arg Glu Gln Met Glu Phe Leu Gly
        195                 200                 205

Gln Gln Lys Gln Pro Ile Lys Val Leu Val Asn Thr Phe His Ala Leu
    210                 215                 220
```

Glu Asn Glu Ala Leu Arg Ala Ile His Glu Leu Glu Met Ile Ala Ile
225 230 235 240

Gly Pro Leu Ile Ser Gln Phe Arg Gly Asp Leu Phe Gln Val Ser Asn
245 250 255

Glu Asp Tyr Tyr Met Glu Trp Leu Asn Ser Lys Ser Asn Cys Ser Val
260 265 270

Val Tyr Leu Ser Phe Gly Ser Ile Cys Val Leu Ser Lys Glu Gln Glu
275 280 285

Glu Glu Ile Leu Tyr Gly Leu Phe Glu Ser Gly Tyr Pro Phe Leu Trp
290 295 300

Val Met Arg Ser Lys Ser Asp Glu Asp Glu Glu Lys Trp Lys Glu Leu
305 310 315 320

Val Glu Gly Lys Gly Lys Ile Val Ser Trp Cys Arg Gln Ile Glu Val
325 330 335

Leu Lys His Pro Ser Leu Gly Cys Phe Met Ser His Cys Gly Trp Asn
340 345 350

Ser Thr Leu Glu Ser Leu Ser Phe Gly Leu Pro Met Val Ala Phe Pro
355 360 365

Gln Gln Val Asp Gln Pro Thr Asn Ala Lys Leu Val Glu Asp Val Trp
370 375 380

Lys Met Gly Val Arg Val Lys Gly Asn Leu Glu Gly Ile Val Glu Arg
385 390 395 400

Glu Glu Ile Arg Arg Cys Leu Asp Leu Val Met Asn Arg Lys Tyr Ile
405 410 415

Asn Gly Glu Arg Glu Glu Thr Glu Lys Asn Val Glu Lys Trp Lys Lys
420 425 430

Leu Ala Trp Glu Ala Met Asp Glu Gly Gly Ser Ser Ile Leu Asn Leu
435 440 445

Ala Asn Phe Val Asp Glu Ile Asp Val Gly Asp Glu Leu Ala Asp Ser
450 455 460

<210> SEQ ID NO 58
<211> LENGTH: 471
<212> TYPE: PRT
<213> ORGANISM: Cucumis sativus

<400> SEQUENCE: 58

Met Gly Leu Ser Pro Thr Asp His Val Leu Leu Phe Pro Phe Pro Ala
1 5 10 15

Lys Gly His Ile Lys Pro Phe Phe Cys Leu Ala His Leu Leu Cys Asn
20 25 30

Ala Gly Leu Arg Val Thr Phe Leu Ser Thr Glu His His His Gln Lys
35 40 45

Leu His Asn Leu Thr His Leu Ala Ala Gln Ile Pro Ser Leu His Phe
50 55 60

Gln Ser Ile Ser Asp Gly Leu Ser Leu Asp His Pro Arg Asn Leu Leu
65 70 75 80

Asp Gly Gln Leu Phe Lys Ser Met Pro Gln Val Thr Lys Pro Leu Phe
85 90 95

Arg Gln Leu Leu Leu Ser Tyr Lys Asp Gly Thr Ser Pro Ile Thr Cys
100 105 110

Val Ile Thr Asp Leu Ile Leu Arg Phe Pro Met Asp Val Ala Gln Glu
115 120 125

Leu Asp Ile Pro Val Phe Cys Phe Ser Thr Phe Ser Ala Arg Phe Leu

```
    130                 135                 140

Phe Leu Tyr Phe Ser Ile Pro Lys Leu Leu Glu Asp Gly Gln Ile Pro
145                 150                 155                 160

Tyr Pro Glu Gly Asn Ser Asn Gln Val Leu His Gly Ile Pro Gly Ala
                165                 170                 175

Glu Gly Leu Leu Arg Cys Lys Asp Leu Pro Gly Tyr Trp Ser Val Glu
            180                 185                 190

Ala Val Ala Asn Tyr Asn Pro Met Asn Phe Val Asn Gln Thr Ile Ala
        195                 200                 205

Thr Ser Lys Ser His Gly Leu Ile Leu Asn Thr Phe Asp Glu Leu Glu
    210                 215                 220

Val Pro Phe Ile Thr Asn Leu Ser Lys Ile Tyr Lys Lys Val Tyr Thr
225                 230                 235                 240

Ile Gly Pro Ile His Ser Leu Leu Lys Lys Ser Val Gln Thr Gln Tyr
                245                 250                 255

Glu Phe Trp Lys Glu Asp His Ser Cys Leu Ala Trp Leu Asp Ser Gln
            260                 265                 270

Pro Pro Arg Ser Val Met Phe Val Ser Phe Gly Ser Ile Val Lys Leu
        275                 280                 285

Lys Ser Ser Gln Leu Lys Glu Phe Trp Asn Gly Leu Val Asp Ser Gly
    290                 295                 300

Lys Ala Phe Leu Leu Val Leu Arg Ser Asp Ala Leu Val Glu Glu Thr
305                 310                 315                 320

Gly Glu Glu Asp Glu Lys Gln Lys Glu Leu Val Ile Lys Glu Ile Met
                325                 330                 335

Glu Thr Lys Glu Glu Gly Arg Trp Val Ile Val Asn Trp Ala Pro Gln
            340                 345                 350

Glu Lys Val Leu Glu His Lys Ala Ile Gly Gly Phe Leu Thr His Ser
        355                 360                 365

Gly Trp Asn Ser Thr Leu Glu Ser Val Ala Val Gly Val Pro Met Val
    370                 375                 380

Ser Trp Pro Gln Ile Gly Asp Gln Pro Ser Asn Ala Thr Trp Leu Ser
385                 390                 395                 400

Lys Val Trp Lys Ile Gly Val Glu Met Glu Asp Ser Tyr Asp Arg Ser
                405                 410                 415

Thr Val Glu Ser Lys Val Arg Ser Ile Met Glu His Glu Asp Lys Lys
            420                 425                 430

Met Glu Asn Ala Ile Val Glu Leu Ala Lys Arg Val Asp Asp Arg Val
        435                 440                 445

Ser Lys Glu Gly Thr Ser Tyr Gln Asn Leu Gln Arg Leu Ile Glu Asp
    450                 455                 460

Ile Glu Gly Phe Lys Leu Asn
465                 470


<210> SEQ ID NO 59
<211> LENGTH: 452
<212> TYPE: PRT
<213> ORGANISM: Cucumis sativus

<400> SEQUENCE: 59

Met Asp Val Gln Lys Ser Arg Asp Thr Pro Thr Thr Ile Leu Met Leu
1               5                   10                  15

Pro Trp Ile Gly Tyr Gly His Leu Ser Ala Tyr Leu Glu Leu Ala Lys
            20                  25                  30
```

-continued

```
Val Leu Ser Arg Arg Asn Asn Phe Leu Ile Tyr Phe Cys Ser Thr Pro
        35                  40                  45

Val Asn Leu Asp Ser Ile Lys Pro Arg Leu Ile Pro Ser Ser Ser Ile
    50                  55                  60

Gln Phe Val Glu Leu His Leu Pro Ser Ser Pro Glu Phe Pro Pro His
65                  70                  75                  80

Leu His Thr Thr Asn Ala Leu Pro Pro Arg Leu Thr Pro Thr Leu His
                85                  90                  95

Lys Ala Phe Ala Ala Ala Ala Ser Pro Phe Glu Ala Ile Leu Gln Thr
            100                 105                 110

Leu Cys Pro His Leu Leu Ile Tyr Asp Ser Leu Gln Gln Trp Ala Pro
        115                 120                 125

Gln Ile Ala Ser Ser Leu Asn Ile Pro Ala Ile Asn Phe Asn Thr Thr
    130                 135                 140

Ala Ala Ser Ile Ile Ser His Ala Leu His Asn Ile Asn Tyr Pro Asp
145                 150                 155                 160

Thr Lys Phe Pro Leu Ser Asp Trp Val Leu His Asn Tyr Trp Lys Gly
                165                 170                 175

Lys Tyr Thr Thr Ala Asn Glu Ala Thr Leu Glu Arg Ile Arg Arg Val
            180                 185                 190

Arg Glu Ser Phe Leu Tyr Cys Leu Ser Ala Ser Arg Asp Ile Thr Leu
        195                 200                 205

Ile Ser Ser Cys Arg Glu Ile Glu Gly Glu Tyr Met Asp Tyr Leu Ser
    210                 215                 220

Val Leu Leu Lys Lys Lys Val Ile Ala Val Gly Pro Leu Val Tyr Glu
225                 230                 235                 240

Pro Arg Glu Asp Asp Glu Asp Glu Asp Tyr Ser Arg Ile Lys Asn Trp
                245                 250                 255

Leu Asp Lys Lys Glu Ala Leu Ser Thr Val Leu Val Ser Phe Gly Ser
            260                 265                 270

Glu Phe Phe Pro Ser Lys Glu Glu Met Glu Glu Ile Gly Cys Gly Leu
        275                 280                 285

Glu Glu Ser Gly Ala Asn Phe Ile Trp Val Ile Arg Ser Pro Lys Gly
    290                 295                 300

Glu Glu Asn Lys Arg Val Glu Glu Ala Leu Pro Glu Gly Phe Val Glu
305                 310                 315                 320

Lys Ala Gly Glu Arg Ala Met Ile Val Lys Glu Trp Ala Pro Gln Gly
                325                 330                 335

Lys Ile Leu Lys His Arg Ser Ile Gly Gly Phe Val Ser His Cys Gly
            340                 345                 350

Trp Asn Ser Val Met Glu Ser Ile Met Leu Gly Val Pro Val Ile Ala
        355                 360                 365

Val Pro Met His Val Asp Gln Pro Tyr Asn Ala Gly Leu Val Glu Glu
    370                 375                 380

Ala Gly Leu Gly Val Glu Ala Lys Arg Asp Pro Asp Gly Met Ile Gln
385                 390                 395                 400

Arg Glu Glu Val Ala Lys Leu Ile Arg Glu Val Val Val Asp Lys Ser
                405                 410                 415

Arg Glu Asp Leu Arg Thr Lys Val Ile Glu Met Gly Glu Ile Leu Arg
            420                 425                 430
```

-continued

```
Ser Lys Gly Asp Glu Lys Ile Asp Glu Met Val Ala Gln Ile Ser Leu
        435                 440                 445

Leu Leu Lys Ile
    450
```

CELLS COMPRISING MOGROSIDE PATHWAY ENZYMES AND USES THEREOF

RELATED APPLICATIONS

This application is a divisional of U.S. patent application Ser. No. 15/510,708 filed on Mar. 13, 2017, now abandoned, which is a National Phase of PCT Patent Application No. PCT/IL2015/050933 having International Filing Date of Sep. 10, 2015, which claims the benefit of priority under 35 USC § 119(e) of U.S. Provisional Patent Application Nos. 62/089,929 filed on Dec. 10, 2014 and 62/048,924 filed on Sep. 11, 2014. The contents of the above applications are all incorporated by reference as if fully set forth herein in their entirety.

SEQUENCE LISTING STATEMENT

The ASCII file, entitled 90380SequenceListing.txt, created on Dec. 28, 2021, comprising 190,048 bytes, submitted concurrently with the filing of this application is incorporated herein by reference.

FIELD AND BACKGROUND OF THE INVENTION

The present invention, in some embodiments thereof, relates to methods of producing mogrosides and compositions comprising same and uses thereof.

Mogrosides are triterpene-derived specialized secondary metabolites found in the fruit of the Cucurbitaceae family plant *Siraitia grosvenorii* (Luo Han Guo). Their biosynthesis in fruit involves number of consecutive glucosylations of the aglycone mogrol to the final sweet products mogroside V and mogroside VI (FIG. 1).

Mogroside V has been known in the food industry as a natural non-sugar food sweetener, with a sweetening capacity of ~250 times that of sucrose (Kasai R., et al., Sweet cucurbitane glycosides from fruits of *Siraitia siamensis* (chi-zi luo-han-guo), a Chinese folk medicine. Agric Biol Chem 1989, 53(12):3347-3349). Moreover, additional health benefits of mogrosides have been revealed in recent studies (Li et al., Chemistry and pharmacology of *Siraitia grosvenorii*: a review. Chin J Nat Med. 2014 12(2):89-102).

The parent aglycone compound mogrol is derived by successive hydroxylations of cucurbitadienol, the initial product of the stereospecific triterpene synthase, cucurbitadienol synthase. Cucurbitadienol is subsequently hydroxylated, by as yet undetermined enzymes, at the C11, C24 and C25 positions, leading to mogrol (FIG. 1). The trans C24, C25 di-hydroxylations are rare among the triterpenoid cucurbitadienol derivatives (Chen J C, et al., Cucurbitacins and cucurbitane glycosides: structures and biological activities. Nat. Prod. Rep. 2005, 22, 386-399) and thus makes the identification of the enzymes responsible a challenge. The mogrol is subsequently glucosylated at the C3 and C24 positions to varying degrees, from 1 to 6 glucosyl groups, in a temporally successive pattern during fruit development and the glucosylated mogrol compounds are termed mogrosides. The sweetness strength of the mogrosides increases with the additional glucose moieties such that M6 (with 6 glucosyl groups) is sweeter than M5, followed by M4, respectively (Kasai R., et al., Sweet cucurbitane glycosides from fruits of *Siraitia siamensis* (chi-zi luo-han-guo), a Chinese folk medicine. Agric Biol Chem 1989, 53(12): 3347-3349). The purified mogroside V, has been approved as a high-intensity sweetening agent in Japan (Jakinovich, W., Jr., Moon, C., Choi, Y. H., & Kinghorn, A. D. 1990. Evaluation of plant extracts for sweetness using the Mongolian gerbil. Journal of Natural Products, 53, 190-195) and the extract has gained generally recognized as safe (GRAS) status in the USA as a non-nutritive sweetener and flavor enhancer.

Extraction of mogrosides from the fruit can yield a product of varying degrees of purity, often accompanied by undesirable aftertaste. In addition, yields of mogroside from cultivated fruit are limited due to low plant yields and particular cultivation requirements of the plant. It is therefore advantageous to be able to produce sweet mogroside compounds via biotechnological processes.

Additional background art includes:

WO2013/076577 discloses enzymes of the UGT family (UDPglucose glycosyl transferase) from *Arabidopsis thaliana* and *Stevia rebaudiana*, plants which do not naturally produce mogroside. Four of these enzymes were capable of performing glycosylation of the aglycone mogrol, specifically the addition of single glucose moieties at the C24 positions to produce M1b. The fifth enzyme UGT73C5 from *Stevia rebaudiana* showed glycosylation at both C3 and C24.

WO 2014086842 discloses the cucurbitadienol synthase, the cyp450 that catalyzes C-11 OH production and some UGT polypeptides from *Siraitia grosvenorii*, shows that these enzymes function in yeast, and provide as well for methods for producing mogrosides. In addition, they also disclose 2 epoxide hydrolases, and demonstrate their ability to hydrate epoxysqualene, suggesting that they can hydrate epoxy cucurbitadienol as well. In particular the invention proposes various biosynthetic pathways useful for mogroside production and enzymes useful for mogroside production are provided. Furthermore, the invention provides recombinant hosts useful in performing the methods of the invention. Tang et al., An efficient approach to finding *Siraitia grosvenorii* triterpene biosynthetic genes by RNA-seq and digital gene expression analysis. BMC Genomics. 2011; 12: 343.

SUMMARY OF THE INVENTION

According to an aspect of some embodiments of the present invention there is provided an isolated uridine diphospho-glucosyl transferase enzyme (UGT) polypeptide comprising an amino acid sequence, wherein the polypeptide catalyzes primary glucosylation of mogrol at C24 and primary glucosylation of mogroside at C3.

According to some embodiments of the present invention the isolated UGT polypeptide catalyzes:

(a) primary glucosylation of mogrol at C24;

(b) primary glucosylation of mogroside at C3; and (c) branching glucosylation of mogroside at C3.

According to some embodiments of the present invention the amino acid sequence at least 34% identical to SEQ ID NO: 34.

According to some embodiments of the present invention the amino acid sequence is as set forth in SEQ ID NO: 34.

According to an aspect of some embodiments of the present invention there is provided an isolated uridine diphospho-glucosyl transferase enzyme (UGT) polypeptide comprising an amino acid sequence, wherein the polypeptide catalyzes branching glucosylation of mogroside at the (1-2) and (1-6) positions of C3 and branching glucosylation of mogroside at the (1-2) and (1-6) positions of C24.

According to an aspect of some embodiments of the present invention there is provided an isolated uridine diphospho-glucosyl transferase enzyme (UGT) polypeptide comprising an amino acid sequence wherein the polypeptide catalyzes branching glucosylation of mogroside M5 to mogroside M6.

According to some embodiments of the present invention the isolated UGT polypeptide catalyzes:

(a) branching glucosylation of mogroside at the (1-2) and (1-6) positions of C3;

(b) branching glucosylation of mogroside at the (1-2) and (1-6) positions of C24, and (c) branching glucosylation of mogroside M5 to mogroside M6.

According to some embodiments of the present invention the amino acid sequence is at least 89% identical to SEQ ID NO: 38.

According to an aspect of some embodiments of the present invention the amino acid sequence is as set forth in SEQ ID NO: 38.

According to an aspect of some embodiments of the present invention there is provided an isolated uridine diphospho-glucosyl transferase enzyme (UGT) polypeptide comprising an amino acid sequence, wherein the polypeptide catalyzes branching glucosylation of mogroside IV (M4) to mogroside V (M5).

According to some embodiments of the present invention the amino acid sequence is selected from the group consisting of a sequence at least 34% identical to SEQ ID NO: 34, a sequence at least 84% identical to SEQ ID NO: 6 and a sequence at least 89% identical to SEQ ID NO:38.

According to some embodiments of the present invention the amino acid sequence is as set forth in SEQ ID NO:6.

According to some embodiments of the present invention the amino acid sequence is as set forth in SEQ ID NO:38.

According to some embodiments of the present invention the amino acid sequence is as set forth in SEQ ID NO: 34.

According to some embodiments of the present invention the UGT is a plant UGT.

According to some embodiments of the present invention the plant is a plant of the Cucurbitaceae family.

According to some embodiments of the present invention the plant is *Siraitia grosvenorii.*

According to an aspect of some embodiments of the present invention there is provided an isolated squalene epoxidase (SQE) polypeptide comprising an amino acid sequence at least 94% identical to SEQ ID NO: 14 or 89% identical to SEQ ID NO: 16, wherein the polypeptide catalyzes diepoxysqualene synthesis from squalene or oxidosqualene.

According to some embodiments of the present invention the amino acid sequence is as set forth in SEQ ID NO: 14 or SEQ ID NO: 16.

According to some embodiments of the present invention the SQE is a plant SQE.

According to an aspect of some embodiments of the present invention there is provided an isolated epoxide hydrolase (EH) polypeptide comprising an amino acid sequence at least 75% identical to SEQ ID NO: 18, SEQ ID NO: 22 or SEQ ID NO: 24, wherein the polypeptide catalyzes 3, 24, 25 trihydroxy cucurbitadienol synthesis from 3-hydroxy, 24-25 epoxy cucurbitadienol.

According to some embodiments of the present invention the amino acid sequence is as set forth in any one of SEQ ID NO: 18, SEQ ID NO: 22 and SEQ ID NO: 24.

According to some embodiments of the present invention the EH is a plant EH.

According to an aspect of some embodiments of the present invention there is provided a method of synthesizing a mogrol or mogrol precursor product from a mogrol precursor substrate, the method comprising contacting at least one mogrol precursor substrate with a mogroside pathway enzyme, wherein:

(a) when the mogrol precursor product comprises diepoxy squalene and the mogrol precursor substrate comprises squalene or oxidosqualene, the mogroside pathway enzyme comprises a squalene epoxidase polypeptide as described in the present invention, thereby producing diepoxy squalene, (b) when the mogrol precursor product comprises 3 hydroxy, 24-25 epoxy cucurbitadienol and the mogrol precursor substrate comprises diepoxy squalene, the mogrol pathway enzyme comprises a cucurbitadienol synthetase polypeptide as set forth in SEQ ID NO: 12 or 60% homologous or identical thereto, thereby producing a 3 hydroxy, 24-25 epoxy cucurbitadienol, (c) when the product comprises 3, 24, 25 trihydroxy cucurbitadienol and the substrate comprises 3-hydroxy, 24-25 epoxy cucurbitadienol, the mogrol pathway enzyme comprises an epoxy hydratase polypeptide as described in the present invention, thereby producing a 3, 24, 25 trihydroxy cucurbitadienol, (d) when the product comprises mogrol and the mogrol precursor substrate comprises 3, 24, 25 trihydroxy cucurbitadienol, the mogrol pathway enzyme is Cytochrome P 450 enzyme as set forth in SEQ ID NO: 10 or 60% homologous or identical thereto, thereby producing 3, 11, 24, 25 tetrahydroxy cucurbitadienol (mogrol).

According to some embodiments of the present invention the Cytochrome P 450 enzyme comprises an amino acid sequence as set forth in SEQ ID NO: 10.

According to some embodiments of the present invention producing the mogrol product comprises at least one of:

(i) contacting the squalene or oxido squalene with the squalene epoxidase enzyme polypeptide, thereby producing diepoxy squalene;

(ii) contacting the diepoxy squalene with a cucurbitadienol synthase, thereby producing 3 hydroxy, 24-25 epoxy cucurbitadienol;

(iii) contacting the 3 hydroxy, 24-25 epoxy cucurbitadienol with the epoxy hydratase enzyme, thereby producing 3, 24, 25 trihydroxy cucurbitadienol; and (iv) contacting the 3, 24-25 trihydroxy cucurbitadienol with the Cytochrome P 450 enzyme, thereby producing the mogrol product (3, 11, 24, 25 tetrahydroxy cucurbitadienol).

According to some embodiments of the present invention producing the mogrol product comprises at least (i) and (iv), at least (ii) and (iv), at least (iii) and (iv), at least (i), (ii) and (iii), at least (i), (ii) and (iv), at least (i), (iii) and (iv), at least (ii), (iii) and (iv).

According to some embodiments of the present invention producing the mogrol product comprises all of (i) (ii), (iii) and (iv).

According to an aspect of some embodiments of the present invention there is provided a method of synthesizing a mogroside, the method comprising contacting at least one UGT polypeptide of the invention or a combination thereof with at least one UGT substrate mogroside precursor.

According to some embodiments of the present invention the at least one UGT polypeptide comprises the UGT polypeptide catalyzing primary glucosylation of mogrol at C24 and primary glucosylation of mogroside at C3 of the invention.

According to some embodiments of the present invention the at least one UGT polypeptide comprises the UGT polypeptide having an amino acid sequence as set forth in SEQ ID NO: 34.

According to some embodiments of the present invention the at least one UGT polypeptide comprises the UGT polypeptide of the invention catalyzing branching glucosylation of mogroside at the (1-2) and (1-6) positions of C3 and branching glucosylation of mogroside at the (1-2) and (1-6) positions of C24, and/or catalyzing branching glucosylation of mogroside M5 to mogroside M6.

According to some embodiments of the present invention the at least one UGT polypeptide comprises a UGT polypeptide of having an amino acid sequence as set forth in SEQ ID NO: 38.

According to some embodiments of the present invention the at least one UGT polypeptide comprises the UGT polypeptide of the invention catalyzing branching glucosylation of mogroside IV (M4) to mogroside V (M5).

According to some embodiments of the present invention the at least one UGT polypeptide comprises the UGT polypeptide having an amino acid sequence selected from the group consisting of a sequence at least 34% identical to SEQ ID NO: 34, a sequence at least 84% identical to SEQ ID NO: 6 and a sequence at least 89% identical to SEQ ID NO:38.

According to some embodiments of the present invention the at least one UGT polypeptide comprises the UGT polypeptide having an amino acid sequence as set forth in SEQ ID NO: 34 and the UGT polypeptide having an amino acid sequence as set forth in SEQ ID NO: 38.

According to some embodiments of the present invention, wherein the UGT substrate mogroside precursor substrate is a mogrol, the method comprises:

(a) producing a mogrol according to the method of the invention, and (b) synthesizing the mogroside from the mogrol according to the method of synthesizing mogroside of the invention.

According to some embodiments of the present invention the mogroside is selected from the group consisting of mogroside I-A1, mogroside I-E1, mogroside IIE, mogroside III, siamenoside, mogroside V and mogroside VI.

According to some embodiments of the present invention, the method, further comprises isolating the mogroside.

According to some embodiments of the present invention the method is performed in a recombinant cell exogenously expressing at least one of the mogroside pathway enzyme polypeptides of the invention or any combination thereof.

According to some embodiments of the present invention the at least one polypeptide is selected from the group consisting of a polypeptide having an amino acid sequence as set forth in SEQ ID NO: 34, a polypeptide having an amino acid sequence as set forth in SEQ ID NO: 38, a polypeptide having an amino acid sequence as set forth in SEQ ID NO: 14 or 16 and a polypeptide having an amino acid sequence as set forth in SEQ ID NO: 18, 22 or 24.

According to an aspect of some embodiments of the present invention there is provided a composition comprising a mogroside generated according to the method of mogroside biosynthesis of the invention.

According to an aspect of some embodiments of the present invention there is provided an isolated polynucleotide comprising a nucleic acid sequence encoding the isolated polypeptide of any one of the SE, CDS, EH, Cyt p450 and UGT enzyme polypeptides of the invention.

According to some embodiments of the present invention nucleic acid sequence is selected from the group consisting of SEQ ID NOs. 5, 9, 11, 13, 15, 17, 21, 23, 33 and 37.

According to an aspect of some embodiments of the present invention there is provided a nucleic acid construct comprising the isolated polynucleotide of the invention and a cis-acting regulatory element for directing expression of the isolated polynucleotide.

According to some embodiments of the present invention the cis-acting regulatory element comprises a promoter.

According to an aspect of some embodiments of the present invention there is provided a host cell heterologously expressing the isolated polynucleotide of the invention.

According to some embodiments of the present invention the host cell is of a microorganism.

According to some embodiments of the present invention the microorganism is selected from the group of yeast and bacteria.

According to some embodiments of the present invention the host cell is a plant host cell.

According to some embodiments of the present invention the host cell forms a part of a plant.

According to some embodiments of the present invention the plant is a transgenic plant.

According to some embodiments of the present invention the plant is of the Cucurbitaceae family.

According to some embodiments of the present invention the host cell forms a part of a fruit or root of the plant.

According to some embodiments of the present invention the host cell produces a mogroside or mogroside precursor in the host cell.

According to an aspect of some embodiments of the present invention there is provided a cell lysate of the host cell of the invention.

According to an aspect of some embodiments of the present invention there is provided a composition enriched in mogroside VI to a total concentration of mogroside VI of at least 10% (wt/wt).

According to an aspect of some embodiments of the present invention there is provided a composition comprising mogroside VI (M6) and mogroside II (M2).

According to an aspect of some embodiments of the present invention there is provided a composition comprising mogroside V (M5), VI (M6) and mogroside II (M2) According to some embodiments of the present invention concentration of the mogroside VI or mogroside V is sufficient to cause an enhancement in flavor.

According to some embodiments of the present invention a concentration of the mogroside VI is at least 0.2 ppm.

According to some embodiments of the present invention the composition is a sweetener.

According to some embodiments of the present invention the composition further comprises a flavor ingredient selected from the group consisting of sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, *stevia*, trilobatin.

According to some embodiments of the present invention the composition is a consumable composition.

According to some embodiments of the present invention the composition further comprises one or more additional flavor ingredients.

According to some embodiments of the present invention the composition is a beverage.

According to some embodiments of the present invention the beverage is selected from the group consisting of an aqueous beverage, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacao, tea-based drink, coffee-based drinks, cacao-based drink, syrup, dairy products, frozen fruit, frozen fruit juice, water-based ice, fruit ice, sorbet, dressing, salad dressing, sauce, soup, and beverage botanical materials, or instant powder for reconstitution.

According to some embodiments of the present invention the composition is Coca-Cola® and the like.

According to some embodiments of the present invention the composition is a solid consumable.

According to some embodiments of the present invention the solid consumable is selected from the group consisting of cereals, baked food products, biscuits, bread, breakfast cereal, cereal bar, dairy product, energy bars/nutritional bars, granola, cakes, cookies, crackers, donuts, muffins, pastries, confectioneries, chewing gum, chocolate, fondant, hard candy, marshmallow, pressed tablets, snack foods, botanical materials (whole or ground), and instant powders for reconstitution.

According to some embodiments of the present invention the composition is a foodstuff.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
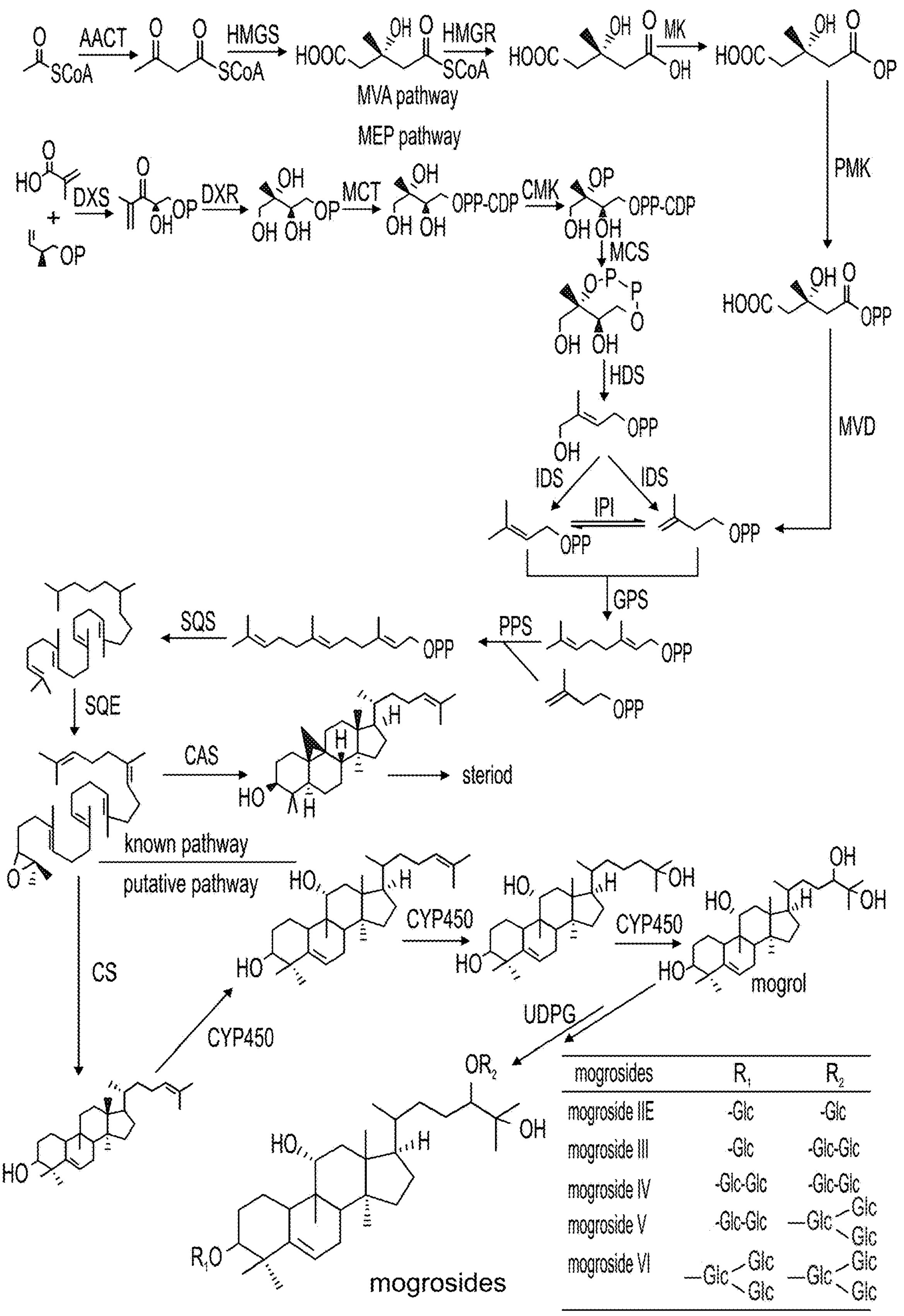
Figure 2:
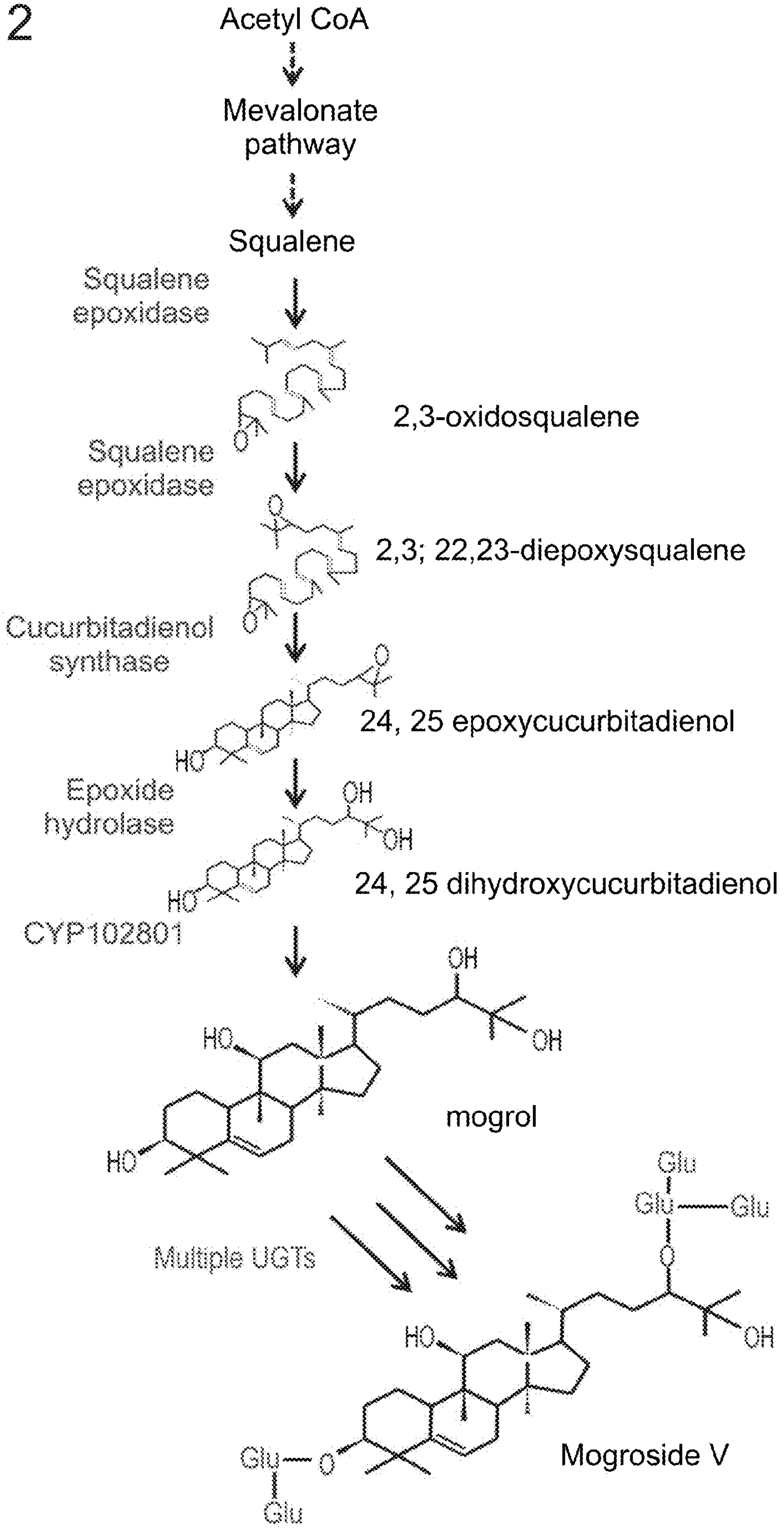
Figure 5A:
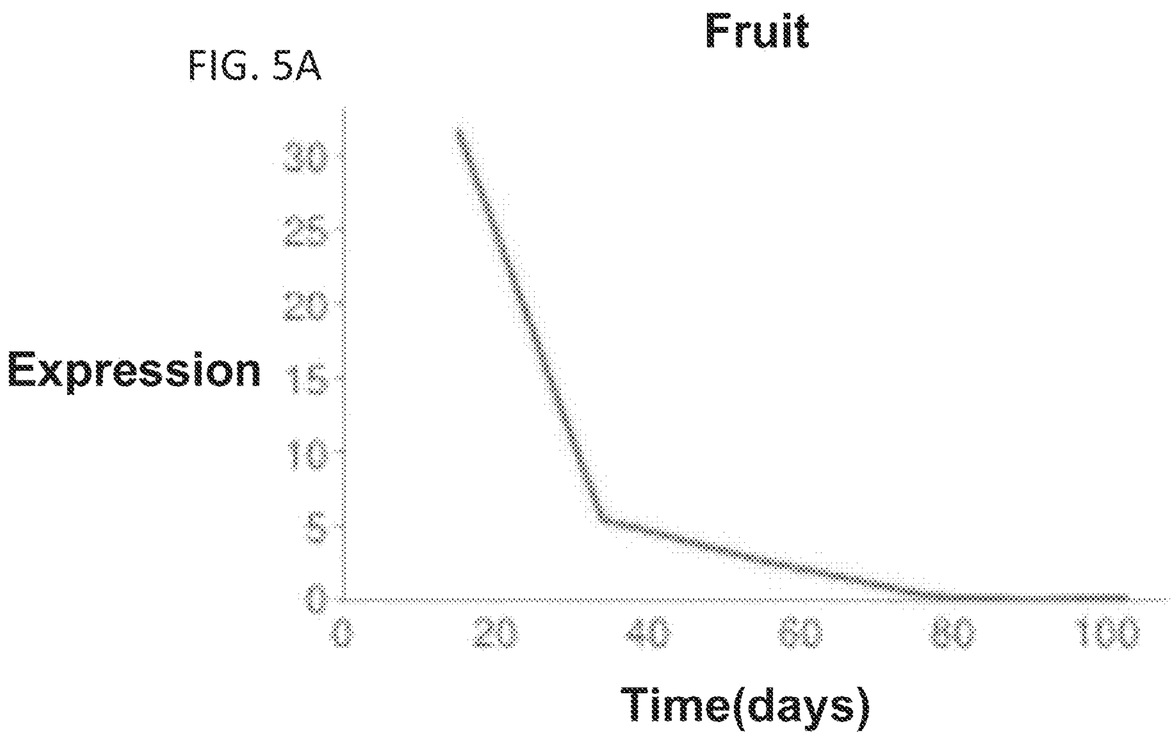
Figure 5B:
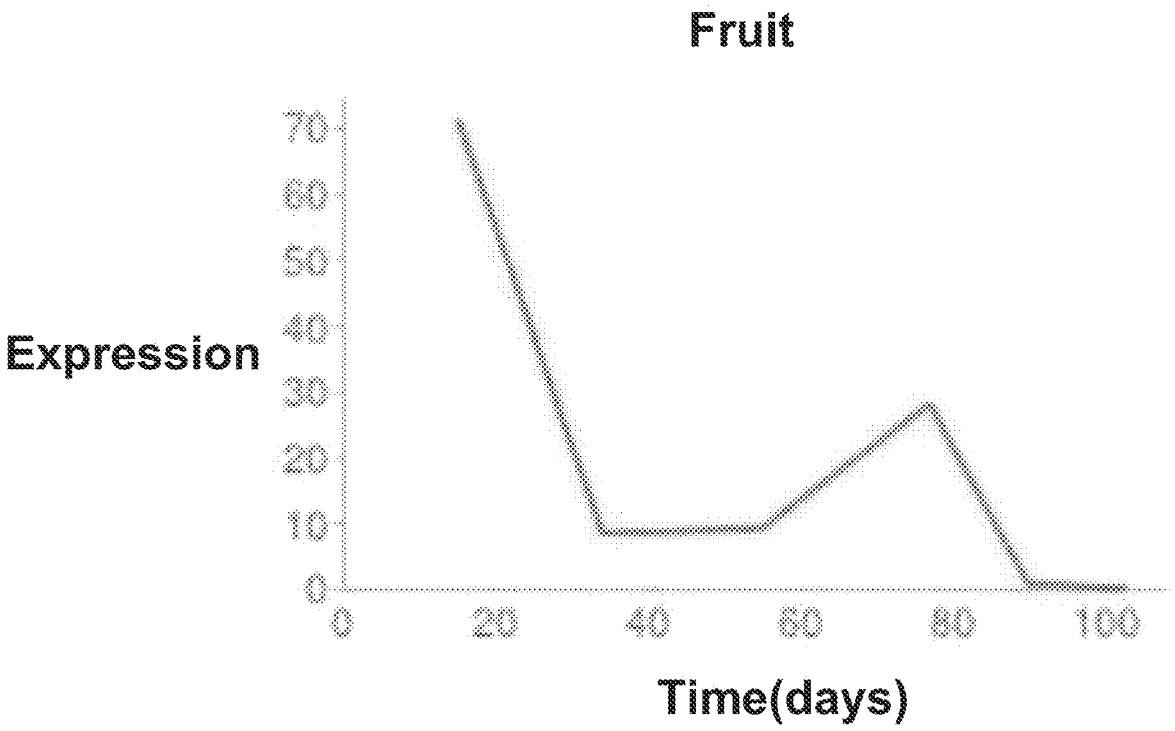
Figures 6A, 6B, 6C:
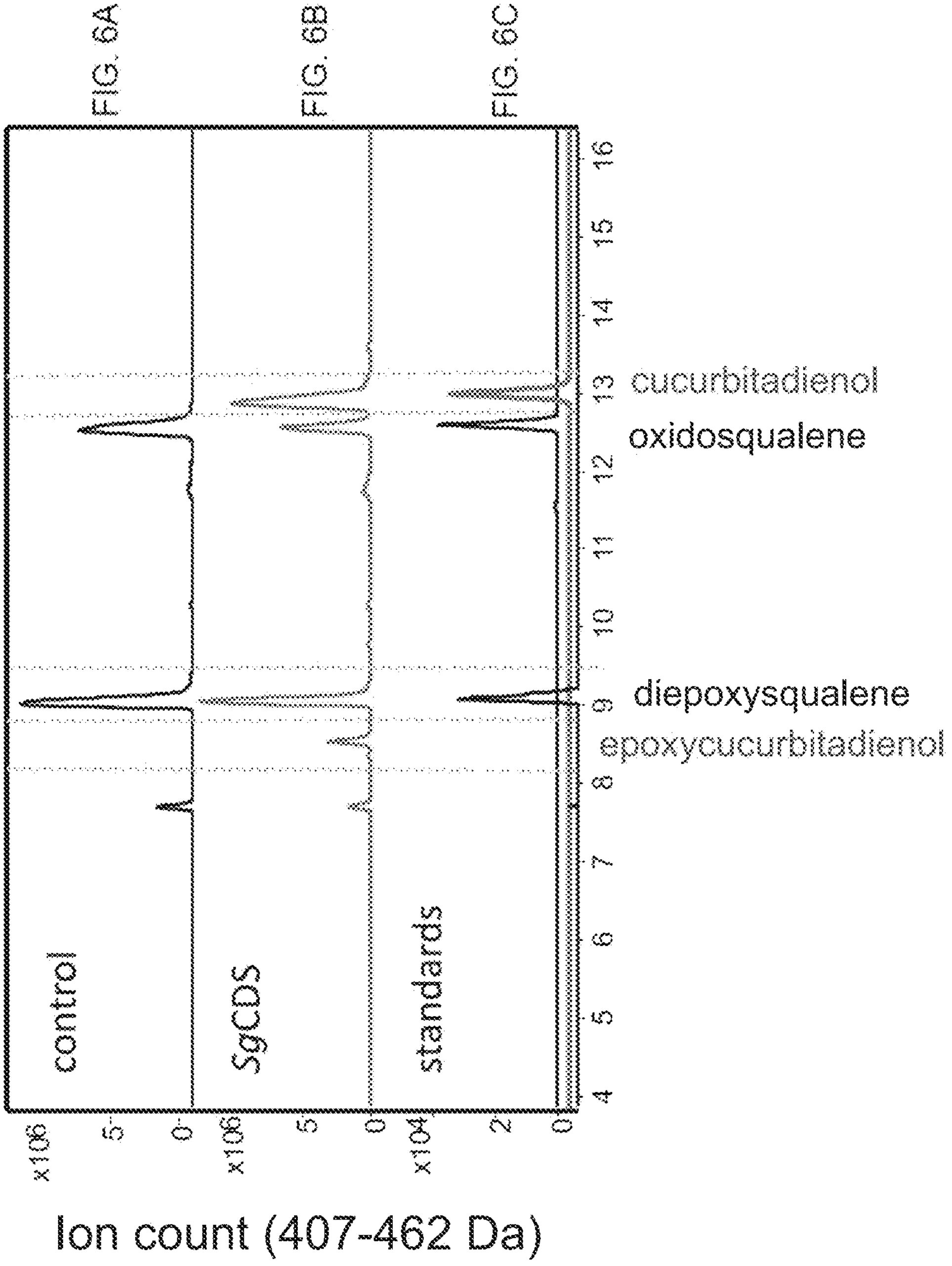
Figure 7:
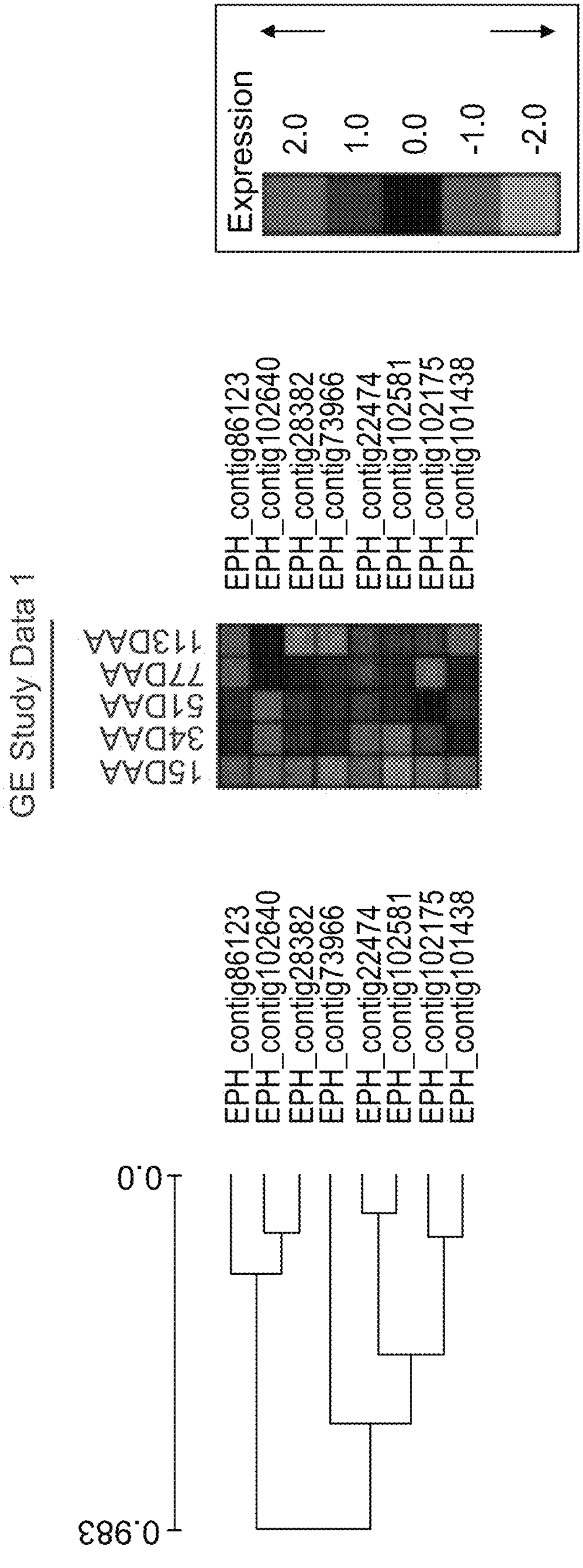
Figure 8A:
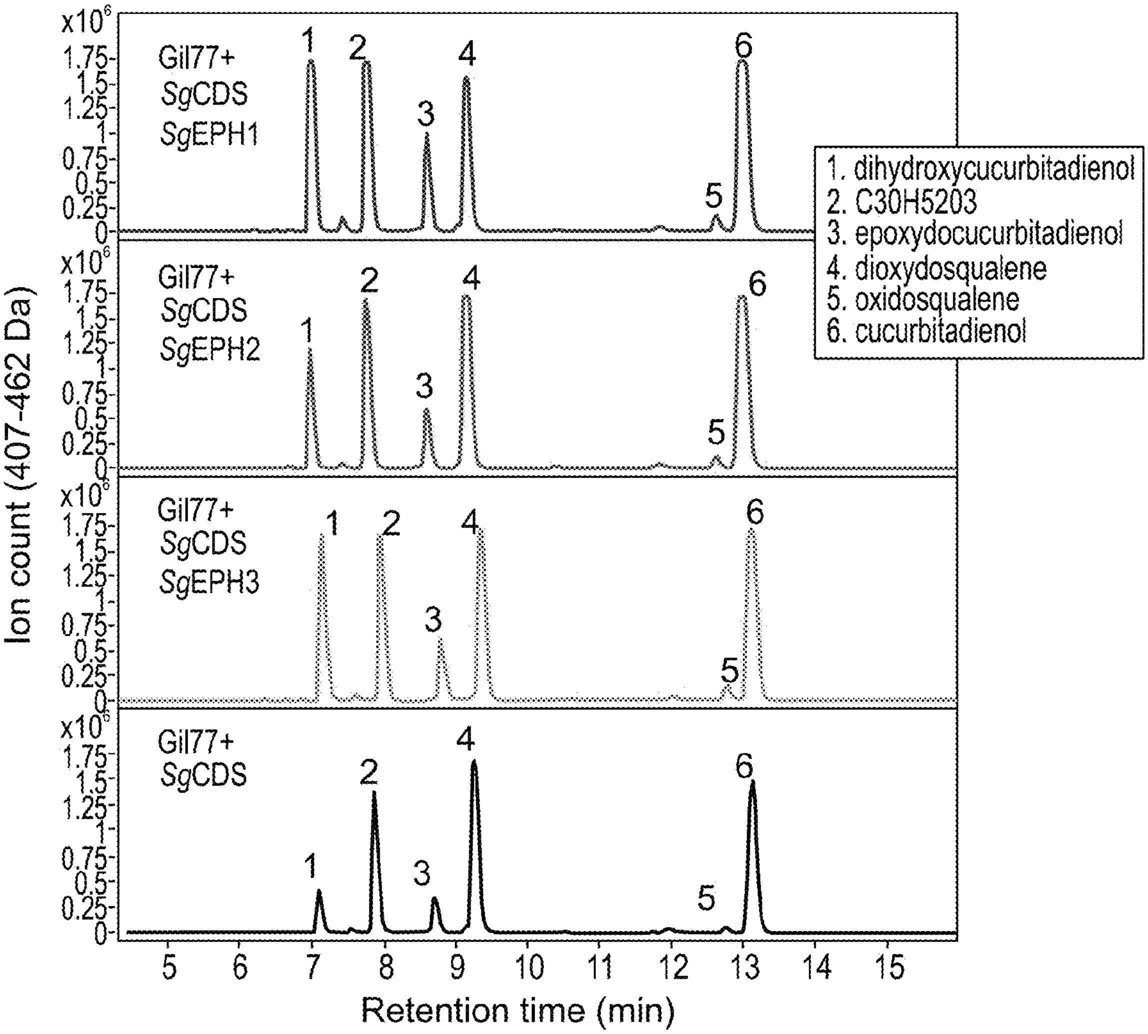
Figure 8B:
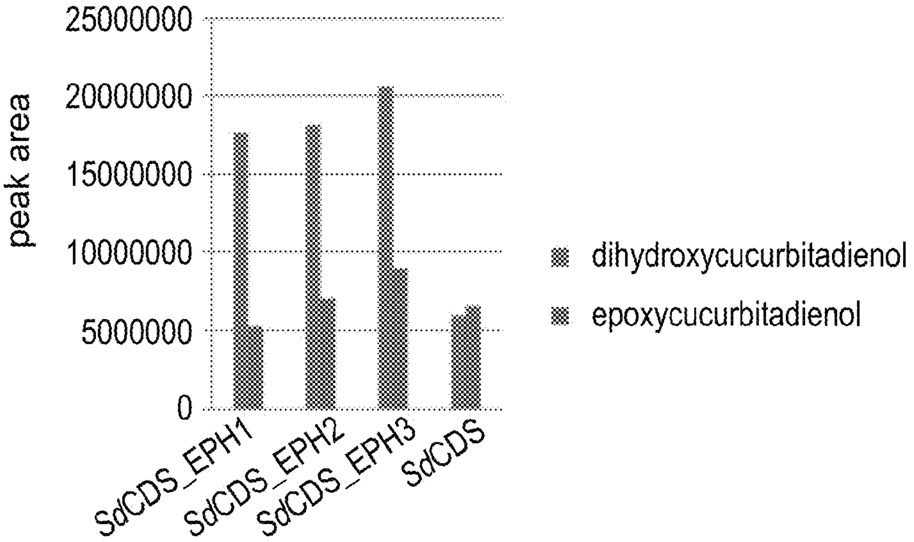
Figure 10:
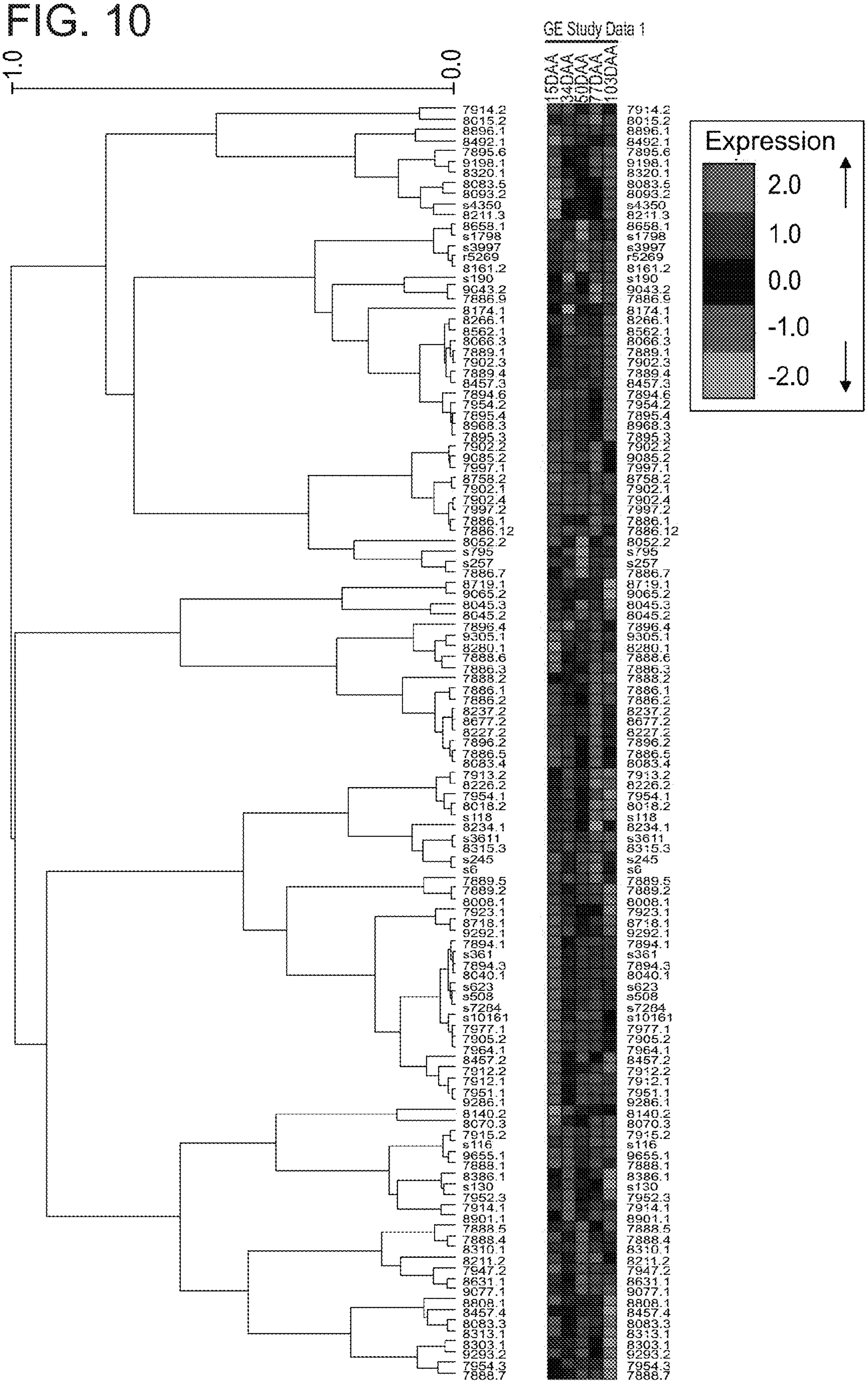
Figures 11A, 11B, 11C:
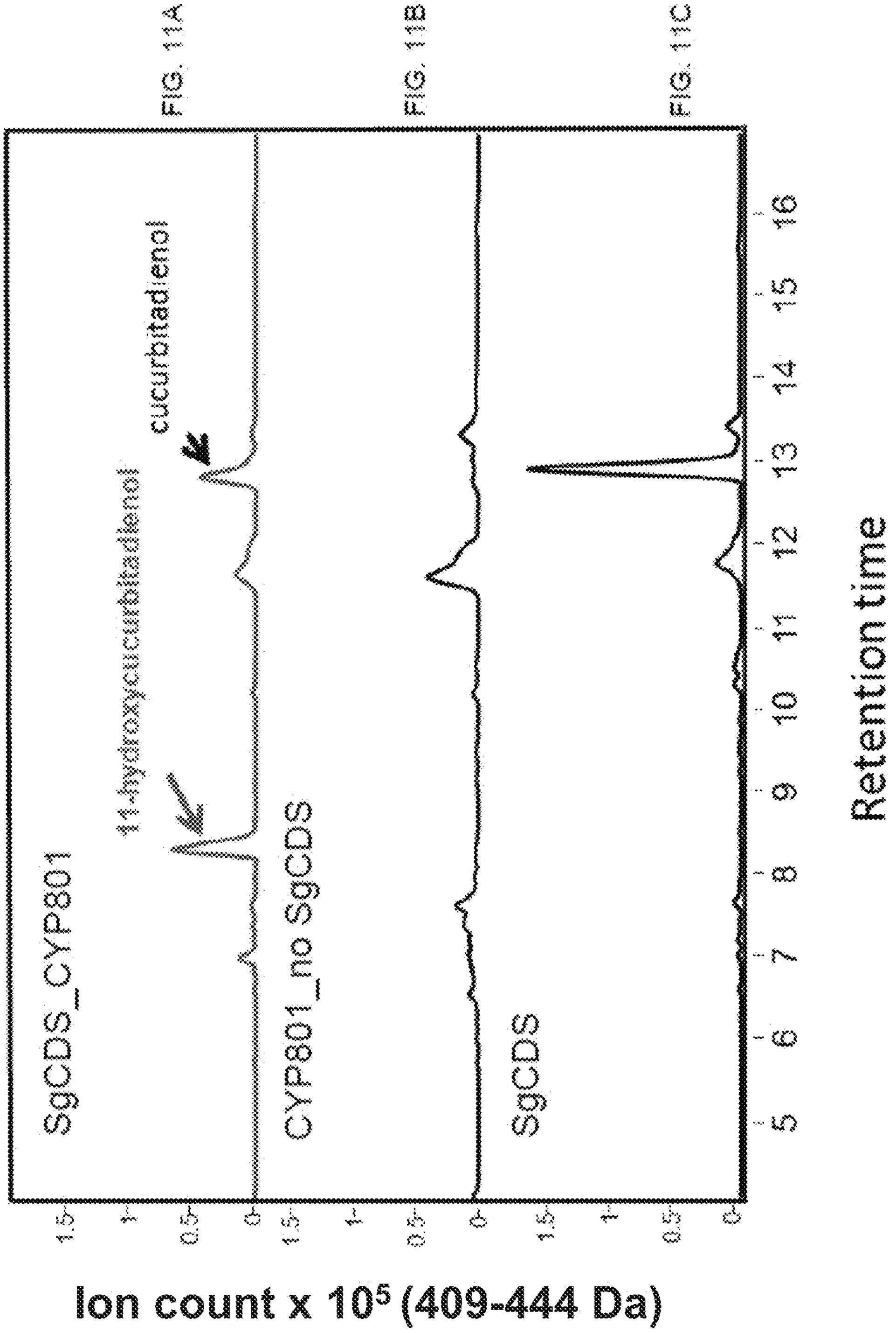

FIG. 1 is an illustration (adapted from Tang et al., An efficient approach to finding Siraitia grosvenorii triterpene biosynthetic genes by RNA-seq and digital gene expression analysis. BMC Genomics. 2011; 12: 343). Putative mogrosides biosynthesis pathway in Siraitia grosvenorii. AACT: acetyl-CoA acetyltransferase, EC:2.3.1.9; HMGS: hydroxymethylglutaryl-CoA synthase, EC:2.3.3.10; HMGR: 3-hydroxy-3-methylglutaryl-coenzyme A reductase, EC:1.1.1.34; MK: mevalonate kinase, EC:2.7.1.36; PMK: phosphomevalonate kinase, EC:2.7.4.2; MVD: diphosphomevalonate decarboxylase, EC:4.1.1.33; DXS: 1-deoxy-D-xylulose-5-phosphate synthase, EC:2.2.1.7; DXR: 1-deoxy-D-xylulose-5-phosphate reductoisomerase, EC:1.1.1.267; MCT: 2-C-methyl-D-erythritol 4-phosphate cytidylyltransferase, EC:2.7.7.60; CMK: 4-diphosphocytidyl-2-C-methyl-D-erythritol kinase, EC:2.7.1.148; MCS: 2-C-methyl-D-erythritol 2,4-cyclodiphosphate synthase, EC:4.6.1.12; HDS: 4-hydroxy-3-methylbut-2-enyl diphosphate synthase, EC:1.17.7.1; IDS: 4-hydroxy-3-methylbut-2-enyl diphosphate reductase (isopentenyl/dimethylallyl diphosphate synthase), EC:1.17.1.2; IPI: isopentenyl-diphosphate delta-isomerase, EC:5.3.3.2; GPS: geranyl diphosphate synthase, EC:2.5.1.1; FPS: farnesyl diphosphate synthase/farnesyl pyrophosphate synthetase, EC:2.5.1.10; SQS: squalene synthetase; CAS: cycloartenol synthase, EC:2.5.1.21; SQE: squalene epoxidase, EC:1.14.99.7; CS: cucurbitadienol synthase, EC:5.4.99.8; P450: cytochrome P450, EC:1.14.-.-; and UDPG: UDP-glucosyltransferase, EC:2.4.1. E.C. 2.4.1 are UGTs;

FIG. 2 is an illustration of the proposed pathway of mogroside synthesis in Siraitia fruit;

FIG. 3 illustrates the numbering system for compounds related to 2,3;22,23-dioxidosqualene (linear, above) and mogrol (cyclized, below), showing the key numbered carbons (blue);

FIGS. 4A-4B are graphic illustrations showing mogroside levels in a course of Siraitia fruit development and ripening. Note the progressive loss of M2 and M3, and concomitant increase in M4 and M5 (FIG. 4B), indicating sequential glucosylation. Values are expressed as relative to highest mogroside content in FIG. 4A, and the relative amount of each compound in FIG. 4B, based on peak area of the chromatograms;

FIGS. 5A and 5B are graphs illustrating the relative expression patterns of squalene epoxidase 1 (FIG. 5A) and squalene epoxidase 2 (FIG. 5B). In the developing Siraitia fruit showing relatively high expression in the youngest fruit;

FIGS. 6A-6C show HPLC-MS chromatograms illustrating production of both 2,3-monooxidosqualene and 2,3;22,23-dioxidosqualene in the yeast host (FIG. 6A); cyclicization of these substrates to both cucurbitadienol and 24,25-epoxycucurbitadienol in yeast hosts expressing Siraitia cucurbitadienol synthase (SgCDS) (FIG. 6B). FIG. 6C—substrate and product standards. Both cucurbitadienol and 24,25-epoxycucurbitadienol were identified by MS and NMR in the yeast extracts;

FIG. 7 is a hierarchical cluster heat map of expression patterns of the 8 epoxide hydrolase genes expressed in the developing Siraitia fruit. The five stages of fruit development presented are 15, 34, 51, 77 and 103 days and correspond to the fruit development stages in FIGS. 4A and 4B;

FIGS. 8A-8B illustrate the effect of epoxide hydrolase expression on 24,25-dihydroxycucurbitadienol. FIG. 8A shows LC-MS chromatograms demonstrating the increase in 24,25-dihydroxycucurbitadienol due to the expression of epoxide hydrolase genes in extracts of yeast expressing cucurbitadienol synthase (SgCDS). The top three chromatograms show the effect of EPH1, 2 and 3 (SEQ ID NOs. 17, 19 and 21), respectively. The bottom chromatogram shows the control yeast harboring the CDS without the additional EPH genes. FIG. 8B is a graph showing the relative levels of 24,25-dihydroxycucurbitadienol (compound 1 of FIG. 8A) and 24,25-epoxycucurbitadienol (compound 3 of FIG. 8A) in the control and EPH-expressing yeast lines;

FIG. 9 is an identity-similarity matrix of reported *Siraitia* Epoxide Hydrolase protein sequences. The sequences in green [encoded by contig_6184 (SEQ ID NO: 39) and contig_8262 (SEQ ID NO: 40)] are from the database reported in Tang et al., (2011) and reported as SEQ ID NOs. 38 and 40, respectively of US2015/0064743. Sequences encoded by contigs 101438, 102175, 102581 and 22474 are SEQ ID NOs. 41, 42, 43 and 44, respectively. The matrix was prepared using the ClustalOmega program (www(dot)ebi(dot)ac(dot)uk/Tools/msa/clustalo/);

FIG. 10 is a hierarchical cluster heat map of expression patterns of the cytochrome P450 genes expressed in the developing *Siraitia* fruit. The five stages of fruit development presented are 15, 34, 51, 77 and 103 days and correspond to the fruit development stages in FIGS. 4A and 4B; Approximately 40 candidates were functionally expressed and assayed for cucurbitadienol hydroxylation activity;

FIGS. 11A-11C are HPLC-MS chromatograms showing the C11-hydroxylation of cucurbitadienol by the Cytochrome P 450 cyp102801 (SEQ ID NO: 10) (FIG. 11A).

Figure 13A:
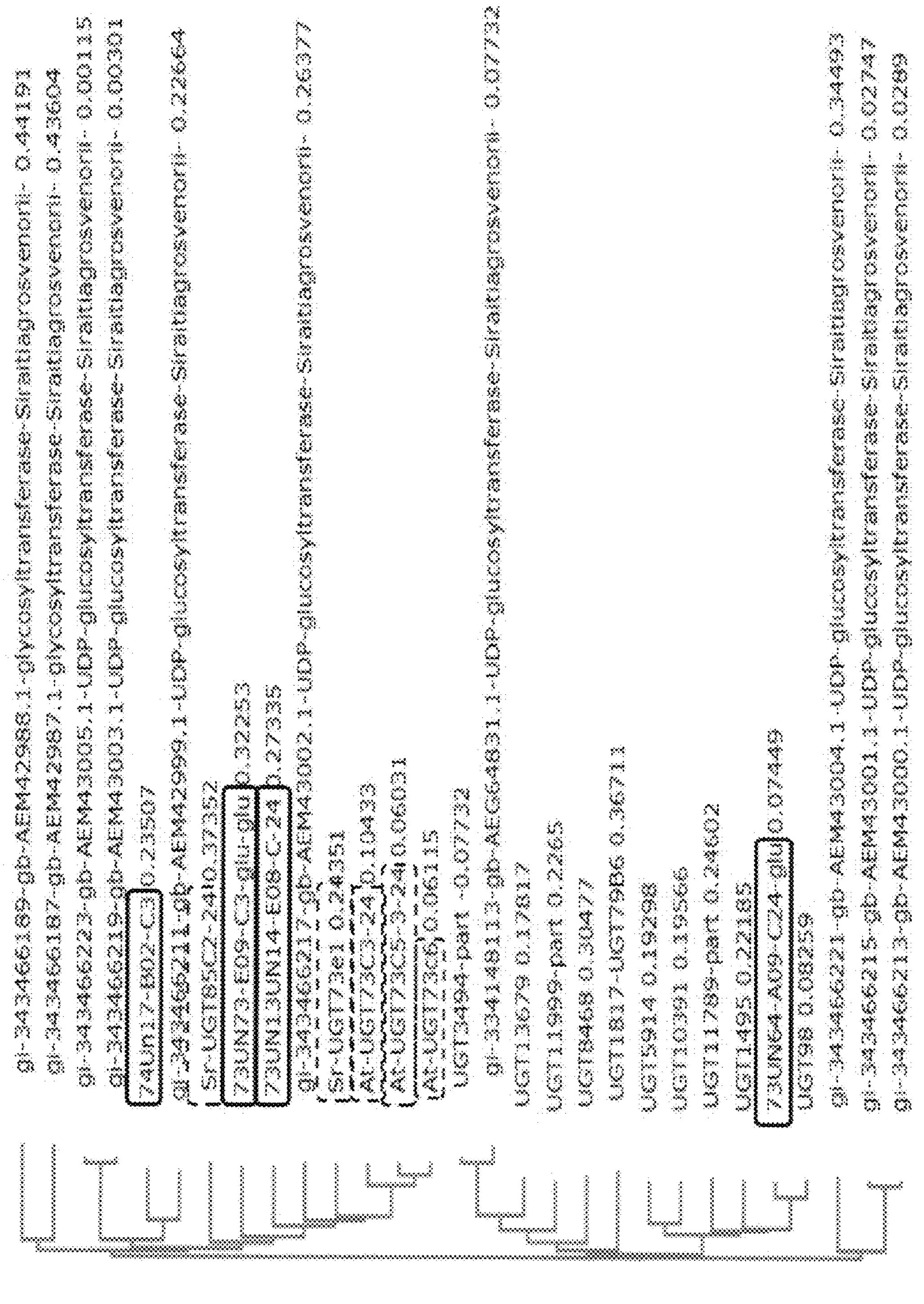
Figure 13A:
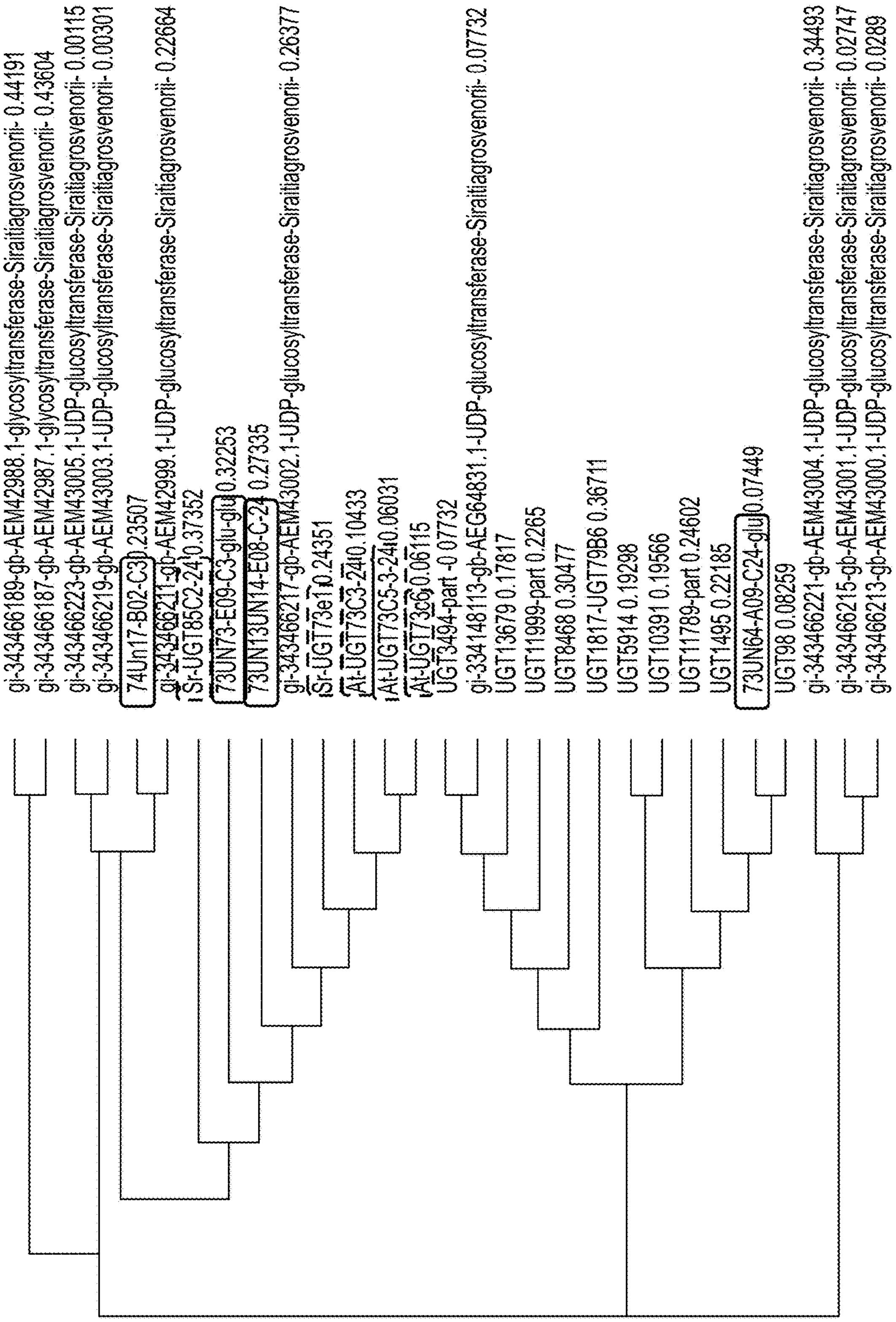
Figure 13B:
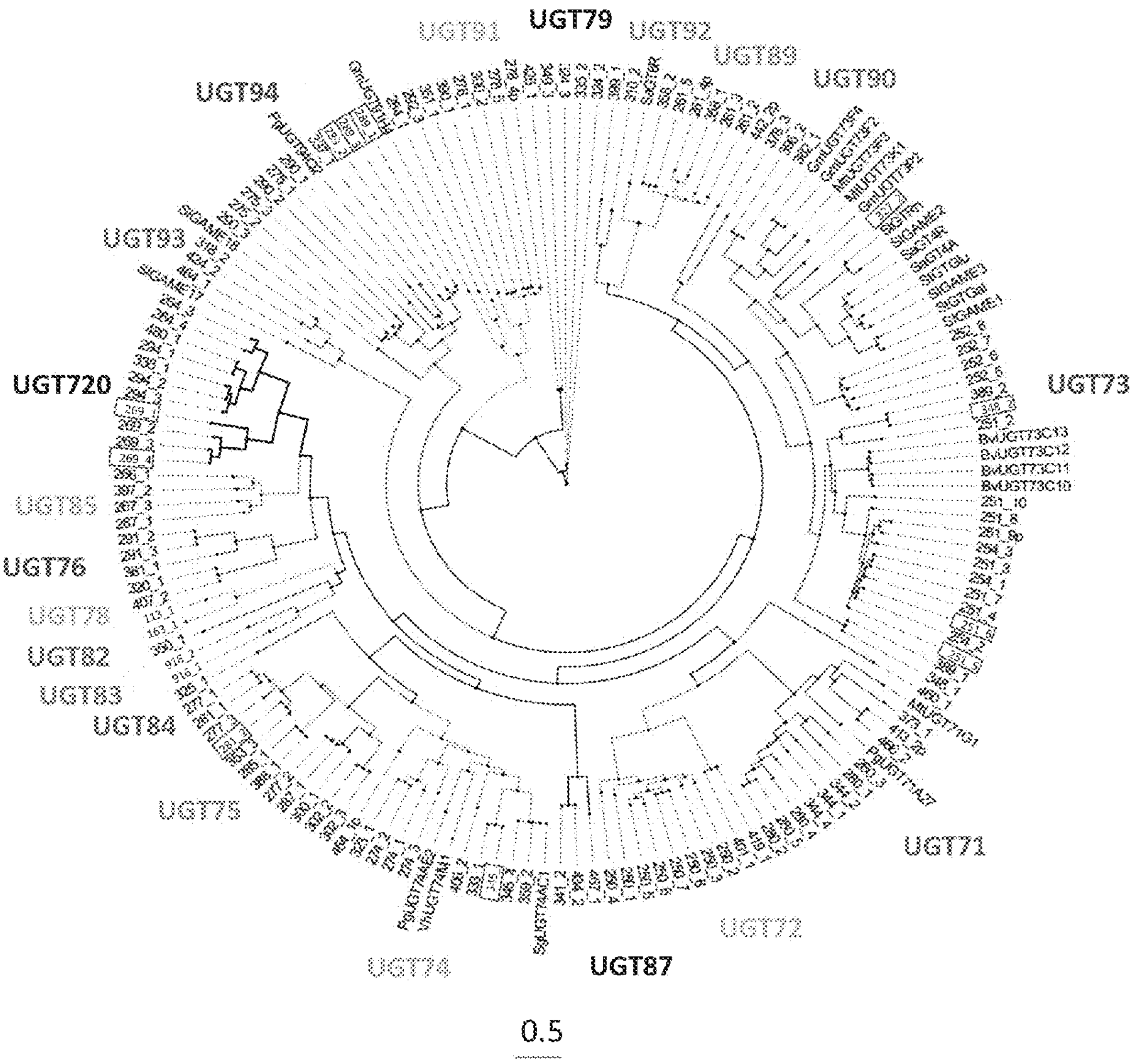

FIG. 11B shows a chromatogram of the extract from the yeast line (devoid of CDS (cucurbitadienol synthase expression) expressing cyp102801. FIG. 11C shows a chromatogram of yeast extract from yeast hosts expressing CDS but not cyp102801;

FIG. 12 is a list of the mogroside substrates used for the screening of glucosyltransferase activity, identifying the substrates according to various nomenclature, and their source and the method used to identify them;

FIGS. 13A-13B show a phylogenetic analysis of Uridine diphosphate glucosyl transferase (UGT) sequences of some embodiments of the invention. FIG. 13A is a phylogenetic analysis of UGT protein sequences from a Clustal Omega alignment.

Figure 14:
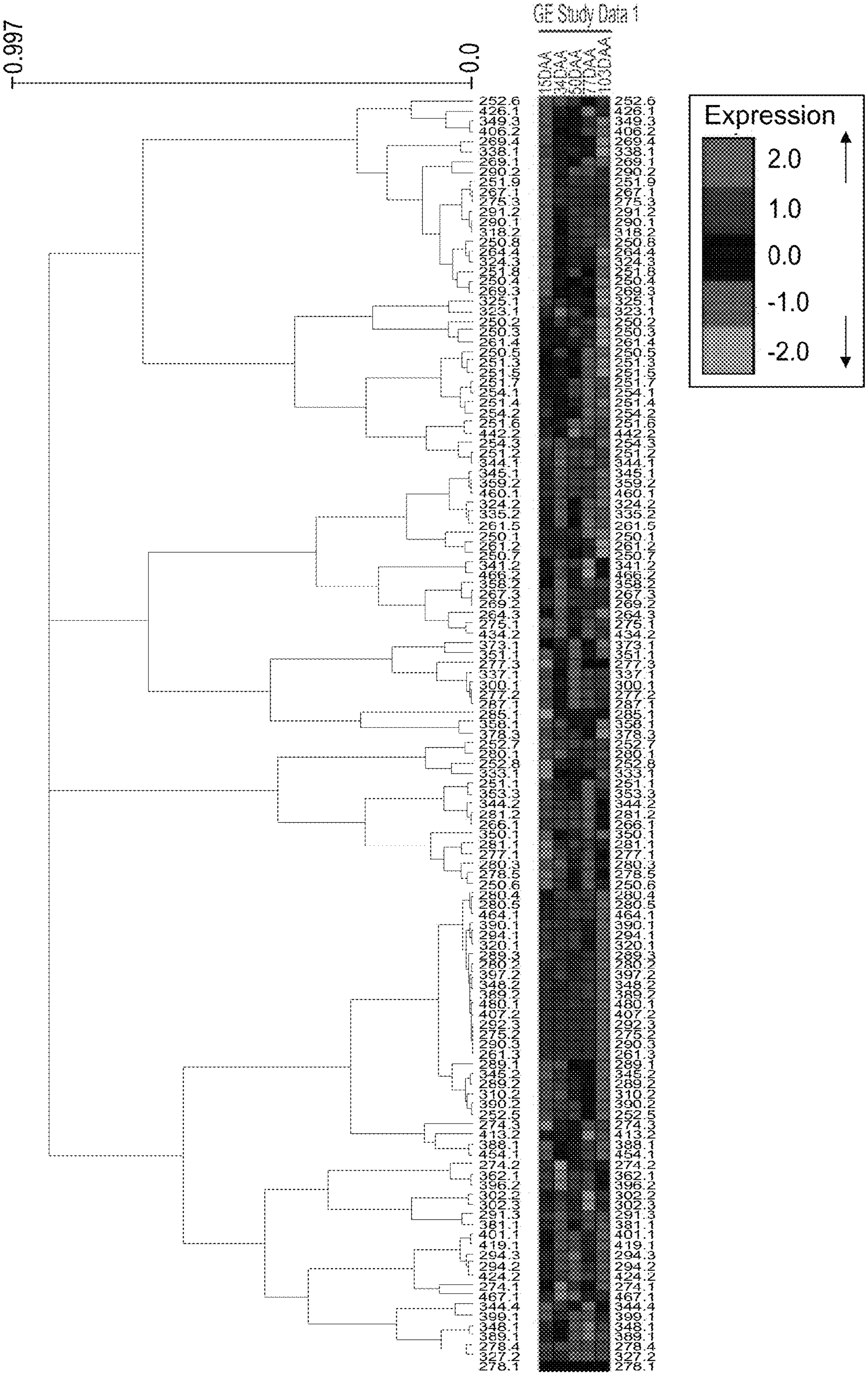
Figure 15A:
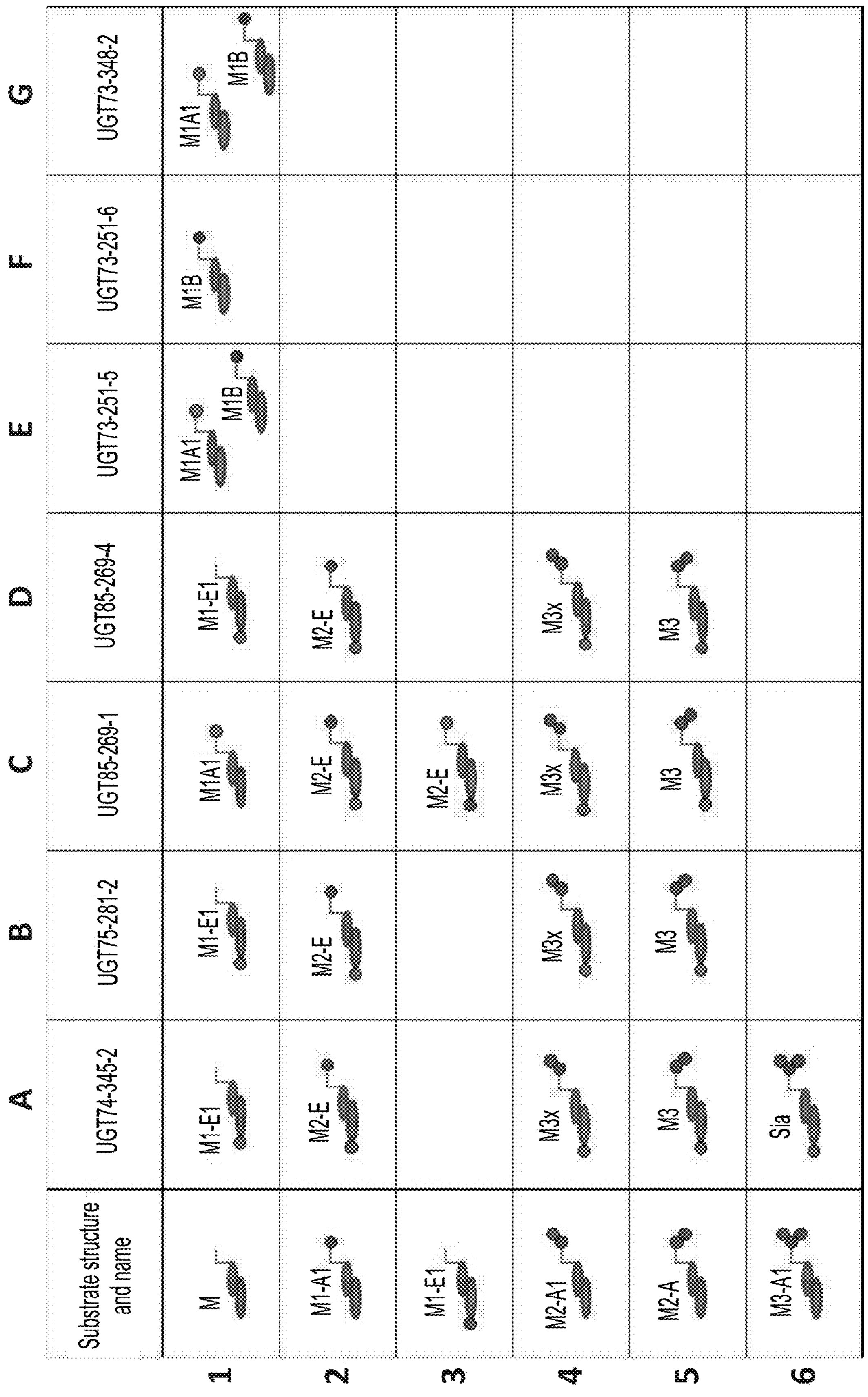
Figure 15B:
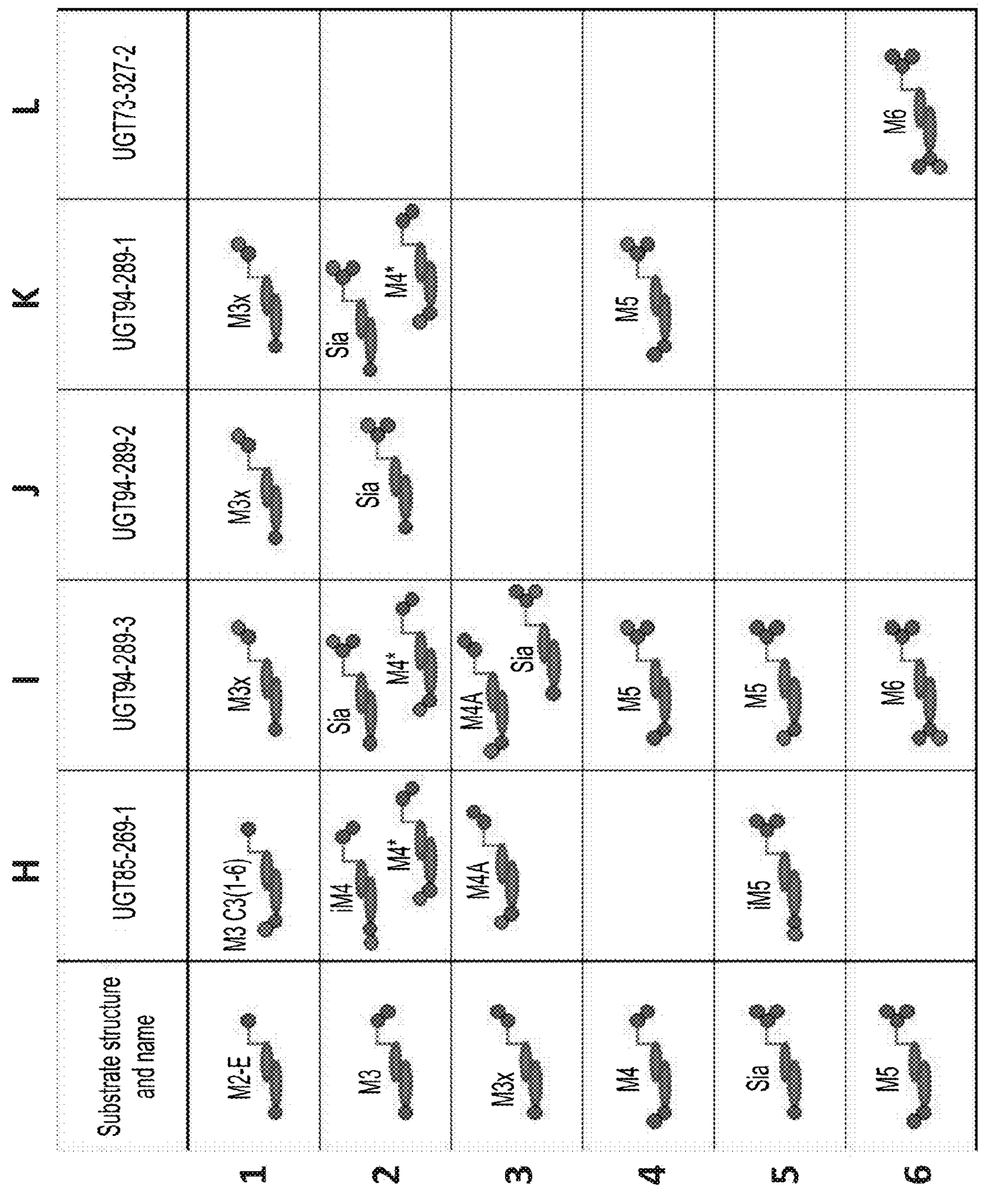
Figure 15C:
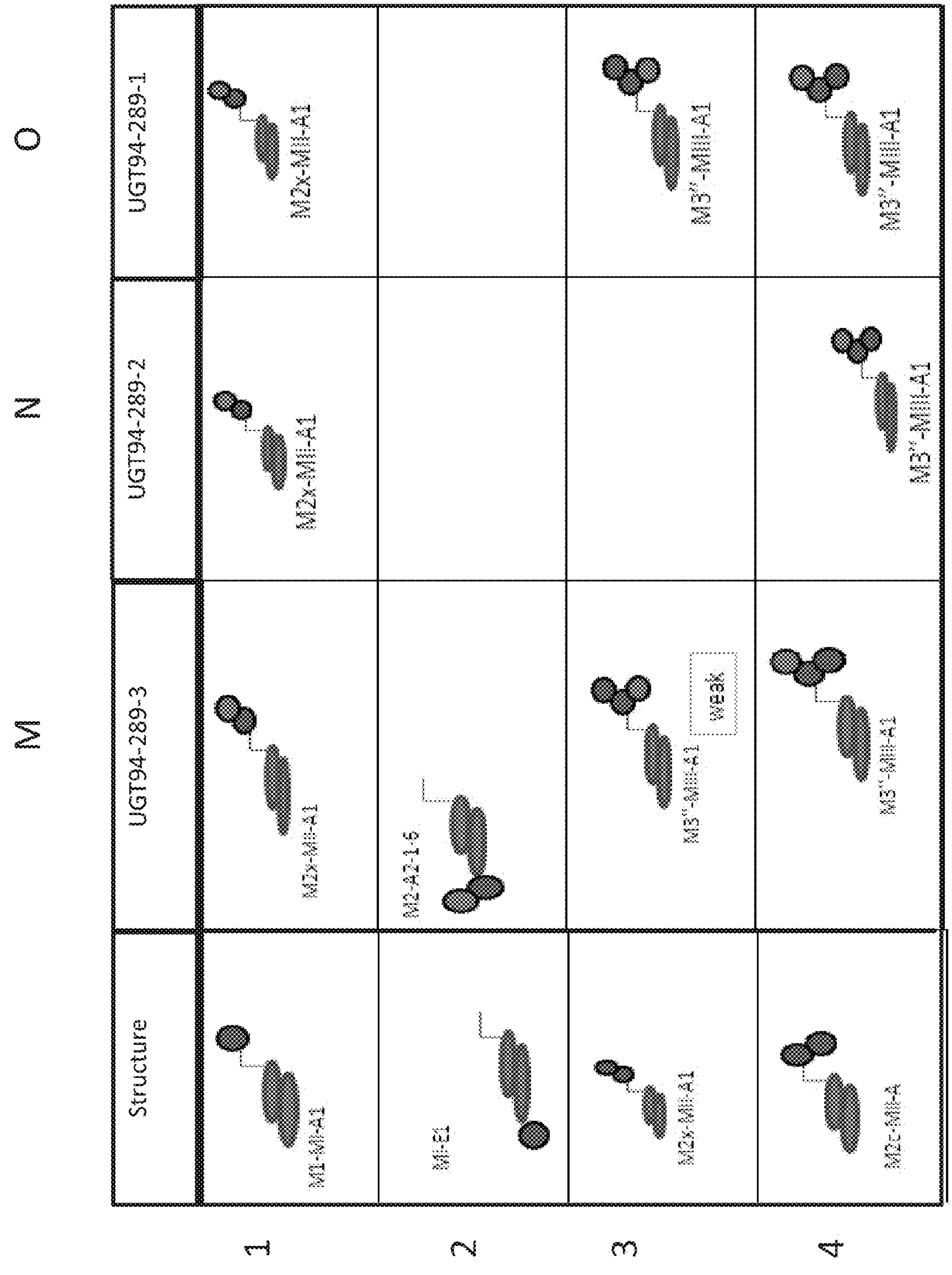
Figure 16:
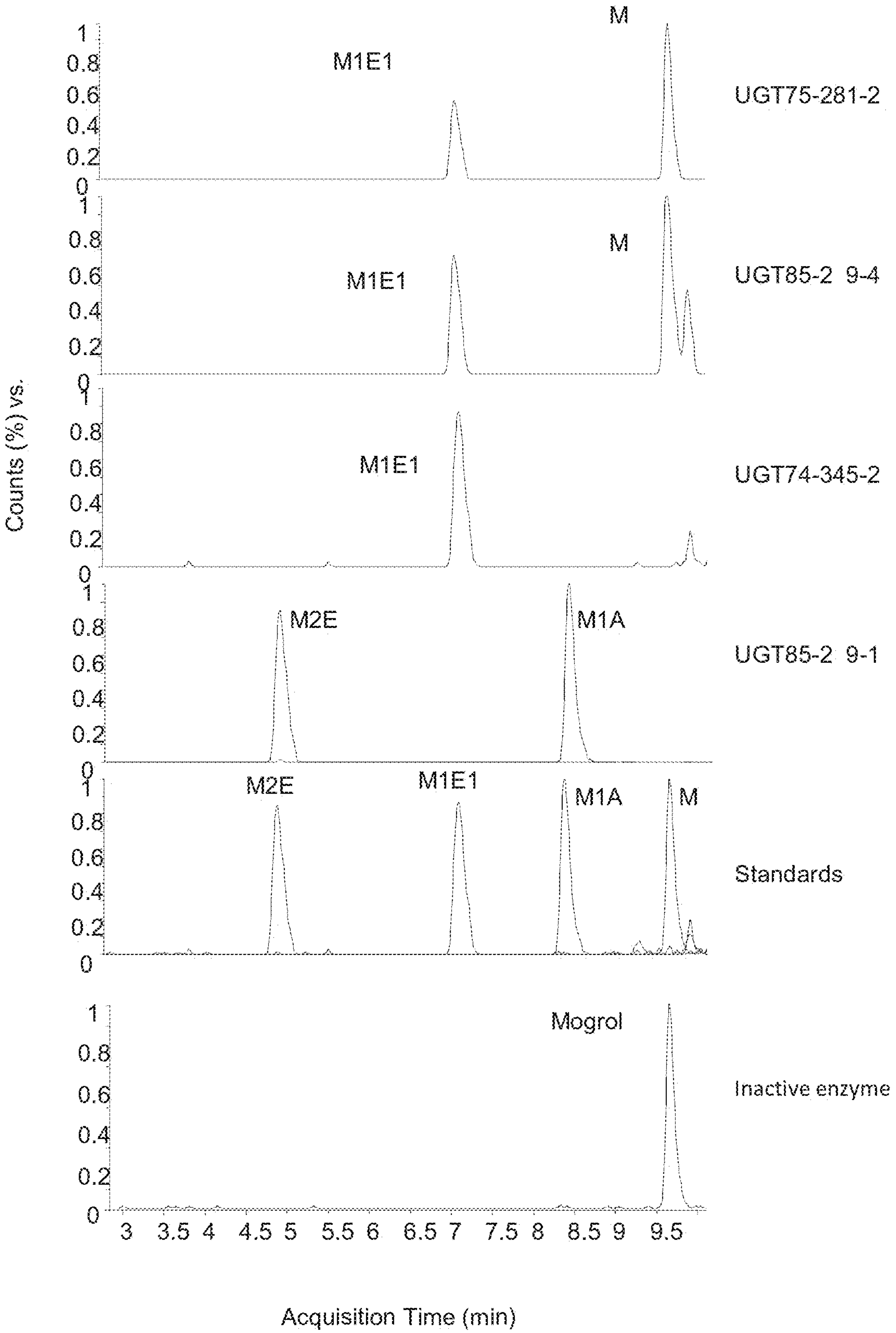
Figures 17A, 17B, 17C, 17D:
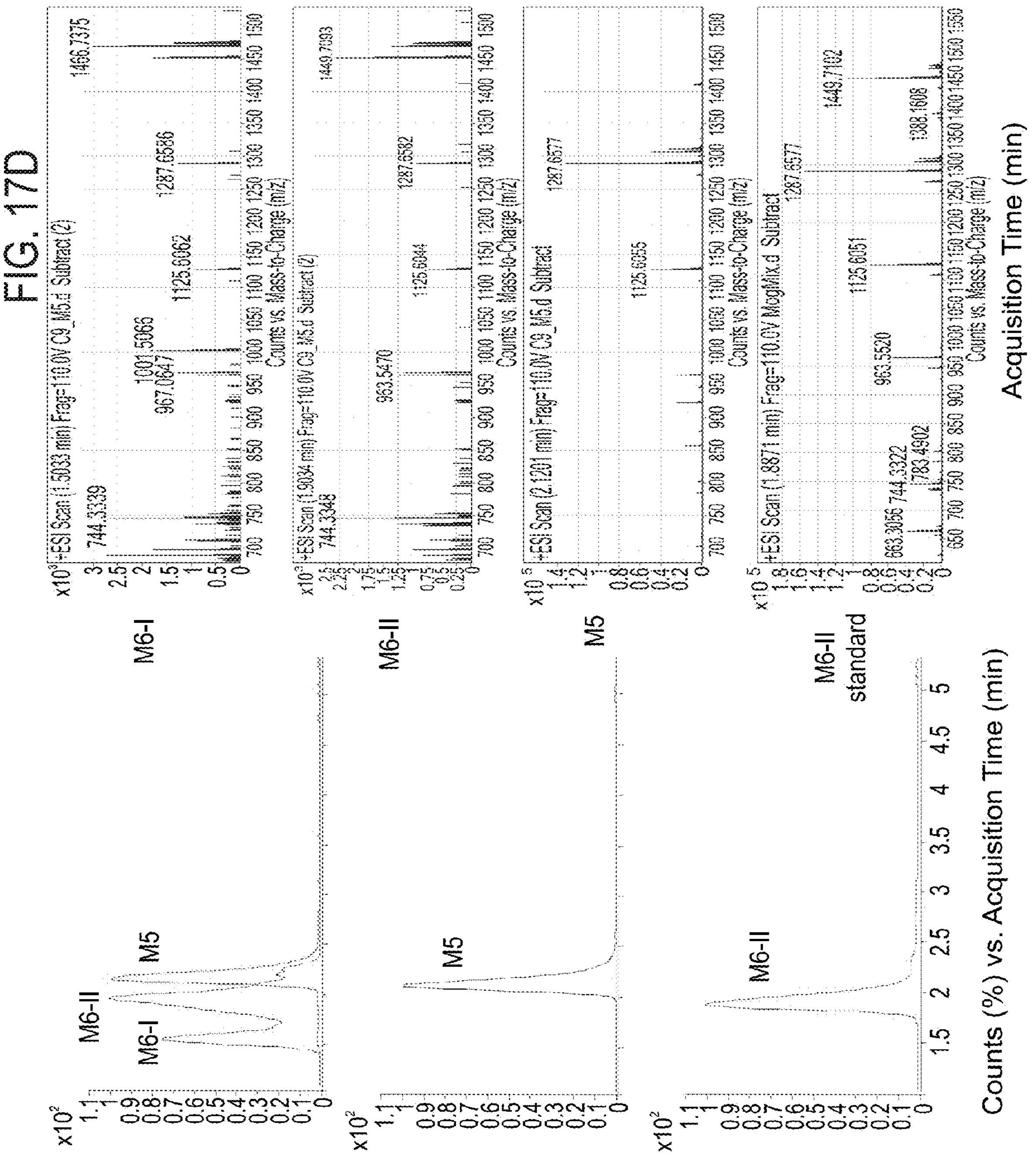
Figure 19B:
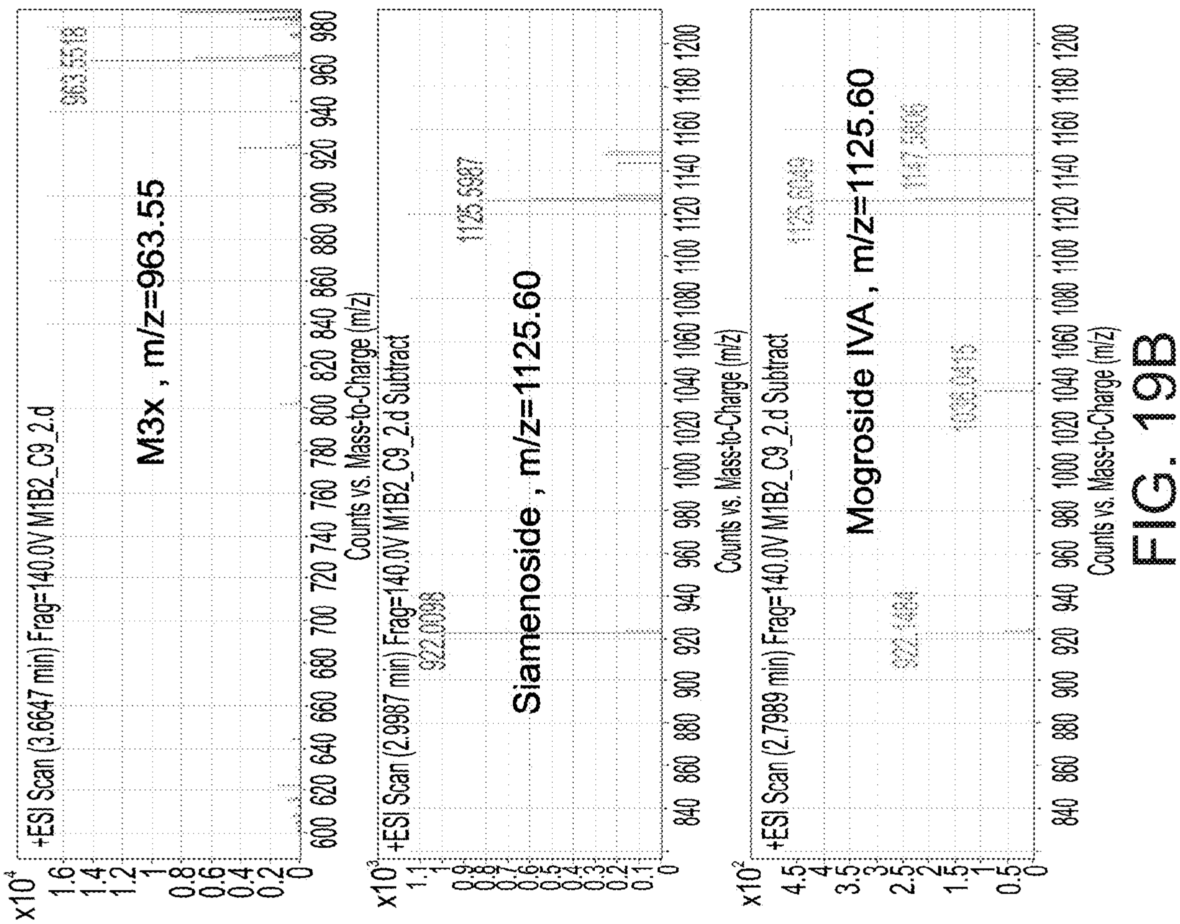
Figure 19A:
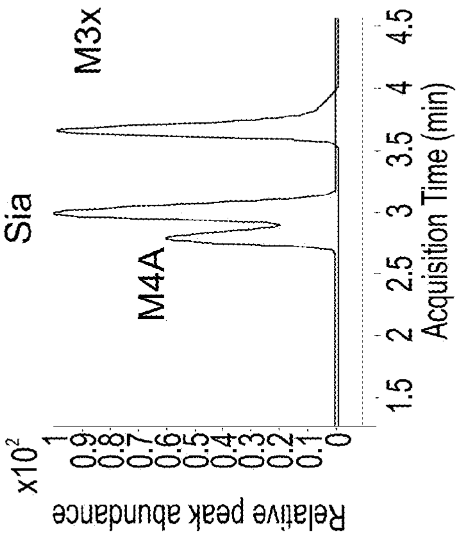
Figure 20:
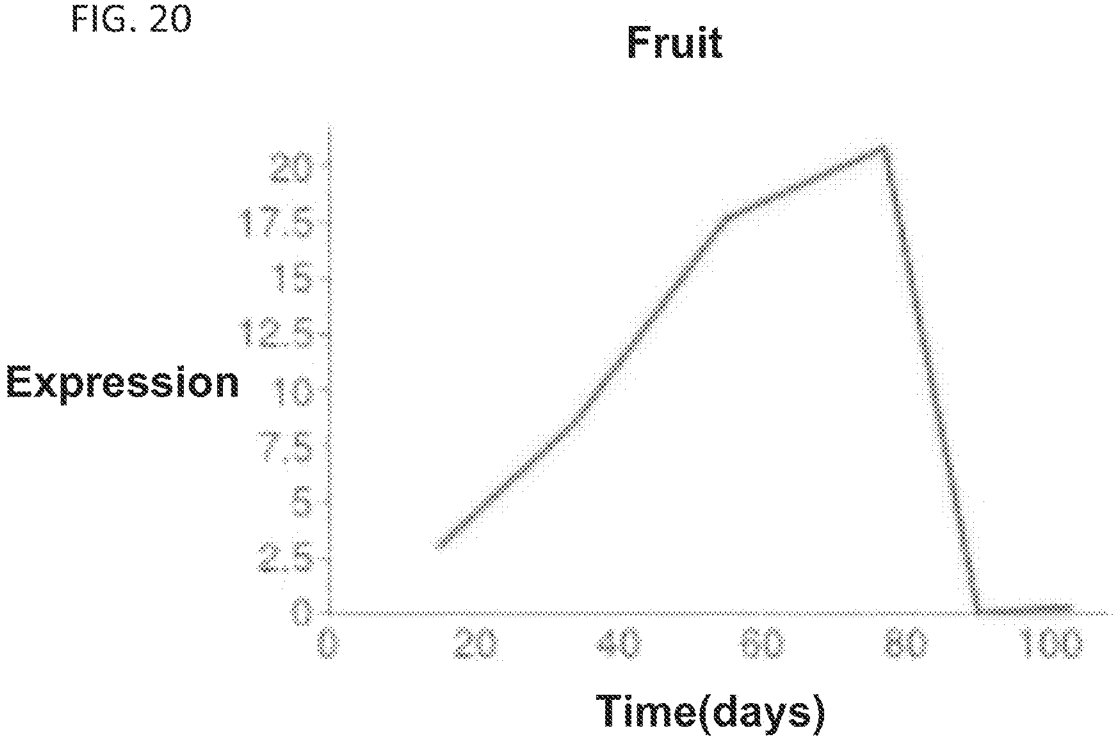
Figure 21:
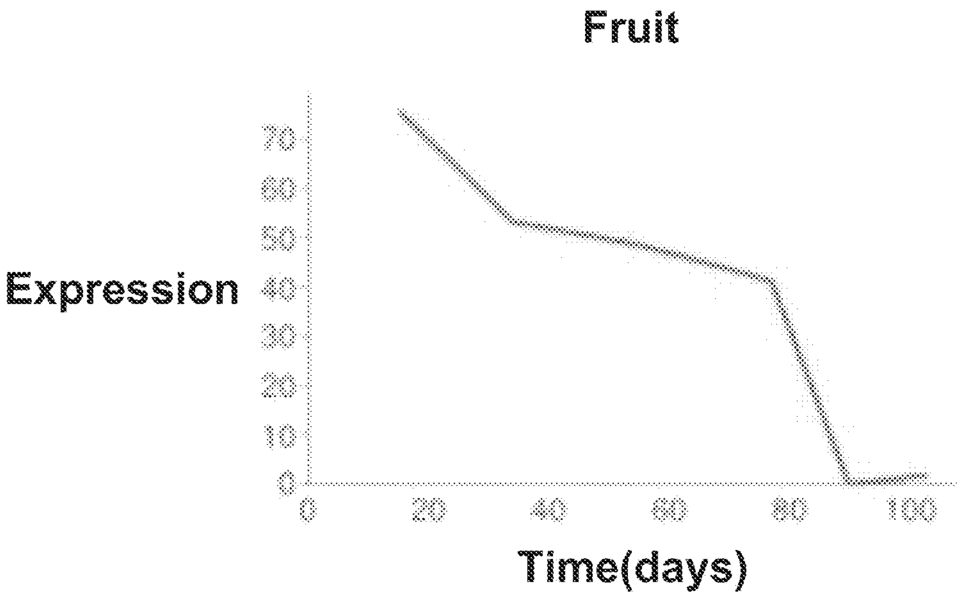
Figure 22:
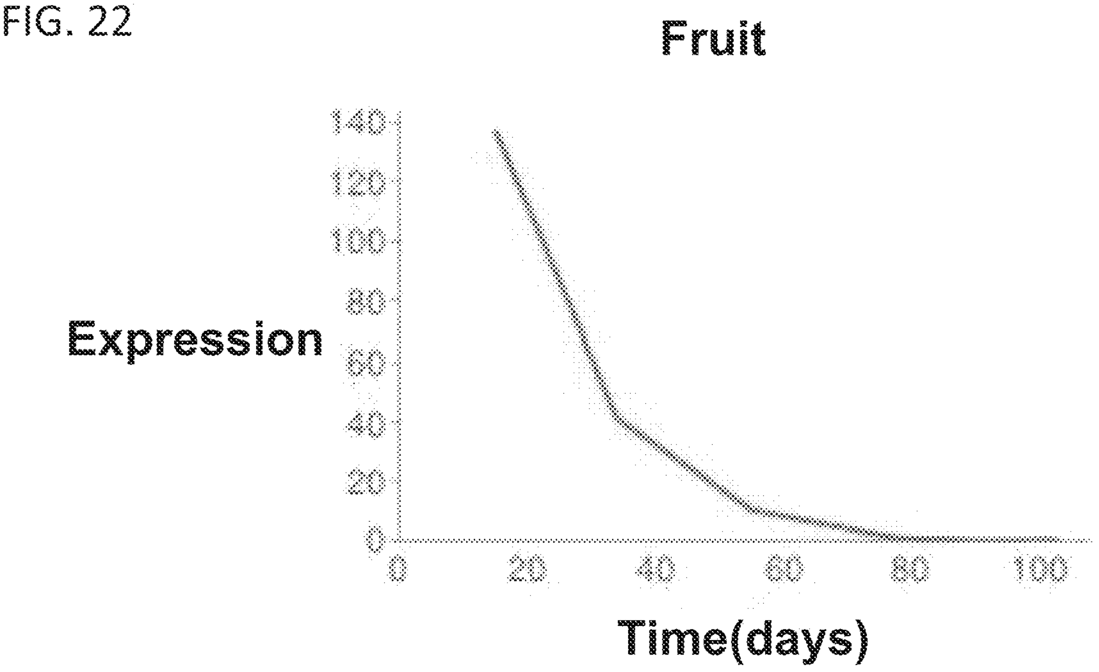
Figure 23:
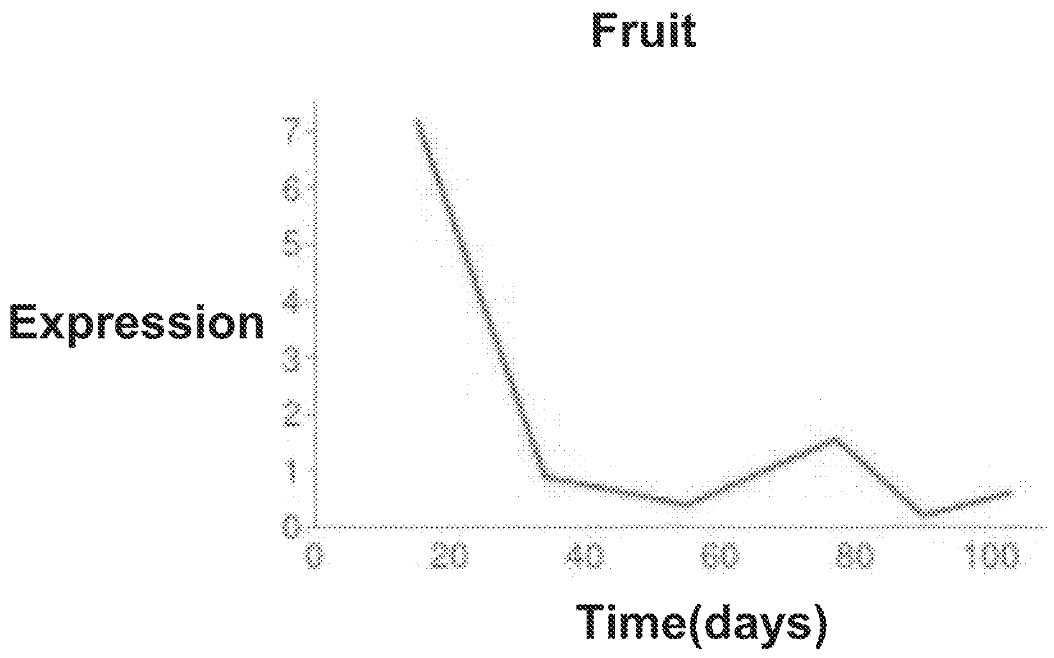
Figure 24:
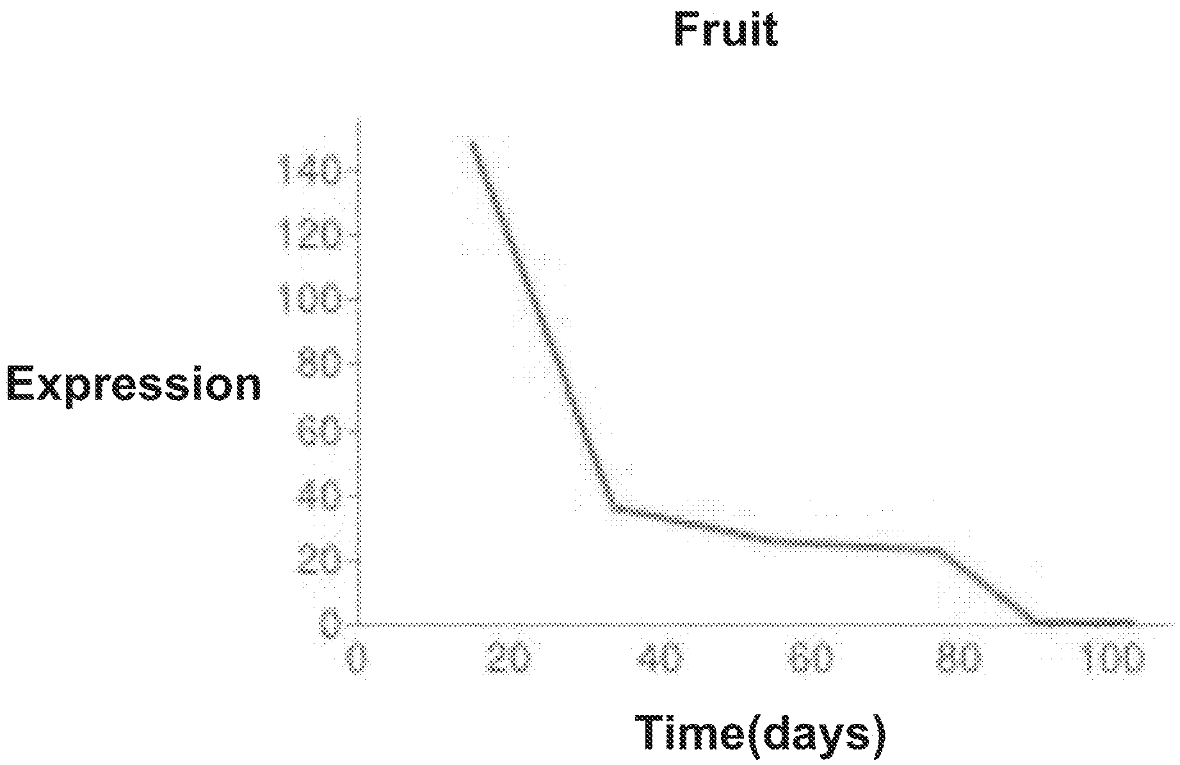

FIG. 13B is a phylogenetic tree of *Siraitia* UGTs. Branches, corresponding to same gene family are marked by color. *Siraitia* UGTs that were shown to glucosylate mogrol and mogrosides in this application are boxed in red;

FIG. 14 is a hierarchical cluster heat map of expression patterns of the UGT genes expressed in the developing *Siraitia* fruit. The five stages of fruit development presented are 15, 34, 51, 77 and 103 days and correspond to the fruit development stages in FIGS. 4A and 4B. Approximately 100 candidates were functionally expressed and assayed for UGT activity with the mogroside substrates;

FIG. 15A-15C are a schematic of UGT enzyme—sugar-acceptor molecule activities, based on products identified from cell-free glucosylation reactions with individual recombinant UGT enzymes expressed in *E. coli* and mogrol and mogroside substrates. FIG. 15A shows primary glucosylations, while FIG. 15B shows branching glucosylation and FIG. 15C shows the primary glucosylations that the branching enzymes presented in FIG. 15B perform. Schematic representation of sugar molecules are shown as circles, when each pair of cyclic cucrbitane rings are represented by blue ovals (rings A and B are schematically combined into the lower oval and rings C and D are combined into the upper oval), and the non-cyclic branched portion of the cucurbitadienol molecule leading towards C-24 and C-25 is represented by a short line. Newly attached glucose moieties from the UGT reaction are marked by green circles, glucose molecules derived from the substrate are in red, and a purple circle indicates where the position of the glucose added was identified by NMR as position C-25 glucose. When the circle points up (diagonally left or right) it represents a (1-6) glycosidic bond, whereas down-pointing circle (diagonally left or right) represents a (1-2) glycosidic bond. Circle pointing left represents a (1-4) glycosidic bond. Asterisk indicates trace amounts of substance;

FIG. 16 shows HPLC/DAD chromatograms of the mogroside products synthesized from each of the primary glucosylation enzymes upon inclusion of the aglycone mogrol (M) in the cell-free reaction media as described in FIGS. 15A-15C. The top three enzymes each synthesize the C-3 glucosidic mogrol, M1E1. UGT85E5 (269-1) synthesizes both the C-24 glucosidic mogrol, MIA and the C3,C24-diglucoside, M2E. The products were identified by MS and by NMR;

FIGS. 17A-17D show HPLC/DAD chromatograms showing that UGT94C9 (289-3) catalyzes cell-free production of Mogroside VI using Mogroside V as a substrate [Peak eluting at 1.9 min (m/z=1449.7113)]. FIG. 17A illustrates the accumulation of Mogroside VI in the reaction mixture, compared to inactive enzyme control (FIG. 17B). Residual Mogroside V that was not completely converted to Mogroside VI in reaction mix, elutes at 2.1 min. (FIG. 17A). FIG. 17C is a chromatogram of a standard of Mogroside VI (identified as M6-II). The reaction products were verified using LC-MS. The resulting spectrum is shown for two Mogroside VI (M6) compounds, Mogroside V (M5) from 17A and Mogroside VI (M6) standard. To discriminate between two Mogrosides VI they were marked M6-I (eluting at 1.5 min) and M6-II (eluting at 1.9 min);

FIG. 18 is a similarity and identity pairwise matrix of alignments of UGT amino acid sequences. The matrix was calculated using MatGAT 2.02 (www(dot)bitincka(dot)com/ledion/matgat/) run with BLOSUM62. Percentage similarity between the amino acid sequences is presented to the left and below the "100% self" diagonal, and percent identity presented to the right and above the "100% self" diagonal;

FIGS. 19A and 19B are chromatograms showing that UGT94-289-3 performs sequential glucosylations to generate Siamenoside and Mogroside 4A from Mogroside 2E in a cell free reaction system. FIG. 19A is an example of a LC-MS chromatogram of the products from the reaction with Mogroside 1A as substrate in the presence of UGT74-345-2 and UGT94-289-3. FIG. 19B shows the spectra for Mogroside 3x and for two Mogroside IV moieties: Mogroside IVA and Siamenoside;

FIG. 20 shows the expression pattern of a candidate squalene epoxidase homologue from *S. grosvenorii*, encoded by contig 19984, which was not selected due to the late expression in fruit development, as well as its sharp decline thereafter;

FIG. 21 shows the expression pattern of a candidate epoxy hydratase homologue from *S. grosvenorii*, encoded by contig 73966 (SEQ ID NO:17), selected for high and early expression in fruit development, and the gradual decline in expression during ripening;

FIG. 22 shows the expression pattern of a candidate epoxy hydratase homologue from *S. grosvenorii*, encoded by contig 86123 (SEQ ID NO: 19), selected for high and early expression in fruit development and gradual decline in expression during ripening;

FIG. 23 shows the expression pattern of a candidate epoxy hydratase homologue from *S. grosvenorii*, encoded by contig 102640 (SEQ ID NO: 3), selected for high and early expression in fruit development and gradual decline in expression during ripening;

FIG. 24 shows the expression pattern of a candidate epoxy hydratase homologue from *S. grosvenorii*, encoded by contig 28382 (SEQ ID NO: 4), selected for high and early expression in fruit development and gradual decline in expression during ripening.

DESCRIPTION OF SPECIFIC EMBODIMENTS OF THE INVENTION

The present invention, in some embodiments thereof, relates to methods of producing mogrol, mogrosides and compositions comprising same and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Mogrol (3, 11, 24, 25 tetrahydroxy cucurbitadienol) is the substrate for the biosynthesis of mogrosides (glycosylated mogrol), the glycosylation of carbons at positions 3, 24 and/or 25 being catalyzed by glucosyltransferase enzymes, such as uridine-5-dipospho-dependent glucosyltransferase (UGT). Mogrol biosynthesis requires the steroid precursor squalene as a substrate, and involves cyclization and hydroxylation of residues. The exact biochemical pathways are not currently known, however, the instant inventors have identified a mogrol synthetic pathway likely prominent in the endogenous biosynthesis of mogrol, have identified *S. grosvenorii* enzymes critical to the production of mogrol, mogrol precursors, mogroside precursors and mogrosides, have successfully reconstituted significant portions of the biosynthetic pathway with the recombinantly synthesized mogrol/mogroside pathway enzymes (see Examples 5 and 6, and FIGS. 15A-15C). Based on the combined metabolic profiling, functional expression and protein modeling results the present inventors suggest the following metabolic pathway for *S. grosvenorii* mogroside biosynthesis: During the initial stage of fruit development squalene is metabolized to the diglucosylated M2, via the progressive actions of squalene synthase, squalene epoxidase, cucurbitadienol synthase, epoxide hydrolase, cytochrome p450 (cyp102801) and UGT85. During fruit maturation there is the progressive activity of the UGT94 members, and perhaps also the UGT85, adding branched glucosyl groups to the primary glucosyl moieties of M2, leading to the sweet-flavored M4, M5 and M6 compounds.

Mogroside synthesis from mogrol is initiated by primary glucosylation of the mogrol molecule at carbons C3 and C24, and proceeds with further additions of glucose moieties, all catalyzed by uridine diphospho-glucosyl transferases (EC 2.4.1). The present inventors have unexpectedly uncovered key UTG enzymes having catalytic activity which may be critical to the *S. grosvenorii* mogroside biosynthesis.

Thus, according to some embodiments of some aspects of the invention there is provided an isolated uridine diphospho-glucosyl transferase enzyme (UGT) polypeptide comprising an amino acid sequence, wherein the polypeptide catalyzes primary glucosylation of mogrol at C24 and primary glucosylation of mogroside at C3. The present inventors have shown that this UGT is promiscuous in its substrate specificity: thus, in some embodiments, using mogrol as a substrate, the isolated UGT polypeptide can catalyze primary glycosylation of mogrol at C24, can catalyze primary glucosylation of a C24 glucosylated mogroside at C3, and can catalyze branched glucosylation of a mogroside. In a specific embodiment, the branching glucosylation is on a primary glucose of C3.

The present inventors have identified this UGT polypeptide as a member of the UGT85 family. In some embodiments, the isolated UGT polypeptide catalyzing primary glucosylation of mogrol at C24 and primary glucosylation of mogroside at C3 comprises an amino acid sequence at least 34% identical to SEQ ID NO: 34. In some embodiments, the amino acid sequence is at least 34% homologous to SEQ ID NO: 34. In some embodiments, the isolated UGT polypeptide catalyzing primary glucosylation of mogrol at C24 and primary glucosylation of mogroside at C3 comprises an amino acid sequence having at least 35%, at least 37%, at least 40%, at least 42%, at least 45%, at least 47%, at least 50%, at least 55%, at least 58%, at least 60%, at least 65%, at least 70%, at least 75%, at least 78%, at least 80%, at least 83%, at least 88%, at least 90%, at least 91%, at least 92%, at least 93%, at least 94%, at least 95%, at least 96%, at least 97%, at least 98%, at least 99%, or 100% homology or identity to SEQ ID NO: 34. In some embodiments, the UTG polypeptide comprises an amino acid sequence having homology or identity in the range of 34-100%, 40-90%, 37-85%, 45-80%, 50-75%, 55-65%, 80-90%, 93-100% to SEQ ID NO: 34. In a specific embodiment, the amino acid sequence of the isolated UGT polypeptide catalyzing primary glucosylation of mogrol at C24 and primary glucosylation of mogroside at C3 is as set forth in SEQ ID NO:34. In some cases, SEQ ID NO:34 is also referred to as UGT85E5, 85E5, and UGT85-269-1.

The present inventors have identified UGT enzymes having branching glucosylation activity critical to mogroside synthesis. Thus, according to some aspects of the invention there is provided an isolated uridine diphospho-glucosyl transferase enzyme (UGT) polypeptide comprising an amino acid sequence wherein the polypeptide catalyzes branching glucosylation of mogroside at the (1-2) and (1-6) positions of C3 and branching glucosylation of mogroside at the (1-2) and (1-6) positions of C24.

According to some aspects of the invention there is provided an isolated uridine diphospho-glucosyl transferase enzyme (UGT) polypeptide comprising an amino acid sequence wherein the polypeptide catalyzes branching glucosylation of mogroside M5 to mogroside M6. This catalytic activity is highly important, since the M6 mogroside is the mogroside with the sweetest taste of all the *Siraitia grosvenorii* mogroside compounds.

The present inventors have uncovered UGT polypeptides catalyzing branching glucosylation of mogroside at the (1-2) and (1-6) positions of C3 and branching glucosylation of mogroside at the (1-2) and (1-6) positions of C24, as well as branching glucosylation of mogroside M5 to mogroside M6.

The present inventors have identified UGT polypeptides catalyzing branching glucosylation of mogroside at the (1-2) and (1-6) positions of C3 and branching glucosylation of mogroside at the (1-2) and (1-6) positions of C24, and/or branching glucosylation of mogroside M5 to mogroside M6 as members of the UGT94 family. In some embodiments, the isolated UGT polypeptide catalyzing branching glucosylation of mogroside at the (1-2) and (1-6) positions of C3 and branching glucosylation of mogroside at the (1-2) and (1-6) positions of C24, and/or branching glucosylation of mogroside M5 to mogroside M6 comprises an amino acid sequence at least 89% identical to SEQ ID NO: 38. In some embodiments, the amino acid sequence is at least 89% homologous to SEQ ID NO: 38. In some embodiments, the isolated UGT polypeptide catalyzing branching glucosylation of mogroside at the (1-2) and (1-6) positions of C3 and branching glucosylation of mogroside at the (1-2) and (1-6) positions of C24, and/or branching glucosylation of mogroside M5 to mogroside M6 comprises an amino acid sequence having at least 89%, at least 90%, at least 91%, at least 92%, at least 93%, at least 94%, at least 95%, at least 96%, at least 97%, at least 98%, at least 99 or 100% homology or identity to SEQ ID NO: 38. In some embodiments, the UTG polypeptide comprises an amino acid sequence having a homology or identity in the range of 89-100%, 90-100%, 92-85%, 94-80%, 95-100%, 96-100%, 97-100% or 99-100% to SEQ ID NO: 38. In a specific embodiment, the isolated UGT polypeptide catalyzing branching glucosylation of mogroside at the (1-2) and (1-6) positions of C3 and branching glucosylation of mogroside at the (1-2) and (1-6) positions of C24, and/or branching glucosylation of mogroside M5 to mogroside M6 comprises an amino acid sequence as set forth in SEQ ID NO:38. In some cases, SEQ ID NO: 38 is also referred to as UGT94C9 and UGT94-289-3.

Additional UTG enzyme polypeptides which may catalyze branching glucosylation of mogroside M5 to mogroside M6 include, but are not limited to UGT polypeptides comprising an amino acid sequence at least 41% identical or homologous to SEQ ID NO: 8. In some embodiments, the UGT polypeptide comprises an amino acid sequence as set forth in SEQ ID NO: 8. SEQ ID NO: 8 is also referred to as UGT73-327-2, UGT73E7 and E07.

According to some aspects of the invention there is provided an isolated uridine diphospho-glucosyl transferase enzyme (UGT) polypeptide comprising an amino acid sequence wherein the polypeptide catalyzes branching glucosylation of mogroside IV (M4) to mogroside V (M5). In some embodiments, the isolated UGT polypeptide catalyzing branching glucosylation of mogroside IV (M4) to mogroside V (M5) comprises an amino acid sequence having at least 89%, at least 90%, at least 91%, at least 92%, at least 93%, at least 94%, at least 95%, at least 96%, at least 97%, at least 98%, at least 99 or 100% homology or identity to SEQ ID NO: 38, or an amino acid sequence at least 35%, at least 37%, at least 40%, at least 42%, at least 45%, at least 47%, at least 50%, at least 55%, at least 58%, at least 60%, at least 65%, at least 70%, at least 75%, at least 78%, at least 80%, at least 83%, at least 88%, at least 90%, at least 91%, at least 92%, at least 93%, at least 94%, at least 95%, at least 96%, at least 97%, at least 98%, at least 99%, or 100% homology or identity to SEQ ID NO: 34, or an amino acid sequence least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homology or identity to SEQ ID NO: 6. In some embodiments, the isolated UGT polypeptide catalyzing branching glucosylation of mogroside IV (M4) to mogroside V (M5) comprises an amino acid sequence having a homology or identity in the range of 89-100%, 90-100%, 92-85%, 94-80%, 95-100%, 96-100%, 97-100% or 99-100% to SEQ ID NO: 38, or 84-100%, 86-100%, 88-100%, 85-95%, 89-100%, 90-100%, 92-85%, 94-86%, 95-100%, 96-100%, 97-100% or 99-100% to SEQ ID NO: 6, or in the range of 34-100%, 40-90%, 37-85%, 45-80%, 50-75%, 55-65%, 80-90%, 93-100% to SEQ ID NO: 34. In a specific embodiment, the isolated UGT polypeptide catalyzing branching glucosylation of mogroside IV (M4) to mogroside V (M5) comprises an amino acid sequence as set forth in SEQ ID NO:38 or SEQ ID NO: 6 or SEQ ID NO:34. In some cases, SEQ ID NO:6 is also referred to as UGT94A9, A09 or UGT94-289-1.

In some embodiments, the UTG enzyme polypeptide catalyzes the branched glucosylation of C3 or C24 of mogroside or mogrol at the (1-2) and/or (1-6) position. However, it will be appreciated that, in some embodiments, the UGT enzyme polypeptides of the invention can comprise glucosylation activity at the (1-4) position as well.

According to some embodiments of some aspects of the invention, the enzyme polypeptides are enzymes catalyzing synthesis of mogrol, namely squalene synthase, squalene epoxidase, cucurbitadienol synthase, epoxide hydrolase (also known as epoxy hydratase) and cytochrome p450.

Thus, according to some aspects of the invention there is provided an isolated squalene epoxidase (SQE, also referred to as SE) polypeptide comprising an amino acid sequence at least 94% identical to SEQ ID NO: 14 or 89% identical to SEQ ID NO: 16, wherein the polypeptide catalyzes diepoxysqualene synthesis from squalene or oxidosqualene. In some embodiments, the squalene epoxidase (SQE) polypeptide comprises an amino acid sequence at least 94, at least 95%, at least 96%, at least 97%, at least 98%, at least 99%, or 100% homologous or identical to SEQ ID NO: 14, or at least 89%, at least 90%, at least 91%, at least 92%, at least 93%, at least 94%, at least 95%, at least 96%, at least 97%, at least 98%, at least 99%, or 100% homologous or identical to SEQ ID NO: 16. In some embodiments, the isolated SQE polypeptide comprises an amino acid sequence having a homology or identity in the range of 95-100%, 96-100%, 97-100% or 99-100% to SEQ ID NO: 14, or 89-100%, 90-100%, 92-100%, 93-100%, 94-100%, 95-100%, 96-100%, 97-100% or 99-100% to SEQ ID NO: 16. In a specific embodiment, the isolated SQE polypeptide catalyzing diepoxysqualene synthesis from squalene or oxidosqualene comprises an amino acid sequence as set forth in SEQ ID NO:14 or SEQ ID NO: 16. In some cases, SEQ ID NO: 14 is also referred to as SE1, SQE1 and contig 18561. In some cases, SEQ ID NO: 14 is also referred to as SE2, SQE2 and contig 16760.

According to some aspects of the invention there is provided an isolated epoxide hydrolase (EH, EPH) polypeptide comprising an amino acid sequence at least 75% identical to SEQ ID NO: 18, SEQ ID NO: 22 or SEQ ID NO: 24, the polypeptide catalyzing 3, 24, 25 trihydroxy cucurbitadienol synthesis from 3-hydroxy, 24-25 epoxy cucurbitadienol. In some embodiments, the epoxide hydrolase (EH) polypeptide comprises an amino acid sequence at least 75%, at least 78%, at least 80%, at least 83%, at least 88%, at least 90%, at least 91%, at least 92%, at least 93%, at least 94%, at least 95%, at least 96%, at least 97%, at least 98%, at least 99%, or 100% homologous or identical to SEQ ID NO: 18, SEQ ID NO: 22 or SEQ ID NO: 24. In some embodiments, the isolated EH polypeptide comprises an amino acid sequence having a homology or identity in the range of 75-100%, 78-97%, 80-95%, 85-92%, 87-98%, 90-99%, 92-100%, 95-100%, 96-100%, 97-100% or 99-100% to SEQ ID NO: 18, or 22 or 24. In a specific embodiment, the isolated EH polypeptide catalyzing 3, 24, 25 trihydroxy cucurbitadienol synthesis from 3-hydroxy, 24-25 epoxy cucurbitadienol comprises the amino acid sequence as set forth in SEQ ID NO:18 or SEQ ID NO: 22 or SEQ ID NO: 24. In some cases, SEQ ID NO: 18 is also referred to as EH1, EPH1 and contig 73966. In some cases, SEQ ID NO: 22 is also referred to as EH3, EPH3 and contig 102640. In some cases, SEQ ID NO: 24 is referred to as EH4, EPH4 and contig 28382.

The UGT, SQE and EH enzyme polypeptides of the invention, having the indicated catalytic activity, can include UGT, SQE and EH enzyme polypeptides of any organism, having the indicated catalytic activity. In some embodiments isolated UGT, SQE or EH polypeptide is a plant UGT, SQE or EH polypeptide. In some embodiments, the plant is a plant of the Cucurbitaceae family. A detailed, non-limiting list of members of the Cucurbitaceae family is found below. In specific embodiments, the isolated UGT polypeptide is a *Siraitia grosvenorii* UGT, SQE or EH polypeptide. As used herein, the phrase "mogrol precursors" or "mogrol pathway precursors", "mogrol precursor", "mogrol precursor substrate" refers to at least squalene, monoepoxy squalene, diepoxy squalene, 3 hydroxy, 24-25 epoxy cucurbitadienol, 3, 11 dihydroxy 24-25 epoxy cucurbitadienol, 3, 24, 25 trihydroxy cucurbitadienol. It will be appreciated that, since mogrol is the substrate for mogroside synthesis, mogrol precursors (precursor substrates, mogrol pathway precursors) also constitute mogroside pathway precursors/substrates.

As used herein, the phrase "mogrol pathway enzymes" refers to at least a squalene epoxidase or at least 89% homologous or identical thereto capable of catalyzing diepoxy squalene synthesis from squalene, or at least a cucurbitadienol synthetase or 60% homologous or identical thereto, capable of catalyzing 3 hydroxy, 24-25 epoxy cucurbitadienol synthesis from diepoxy squalene, at least an epoxy hydratase or 75% homologous or identical thereto capable of catalyzing 3, 24, 25 trihydroxy cucurbitadienol synthesis from 3-hydroxy, 24-25 epoxy cucurbitadienol, and a Cytochrome P 450 enzyme or 60% homologous or identical thereto capable of catalyzing 3, 11, 24, 25 tetrahydroxy cucurbitadienol synthesis from 3, 24, 25 trihydroxy cucurbitadienol. (SQE: squalene epoxidase, EC:1.14.99.7; CS: cucurbitadienol synthase, EC:5.4.99.8; P450: cytochrome P450, EC:1.14.-.-; and UDPG: UDP-glucosyltransferase, EC:2.4.1. E.C. 2.4.1 are UGTs)

As used herein, the term "mogroside pathway enzyme" refers to at least one or more uridine diphospho-glucosyl transferase (UGT) enzyme which catalyzes the glucosylation of a mogrol (un-glucosylated) or mogroside substrate.

Table 1 below comprises a non-limiting list of some mogrol and mogroside pathway enzymes useful in the methods and compositions of the present invention, including examples of homologues which can be suitable for use in some of the embodiments of the invention.

TABLE 1

MOGROL/MOGROSIDE PATHWAY ENZYMES

| ENZYME | SEQ ID NO: DNA | SEQ ID NO: PROT | CLOSEST HOMOLOG | ALSO REFERRED TO AS |
|---|---|---|---|---|
| CDS cucurbitadienol synthase | | | | |
| >SgCDS | 11 | 12 | cucurbitadienol synthase [*Siraitia grosvenorii*] gb\|AEM42982.11 SEQ ID NO: 45 | |
| CYP cytochrome P450 | | | | |
| >Sg_cyp102801 | 9 | 10 | cytochrome P450 [*Siraitia grosvenorii*] gb\|AEM42986.1\| SEQ ID NO: 52 | CYP801 |

TABLE 1-continued

MOGROL/MOGROSIDE PATHWAY ENZYMES

| ENZYME | SEQ ID NO: DNA | SEQ ID NO: PROT | CLOSEST HOMOLOG | ALSO REFERRED TO AS |
|---|---|---|---|---|
| SQE Squalene Epoxidase | | | | |
| >SQE18561p | 13 | 14 | squalene monooxygenase-like [*Cucumis melo*] ref\|XP_008452686.1\| SEQ ID NO: 46 | SE1, SQE1, contig 18561 |
| >SQE16760p | 15 | 16 | squalene monooxygenase [*Cucumis sativus*] ref\|XP_004142907.1\| SEQ ID NO: 47 | SE2, SQE2, Contig16760 |
| EPH Epoxide hydrolase | | | | |
| >EPH73966p | 17 | 18 | bifunctional epoxide hydrolase 2-like [*Cucumis sativus*] ref\|XP_004152243.1 SEQ ID NO: 48 | Epoxide Hydratase, EH1, EPH1, Contig73966 |
| >EPH86123p | 19 | 20 | bifunctional epoxide hydrolase 2-like isoform X1 [*Cucumis melo*] ref\|XP_008454322.1 SEQ ID NO: 49 | Epoxide Hydratase, EH2, EPH2, Contig86123 |
| >EPH102640 | 21 | 22 | bifunctional epoxide hydrolase 2-like [*Cucumis melo*] ref\|XP_008454327.1\| SEQ ID NO: 50 | Epoxide Hydratase, EH3, EPH3, Contig 102640 |
| >EPH28382p | 23 | 24 | bifunctional epoxide hydrolase 2-like [*Cucumis sativus*] ref\|XP_004152361.1\| SEQ ID NO: 51 | Epoxide Hydratase, EH4, EPH4, Contig28382 |
| UGT Uridine diphospho-glucosyl transferase | | | | |
| >UGT73-251_5 | 25 | 26 | UDP-glycosyltransferase 73C3-like [*Cucumis melo*] ref\|XP_008442743.1\| SEQ ID NO: 53 | UDPGT |
| >UGT73-251-6 | 27 | 28 | UDP-glycosyltransferase 73C3-like [*Cucumis melo*] ref\|XP_008442743.1\| SEQ ID NO: 53 | UDPGT |
| >UGT73-348-2 | 3 | 4 | UDP-glycosyltransferase 73D1-like [*Cucumis melo*] ref\|XP_008462511.1 SEQ ID NO: 54 | UGT73E8, EO8, UDPGT |
| >UGT73-327-2 | 7 | 8 | UDP-glucose flavonoid 3-O-glucosyltransferase 7-like [*Cucumis sativus*] ref\|XP_004140708.1\| SEQ ID NO: 55 | UGT73E7, EO7, UDPGT |
| >UGT74-345-2 | 1 | 2 | UDP-glycosyltransferase 74E2-like [*Cucumis melo*] ref\|XP_008445481.1 SEQ ID NO: 56 | UGT74B2, B02 UDPGT |
| >UGT75-281-2 | 29 | 30 | crocetin glucosyltransferase, chloroplastic-like [*Cucumis sativus*] ref\|XP_004140604.2 SEQ ID NO: 57 | 75 contig 103243, E8, UGT75nE8 UDPGT |

TABLE 1-continued

MOGROL/MOGROSIDE PATHWAY ENZYMES

| ENZYME | SEQ ID NO: DNA | PROT | CLOSEST HOMOLOG | ALSO REFERRED TO AS |
|---|---|---|---|---|
| >UGT85-269-4 | 31 | 32 | 7-deoxyloganetic acid glucosyltransferase-like [*Cucumis sativus*] ref\|XP_004147933.2 SEQ ID NO: 58 | UGT85E6, UDPGT |
| >UGT85-269-1 | 33 | 34 | 7-deoxyloganetic acid glucosyltransferase-like [*Cucumis sativus*] ref\|XP_004147933.2\| SEQ ID NO: 58 | UGT85E5, 85E5 UDPGT |
| >UGT94-289-1 | 5 | 6 | beta-D-glucosyl crocetin beta-1,6-glucosyltransferase-like [*Cucumis sativus*] ref\|XP_004142256.1 SEQ ID NO: 59 | UGT94A9, A09, UDPGT |
| >UGT94-289-2 | 35 | 36 | beta-D-glucosyl crocetin beta-1,6-glucosyltransferase-like [*Cucumis sativus*] ref\|XP_004142256.1 SEQ ID NO: 59 | UGT9498, UDPGT |
| >UGT94-289_3 | 37 | 38 | beta-D-glucosyl crocetin beta-1,6-glucosyltransferase-like [*Cucumis sativus*] ref\|XP_004142256.1 SEQ ID NO: 59 | UGT94C9, UDPGT |

As used herein the term “mogrol” refers to the aglycone compound mogrol.

Glycosylated mogrol or mogroside refers to a mogrol having at least one primary glucose or branched glucose at positions 3, 24 and/or 25. According to a specific embodiment, the glycosylated or glucosylated mogrol or mogroside refers to a mogrol having at least one primary glucose or branched glucose at positions 3 and/or 24.

The UGT enzyme polypeptides of the present invention can catalyze primary glucosylation and/or branching glucosylation of the mogrol or mogroside substrates. As used herein, the term “primary glucosylation” refers to covalent addition of a glucose moiety to an un-glucosylated carbon of the mogrol or mogroside substrate, resulting in a mono-glucosylated (M1) (when substrate is an aglycol mogrol) or di-glucosylated (when substrate is a mono-glucosylated mogroside) mogroside (M2). Glucosylations are typically at the C3 and C24 carbons of the mogrol backbone.

As used herein, the term “branching glucosylation” or “branched glucosylation” refers to the covalent addition of a glucose moiety to a glucose of a glucosylated carbon of a mogroside substrate, resulting in a multi-glucosylated mogroside (M2, M3, M4, M5 or M6), depending on the level of glucosidation of the mogroside substrate. Glucosylations are typically at the C3 and C24 carbons of the mogrol backbone. A table illustrating a non-limiting number of unglucosylated mogrol and different forms of mogroside, glucosylated at different carbons, and with different linkages, is shown in FIG. 12.

The mogrol biosynthetic pathway enzyme and mogroside biosynthetic pathway enzyme polypeptides of the invention can be used to synthesize a mogrol, mogrol precursor or mogroside or mogroside precursor.

Thus, according to some embodiments of some aspects of the invention there is provided a method of synthesizing a mogrol or mogrol precursor product from a mogrol precursor substrate, the method comprising contacting at least one mogrol precursor substrate with a mogroside pathway enzyme. The mogroside pathway enzymes catalyzing the steps of mogrol, mogroside or mogrol or mogroside precursor biosynthesis can be as follows:

(a) when the mogrol precursor product comprises diepoxy squalene and the mogrol precursor substrate comprises squalene or oxidosqualene, the mogroside pathway enzyme comprises a squalene epoxidase polypeptide as described herein, thereby producing diepoxy squalene. Squalene epoxidase polypeptides of the invention suitable for use in the method include SQE polypeptides comprising SEQ ID NO: 14, or at least 94% identical or homologous thereto, or SEQ ID NO: 16 or at least 89% identical or homologous thereto, or (b) when the mogrol precursor product comprises 3 hydroxy, 24-25 epoxy cucurbitadienol and the mogrol precursor substrate comprises diepoxy squalene, the mogrol pathway enzyme comprises a cucurbitadienol synthetase polypeptide as set forth in SEQ ID NO: 12 or 60% homologous or identical thereto, thereby producing a 3 hydroxy, 24-25 epoxy cucurbitadienol, or (c) when the product comprises 3, 24, 25 trihydroxy cucurbitadienol and the substrate comprises 3-hydroxy, 24-25 epoxy cucurbitadienol, the mogrol pathway enzyme comprises an epoxy hydratase polypeptide as described in the present invention, thereby producing a 3, 24, 25 trihydroxy cucurbitadienol. Epoxy hydratase (also known as epoxide hydrolase) polypeptides of the invention suitable for use in the method include EH polypeptides comprising SEQ ID NO: 18, 22 or 24 or at least 75% identical or homologous thereto, or (d) when the product comprises mogrol and the mogrol precursor substrate comprises 3, 24, 25 trihydroxy cucurbitadienol, the mogrol pathway enzyme is Cytochrome P 450 enzyme as set forth in SEQ ID NO: 10 or 60% homologous or identical thereto, thereby producing 3, 11, 24, 25 tetrahydroxy cucurbitadienol (mogrol).

Biosynthesis of the mogrol or mogroside can be reconstituted in a cell expressing one or more of the mogroside biosynthesis enzyme polypeptides of the invention. Depending upon the availability of mogrol precursors and biosynthetic enzymes in the cell (or cell lysate), the individual reactions, or combinations thereof can be reconstituted using any one of, some of or all of the steps described above. Thus, in some embodiments, producing the mogrol product comprises at least one of the steps of:

(i) contacting the squalene or oxido squalene with a squalene epoxidase enzyme polypeptide of the invention, thereby producing diepoxy squalene;

(ii) contacting the diepoxy squalene with a cucurbitadienol synthase of the invention, thereby producing 3 hydroxy, 24-25 epoxy cucurbitadienol;

(iii) contacting the 3 hydroxy, 24-25 epoxy cucurbitadienol with an epoxy hydratase (epoxide hydrolase) enzyme of the invention, thereby producing 3, 24, 25 trihydroxy cucurbitadienol; and (iv) contacting the 3, 24-25 trihydroxy cucurbitadienol with a Cytochrome P 450 enzyme of the invention, thereby producing the mogrol product (3, 11, 24, 25 tetrahydroxy cucurbitadienol).

In some embodiments, producing the mogrol product comprises at least (i) and (iv), at least (ii) and (iv), at least (iii) and (iv), at least (i), (ii) and (iii), at least (i), (ii) and (iv), at least (i), (iii) and (iv), at least (ii), (iii) and (iv), and optionally all of (i) (ii), (iii) and (iv). For example, in order to reconstitute or enhance dioxidosqualene synthesis in a cell lacking or deficient in squalene epoxidase, but having the biosynthetic capabilities for completing the synthesis of mogrol from dioxidosqualene, the method can comprise (i). In a cell capable of synthesizing dioxidosqualene, 3 hydroxy, 24-25 epoxy cucurbitadienol, and 3, 24-25 trihydroxy cucurbitadienol, but deficient or lacking in epoxide hydrolase (epoxy hydratase), the method can comprise (iii). In a cell capable of synthesizing 3 hydroxy, 24-25 epoxy cucurbitadienol, and 3, 24-25 trihydroxy cucurbitadienol, but deficient or lacking in squalene epoxidase and epoxide hydrolase (epoxy hydratase), the method can comprise (i) and (iii).

The present invention contemplates mogroside biosynthesis. According to some embodiments of some aspects of the invention there is provided a method of synthesizing a mogroside, the method comprising contacting at least one UGT polypeptide of the invention or a combination thereof with at least one UGT substrate mogroside precursor.

According to some embodiments, the method comprises the steps of primary and branching glucosylation of the mogrol or mogroside precursor substrates. The mogroside pathway enzymes catalyzing the steps of mogroside or mogroside precursor biosynthesis can be as follows:

(aa) When the substrate is mogrol, or mogroside unglucosylated at C3, the UGT catalyzing primary glucosylation of mogrol at C24 and primary glucosylation of mogroside at C3 is a UGT comprising an amino acid sequence set forth in SEQ ID NO: 34 or at least 34% homologous or identical thereto.

(bb) When the substrate is a mogroside, the UGT catalyzing branching glucosylation of mogroside at the (1-2) and (1-6) positions of C3 and/or branching glucosylation of mogroside at the (1-2) and (1-6) positions of C24 comprises an amino acid sequence as set forth in SEQ ID NO: 38 or at least 89% homologous or identical thereto.

(cc) When the substrate is a mogroside M5, the UGT catalyzing branching glucosylation of mogroside M5 to mogroside M6 comprises an amino acid sequence as set forth in SEQ ID NO: 38 or at least 89% homologous or identical thereto, or SEQ ID NO: 8, or at least 41% homologous or identical thereto.

(dd) When the substrate is a mogroside IV (M4), the UGT catalyzing branching glucosylation of M4 to mogroside V (M5) comprises an amino acid sequence as set forth in any one of SEQ ID NO: 38, or at least 89% homologous or identical thereto, SEQ ID NO: 34, or at least 34% homologous or identical thereto, and SEQ ID NO: 6, or at least 84% homologous or identical thereto.

Thus, in some embodiments, the method comprises contacting the mogroside substrate with at least one UGT polypeptide selected from the group comprising an amino acid sequence as set forth in SEQ ID NO: 38, or at least 89% homologous or identical thereto, SEQ ID NO: 34, or at least 34% homologous or identical thereto, SEQ ID NO: 8, or at least 41% homologous or identical thereto and SEQ ID NO: 6, or at least 84% homologous or identical thereto.

In some embodiments, producing the mogroside product comprises at least (aa) and (bb), at least (aa) and (cc), at least (aa) and (dd), at least (aa), (bb) and (cc), at least (aa), (cc) and (dd), at least (bb), (cc) and (dd), at least (bb) and (cc), at least (cc) and (dd), and optionally all of (aa) (bb), (cc) and (dd). For example, in order to reconstitute or enhance mogroside synthesis in a cell lacking or deficient in UGT catalyzing primary glucosylation at C3 or C24, but having the biosynthetic capabilities for completing the synthesis of mogroside from mono-glucosylated mogroside, the method can comprise (aa). In a cell capable of synthesizing M5, but deficient or lacking in UGT catalyzing branching glucosylation of M5 to M6, the method can comprise (cc). In a cell capable of having the biosynthetic capabilities for completing the synthesis of mogroside M5 from mono-glucosylated mogroside, but deficient or lacking in primary glucosylation of C3 or C24 and in branching glucosylation of M5 to M6, the method can comprise (aa) and (cc). In some embodiments, the method comprises contacting the mogroside substrate with at least a UGT polypeptide comprising an amino acid sequence as set forth in SEQ ID NO: 34, or at least 34% homologous or identical thereto and one or more of a UGT polypeptide comprising an amino acid sequence as set forth in SEQ ID NO: 8, or at least 41% homologous or identical thereto, a UGT polypeptide comprising an amino acid sequence as set forth in SEQ ID NO: 6 or 84% homologous or identical thereto, and a UGT polypeptide comprising an amino acid sequence as set forth in SEQ ID NO: 38, or 89% homologous or identical thereto. In a specific embodiment, the method comprises contacting the mogroside substrate with at least a UGT polypeptide comprising an amino acid sequence as set forth in SEQ ID NO: 34, or at least 34% homologous or identical thereto and a UGT polypeptide comprising an amino acid sequence as set forth in SEQ ID NO: 38, or 89% homologous or identical thereto.

The present invention contemplates mogroside biosynthesis from mogrol substrates and/or precursors. Thus, the methods of the invention for synthesizing a mogroside comprises combining producing a mogrol according to a method of the invention, and synthesizing the mogroside as described hereinabove, i.e. combining any one or more, or all of the steps of the mogrol synthesis described herein with any one or more, or all of the steps of the mogroside synthesis described herein.

Production of all possible mogroside products is contemplated. Thus, in some embodiments, the mogroside is selected from the group consisting of mogroside I-A1, mogroside I-E1, mogroside IIE, mogroside III, siamenoside, mogroside V and mogroside VI.

According to some embodiments, the method further comprises isolating the mogroside. Methods for isolation and purification of mogroside compounds are well known in the art, for example, Li, D. et al J. Nat. Med. 2007, 61, 307-312; Venkata Chaturvedula and Indra Prakash., J. Carb. Chem. 2011 30, 16-26; Venkata Sai Prakash Chaturvedula, Indra Prakash. IOSR Journal of Pharmacy (IOSRPHR) 2012. 2, 7-12.

As used herein, the term "polypeptide" refers to a linear organic polymer consisting of a large number of amino-acid residues bonded together by peptide bonds in a chain, forming part of (or the whole of) a protein molecule. The amino acid sequence of the polypeptide refers to the linear consecutive arrangement of the amino acids comprising the polypeptide, or a portion thereof.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein "expressing" refers to expression at the mRNA and optionally polypeptide level.

As used herein, the phrase “exogenous polynucleotide” refers to a heterologous nucleic acid sequence which may not be naturally expressed within the plant (e.g., a nucleic acid sequence from a different species) or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term “endogenous” as used herein refers to any polynucleotide or polypeptide which is present and/or naturally expressed within a plant or a cell thereof.

Homologous sequences include both orthologous and paralogous sequences.

The term “paralogous” relates to gene-duplications within the genome of a species leading to paralogous genes. The term “orthologous” relates to homologous genes in different organisms due to ancestral relationship. Thus, orthologs are evolutionary counterparts derived from a single ancestral gene in the last common ancestor of given two species and therefore have great likelihood of having the same function.

One option to identify orthologues in monocot plant species is by performing a reciprocal BLAST search. This may be done by a first blast involving blasting the sequence-of-interest against any sequence database, such as the publicly available NCBI database which may be found at: ncbi(dot)nlm(dot)nih(dot)gov. If orthologues in rice were sought, the sequence-of-interest would be blasted against, for example, the 28,469 full-length cDNA clones from *Oryza sativa* Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [ebi(dot)ac(dot)uk/Tools/clustalw2/index(dot)html], followed by a neighbor-joining tree (wikipedia(dot)org/wiki/Neighbor-joining) which helps visualizing the clustering.

Homology (e.g., percent homology, sequence identity+sequence similarity) can be determined using any homology comparison software computing a pairwise sequence alignment.

As used herein, “sequence identity” or “identity” in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have “sequence similarity” or “similarity”. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

According to some embodiments of the invention, the term “homology” or “homologous” refers to identity of two or more nucleic acid sequences; or identity of two or more amino acid sequences; or the identity of an amino acid sequence to one or more nucleic acid sequence.

According to some embodiments of the invention, the homology is a global homology, i.e., an homology over the entire amino acid or nucleic acid sequences of the invention and not over portions thereof.

The degree of homology or identity between two or more sequences can be determined using various known sequence comparison tools which are described in WO2014/102774.

Local alignments tools, which can be used include, but are not limited to, the tBLASTX algorithm, which compares the six-frame conceptual translation products of a nucleotide query sequence (both strands) against a protein sequence database. Default parameters include: Max target sequences: 100; Expected threshold: 10; Word size: 3; Max matches in a query range: 0; Scoring parameters: Matrix—BLOSUM62; filters and masking: Filter—low complexity regions.

Microorganisms, plant cells, or plants can be developed that express polypeptides useful for the biosynthesis of mogrol (the triterpene core) and various mogrol glycosides (mogrosides). The aglycone mogrol is glycosylated with different numbers of glucose moieties to form various mogroside compounds.

In general, the method of producing a mogroside may be performed either in vitro or in vivo. It is also comprised within the invention that some steps are performed in vitro, whereas others may be performed in vivo. Thus, for example the first steps may be performed in vitro and where after an intermediate product may be fed to recombinant host cells, capable of performing the remaining steps of the method. Alternatively, the first steps may be performed in vivo and where after an intermediate product may be used as substrate for the subsequent step(s) performed in vitro. Other combinations can also be envisaged. When the methods are performed in vitro each of the steps of the methods may be performed separately. Alternatively, one or more of the steps may be performed within the same mixture. In embodiments wherein some or all of the steps of the methods are performed separately, then the intermediate product of each of the steps may be purified or partly purified before performing the next step.

When the methods are performed in vivo, the methods employ use of a recombinant host expressing one or more of the enzymes or the methods may employ use of several recombinant hosts expressing one or more of the enzymes.

The present invention contemplates the recombinant production of mogrol, or mogroside. Thus, in some embodiments, the method of mogrol and/or mogroside biosynthesis is performed in a recombinant cell exogenously expressing at least one of the SQE, CDS, EH, Cyt p450 and UGT enzyme polypeptides of the invention. In some embodiments, the recombinant cell expresses at least one enzyme polypeptide selected from the group consisting of a UGT polypeptide comprising the amino acid sequence as set forth in SEQ ID NO: 34 or at least 34% identical or homologous thereto, a UGT polypeptide comprising the amino acid sequence as set forth in SEQ ID NO: 6 or at least 84% identical or homologous thereto, a UGT polypeptide comprising the amino acid sequence as set forth in SEQ ID NO: 38 or at least 89% identical or homologous thereto, a SQE polypeptide comprising the amino acid sequence as set forth in SEQ ID NO: 14 or at least 94% identical or homologous thereto, or SEQ ID NO: 16 or at least 89% identical or homologous thereto, and an EH polypeptide comprising the amino acid sequence as set forth in any one of SEQ ID NOs: 18, 22 or 24 or at least 75% identical or homologous thereto.

Recombinant expression of the polypeptides of the invention, or recombinant production of mogrol substrates, mogrol and/or mogroside compounds can be performed in a host cell expressing an isolated polynucleotide comprising a nucleic acid sequence encoding the isolated polypeptide of the mogrol and or mogroside biosynthetic pathway enzyme of the invention. In some embodiments, the isolated polynucleotide is provided in a nucleic acid construct useful in transforming the host cell. Suitable host cells include bacteria, yeast and other microorganisms that can be cultured or grown in fermentation, plant and other eukaryotic cells. In some embodiments, the nucleic acid construct of some embodiments of the invention can be utilized to transform plant cells.

Isolated polynucleotides suitable for use with the methods of the invention include, but are not limited to, polynucleotides encoding any of the mogrol and mogroside biosynthesis pathway enzymes as shown in Table 1. Thus, in some embodiments, there is provided an isolated polynucleotide comprising a nucleic acid sequence encoding the amino acid sequence as set forth in any one of SEQ ID NOs: 6, 10, 12, 14, 16, 22, 24, 34 and 38, or functional homologs thereof.

Functional homologs of the polypeptides described above are also suitable for use in the methods and recombinant hosts described herein. A functional homolog is a polypeptide that has sequence similarity to a reference polypeptide, and that carries out one or more of the biochemical or physiological function(s) of the reference polypeptide. Thus, functional homologues of the enzymes described herein are polypeptides that have sequence similarity to the reference enzyme, and which are capable of catalyzing the same step or part of a step of the methods of the invention as the reference enzyme. In general it is preferred that functional homologues share at least some degree of sequence identity with the reference polypeptide, for example, as indicated hereinabove for the UGT, SE, EH, CDS, Cyt p450 enzyme polypeptides of the invention.

According to some embodiments of the invention, the heterologous polynucleotide of the invention encodes a UGT polypeptide comprising the amino acid sequence as set forth in SEQ ID NO: 34 or at least 34% identical or homologous thereto, a UGT polypeptide comprising the amino acid sequence as set forth in SEQ ID NO: 6 or at least 84% identical or homologous thereto, a UGT polypeptide comprising the amino acid sequence as set forth in SEQ ID NO: 38 or at least 89% identical or homologous thereto, a SQE polypeptide comprising the amino acid sequence as set forth in SEQ ID NO: 14 or at least 94% identical or homologous thereto, or SEQ ID NO: 16 or at least 89% identical or homologous thereto, and an EH polypeptide comprising the amino acid sequence as set forth in any one of SEQ ID NOs: 18, 22 or 24 or at least 75% identical or homologous thereto.

In some embodiments, the isolated polynucleotide comprises a nucleic acid sequence selected from the group consisting of SEQ ID NOs. 5, 9, 11, 13, 15, 17, 21, 23, 33 and 37.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising Acacia spp., Acer spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., Centroema *pubescens*, Chacoomeles spp., *Cinnamomum cassia, Coffea arabica, Colophospermum mopane*, Coronillia *varia, Cotoneaster serotina, Crataegus* spp., *Cucumis* spp., *Cupressus* spp., *Cyathea dealbata, Cydonia oblonga, Cryptomeria japonica, Cymbopogon* spp., Cynthea *dealbata, Cydonia oblonga, Dalbergia monetaria, Davallia divaricata, Desmodium* spp., *Dicksonia squarosa*, Dibeteropogon *amplectens, Dioclea* spp, *Dolichos* spp., *Dorycnium* rectum, *Echinochloa pyramidalis*, Ehraffia spp., *Eleusine coracana*, Eragrestis spp., *Erythrina* spp., Eucalypfus spp., Euclea *schimperi, Eulalia* vi/losa, Pagopyrum spp., *Feijoa* sellowlana, *Fragaria* spp., *Flemingia* spp, *Freycinetia* banksli, *Geranium thunbergii*, GinAgo *biloba, Glycine javanica, Gliricidia* spp, *Gossypium hirsutum, Grevillea* spp., *Guibourtia coleosperma, Hedysarum* spp., Hemaffhia *altissima, Heteropogon contoffus, Hordeum vulgare, Hyparrhenia rufa, Hypericum erectum*, Hypeffhelia dissolute, Indigo incamata, Iris spp., *Leptarrhena pyrolifolia*, Lespediza spp., Lettuca spp., *Leucaena leucocephala, Loudetia simplex*, Lotonus bainesli, *Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum* sativam, *Podocarpus totara, Pogonarthria fleckii*, Pogonaffhria *squarrosa, Populus* spp., *Prosopis cineraria, Pseudotsuga menziesii, Pterolobium stellatum, Pyrus communis, Quercus* spp., Rhaphiolepsis *umbellata, Rhopalostylis sapida, Rhus natalensis, Ribes grossularia, Ribes* spp., *Robinia pseudoacacia, Rosa* spp., *Rubus* spp., *Salix* spp., Schyzachyrium *sanguineum, Sciadopitys* vefficillata, *Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla,*

*Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention. In specific embodiments, the plant is a plant of the Cucurbitacae family, such as *S. grosvenorii*. In some embodiments, the plant cells expressing the polypeptides of the invention comprise fruit or root cells of a Cucurbitaceae plant.

The present invention contemplates the use of nucleic acid constructs for transformation of cells for expression of the mogroside biosynthesis pathway enzyme polypeptides and production of mogrol, mogrol precursors and mogroside. Thus, in some embodiments, there is provided a nucleic acid construct comprising an isolated polynucleotide of the invention and a cis-acting regulatory element for directing expression of the isolated polynucleotide.

Constructs useful in the methods according to some embodiments of the invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of preferred promoters useful for the methods of some embodiments of the invention are presented in Table 2, 3, 4 and 5.

TABLE 2

Exemplary constitutive promoters for use in the performance of some embodiments of the invention

| Gene Source | Expression Pattern | Reference |
|---|---|---|
| Actin | constitutive | McElroy etal, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100:456-462, 1997 |
| GOS2 | constitutive | de Pater et al, Plant J November; 2(6):837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1);107-121, 1996 |

TABLE 3

Exemplary seed-preferred promoters for use in the performance of embodiments of the invention

| Gene Source | Expression Pattern | Reference |
|---|---|---|
| Seed specific genes | seed | Simon, et al., Plant Mol. Biol. 5. 191, 1985; Scofield, etal., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235- 245, 1992. |
| legumin | seed | Ellis, et al.Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143).323-32 1990 |
| napA | seed | Stalberg, et al, Planta 199: 515-519, 1996 |
| wheat LMW and HMW, glutenin-1 | endosperm | Mol Gen Genet 216:81-90, 1989; NAR 17:461-2, |
| Wheat SPA | seed | Albanietal, Plant Cell, 9: 171-184, 1997 |
| wheat a, b and g gliadins | endosperm | EMBO3:1409-15, 1984 |
| Barley Itrl promoter | endosperm | |
| barley B1, C, D hordein | endosperm | Theor Appl Gen 98:1253-62, 1999; Plant J 4:343-55, 1993; Mol Gen Genet 250:750- 60, 1996 |
| Barley DOF | endosperm | Mena et al, The Plant Journal, 116(1): 53- 62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885- 889, 1998 |
| rice -globulin Glb-1 | endosperm | Wu et al, Plant Cell Physiology 398) 885-889, 1998 |
| rice OSH1 | emryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6:157-68, 1997 |
| maize ESR gene family | endosperm | Plant J 12:235-46, 1997 |
| sorgum gamma-kafirin | endosperm | PMB 32:1029-35, 1996 |
| KNOX | emryo | Postma-Haarsma ef al, Plant Mol. Biol. 39:257-71, 1999 |
| rice oleosin | Embryo and aleuton | Wu et at, J. Biochem., 123:386, 1998 |
| sunflower oleosin | Seed (embryo and dry seed) | Cummins, etal., Plant Mol. Biol. 19: 873- 876, 1992 |
| Tobacco NsCBTS | trichomes | Ennajdaoui et al., Plant Mol Biol. 73:6730685. 2010 |

TABLE 4

Exemplary flower-specific promoters for use in the performance of the invention

| Gene Source | Expression Pattern | Reference |
|---|---|---|
| AtPRP4 | flowers | www(dot)salus(dot) medium(dot)edu/m mg/tierney/html |
| chalene synthase (chsA) | flowers | Van der Meer, et al., Plant Mol. Biol. 15, 95-109, 1990. |

TABLE 4-continued

| Exemplary flower-specific promoters for use in the performance of the invention | | |
|---|---|---|
| Gene Source | Expression Pattern | Reference |
| LAT52 | anther | Twell et al Mol. Gen Genet. 217:240-245 (1989) |
| apetala- 3 | flowers | |

TABLE 5

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer o fembryo + calli |
| PR00081 | putative caffeoyl- CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |

TABLE 5-continued

Alternative rice promoters for use in the performance of the invention

| PRO # | gene | expression |
|---|---|---|
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PR00228 | BLZ-2_long (barley) | |

Nucleic acid sequences of the polypeptides of some embodiments of the invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot) or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, some embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Plant cells may be transformed stably or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane. According to some embodiments of the invention, there is provided a host cell heterologously expressing an isolated polynucleotide of the invention, as described hereinabove. The host cell can be any suitable host cell include bacteria, yeast and other microorganisms that can be cultured or grown in fermentation, plant and other eukaryotic cells. For example, the host cell a bacterial cell (e.g., *E. coli* and *B. subtilis*) transformed with a heterologous nucleic acid, such as bacteriophage DNA, plasmid DNA, or cosmid DNA expression vectors containing the nucleic acid molecules described herein, or yeast (e.g., *S. cerevisiae* or *S. pombe*) transformed with recombinant yeast expression vectors containing the nucleic acid molecules described herein.

In some embodiments, the host cell is a yeast cell. In a specific embodiment, the yeast cell is a yeast cell deprived of endogenous sterol biosynthesis, such as GIL77, or a yeast line deficient in the endogenous squalene epoxidase erg1 gene such as described in Rasbery J M et al. (Jour. Biol. Chem. 2007. 282:17002-17013).

In some embodiments, the host cell produces mogrol, mogrol or mogroside precursor, or mogroside.

The methods may also employ a mixture of recombinant and non-recombinant host. If more than one host is used then the hosts may be co-cultivated, or they may be cultured separately. If the hosts are cultivated separately the intermediate products may be recovered and optionally purified and partially purified and fed to recombinant hosts using the intermediate products as substrates.

Recombinant hosts described herein can be used in methods to produce mogroside compounds. For example, if the recombinant host is a microorganism, the method can include growing the recombinant microorganism in a culture medium under conditions in which one or more of the enzymes catalyzing step(s) of the methods of the invention, e.g. synthases, hydrolases. CYP450s and/or UGTs are expressed. The recombinant microorganism may be grown in a fed batch or continuous process.

Typically, the recombinant microorganism is grown in a fermenter at a defined temperature(s) for a desired period of time. A cell lysate can be prepared from the recombinant host expressing one or more enzymes and be used to contact a substrate, such that mogroside compounds can be produced. For example, a cell lysate can be prepared from the recombinant host expressing one or more UGTs and used to contact mogrol or mogroside, such that mogroside compounds can be produced.

In some embodiments, mogroside compounds can be produced using whole cells that are fed raw materials that contain precursor molecules, e.g., mogrol. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

Levels of products, substrates and intermediates can be determined by extracting samples from culture media for analysis according to published methods. Mogroside compounds can be recovered from the culture or culture medium using various techniques known in the art.

In some embodiments, there is provided a cell lysate of the host cell. Such a cell lysate can comprise both the mogroside pathway enzymes of the present invention, and the mogrol, mogrol and mogroside precursors and mogroside products of the pathways. Thus, the cell lysate can be used either for recovery of the products of the mogroside pathway (e.g. mogrol, mogroside M4, M5 and M6) or recovery of the recombinantly expressed enzymes polypeptides. Methods for extraction of active enzyme polypeptides are well known in the art.

Cell lysate of the invention can also be used for cell-free synthesis of mogrol, mogrol or mogroside precursors and mogroside, alone or in combination with other suitable substrates or enzymes.

Recombinant Host

This document also feature recombinant hosts. As used herein, the term recombinant host is intended to refer to a host, the genome of which has been augmented by at least one incorporated DNA sequence. The incorporated DNA sequence may be a heterologous nucleic acid encoding one or more polypeptides. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. The recombinant gene may also be a heterologous nucleic acid encoding one or more polypeptides. Generally, the introduced DNA or heterologous nucleic acid is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA or heterologous nucleic acid will modify or even replace an endogenous gene or DNA sequence by, e.g., homologous recombination or site-directed mutagenesis.

According to a specific embodiment, the plant is of the Cucurbitaceae family. Exemplary species are provided below.

Subfamily Zanonioideae (Small Striate Pollen Grains)

Tribe Zanonieae

Subtribe Fevilleinae: *Fevillea*

Subtribe Zanoniinae: *Alsomitra Zanonia Siolmatra Gerrardanthus Zygosicyos Xerosicyos Neoalsomitra*
Subtribe Gomphogyninae: *Hemsleya Gomphogyne Gynostemma*
Subtribe Actinostemmatinae: *Bolbostemma Actinostemma*
Subtribe Sicydiinae: *Sicydium Chalema Pteropepon Pseudosicydium Cyclantheropsis*
Subfamily Cucurbitoideae (Styles United into a Single Column)
Tribe Melothrieae
Subtribe Dendrosicyinae: *Kedrostis Dendrosicyos Corallocarpus Ibervillea Tumamoca Halosicyos Ceratosanthes Doyerea Trochomeriopsis Seyrigia Dieterlea Cucurbitella Apodanthera Guraniopsis Melothrianthus Wilbrandia*
Subtribe Guraniinae: *Helmontia Psiguria Gurania*
Subtribe Cucumerinae: *Melancium Cucumeropsis Posadaea Melothria* Muellarargia *Zehneria Cucumis* (including: *Mukia*, *Dicaelospermum*, *Cucumella*, *Oreosyce*, and *Myrmecosicyos*[4]).
Subtribe Trochomeriinae: *Solena Trochomeria Dactyliandra Ctenolepsis*
Tribe Schizopeponeae: *Schizopepon*
Tribe Joliffieae
Subtribe Thladianthinae: *Indofevillea Siraitia Thladiantha Momordica*
Subtribe Telfairiinae: *Telfaria*
Tribe Trichosantheae
Subtribe Hodgsoniinae: *Hodgsonia*
Subtribe Ampelosicyinae: *Ampelosicyos Peponium*
Subtribe Trichosanthinae: *Gymnopetalum Trichosanthes Tricyclandra*
Subtribe Herpetosperminae: *Cephalopentandra Biswarea Herpetospermum Edgaria*
Tribe Benincaseae
Subtribe Benincasinae: *Cogniauxia Ruthalicia Lagenaria Benincasa Praecitrullus Citrullus Acanthosicyos Eureiandra Bambekea Nothoalsomitra Coccinia Diplocyclos Raphidiocystis Lemurosicyos Zombitsia Ecballium Bryonia*
Subtribe Luffinae: *Luffa*
Tribe Cucurbiteae (pantoporate, spiny pollen): *Cucurbita Sicana Tecunumania Calycophysum Peponopsis Anacaona Polyclathra Schizocarpum Penelopeia Cionosicyos Cayaponia Selysia Abobra*
Tribe Sicyeae (trichomatous nectary, 4- to 10-colporate pollen grains)
Subtribe Cyclantherinae: *Hanburia Echinopepon Marah Echinocystis Vaseyanthus Brandegea Apatzingania Cremastopus Elateriopsis Pseudocyclanthera Cyclanthera Rytidostylis*
Subtribe Sicyinae: *Sicyos Sicyosperma Parasicyos Microsechium Sechium Sechiopsis Pterosicyos*
incertae *sedis*: *Odosicyos*
Alphabetical list of genera: *Abobra Acanthosicyos Actinostemma Alsomitra* Ampelosycios *Anacaona Apatzingania Apodanthera Bambekea Benincasa Biswarea Bolbostemma Brandegea Bryonia Calycophysum Cayaponia Cephalopentandra Ceratosanthes Chalema* Cionosicyos *Citrullus Coccinia Cogniauxia Corallocarpus Cremastopus Ctenolepis Cucumella Cucumeropsis Cucumis Cucurbita Cucurbitella Cyclanthera Dactyliandra Dendrosicyos Dicaelospermum Dieterlea Diplocyclos Doyerea Ecballium Echinocystis Echinopepon Edgaria Elateriopsis Eureiandra Fevillea Gerrardanthus Gomphogyne Gurania Guraniopsis Gymnopetalum Gynostemma Halosicyos Hanburia Helmontia Hemsleya Herpetospermum Hodgsonia Ibervillea Indofevillea Kedrostis Lagenaria Lemurosicyos Luffa Marah Melancium Melothria Melothrianthus Microsechium Momordica Muellerargia Mukia Myrmecosicyos Neoalsomitra Nothoalsomitra Odosicyos Oreosyce Parasicyos Penelopeia Peponium Peponopsis Polyclathra Posadaea Praecitrullus Pseudocyclanthera Pseudosicydium Psiguria Pteropepon Pterosicyos Raphidiocystis Ruthalicia Rytidostylis Schizocarpum Schizopepon Sechiopsis Sechium Selysia Seyrigia Sicana Sicydium Sicyos Sicyosperma Siolmatra Siraitia Solena Tecunumania Telfairia Thladiantha Trichosanthes Tricyclandra Trochomeria Trochomeriopsis* Tumacoca *Vaseyanthus Wilbrandia Xerosicyos Zanonia Zehneria Zombitsia Zygosicyos*.

*Cucurbita* genus refers to genus in the gourd family Cucurbitaceae native to and originally cultivated in the Andes and Mesoamerica. The *Cucurbita* species may be domesticated or non-domesticated.

Exemplary species include, but are not limited to:
*C. argyrosperma* (synonym *C. mixta*)—pipian, cushaw pumpkin; origin-Panama, Mexico
*C. kellyana*, origin-Pacific coast of western Mexico
*C. palmeri*, origin-Pacific coast of northwestern Mexico
*C. sororia*, origin-Pacific coast Mexico to Nicaragua, northeastern Mexico
*C. digitata*—fingerleaf gourd; origin-southwestern USA, northwestern Mexico
*C. californica*
*C. cordata*
*C. cylindrata*
*C. palmata*
*C. ecuadorensis*, origin-Ecuador's Pacific coast
*C. ficifolia*—figleaf gourd, chilacayote; origin-Mexico, Panama, northern Chile and Argentina
*C. foetidissima*—stinking gourd, buffalo gourd; origin-Mexico
*C. scabridifolia*, likely a natural hybrid of *C. foetidissima* and *C. pedatifolia*[67][68]
*C. galeottii* is little known; origin-Oaxaca, Mexico
*C. lundelliana*, origin-Mexico, Guatemala, Belize
*C. maxima*—winter squash, pumpkin; origin-Argentina, Bolivia, Ecuador
*C. andreana*, origin-Argentina
*C. moschata*—butternut squash, 'Dickinson' pumpkin, golden cushaw; origin-Bolivia, Colombia, Ecuador, Mexico, Panama, Puerto Rico, Venezuela
*C. okeechobeensis*, origin-Florida
*C. martinezii*, origin-Mexican Gulf Coast and foothills
*C. pedatifolia*, origin-Querétaro, Mexico
*C. moorei*
*C. pepo*—field pumpkin, summer squash, zucchini, vegetable marrow, courgette, acorn squash; origin-Mexico, USA
*C. fraterna*, origin-Tamaulipas and Nuevo Le6n, Mexico
*C. texana*, origin-Texas, USA
*C. radicans*—calabacilla, calabaza de coyote; origin-Central Mexico
*C. gracilior*

The polypeptides, polynucleotides, cells and methods of the present invention can be used to produce mogroside VI. Thus, according to some embodiments, there is provided a composition enriched in mogroside VI to a total concentration of mogroside VI of at least 10% (wt/wt).

In some embodiments, and especially in populations of recombinant cells producing mogroside, mogrosides MII and MV or MVI may be found together in significant amounts. Thus, according to one embodiment, there is provided a composition comprising mogroside VI (M6) and mogroside II (M2), and or a composition comprising mogroside V (M5), VI (M6) and mogroside II (M2).

In some embodiments, especially where the composition comprising the mogroside is produced in recombinant cells heterologously expressing one or more of the mogrol biosynthesis pathway enzymes of the invention, the composition comprises mogroside M4, and/or M5 and or M6, and DNA comprising at least one DNA sequence encoding the one or more mogrol biosynthesis pathway enzymes, the DNA sequence lacking at least one intron. In some embodiments, the sequence is 10%, 20%, 30%, 40%, 50%, 60% or more of the complete coding sequence of the mogrol biosynthesis pathway polypeptide. In some cases the at least one DNA sequence comprising the coding sequence comprises a coding sequence optimized for expression in a recombinant host, and differing in the nucleic acid sequence from the native (e.g. *S. grosvenorii*) sequence by at least 5%, at least 10%, at least 15%, at least 20% or more.

In some embodiments, wherein an enhanced sweetness is desired, a concentration of the mogroside VI or mogroside V is sufficient to cause an enhancement in flavor, and can be used as a sweetener. Such a composition can comprise a concentration of the mogroside VI of at least 0.2 ppm (e.g., 0.2-300) ppm or more.

In some embodiments, the composition of the invention is a consumable composition.

Consumables include all food products, including but not limited to, cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

Mogroside compositions of the invention can be used in various consumables including but not limited to water-based consumables, solid dry consumables and dairy products, dairy-derived products and dairy-alternative products. In some embodiments the composition is a foodstuff.

Water-based consumables include but are not limited to beverage, water, aqueous drink, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacao (water-based), tea-based drink, coffee-based drink, cacao-based drink, syrup, frozen fruit, frozen fruit juice, water-based ice, fruit ice, sorbet, dressing, salad dressing, sauce, soup, and beverage botanical materials (whole or ground), or instant powder for reconstitution (coffee beans, ground coffee, instant coffee, cacao beans, cacao powder, instant cacao, tea leaves, instant tea powder). In some embodiments, the composition can be a beverage such as Coca-Cola® and the like.

Solid dry consumables include but are not limited to cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, and botanical materials (whole or ground), and instant powders for reconstitution as mentioned above.

For water-based or solid dry consumables a useful concentration may be from 0.2 ppm (e.g., 0.2-300) ppm or more.

In certain products a higher sweetener concentration is usually necessary to reach similar sweetness intensity, for example in dairy products, dairy-derived products and dairy-alternative products. Dairy-derived food products contain milk or milk protein. Dairy-alternative products contain (instead of dairy protein derived from the milk of mammals) protein from botanical sources (soy, rice, and other protein-rich plant materials). Dairy products, dairy-derived products and dairy-alternative products include but are not limited to milk, fluid milk, cultured milk product, cultured and non-cultured dairy-based drinks, cultured milk product cultured with *lactobacillus*, yoghurt, yoghurt-based beverage, smoothy, lassi, milk shake, acidified milk, acidified milk beverage, butter milk, kefir, milk-based beverage, milk/juice blend, fermented milk beverage, icecream, dessert, sour cream, dip, salad dressings, cottage cheese, frozen yoghurt, soy milk, rice milk, soy drink, rice milk drink.

Milk includes, but is not limited to, whole milk, skim milk, condensed milk, evaporated milk, reduced fat milk, low fat milk, nonfat milk, and milk solids (which may be fat or nonfat).

For dairy products, dairy-derived products and dairy-alternative products, a useful concentration will be from about 0.3 to 500 ppm or higher, and may be up to 550 ppm, 600 ppm, 650 ppm, 700 ppm, or 750 ppm.

The composition of the invention can also include one or more additional flavor ingredients, such as additional sweeteners. A non-limiting list of suitable flavor ingredients useful with the composition of the invention includes sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, *stevia* and trilobtain.

Sweeteners commonly used in consumables include:

Acesulfame K—Artificial Sweetener (E950)
Agave Syrup—Modified Sugar
Alitame—Artificial Sweetener (E956)
Aspartame—Artificial Sweetener (E951)
Aspartame-Acesulfame Salt—Artificial Sweetener (E962)
Barley Malt Syrup—Modified Sugar
Birch Syrup—Sugar Extract
Blackstrap Molasses—Sugar Extract
Brazzein—Natural Sweetener
Brown Rice Syrup—Modified Sugar
Cane Juice—Sugar Extract
Caramel—Modified sugar
Coconut Palm Sugar—Sugar Extract
Corn Sugar (HFCS)—Modified sugar
Corn Sweetener (HFCS)—Modified sugar
Corn Syrup (HFCS)—Modified sugar
Curculin—Natural Sweetener
Cyclamate—Artificial Sweetener (E952)

Dextrose—Sugar
Erythritol—Sugar Alcohol (E968)
Fructose Glucose Syrup (HFCS)—Modified sugar
Fructose—Sugar
Galactose—Sugar
Glucitol (Sorbitol)—Sugar Alcohol (E420)
Glucose—Sugar
Glucose Fructose Syrup (HFCS)—Modified sugar
Glycerol (Glycerin)—Sugar Alcohol (E422)
Glycyrrhizin—Natural Sweetener (E958)
Golden Syrup—Modified sugar
High Fructose Corn Syrup (HFCS)—Modified Sugar
HFCS-42—Modified Sugar
HFCS-55—Modified Sugar
HFCS-90—Modified Sugar
Honey—Natural Sugar
HSH—Sugar Alcohol
Hydrogenated Starch Hydrolysate (HSH)— Sugar Alcohol
Isoglucose (HFCS)—Modified sugar
Inulin—Sugar Fiber
Inverted Sugar—Modified sugar
Isomalt—Sugar Alcohol (E953)
Lactitol—Sugar Alcohol (E966)
Lactose—Sugar
Levulose (Fructose)—Sugar
Luo Han Guo—Natural Sweetener
Maltitol—Sugar Alcohol (E965)
Maltodextrin—Sugar
Maltose—Sugar
Mannitol—Sugar Alcohol (E421)
Maple Syrup—Sugar Extract
Miraculin—Natural Sweetener
Molasses—Sugar Extract
Monellin—Natural Sweetener
Monk Fruit (Luo Han Guo)—Natural Sweetener
Neohesperidin DC—Artificial Sweetener (E959)
Neotame—Artificial Sweetener (E961)
Oligofructose—Sugar Fiber
Palm Sugar—Sugar Extract
Pentadin—Natural Sweetener
Rapadura—Sugar Extract
Refiners Syrup—Modified Sugar
Saccharin—Artificial Sweetener (E954)
Saccharose (Sucrose)—Sugar
Sorbitol—Sugar Alcohol (E420)
*Sorghum* Syrup—Sugar Extract
*Stevia*—Natural Sweetener
Stevioside—Natural Sweetener (E960)
Sucralose—Artificial Sweetener (E955)
Sucrose—Sugar
Tagatose—Modified Sugar
Thaumatin—Natural Sweetener (E957)
Trehalose—Sugar
Xylitol—Sugar Alcohol (E967)
Yacon Syrup—Natural Sweeten As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures

Gene Screen

In order to identify candidate *Siraitia* genes that may be involved in mogroside biosynthesis the present inventors have performed a detailed transcriptome analysis of 6 stages of developing *Siraitia* fruit. The fruit stages were 15, 34, 55, 77, 93 and 103 days after fruit set, which was accomplished by spraying the anthesis female flowers with a commercial fruit set hormone (20 ppm NAA naphthaleneacetic acid, commercial formulation Alphatop, Perelman Co. Tel Aviv, Israel) treatment commonly used for the production of parthenocarpic squash fruit. Developing fruits were sampled, stored at −80C and used for further analyses. RNA from powdered fruit samples was extracted and transcripts were prepared using the Tru Seq® RNA Sample Preparation Kit v2 (Illumina San Diego, California, USA) according to manufacturer's directions. RNA-seq libraries were analyzed using Illumina HiSeq2500 technology at the University of Illinois Genome Research Center and reads were assembled into transcript contigs using standard de novo assembly packages. Transcripts were annotated against public genome databases including NCBI non-redundant proteins (nr), and cucurbit genomics databases such as the melon genome (https://melonomics(dot)net/) and cucumber genome (www(dot)cugi(dot)org). Transcripts annotated as candidate genes for the various enzymes involved in the metabolism of mogrosides (squalene epoxidase, cucurbitadienol synthase, epoxide hydrolase, cytochrome P450 and UDPglucose glucosyltransferase) were selected for heterologous expression and functional analysis. The same fruit samples were analyzed for mogroside content in order to determine the stages of successive additions of glucosyl groups.

Tissue Sampling for Metabolic Profiling

Tissue preparation—For HPLC, fresh or frozen (−80° C.) fruit tissue was ground in liquid nitrogen using IKA All grinder. Then 600 μl of methanol:water (1:1) was added to 200 mg fine ground powder and the resulting mixture was vortexed for 30 seconds, sonicated for 15 min and vortexed again for 30 seconds. The sample was clarified of debris by centrifugation (20,000×g) and by filtration using Axiva syringe filters (PTFE, 0.2 m).

HPLC-DAD—The analysis was carried out on an Agilent 1200 HPLC system with an Agilent 1200 Diode Array Detector (DAD). The analytical column: Zorbax Stable Bond—C18 column (4.6×150.0 mm, 5.0 m, Agilent Technologies, USA). The mobile phase contained A, H2O with 0.1% formic acid; B, 100% HPLC grade acetonitrile. The column was equilibrated with 80% A, and then the sample was injected, reaching 90% B gradient after 10 min. The mobile phase flow was 1.5 ml $min^{-1}$. Each substance was identified by co-migration with commercial standards and by matching the spectrum of each nucleoside peak against that of a standard.

HPLC-MS—The analysis was carried out on an Agilent 1290 Infinity series liquid chromatograph coupled with an Agilent 1290 Infinity DAD and Agilent 6224 Accurate Mass Time of Flight (TOF) mass spectrometer (MS). The analytical column was: Zorbax Extend-C18 Rapid Resolution HT column (2.1×50.0 mm, 1.8 m, Agilent Technologies, Waldbronn, Germany) Mass spectrometry was performed using an Agilent 6224 Accurate Mass TOF LC/MS System equipped with a dual-sprayer orthogonal ESI source, with one sprayer for analytical flow and one for the reference compound (Agilent Technologies, Santa Clara, USA). The mobile phase contained A, H2O with 0.1% formic acid; B, 100% HPLC grade acetonitrile. The column was equilibrated with 80% A, and then the sample was injected, reaching 90% B gradient after 10 min. The mobile phase flow was 0.4 ml $min^{-1}$. Each substance was identified by co-migration with commercial standards and by matching the mass spectrum of putative peak against that of a standard. The chromatogram was initially analyzed by MassHunter Qualitative Analysis software v.B.05.00 (Agilent) and further analyzed by MassHunter Mass Profiler software v.B.05.00 (Agilent).

UGT Expression and Functional Analysis

For UGT expression, which was carried out in an *E. coli* expression system, the resulting plasmid was transformed to *E. coli* Arctic Express (Agilent). For expression of the UGT enzyme, a fresh overnight culture was diluted 1:100 in 25 ml LB medium with 50 μg/ml kanamycin and gentamicin, and incubated at 37° C. and 250 rpm until an A600 of 0.4 was reached. Subsequently, IPTG was added to a concentration of 0.5 mM, and the incubation was continued overnight at 18° C. and 250 rpm. The next day, cells were harvested by centrifugation, and the pellet resuspended in 2 ml of 50 mM Tris HCl pH=7.0 and 5 mM β-mercaptoethanol. After breaking the cells by sonication, insoluble material was removed by centrifugation, and the soluble fraction was used for characterization of the enzyme. Protein was stored at −20° C. until further analysis.

UGT Assays:

Substrates (mogrosides) were dissolved to 1 mM in 50% DMSO. Enzyme assays were carried out in 50 mM Tris HCl pH=7.0 and 5 mM β-mercaptoethanol using 8 mM UDP-xylose and 0.1 mM substrate and 25 ul of enzyme crude extract (reaction in an end volume of 100 μl). After overnight incubation at 30° C., reactions were stopped by addition of 300 μl methanol and 0.1% formic acid. Samples were prepared by brief vortexing. Then the extracts were centrifuged for 15 min at 13,000 rpm and analyzed on LC-MS. The product was compared to a control incubation which contained an enzyme preparation of an *E. coli* harboring an empty pET28a.

Example 1

Temporal Pattern of Mogroside Accumulation

Mogroside accumulation during development of the *Siraitia* fruit is shown in FIGS. 4A and 4B. Targeted metabolic profiling of *Siraitia* mogrosides during fruit ripening was carried out on methanolic extracts of the frozen powders and analyzed by HPLC with photodiode array and mass spec detection. Results reveal their unique temporal distribution. Mogrosides were limited to the developing fruit and were not observed in the root, stem or leaf tissue.

Already in the youngest stage of immature fruit analyzed, at 15 DAA (Days After Anthesis), the majority of the mogrols were present in the di-glucosylated form in which the C-3 and C-24 mogrol carbons are each mono-glucosylated. Non-glucosylated, mono-glucosylated or alternative M2 compounds, in which the second glucosyl moiety was present as a branched glucose on one of the primary glucose moieties, were not observed, indicating that the initial metabolic steps of mogroside glucosylations are limited to the two primary glucosylations and that these occur early in fruit development.

The total mogroside levels in the developing fruitlets remained similar throughout development and there was no indication of a net accumulation of mogrosides with development. These results indicate a strong temporal division of mogroside metabolism and that the early steps of mogrol synthesis and the initial primary glucosylations are limited to early fruit development, preparing the reservoir of mogrosides for subsequent glucosylations.

Following the synthesis of M2 there is an additional branched 1-6 glycosylation at the C24 position leading to the accumulation of M3X. During the later stages (77 and 90 DAA) a number of M4 compounds appeared, primarily siaminoside which was confirmed by NMR as the third branched glucosylation at the C24 position. Alternative tetra-glucosylated mogrosides, such as M4A, were also present, but in low amounts. M5, with a second glucosylation at the C3 position, began to accumulate at the expense of the M4 compounds at 77 DAA and increased sharply during the final stages of ripening. In the ripe 103 DAA fruit M5, along with small traces of IM5, comprised the majority of fruit mogroside components. (FIG. 4B).

Thus, at the youngest stage analyzed there was already the full complement of mogroside metabolites up to the diglucosylated mogrol, M2. Expression of candidate genes for the early stages of mogroside synthesis, including specifically squalene epoxidase, epoxide hydrolase, cucurbitadienol synthase, cyp450 and the primary glucosylation UGTs, was then undertaken Gene Cloning and Synthesis In general, synthetic genes were ordered from Gen9Bio (Cambridge MA, USA) and subcloned into pET28a vector using NheI and NotI restriction enzymes, and the inserts were verified by sequencing.

The following examples indicate the process used to identify the genes responsible for the pathway.

Example 2

Identification of *Siraitia* Cucurbitadienol Synthase (SgCDS) as the Enzyme which Cyclicizes Both 2,3-Monoepoxysqualene and 2,3;22,23-Diepoxysqualene, Leading to, Respectively, Cucurbitadienol and 24,25-Epoxycucurbitadienol The preferred substrate for the synthesis of the novel trans-C24,C25-dihydroxycucurbitadienol is 2,3;22,23-diepoxysqualene which is symmetrically epoxidated at both ends of the squalene molecule at the squalene numbered positions of C2,3 and C22,23 (FIG. 3). 2,3;22,23-diepoxysqualene is synthesized by the enzyme squalene epoxidase (SQE) which is ubiquitous in squalene metabolizing organisms, including the yeast strain GIL77. The yeast strain GIL77 is one of the strains in which the yeast gene erg7 encoding lanosterol synthase is mutated and non-functional, thereby making available the 2,3-epoxysqualene precursor to the cucurbitadienol synthase cyclization reaction and allowing for the synthesis of cucurbitadienol. This has previously been shown for the *Cucurbita* species CDS gene (referred to as CPQ in Shibuya M et al 2004. Tetrahedron 60:6995-7003). While it is known that cucurbitadienol synthase can cyclicise 2,3epoxysqualene to cucurbitadienol (FIG. 1), it was not known whether it can cyclicize the 2,3;22,23-diepoxysqualene to the 24,25-diepoxycucurbitadienol, which is the key intermediate in the proposed mogroside synthesis pathway of *Siraitia* (FIG. 2).

Surprisingly, it was found that the *Siraitia* gene coding for cucurbitadienol synthase SgCDS carries out the cyclization of both 2,3-epoxysqualene, leading to cucurbitadienol, and of 2,3;22,23-diepoxysqualene, leading to the critical substrate for the mogrol synthetic pathway, 24,25-epoxycucurbitadienol. The SgCDS gene (sequence gb/AEM42982) was heterologously expressed in the GIL77 yeast strain as described in Davidovich-Rikanati et al. (Yeast. 2015. 32(1): 103-114). In brief, transformed yeast were cultured and the GAL1 promoter was induced by replacing the glucose carbon source by galactose. Following 2 days of induction the yeast were disrupted in presence of 20% KOH: 50% EtOH sterols were extracted with hexane. The resulting cell extracts were subjected to LC-TOF-MS analysis using APCI interphase and the chromatograms are presented in FIG. 6B. The GIL77 control culture (FIG. 6A) produced both 2,3-epoxysqualene (R.T. 12.6) and 2,3;22,23-diepoxysqualene (R.T. 9.0), due to endogenous yeast erg1 squalene epoxidase enzyme activity. Expression of SgCDS (FIG. 6B) led to the accumulation of not only cucurbitadienol but also to the accumulation of the 24,25-epoxycucurbitadienol, the appropriate substrate for the following reaction of epoxide hydrolase.

Squalene epoxidase enzymes have previously been reported to carry out both mono and diepoxidation of squalene. This has been shown to function in both animal systems (i.e., the synthesis of 24,25-epoxycholesterol in cholesterol metabolism, Nelson J A et al., Jour. Biol. Chem. 1981. 256, 1067-1068; Bai M, et al., Bioch. Biophys. Res. Comm. 1992. 185:323-329) and plant systems (i.e., Rasbery J M et al., Jour. Biol. Chem. 2007. 282:17002-17013).

In order to identify candidate *Siraitia* squalene epoxidase genes that may be involved in mogrol biosynthesis a detailed transcriptome analysis of 6 stages of developing *Siraitia* fruit was performed. The fruit stages were 15, 34, 55, 77, 93 and 103 days after fruit set, and used for the production of transcriptome and mogroside metabolome that are described above. Data mining of *Siraitia* transcriptome led to the selection of 2 candidate squalene epoxidase enzymes (contigs 16760 and 18561) with high and early expression during fruiting (FIGS. 5A and 5B). These squalene epoxidase genes can be cloned and expressed in yeast, such as the line deprived of endogenic sterol biosynthesis (Gil77) as above) or a yeast line deficient in the endogenous squalene epoxidase erg1 gene such as described in Rasbery J M et al. (Jour. Biol. Chem. 2007. 282:17002-17013) and the products assayed for production of the mogrol precursor, 2,3;24,25-diepoxysqualene which can then be cyclized to 24,25-epoxycucurbitadienol and proceed through the mogrol biosynthetic pathway.

Example 3

Identification of *S. Grosvenorii* Epoxy Hydratase Enzymes Catalyzing the Hydration of 24,25-Epoxycucurbitadienol in Mogrol Biosynthesis In order to identify candidate *Siraitia* epoxy hydratase genes that may be involved in mogrol biosynthesis a detailed transcriptome analysis of 6 stages of developing *Siraitia* fruit was performed. The fruit stages were 15, 34, 55, 77, 93 and 103 days after fruit set, and used for the productions of transcriptome and mogroside metabolome that are described above. Data mining of *Siraitia* transcriptome led to the identification and isolation of 4 candidate epoxy hydratase enzymes (contigs 73966, 86123, 102640 and 28382) with high levels of expression early in fruit development (FIGS. 7 and 21-24).

The epoxy hydratase genes were expressed in GIL77 yeast, and the products assayed for production of 24,25-dihydroxycucurbitadienol from 24,25-epoxycucurbitadienol, the product of the previously described SgCDS reaction. FIGS. 8A and 8B show the effect of heterologous expression the three EPH candidate genes (coding sequences EPH1—SEQ ID NO: 17, EPH2-SEQ ID NO: 19 and EPH3-SEQ ID NO: 21) in the GIL77 yeast strain harboring the SgCDS gene. Cmp1(peak) represents the 24,25-dihydroxycucurbitadienol product and Cmp3(peak) represents the 24,25-epoxycucurbitadienol substrate. The results show that the expression of the *S. grosvenorii* SgEPH genes led to a large increase in the amount of the 24,25-dihydroxycucurbitadienol product (quantitative display—by area under peak—is shown in FIG. 8B). Due to endogenous yeast epoxide hydrolase activity, the control strain without the SgEPH) genes also accumulates 24,25-dihydroxycucurbitadienol, but to a much lower level (Gil77+SgCDS).

FIG. 9 shows the amino acid sequence identity matrix between the eight EPH genes of *Siraitia* which were identified in our transcriptomic and genomic analyses and the two EPH sequences reported by Tang et al., (2011) and subsequently used to produce tetrahydroxy squalene in WO2014086842 (identified as Seq Id Nos. 38 and 40 of WO2014086842).

Accordingly, the results of this example show that the genes identified as EPH genes in the *Siraitia* transcriptome are capable of carrying out the novel trans-24,25 dihydroxylation step following the CDS catalyzed cyclization of squalene diepoxide.

Example 4

Identification of Cucurbitadienol 11-Hydrolase

In order to identify candidate *Siraitia* cytochrome p450 genes that may be involved in mogrol biosynthesis a detailed transcriptome analysis of 6 stages of developing *Siraitia* fruit was performed. The fruit stages were 15, 34, 55, 77, 93 and 103 days after fruit set, and used for the productions of transcriptome and mogroside metabolome that are described above.

The *Siraitia* transcriptome indicated that the cyp450 family comprises over 100 members. Data mining of the *Siraitia* transcriptome based on homology analysis and expression patterns resulted in about 50 cytochrome CYP450 homologs that were expressed in developing fruits (FIG. 10) and therefore chosen for functional expression to test their activity in presence of cucurbitadienol.

To test the possible involvement of the candidate p450s in mogrol biosynthesis and test their functionality, nucleotide sequences of all candidates were synthesized (Gen9Bio, Cambridge, MA, USA) according to their deduced full length open reading frames, and cloned in a yeast expression vector system. The candidate p450 were cloned into the dual expression pESC-URA vector system (Agilent Technologies) possessing two multiple cloning sites (MCS) for gene expression of two genes under the galactose inducible GAL1 and GAL10 promoters. Each candidate CYP was introduced into MCS 2 while the SgCDS was cloned in MCS1 and produced cucurbitadienol when induced. The resulting plasmids were transferred to *S. cerevisiae* strain BY4743_YHR072 (MATa/α his3Δ1/his3Δ1 leu2Δ0/leu2Δ0 LYS2/lys2Δ0 met15Δ0/MET15 ura3Δ0/ura3Δ0 kanMax::erg7/ERG7) originating from the yeast deletion project collection (Brachmann C B et al Yeast 14(2): 115-32) that is heterozygous for lanosterol synthase, Erg7 (Corey E J et al. Proc Natl Acad Sci USA 91: 2211-2215). To aid p450 activity by supplying a proton source, all yeasts were transformed with the pESC-HIS vector harboring the *Arabidopsis thaliana* NADPH cytochrome p450 reductase (AtCPR1). Transformed yeast were cultured and the GAL1 promoter was induced by replacing the glucose carbon source by galactose and extracted as described in Example 2. The resulting cell extracts were subjected to LC-TOF-MS analysis using APCI interphase. The extracted ion chromatograms of the transformed yeast extracts are shown in FIG. 11A-11C. The heterologous expression of contig102801 next to SgCDS and AtCRP1 resulted in two major eluting compounds at 8.25 and 8.3 min with the designated molecular formula of C30H5002 and C30H4802 according to their exact mass of 443.3883 and 441.3727 respectively (FIG. 11A). The main product eluting at 8.3 min was further isolated for its chemical analysis by NMR to identify the OH position that was found to be on C11 of cucurbitadienol. The expression of the same contig without SgCDS resulted in no new compounds (FIG. 11B) indicating that the encoded enzyme acts on cucurbitadienol and not on lanosterol that is endogenically produced by yeast.

Example 5

Preparation of Mogroside Precursor Substrates for UGT Assays

Candidate UGT gene sequences were synthesized (BioGen9, Cambridge, MA, USA) and genes were individually expressed in *E. coli* cells. In parallel, substrates for each of the glucosylation reactions were purified, including mogrol, M1-E1 M2-A1, M2A, M3, M3x, siamenoside, M4, M5 (depicted in FIG. 12). These substrates were either purified from commercial mogroside powder (for compounds of M4 and above, described in (VSP Chaturvedula, I Prakash, Journal of Carbohydrate Chemistry, 2011 30:16-26 DOI: 10.1080/07328303.2011.583511 and additional mogrosides described in Sai Prakash Chaturvedula V. and Prakash I., IOSR Journal of Pharmacy. 2012 2(4):2250-3013) or by chemical and enzymatic hydrolysis of purified M5 and subsequent purification by HPLC.

Primary Glucosylations

In order to identify the UGT family enzymes responsible for mogrol glucosylation, nearly 100 genes of the total about 160 UGTs in the *Siraitia* genome (FIGS. 13A and 13B) which showed expression in the developing fruit (FIG. 14) were functionally expressed in *E. coli* as described above. The extracted recombinant enzymes were assayed with 0.1 mM of each of the 10 substrates (M, M1-E1, M2-A1, M2A, M2-E, M3x, M3, Siamenoside, M4, and M5), and 8 mM UDP-glucose, as glucose donor.

The overall results for the screening are presented in the activity matrices in FIGS. 15A-15C. The results identified three genes that carried out strictly the primary C3 glucosylation, members of UGT families 74, 75 and 85 (FIG. 15A columns A-D). A fourth gene, UGT85E5 (SEQ ID NO: 33) was the only identified gene capable of strictly carrying out the specific C24 primary glucosylation (FIG. 15A, C1). Additional enzymes of the UGT73 family were identified which carried either C25 glucosylation or a mix of C24 and C25 glucosylation (FIG. 15A, columns E-G), as identified by NMR.

Significantly, UGT85-269-1 was not only capable of carrying out the primary C-24 glucosylation of mogrol, but subsequently also the C-3 primary glucosylation of C-24-glucosylated mogrol, thus accounting itself for the synthesis of the diglucosylated M2. Thus, the UGT85-269-1 enzyme yielded both M1-C24 and M2-C3, C24 when incubated with mogrol, but not M1-C3 (FIG. 15A, C2-3, FIG. 16). It can furthermore be seen in FIG. 15A that the enzymes performing primary C3 glucosylation are also capable of performing the reaction irrespective of the glucosylation status C24, whether 0, 1, 2 or 3 glucose moieties occupy the position (FIG. 15A, columns A-D, rows 2-6).

Branched Glucosylations

The subsequent secondary branching glycosylations were carried out by three members of a single UGT family, UGT94, which were specific for branching and did not perform primary glucosylations (FIG. 15B columns I, J, K; FIG. 15C, columns M, N, O). The three UGT94 enzymes show differences in substrate specificity and activity as depicted in FIGS. 15B and 15C. UGT94 (289-3) and UGT94 (289-1) appear to be the most versatile, each leading to the pentaglucosylated M5 from M4, while UGT94 (289-2), appears to be most limited in its substrate specificity. FIG. 18 shows the similarity and identity scores between each of the genes described herein and the prior known gene sequences from *Siraitia*, described in Tang et al (2011) and WO2013/076577. The matrix was determined using MatGAT 2.02 (www(dot)bitincka(dot)com/ledion/matgat/) run with BLOSUM62.

Surprisingly, in some of the reactions of UGT94(289-3) with M5 as substrate we observed an M6 product (m/z 1642.5) (FIG. 17A). Furthermore, the branching enzyme UGT94 (289-3) was also capable of carrying out consecutive reactions of branching (FIG. 19A). When M1A1 was incubated with both UGT74-345-2 and UGT94-289-3 we observed M4 products. Since UGT94-289-3 can produce M5 from M4 substrates, as depicted in FIG. 15B, without wishing to be limited to a single hypothesis, it is possible that UGT94-289-3 can carry out the complete array of branching reactions if supplied with adequate substrate and optimal reaction conditions.

Surprisingly, UGT85E5 also showed branching activity, specifically on the C-3 primary glucose (FIG. 15B, column H)) and it too may contribute to the branching portion of the pathway, making it a key enzyme in mogroside synthesis.

In summary, based on the combined metabolic profiling, functional expression and protein modeling results the following metabolic pathway for mogroside biosynthesis is conceivable. During the initial stage of fruit development squalene is metabolized to the diglucosylated M2, via the progressive actions of squalene synthase, squalene epoxidase, cucurbitadienol synthase, epoxide hydrolase, cytochrome p450 (cyp102801) and UGT85. During fruit maturation there is the progressive activity of the UGT94 members, and perhaps also the UGT85, adding branched glucosyl groups to the primary glucosyl moieties of M2, leading to the sweet-flavored M4, M5 and M6 compounds.

The individual reactions summarized in FIGS. 15A-15C are described in the following individual examples.

Example 6

UGT74-345-2 Catalyzes the Addition of the Primary Glucose at Position C3.

Reaction containing UGT74-345-2 recombinant enzyme provided 0.1 mM aglycone Mogrol as substrate and 8 mM UDP-Glucose as sugar donor resulted in accumulation of MI-E1 (FIG. 15A-A1), whilst the same reaction containing 0.1 mM of MI-A1 as a substrate, resulted in accumulation of MII-E (FIG. 15A-A2). Moreover, in reaction containing 0.1 mM of M2-A1 accumulation of M3x was measured and in that containing MII-A accumulation of M3 was observed (FIG. 15A-A4 and A5). Furthermore, in the presence of MIII-A1 siamenoside was produced (FIG. 15A-A6). The analysis of the products of those reactions points to ability of UGT74-345-2 to perform primary glucosylation, attaching glucose moiety on C-3 position of Mogrol/Mogroside.

UGT75-281-2 Catalyzes the Addition of the Primary Glucose at Position C3.

Reaction containing UGT75-281-2 recombinant enzyme provided 0.1 mM aglycone Mogrol as substrate and 8 mM UDP-Glucose as sugar donor resulted in accumulation of MI-E1 (FIG. 15A-B1 and FIG. 16), whilst the same reaction containing 0.1 mM of MI-A1 as a substrate, resulted in accumulation of MII-E (FIG. 15A-B2 and FIG. 16). Moreover, in a reaction containing 0.1 mM of M2-A1 accumulation of M3x was measured and in that containing MII-A accumulation of M3 was observed (FIG. 15A-B4 and B5). The analysis of the products of those reactions points to ability of UGT75-281-2 to perform primary glucosylation, attaching glucose moiety on C-3 position of Mogrol/Mogroside.

UGT85-269-1 is a Promiscuous Enzyme and Catalyzes the Primary and the Branched Addition of Glucose Using 0.1 mM M, M1A1, M1E1, M2A1 or M2A as a substrate and 8 mM UDP-Glucose as sugar donor, accumulation of M1A1, M2E, M2E, M3x or M3, respectively, was observed when UGT85-269-1 recombinant enzyme was added into reaction (FIG. 15A-C1-C5 and FIG. 16). Therefore the UGT85-269-1 is a primary glucosyltransferase from Mogroside biosynthetic pathway, and is able to attach glucose (glucosylate) at C-3 or C-24 of Mogrol/mogroside. Given M2E, M3, M3x or Siamenoside as a substrate, UGT269-1-containing reaction mixes accumulated putative M3-C3(1-6), isomogroside 4 and trace amounts of M4, M4A and isomogroside 5, respectively (FIG. 15B-H1-H3 and H4). Indicating that UGT85-269-1 can act as both a primary and branched glucosyltransferase from Mogroside biosynthetic pathway.

UGT85-269-4 Catalyzes the Addition of the Primary Glucose at Position C3

Using 0.1 mM M, M1A1 M2A1 or M2A as a substrate and 8 mM UDP-Glucose as sugar donor, accumulation of M1E1, M2E, M3x or M3, respectively, was observed when UGT85-269-4 recombinant enzyme was added into reaction (FIG. 15A-D1-D5 and FIG. 16). Therefore the UGT85-269-4 is a primary glucosyltransferase from Mogroside biosynthetic pathway, and is able to attach glucose (glucosylate) at the C-3 position of mogrol.

UGT73-251-5 Catalyzes the Addition of the Primary Glucose at Position C24 or C25

When the UGT73-251-5 recombinant enzyme was added to a reaction mix containing 0.1 mM aglycone Mogrol as substrate and 8 mM UDP-Glucose as sugar donor, accumulation of M1-A1 and M1-B (FIG. 15A-E1) was observed, suggesting that UGT73-251-5 acts as C-24 and C-25 glucosyltransferase.

UGT73-251-6 Catalyzes the Addition of the Primary Glucose at Position C25

When the UGT73-251-6 recombinant enzyme was added to a reaction mix containing 0.1 mM aglycone Mogrol as substrate and 8 mM UDP-Glucose as sugar donor, accumulation of M1-B (FIG. 15A-D1) was observed, suggesting that UGT73-348-2 is C-25 glucosyltransferase.

UGT73-348-2 Catalyzes the Addition of the Primary Glucose at Position C24

[a]When the UGT73-348-2 recombinant enzyme was added to a reaction mix containing 0.1 mM aglycone Mogrol as substrate and 8 mM UDP-Glucose as sugar donor, accumulation of M1-A1 and M1-B (FIG. 15A-G1) was observed, suggesting that UGT73-348-2 is C-24 and C-25 glucosyltransferase.

UGT94-289-1 Catalyzes the Branched Additions of Glucose to the Primary Glucose at Position C24 and C3 in a 1-6 Position Using 0.1 mM Mogroside IIE as a substrate and 8 mM UDP-Glucose as sugar donor, accumulation of M3x was observed when UGT94-289-1 recombinant enzyme was added into reaction (FIG. 15B-K1). When M3 was used as a substrate, Siamenoside and trace amount of M4 accumulated in the reaction mix (FIG. 15B-K2). Finally, when M4 was used as a substrate, M5 was found to accumulate in reaction mix (FIG. 15B-K 4). In addition, when M1A1, M2A1 or M2A were added as substrate for glucosylation, M2A1, M3-A1 and M3-A1 accumulated, respectively (FIGS. 15C-O1, O3 and O4). Therefore the UGT94-289-1 is a branching glucosyltransferase from Mogroside biosynthetic pathway, and is able to attach glucose at (1-6) and (1-2) position on C-24 and C-3 glucosylated mogroside.

UGT94-289-2 Catalyzes the Branched Additions of Glucose to the Primary Glucose at Position C24 in a 1-6 Position Using 0.1 mM Mogroside IIE as a substrate and 8 mM UDP-Glucose as sugar donor, accumulation of M3x was observed when UGT94-289-2 recombinant enzyme was added into reaction (FIG. 15B-J1), whilst when M3 was used as substrate, accumulation of Siamenoside was observed in reaction mix (FIG. 15B-J2). In addition, when M1A1 or M2A were added as substrate for glucosylation, M2A1 and M3-A1 accumulated, respectively (FIG. 15C-N1 and N4). Therefore the UGT94-289-2 is a branching glucosyltransferase from Mogroside biosynthetic pathway, and is able to attach glucose at (1-6) position on C-24 glucosylated mogroside.

UGT94-289-3 is a Promiscuous Enzyme Catalyzes the Branched Additions of Glucose to the Primary Glucose at Position C24 and C3 in a 1-6 or 1-2 Position Using 0.1 mM Mogroside IIE as a substrate and 8 mM UDP-Glucose as sugar donor, accumulation of M3x was observed when UGT94-289-3 recombinant enzyme was added into reaction (FIG. 15B-I1). When M3, M3x M4 or Siamenoside were used as substrates, Siamenoside (with trace amounts of M4), M4A with Siamenoside, M5 and M5 were found in reaction mix, respectively (FIG. 15B-I2-I5 and FIG. 20). In addition, when M1A1, M1E1, M2A1 or M2 were added as substrate for glucosylation, M2A1, M2-A2, M3-A1 and M3-A1 accumulated, respectively (FIG. 165-M1-M4). Therefore the UGT94-289-3 is branching glucosyltransferase from Mogroside biosynthetic pathway, and is able to attach glucose at (1-6) and (1-2) positions on C-24 or C-3 glucosylated mogroside. In some of the reactions of UGT94-289-3 with M5 as substrate we observed an M6 product (m/z 1449.7113) (FIG. 15B-I6 and FIG. 17A).

UGT73-327-2 Catalyzes the Branched Addition of Glucose to the Primary Olucose at Position C3 in a 1-2 Position to Yield M6 from M5

Enzyme UGT73-327-2 was found to catalyze the final step in biosynthesis of Mogroside VI. When heterologously expressed UGT73-327-2 protein was added to reaction containing 0.1 mM Mogroside V and 8 mM UDP-Glucose, Mogroside VI was found among the reaction products, therefore designating UGT73-327-2 as a likely (1-2) C-3-Glu glucosyltransferase (FIG. 15B-L6).

Example 7

Phylogenetic Tree of the UGT Enzymes

Similarity and identity scores between each of the genes described herein and the nine prior known gene sequences from *Siraitia* were determined using MatGAT 2.02 (www (dot)bitincka(dot)com/ledion/matgat/) run with BLOSUM62. FIGS. 13A-B describe phylogenetic trees of the currently known UGTs as well as the novel UGTs of some embodiments of the invention. Alignments were carried out using the Clustal X software using default settings. Bootstrap values were also carried out using the Clustal X software (1000 iterations). The tree was visualized using the NJPLOT software. Numbers on tree branches show bootstrap proportions, which are the frequencies with which groups are encountered in analyses of replicate data sets and therefore provide an index of support for those groups. The length of the branches correspond to the numbers of substitutions per site.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A host cell that expresses an exogenous isolated polynucleotide comprising the nucleic acid sequence of SEQ ID NO: 33.

2. The host cell of claim 1, wherein said host cell is selected from the group consisting of a yeast cell, a bacterial cell and a plant cell.

3. The host cell of claim 2, wherein said plant cell is cell of a plant of the Cucurbitaceae family.

4. The host cell of claim 2, wherein said cell is a plant cell and said plant cell forms a part of a fruit or part of a root of the plant.

5. A cell lysate of the host cell of claim 1.

6. The host cell of claim 1, wherein the host cell comprises a nucleic acid construct comprising the polynucleotide of SEQ ID NO: 33 and a cis-acting regulatory element for directing expression of the polynucleotide of SEQ ID NO: 33.

* * * * *